US012421210B2

(12) United States Patent
Dickson et al.

(10) Patent No.: US 12,421,210 B2
(45) Date of Patent: Sep. 23, 2025

(54) FUSED BICYCLIC HETEROCYCLES AS THERAPEUTIC AGENTS

(71) Applicant: NEW YORK UNIVERSITY, New York, NY (US)

(72) Inventors: John K. Dickson, Apex, NC (US); Andrew S. Chi, New York, NY (US); Xinyan Huang, Paramus, NJ (US); Nadim Shohdy, Garden City, NY (US)

(73) Assignee: NEW YORK UNIVERSITY, New York, NY (US)

( * ) Notice: Subject to any disclaimer, the term of this patent is extended or adjusted under 35 U.S.C. 154(b) by 1077 days.

(21) Appl. No.: 17/282,917

(22) PCT Filed: Oct. 5, 2019

(86) PCT No.: PCT/US2019/054905
§ 371 (c)(1),
(2) Date: Apr. 5, 2021

(87) PCT Pub. No.: WO2020/073031
PCT Pub. Date: Apr. 9, 2020

(65) Prior Publication Data
US 2021/0395222 A1    Dec. 23, 2021

Related U.S. Application Data

(60) Provisional application No. 62/742,041, filed on Oct. 5, 2018.

(51) Int. Cl.
| | |
|---|---|
| *C07D 401/14* | (2006.01) |
| *C07D 209/94* | (2006.01) |
| *C07D 333/54* | (2006.01) |
| *C07D 401/12* | (2006.01) |
| *C07D 403/04* | (2006.01) |
| *C07D 405/14* | (2006.01) |
| *C07D 409/12* | (2006.01) |
| *C07D 413/14* | (2006.01) |
| *C07D 417/14* | (2006.01) |
| *C07D 471/04* | (2006.01) |
| *C07D 487/04* | (2006.01) |
| *C07D 491/048* | (2006.01) |
| *C07D 491/052* | (2006.01) |
| *C07D 495/04* | (2006.01) |
| *C07D 498/04* | (2006.01) |
| *C07D 513/04* | (2006.01) |
| *C07D 513/14* | (2006.01) |

(52) U.S. Cl.
CPC ......... *C07D 401/14* (2013.01); *C07D 209/94* (2013.01); *C07D 401/12* (2013.01); *C07D 405/14* (2013.01); *C07D 409/12* (2013.01); *C07D 413/14* (2013.01); *C07D 417/14* (2013.01); *C07D 471/04* (2013.01); *C07D 487/04* (2013.01); *C07D 491/048* (2013.01); *C07D 491/052* (2013.01); *C07D 495/04* (2013.01); *C07D 498/04* (2013.01); *C07D 513/04* (2013.01); *C07D 513/14* (2013.01)

(58) Field of Classification Search
CPC .. C07D 401/14; C07D 209/94; C07D 401/12; C07D 405/14; C07D 409/12; C07D 413/14; C07D 417/14; C07D 471/04; C07D 487/04; C07D 491/048; C07D 491/052; C07D 495/04; C07D 498/04; C07D 513/04; C07D 513/14; C07D 333/54; C07D 403/04
See application file for complete search history.

(56) References Cited

U.S. PATENT DOCUMENTS

| | | | | |
|---|---|---|---|---|
| 8,865,738 | B2 * | 10/2014 | Abouabdellah | ...... C07D 401/14 546/159 |
| 2009/0012116 | A1 * | 1/2009 | Kumar | ................. C07D 405/12 546/133 |
| 2016/0031813 | A1 | 2/2016 | Curtin et al. | |

FOREIGN PATENT DOCUMENTS

| | | | | |
|---|---|---|---|---|
| EP | 0413455 A2 * | 2/1991 | ........... | C07D 401/04 |
| WO | 2014/074715 A1 | 5/2014 | | |

OTHER PUBLICATIONS

Shah N, Khurana S, Cheng K, Raufman JP. Muscarinic receptors and ligands in cancer. Am J Physiol Cell Physiol. Feb. 2009;296(2):C221-32. doi: 10.1152/ajpcell.00514.2008. Epub Nov. 26, 2008. PMID: 19036940; PMCID: PMC2643856. (Year: 2009).*
Leiter U, Eigentler T, Garbe C. Epidemiology of skin cancer. Adv Exp Med Biol. 2014;810:120-40. doi: 10. 1007/978-1-4939-0437-2_7. PMID: 25207363. (Year: 2014).*
Kim JH, Nam G. Synthesis and evaluation of 6-pyrazoylamido-3N-substituted azabicyclo[3, 1,0]hexane derivatives as T-type calcium channel inhibitors for treatment of neuropathic pain. Bioorg Med Chem. Nov. 1, 2016;24(21):5028-5035. doi: 10.1016/j.bmc.2016.06.006. Epub Jun. 4, 2016. PMID: 27591007. (Year: 2016).*
Cecil Textbook of Medicine, vol. 1, Edition 20, 1997 (Year: 1997).*
Dictionary.com, In Vitro, 2024, https://www.dictionary.com/browse/in-vitro (Year: 2024).*
Cecil Textbook of Medicine, 20th Ed, vol. 1, 1997 (Year: 1997).*
Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022).*

(Continued)

*Primary Examiner* — Jeffrey H Murray
*Assistant Examiner* — Kevin S Martin
(74) *Attorney, Agent, or Firm* — McDonnell Boehnen Hulbert & Berghoff LLP

(57) ABSTRACT

This disclosure relates to compounds, pharmaceutical compositions comprising them, and methods of using the compounds and compositions for treating diseases related to nicotinamide phosphoribosyltransferase (NAM FT) expression. More particularly, this disclosure relates to fused bicyclic heterocyclic compounds and pharmaceutical compositions thereof, methods of inhibiting NAM FT with these compounds, and methods of treating diseases related to NAMPT expression.

10 Claims, No Drawings

(56) References Cited

OTHER PUBLICATIONS

Curtin et al. "SAR and Characterization of non-substrate isoindoline urea inhibitors of nicotinamide phosphoribosyltransferase (NAMPT)." Biooganic and Medicinal Chemistry Letters, vol. 27, p. 3317-3325, (2017).
Zak et al. "Minimizing CYP2C9 Inhibition of Eposed-Pyridine NAMPT (Nicotinamide Phosphoribosyltransferase) Inhibitors." Journal of Medicinal Chemistry, vol. 59, p. 8345-8368, (2016).
Giannetti et al. "Fragment Based Identification of Amides Derived from trans-2-(Pyridin-3-yl)-cyclopropanecarboxylic Acid as Potent Inhibitors of Human Nicotinamide Phosphoribosyltransferase (NAMPT)." Journal of Medicinal Chemistry, vol. 57, p. 770-792, (2014).
Galli et al. "Medicinal Chemistry of Nicotinamide Phosphoribosyltransferase (NAMPT) Inhibitors." Journal of Medicinal Chemistry, vol. 56, p. 6279-6296, (2016).
International Search Report and Written Opinion of International Application PCT/US2019/054905, dated Oct. 12, 2019.

\* cited by examiner

FUSED BICYCLIC HETEROCYCLES AS THERAPEUTIC AGENTS

CROSS-REFERENCE TO RELATED APPLICATIONS

This application is a national stage application under 35 U.S.C. § 371 of International Application No. PCT/US2019/054905, filed Oct. 5, 2019, which claims the benefit of priority of U.S. Provisional Patent Application No. 62/742,041, filed Oct. 5, 2018, the disclosures of each are incorporated by reference in their entirety.

BACKGROUND OF DISCLOSURE

Field of Disclosure

This disclosure relates to compounds, pharmaceutical compositions comprising them, and methods of using the compounds and compositions for treating diseases related to nicotinamide phosphoribosyltransferase (NAMPT) expression. More particularly, this disclosure relates to fused bicyclic heterocyclic compounds and pharmaceutical compositions thereof, methods of inhibiting NAMPT with these compounds, and methods of treating diseases related to NAMPT expression.

Technical Background

Nicotinamide adenine dinucleotide (NAD+) is a coenzyme that plays a critical role in many physiologically essential processes, such as metabolism, energy production, DNA repair, and signaling. For example, NAD is necessary for several signaling pathways including, for example, poly ADP-ribosylation in DNA repair, and mono-ADP-ribosylation in both the immune system and G-protein-coupled signaling. NAD is also required by sirtuins for their deacetylase activity. Cancer cells have a higher basal turnover of NAD+ and also display higher energy requirements compared with normal cells.

NAD+ can be synthesized from nicotinamide, nicotinic acid, or tryptophan. The major route to NAD+ is a two-step salvage pathway from nicotinamide. NAMPT is essential for the biosynthesis of NAD+. Specifically, NAMPT is the rate-limiting enzyme for the first step of the two-step salvage pathway, affecting the conversion of nicotinamide to nicotinamide mononucleotide (NMN).

NAMPT is also found to be upregulated in various cancer cells. Inhibition of NAMPT leads to depletion of NAD+. Without sufficient NAD+, the synthesis of adenosine-5′-triphosphate (ATP) is inhibited by attenuating glycolysis at the NAD+-requiring glyceraldehyde 3-phosphate dehydrogenase (GAPDH) step, among other metabolic perturbations. The depletion of NAD+ results in eventual decrease of cancer cell proliferation.

NAMPT inhibitors, such as FK866 and GMX1778, have been known for the treatment of cancer. However, FK866 and GMX1778 have not been particularly successful in clinical studies. Therefore, there remains a need for potent NAMPT inhibitors with desirable pharmaceutical properties.

SUMMARY OF THE DISCLOSURE

The disclosure provides novel NAMPT inhibitors useful for treating diseases related to NAMPT expression. Thus, one aspect of the disclosure provides a compound of formula (I):

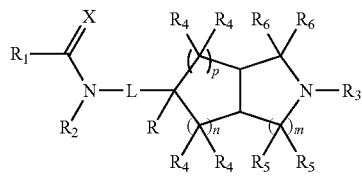

or a pharmaceutically acceptable salt thereof, wherein
m is an integer 1 or 2;
n is an integer 0, 1, or 2;
p is an integer 0 or 1;
L represents a $C_2$-$C_4$ alkylene linker optionally substituted with one or more $R_{15}$,
  wherein each $R_{15}$ is independently halogen, $C_1$-$C_6$ alkyl, —OH, $C_1$-$C_6$ alkoxy, or $C_1$-$C_6$ haloalkoxy, or two $R_{15}$ groups form a $C_3$-$C_4$ cyclyl;
X represents O or N—CN;
R is hydrogen or —F;
$R_1$ is —$R_7$, —$NHR_7$, —$OR_7$, or —$CH_2$—$OR_7$,
  wherein $R_7$ is $C_1$-$C_6$ alkyl optionally substituted with one or more $R_{10}$, aryl($C_0$-$C_4$ alkyl) optionally substituted with one or more $R_{11}$, aryl($C_2$-$C_4$ alkenyl) optionally substituted with one or more $R_{11}$, heteroaryl($C_0$-$C_4$ alkyl) optionally substituted with one or more $R_{11}$, heteroaryl($C_2$-$C_4$ alkenyl) optionally substituted with one or more $R_{11}$, heterocyclyl($C_0$-$C_4$ alkyl) optionally substituted with one or more $R_{11}$, and cyclyl($C_0$-$C_4$ alkyl) optionally substituted with one or more $R_{11}$, where
    each $R_{10}$ is independently selected from the group consisting of halogen, —$NO_2$, —CN, $C_1$-$C_6$ alkyl, $C_1$-$C_6$ haloalkyl, —OH, $C_1$-$C_6$ alkoxy, and $C_1$-$C_6$ haloalkoxy;
    each $R_{11}$ is independently selected from the group consisting of halogen, —$NO_2$, —CN, $C_1$-$C_6$ alkyl, $C_1$-$C_6$ haloalkyl, —$NH_2$, —$NH(C_1$-$C_6$ alkyl), —$N(C_1$-$C_6$ alkyl$)_2$, —OH, $C_1$-$C_6$ alkoxy, $C_1$-$C_6$ haloalkoxy, hydroxy($C_1$-$C_6$ alkyl), alkoxy($C_1$-$C_6$ alkyl), amino($C_1$-$C_6$ alkyl), —$CONH_2$, —CONH($C_1$-$C_6$ alkyl), —CON($C_1$-$C_6$ alkyl$)_2$, —CONH—OH, —$CO_2H$, —$CO_2(C_1$-$C_6$ alkyl), aryl optionally substituted with one or more $R_{12}$, heteroaryl optionally substituted with one or more $R_{12}$, and heterocyclyl optionally substituted with one or more $R_{12}$; or two $R_{11}$ groups when attached to the same carbon atom form =O;
    each $R_{12}$ is independently selected from the group consisting of halogen, —$NO_2$, —CN, $C_1$-$C_6$ alkyl, $C_1$-$C_6$ haloalkyl, —OH, $C_1$-$C_6$ alkoxy, and $C_1$-$C_6$ haloalkoxy;
$R_2$ is hydrogen or $C_1$-$C_6$ alkyl;
$R_3$ is selected from the group consisting of —$R_8$, —C(O)$R_8$, —C(O)O$R_8$, —C(O)$NH_2$, —C(O)$NR_8R_9$, and —$S(O)_{0-2}$—$R_8$, where
  each $R_8$ is independently selected from the group consisting of $C_1$-$C_6$ alkyl optionally substituted with one or more $R_{13}$, aryl($C_0$-$C_4$ alkyl) optionally substituted with one or more $R_{13}$, heteroaryl($C_0$-$C_4$ alkyl) optionally substituted with one or more $R_{13}$, heterocyclyl($C_0$-$C_4$ alkyl) optionally substituted with one or more $R_{13}$, and cyclyl($C_0$-$C_4$ alkyl) optionally substituted with one or more $R_{13}$;

$R_9$ is hydrogen or $C_1$-$C_6$ alkyl;

each $R_{13}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy optionally substituted with one or more $R_{16}$, $C_1$-$C_6$ haloalkoxy, hydroxy($C_1$-$C_6$ alkyl), alkoxy($C_1$-$C_6$ alkyl), amino($C_1$-$C_6$ alkyl), —$CONH_2$, —CONH($C_1$-$C_6$ alkyl), —CON($C_1$-$C_6$ alkyl)$_2$, —CONH—OH, —$CO_2H$, —$CO_2$($C_1$-$C_6$ alkyl), —P(O)(OH)$_2$, —P(O)(O$C_1$-$C_6$ alkyl)$_2$, —P(O)($C_1$-$C_6$ alkyl)$_2$, aryl optionally substituted with one or more $R_{14}$, heteroaryl optionally substituted with one or more $R_{14}$, and heterocyclyl optionally substituted with one or more $R_{14}$; or two $R_{13}$ groups when attached to the same carbon atom form =O;

each $R_{14}$ is independently selected from the group consisting of halogen, —$NO_2$, —CN, $C_1$-$C_6$ alkyl, $C_1$-$C_6$ haloalkyl, —OH, $C_1$-$C_6$ alkoxy, and $C_1$-$C_6$ haloalkoxy;

each $R_{16}$ is independently selected from the group consisting of —OH, $C_1$-$C_6$ alkoxy, —$NH_2$, —NH($C_1$-$C_6$ alkyl), —N($C_1$-$C_6$ alkyl)$_2$, —$CO_2H$, —$CO_2$($C_1$-$C_6$ alkyl), —$CONH_2$, —CONH($C_1$-$C_6$ alkyl), —CON($C_1$-$C_6$ alkyl)$_2$, aryl($C_0$-$C_2$ alkyl) optionally substituted with one or more $R_{14}$, heteroaryl($C_0$-$C_2$ alkyl) optionally substituted with one or more $R_{14}$, heterocyclyl($C_0$-$C_2$ alkyl) optionally substituted with one or more $R_{14}$, and cyclyl($C_0$-$C_2$ alkyl) optionally substituted with one or more $R_{14}$;

each $R_4$ is independently selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy;

each $R_5$ is independently selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy; and each $R_6$ is independently selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy, or two $R_6$ groups form an oxo or a thioxo group.

In certain embodiments of this aspect, the compounds of formula (I) exclude:

ethyl 5-((((2-(2-(5-bromopyridin-2-yl)octahydrocyclopenta[c]pyrrol-5-yl)ethyl)carbamoyl)oxy)methyl)isoxazole-3-carboxylate;

ethyl 5-((((2-(2-(tert-butoxycarbonyl)octahydrocyclopenta[c]pyrrol-5-yl)ethyl)carbamoyl)oxy)methyl)isoxazole-3-carboxylate;

(3-carbamoylisoxazol-5-yl)methyl (2-(2-(5-bromopyridin-2-yl)octahydrocyclopenta[c]pyrrol-5-yl)ethyl)carbamate;

(3-(methylcarbamoyl)isoxazol-5-yl)methyl (2-(2-(5-bromopyridin-2-yl)octahydrocyclopenta[c]pyrrol-5-yl)ethyl)carbamate; or ethyl 7-(6-(2-((tert-butoxycarbonyl)amino)ethyl)-3-azabicyclo[3.1.0]hexan-3-yl)-1-(2,4-difluorophenyl)-6-fluoro-4-oxo-1,4-dihydro-1,8-naphthyridine-3-carboxylate.

Another aspect of the disclosure provides a compound of formula (II):

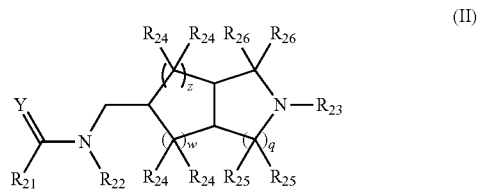

or a pharmaceutically acceptable salt thereof, wherein
q is an integer 1 or 2;
w is an integer 0, 1, or 2;
z is an integer 0 or 1;
Y represents O or N—CN;
$R_{21}$ is —$R_{25}$, —$NHR_{27}$, or —$CH_2$—$OR_{27}$,
wherein $R_{25}$ is heteroaryl($C_2$-$C_4$ alkenyl), pyridinyl($C_0$-$C_4$ alkyl), 1,3-dihydro-2H-pyrrolo[3,4-c]pyridin-2-yl, thieno[2,3-c]pyridin-2-yl, or isoxazolyl, each optionally substituted with one or more $R_{31}$,
wherein $R_{27}$ is $C_1$-$C_6$ alkyl optionally substituted with one or more $R_{30}$, aryl($C_0$-$C_4$ alkyl) optionally substituted with one or more $R_{31}$, aryl($C_2$-$C_4$ alkenyl) optionally substituted with one or more $R_{31}$, heteroaryl($C_0$-$C_4$ alkyl) optionally substituted with one or more $R_{31}$, heteroaryl($C_2$-$C_4$ alkenyl) optionally substituted with one or more $R_{31}$, heterocyclyl($C_0$-$C_4$ alkyl) optionally substituted with one or more $R_{31}$, and cyclyl($C_0$-$C_4$ alkyl) optionally substituted with one or more $R_{31}$, where each $R_{30}$ is independently selected from the group consisting of halogen, —$NO_2$, —CN, $C_1$-$C_6$ alkyl, $C_1$-$C_6$ haloalkyl, —OH, $C_1$-$C_6$ alkoxy, and $C_1$-$C_6$ haloalkoxy;

each $R_{31}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), alkoxy($C_1$-$C_6$ alkyl), amino($C_1$-$C_6$ alkyl), —$CONH_2$, —CONH($C_1$-$C_6$ alkyl), —CON($C_1$-$C_6$ alkyl)$_2$, —CONH—OH, —$CO_2H$, —$CO_2$($C_1$-$C_6$ alkyl), aryl optionally substituted with one or more $R_{32}$, heteroaryl optionally substituted with one or more $R_{32}$, and heterocyclyl optionally substituted with one or more $R_{32}$; or two $R_{31}$ groups when attached to the same carbon atom form =O;

each $R_{32}$ is independently selected from the group consisting of halogen, —$NO_2$, —CN, $C_1$-$C_6$ alkyl, $C_1$-$C_6$ haloalkyl, —OH, $C_1$-$C_6$ alkoxy, and $C_1$-$C_6$ haloalkoxy;

$R_{22}$ is hydrogen or $C_1$-$C_6$ alkyl;
$R_{23}$ is selected from the group consisting of —$R_{28}$, —C(O)$R_{28}$, —C(O)O$R_{28}$, —C(O)$NH_2$, —C(O)N$R_{28}R_{29}$, and —S(O)$_{0-2}$—$R_{28}$, where each $R_{28}$ is independently selected from the group consisting of $C_1$-$C_6$ alkyl optionally substituted with one or more $R_{33}$, aryl($C_0$-$C_4$ alkyl) optionally substituted with one or more $R_{33}$, heteroaryl($C_0$-$C_4$ alkyl) optionally substituted with one or more $R_{33}$, heterocyclyl($C_0$-$C_4$ alkyl) optionally substituted with one or more $R_{33}$, and cyclyl($C_0$-$C_4$ alkyl) optionally substituted with one or more $R_{33}$;

$R_{29}$ is hydrogen or $C_1$-$C_6$ alkyl;
each $R_{33}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), alkoxy($C_1$-$C_6$ alkyl), amino($C_1$-$C_6$ alkyl), —CONH$_2$, —CONH($C_1$-$C_6$ alkyl), —CON($C_1$-$C_6$ alkyl)$_2$, —CONH—OH, —CO$_2$H, —CO$_2$($C_1$-$C_6$ alkyl), aryl optionally substituted with one or more $R_{34}$, heteroaryl optionally substituted with one or more $R_{34}$, and heterocyclyl optionally substituted with one or more $R_{34}$; or two $R_{33}$ groups when attached to the same carbon atom form =O;

each $R_{34}$ is independently selected from the group consisting of halogen, —NO$_2$, —CN, $C_1$-$C_6$ alkyl, $C_1$-$C_6$ haloalkyl, —OH, $C_1$-$C_6$ alkoxy, and $C_1$-$C_6$ haloalkoxy;

each $R_{24}$ is independently selected from the group consisting of hydrogen, halogen, $O_1$-$O6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy;

each $R_{25}$ is independently selected from the group consisting of hydrogen, halogen, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy; and each $R_{26}$ is independently selected from the group consisting of hydrogen, halogen, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy, or two $R_{26}$ groups form an oxo or a thioxo group.

Another aspect of the disclosure provides a pharmaceutical composition including one or more compounds of the disclosure as described herein (e.g., compounds of formula (I) and/or (II)) and a pharmaceutically acceptable carrier, solvent, adjuvant or diluent.

Another aspect of the disclosure provides a method of treating cancer, the method including administering to a subject in need of such treatment one or more compounds of the disclosure as described herein or a pharmaceutical composition of the disclosure as described herein.

In certain embodiments of this aspect, the cancer is a solid tumor (e.g., carcinomas, sarcomas, astrocytomas, glioblastoma, oligodendroglioma, high-grade glioma, malignant glioma, glioma cholangiocarcinoma, thyroid cancer, and melanoma). In certain embodiments of this aspect, the cancer is a hematological malignancy (e.g., leukemia and lymphoma).

In certain embodiments of this aspect, the cancer is an IDH1 mutant cancer or an IDH2 mutant cancer. In certain embodiments of this aspect, the cancer includes mutation or gene amplification of the MYC, MYCN, and/or MYCL genes. In certain embodiments of this aspect, the cancer includes reduced expression of NAPRT1 or DNA methylation of the NAPRT1 promoter.

Another aspect of the disclosure provides a method of inhibiting NAMPT, the method including administering one or more compounds of the disclosure as described herein or a pharmaceutical composition of the disclosure as described herein.

Additional aspects of the disclosure will be evident from the disclosure herein.

DETAILED DESCRIPTION

Before the disclosed processes and materials are described, it is to be understood that the aspects described herein are not limited to specific embodiments, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

In view of the present disclosure, the methods and compositions described herein can be configured by the person of ordinary skill in the art to meet the desired need. In general, the disclosed materials and methods provide improvements in treatment of cancer. Specifically, the inventors found that the compounds of the disclosure inhibit NAMPT with sub-µM IC$_{50}$. For example, in certain embodiments, the compounds of the disclosure inhibit NAMPT at IC$_{50}$ of no more than 1 µM, or no more than 100 nm, or even no more than 10 nm.

Accordingly, one aspect of the disclosure provides compounds of formula (I) as provided above.

In certain embodiments, the compounds of formula (I) exclude:

ethyl 5-((((2-(2-(5-bromopyridin-2-yl)octahydrocyclopenta[c]pyrrol-5-yl)ethyl)carbamoyl)oxy)methyl)isoxazole-3-carboxylate;

ethyl 5-((((2-(2-(tert-butoxycarbonyl)octahydrocyclopenta[c]pyrrol-5-yl)ethyl)carbamoyl)oxy)methyl)isoxazole-3-carboxylate;

(3-carbamoylisoxazol-5-yl)methyl (2-(2-(5-bromopyridin-2-yl)octahydrocyclopenta[c]pyrrol-5-yl)ethyl)carbamate;

(3-(methylcarbamoyl)isoxazol-5-yl)methyl (2-(2-(5-bromopyridin-2-yl)octahydrocyclopenta[c]pyrrol-5-yl)ethyl) carbamate; or ethyl 7-(6-(2-((tert-butoxycarbonyl)amino)ethyl)-3-azabicyclo[3.1.0]hexan-3-yl)-1-(2,4-difluorophenyl)-6-fluoro-4-oxo-1,4-dihydro-1,8-naphthyridine-3-carboxylate.

In some embodiments, the compounds of formula (I) as otherwise described herein are those wherein R is hydrogen.

In some embodiments, the compounds of formula (I) as otherwise described herein are those wherein m is 1. In one embodiment, the disclosure provides compounds of formula (I) as otherwise described herein where m is 1, and both n and p are 0, e.g., the compounds of formula (I-1) or (1-2):

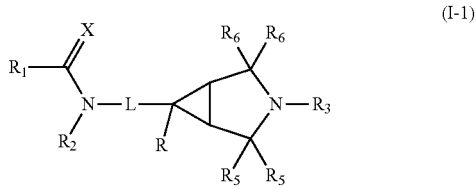

(I-1)

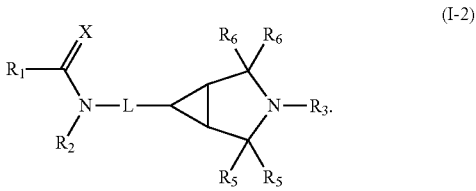

(I-2)

In one embodiment, the disclosure provides compounds of formula (I) as otherwise described herein where m is 1, and both n and p are 1, e.g., the compounds of formula (I-3) or (I-4):

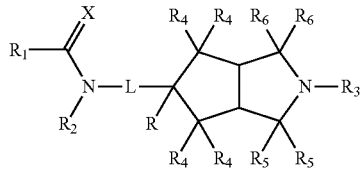

(I-3)

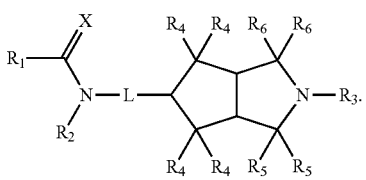

(I-4)

In one embodiment, the disclosure provides compounds of formula (I) as otherwise described herein where m is 1, and n is 2, and p is 1, e.g., the compounds of formula (I-5) or (I-6):

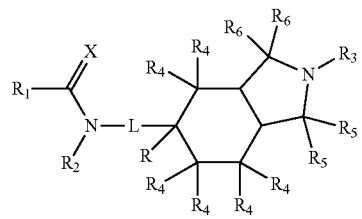

(I-5)

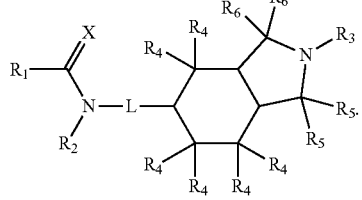

(I-6)

In some embodiments, the compounds of formula (I) as otherwise described herein are those wherein m is 2. In one embodiment, the disclosure provides compounds of formula (I) as otherwise described herein where m is 2, and both n and p are 1. Such compounds are of formula (I-7) or (I-8):

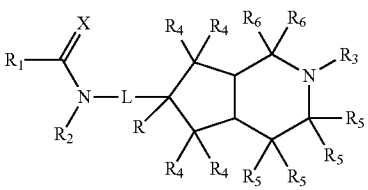

(I-7)

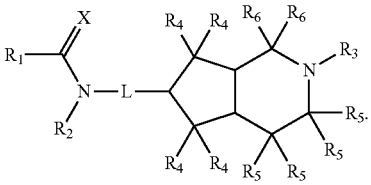

(I-8)

Another embodiment of the disclosure provides compounds of formula (I)-(I-8) as otherwise described herein where L is ethylene optionally substituted with one or more $R_{15}$. For example, in certain embodiments of the disclosure, each $R_{15}$ is independently halogen, $C_1$-$C_3$ alkyl, —OH, $C_1$-$C_3$ alkoxy, or $C_1$-$C_3$ haloalkoxy, or two $R_{15}$ groups form a $C_3$-$C_4$ cyclyl. In certain embodiments of the disclosure, each $R_{15}$ is independently halogen, $C_1$-$C_3$ alkyl, or —OH, or two $R_{15}$ groups form a $C_3$-$C_4$ cyclyl. Some particular embodiments include those wherein L is ethylene optionally substituted with one $R_{15}$, and wherein $R_{15}$ is independently halogen or —OH. Some particular embodiments include those wherein L is ethylene optionally substituted with two $R_{15}$ groups that form a $C_3$-$C_4$ cyclyl (e.g., cyclopropyl). Some particular embodiments include those wherein L is unsubstituted ethylene. Other embodiments are those where L is ethylene, —$CH_2$—CHF—, —$CH_2$—CHOH—, or —C(cyclopropyl)-$CH_2$—.

Another embodiment of the disclosure provides compounds of formula (I)-(I-8) as otherwise described herein where L is $C_3$-$C_4$ alkylene linker optionally substituted with one or more $R_{15}$. In certain embodiments of the disclosure, each $R_{15}$ is independently halogen, $C_1$-$C_3$ alkyl, —OH, $C_1$-$C_3$ alkoxy, or $C_1$-$C_3$ haloalkoxy, or two $R_{15}$ groups form a $C_3$-$C_4$ cyclyl. In certain embodiments of the disclosure, each $R_{15}$ is independently halogen, $C_1$-$C_3$ alkyl, or —OH, or two $R_{15}$ groups form a $C_3$-$C_4$ cyclyl. In certain embodiments of the disclosure, one or more of $R_{15}$ is independently halogen or —OH. In certain embodiments of the disclosure, two $R_{15}$ groups that form a $C_3$-$C_4$ cyclyl (e.g., cyclopropyl).

In certain embodiments of the disclosure, the compounds of formula (I)-(I-8) as otherwise described herein are those wherein X represents O.

Another embodiment of the disclosure provides compounds of formula (I)-(I-8) as otherwise described herein where X represents N—CN.

One embodiment of the disclosure provides compounds of formula (I)-(I-8) as otherwise described herein where $R_1$ is —$R_7$, —$NHR_7$, or —$CH_2$—$OR_7$. Another embodiment of the disclosure provides compounds of formula (I)-(I-8) as otherwise described herein where $R_1$ is —$R_7$, —$NHR_7$, or —$OR_7$. Another embodiment of the disclosure provides compounds of formula (I)-(I-8) as otherwise described herein where $R_1$ is —$R_7$ or —$NHR_7$. Yet another embodiment of the disclosure provides compounds of formula (I)-(I-8) as otherwise described herein where $R_1$ is —$R_7$.

Another embodiment of the disclosure provides compounds of formula (I)-(I-8) as otherwise described herein where $R_1$ is —$R_7$, which is $C_1$-$C_6$ alkyl optionally substituted with one or more $R_{10}$, aryl($C_0$-$C_2$ alkyl) optionally substituted with one or more $R_{11}$, aryl($C_2$-$C_3$ alkenyl) optionally substituted with one or more $R_{11}$, heteroaryl($C_0$-$C_2$ alkyl) optionally substituted with one or more $R_{11}$, heteroaryl($C_2$-$C_3$ alkenyl) optionally substituted with one or more $R_{11}$, heterocyclyl($C_0$-$C_2$ alkyl) optionally substituted with one or more $R_{11}$, or cyclyl($C_0$-$C_2$ alkyl) optionally substituted with one or more $R_{11}$. In certain embodiments of the disclosure, $R_1$ is $C_1$-$C_6$ alkyl optionally substituted with one or more $R_{10}$, aryl optionally substituted with one or more $R_{11}$, aryl(ethenyl) optionally substituted with one or more $R_{11}$, heteroaryl optionally substituted with one or more $R_{11}$, heteroaryl(ethenyl) optionally substituted with one or more $R_{11}$, heterocyclyl optionally substituted with one or more $R_{11}$, or cyclyl optionally substituted with one or more $R_{11}$. In certain embodiments of the disclosure, $R_1$ is $C_1$-$C_6$ alkyl, aryl optionally substituted with one or more $R_{11}$, aryl(ethenyl) optionally substituted with one or more $R_{11}$, heteroaryl optionally substituted with one or more $R_{11}$, heteroaryl(ethenyl) optionally substituted with one or more $R_{11}$, heterocyclyl optionally substituted with one or more $R_{11}$, or cyclyl optionally substituted with one or more $R_{11}$. In certain embodiments of the disclosure, where $R_1$ is $C_1$-$C_6$ alkyl, aryl optionally substituted with one or more $R_{11}$, heteroaryl optionally substituted with one or more $R_{11}$, heteroaryl(ethenyl) optionally substituted with one or more $R_{11}$, heterocyclyl optionally substituted with one or more $R_{11}$, or cyclyl optionally substituted with one or more $R_{11}$. In certain embodiments of the disclosure, $R_1$ is aryl optionally substituted with one or more $R_{11}$, heteroaryl optionally substituted with one or more $R_{11}$, heteroaryl(ethenyl) optionally substituted with one or more $R_{11}$, heterocyclyl optionally substituted with one or more $R_{11}$, or cyclyl optionally substituted with one or more $R_{11}$. In certain embodiments of the disclosure, the compounds of formula (I)-(I-8) as otherwise described herein are those where $R_1$ is heteroaryl optionally substituted with one or more $R_{11}$, heteroaryl(ethenyl) optionally substituted with one or more $R_{11}$, or heterocyclyl optionally substituted with one or more $R_{11}$. In certain embodiments of the disclosure, $R_1$ is heteroaryl optionally substituted with one or more $R_{11}$ or heteroaryl(ethenyl) optionally substituted with one or more $R_{11}$. In certain embodiments of the disclosure, the compounds of formula (I)-(I-8) as otherwise described herein are those where $R_1$ is heteroaryl(ethenyl) optionally substituted with one or more $R_{11}$; or $R_1$ is 4-pyridinyl(ethenyl), 3-pyridinyl(ethenyl), or 2-pyridinyl(ethenyl), each optionally substituted with one or more $R_{11}$.

Another embodiment of the disclosure provides compounds of formula (I)-(I-8) as otherwise described herein where $R_1$ is —$NHR_7$, wherein $R_7$ is $C_1$-$C_6$ alkyl optionally substituted with one or more $R_{10}$, aryl($C_0$-$C_2$ alkyl) optionally substituted with one or more $R_{11}$, aryl($C_2$-$C_3$ alkenyl) optionally substituted with one or more $R_{11}$, heteroaryl($C_0$-$C_2$ alkyl) optionally substituted with one or more $R_{11}$, heteroaryl($C_2$-$C_3$ alkenyl) optionally substituted with one or more $R_{11}$, heterocyclyl($C_0$-$C_2$ alkyl) optionally substituted with one or more $R_{11}$, or cyclyl($C_0$-$C_2$ alkyl) optionally substituted with one or more $R_{11}$. In certain embodiments of the disclosure, are those where $R_7$ is $C_1$-$C_6$ alkyl optionally substituted with one or more $R_{10}$, aryl optionally substituted with one or more $R_{11}$, aryl(methyl) optionally substituted with one or more $R_{11}$, heteroaryl optionally substituted with one or more $R_{11}$, heteroaryl(methyl) optionally substituted with one or more $R_{11}$, heterocyclyl optionally substituted with one or more $R_{11}$, or cyclyl optionally substituted with one or more $R_{11}$. In certain embodiments of the disclosure, $R_7$ is $C_1$-$C_6$ alkyl, aryl optionally substituted with one or more $R_{11}$, aryl(methyl) optionally substituted with one or more $R_{11}$, heteroaryl optionally substituted with one or more $R_{11}$, heteroaryl(methyl) optionally substituted with one or more $R_{11}$, heterocyclyl optionally substituted with one or more $R_{11}$, or cyclyl optionally substituted with one or more $R_{11}$. In certain embodiments of the disclosure, the compounds of formula (I)-(I-8) as otherwise described herein are those where $R_7$ is heteroaryl optionally substituted with one or more $R_{11}$, heteroaryl(methyl) optionally substituted with one or more $R_{11}$, or heterocyclyl optionally substituted with one or more $R_{11}$. In certain embodiments of the disclosure, the compounds of formula (I)-(I-8) as otherwise described herein are those where $R_7$ is pyridinyl, 4-pyridinyl(methyl), 3-pyridinyl(methyl), or 2-pyridinyl(methyl), each optionally substituted with one or more $R_{11}$.

In certain embodiments of the disclosure, the compounds of formula (I)-(I-8) as otherwise described herein are those where each $R_{11}$ is independently selected from the group consisting of halogen, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, aryl optionally substituted with one or more $R_{12}$, heteroaryl optionally substituted with one or more $R_{12}$, and heterocyclyl optionally substituted with one or more $R_{12}$. In certain embodiments of the disclosure, the compounds of formula (I)-(I-8) as otherwise described herein are those where each $R_{11}$ is independently selected from the group consisting of halogen, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, and heteroaryl optionally substituted with one or more $R_{12}$. In certain embodiments of the disclosure, the compounds of formula (I)-(I-8) as otherwise described herein are those where each $R_{11}$ is independently selected from the group consisting of halogen, —$NH_2$, —$NH(C_1$-$C_6$ alkyl), —$N(C_1$-$C_6$ alkyl)$_2$, —OH, $C_1$-$C_6$ alkoxy, and $C_1$-$C_6$ haloalkoxy. In certain embodiments of the disclosure, the compounds of formula (I)-(I-8) as otherwise described herein are those where each $R_{11}$ is independently selected from the group consisting of halogen, —$NH_2$, —$NH(C_1$-$C_6$ alkyl), —$N(C_1$-$C_6$ alkyl)$_2$, —OH, and $C_1$-$C_6$ alkoxy. In certain embodiments of the disclosure, each $R_{11}$ is independently selected from the group consisting of halogen, —$NH_2$, —$NH(C_1$-$C_6$ alkyl), and —$N(C_1$-$C_6$ alkyl)$_2$. In certain embodiments of the disclosure, each $R_{11}$ is independently selected from the group consisting of halogen, —$NH_2$, and —OH. In certain embodiments of the disclosure, each $R_{11}$ is independently selected from the group consisting of halogen, and —$NH_2$.

Another embodiment of the disclosure provides compounds of formula (I)-(I-8) as otherwise described herein where $R_7$ is unsubstituted or substituted with one $R_{11}$ selected from halogen and —$NH_2$. Other embodiment of the disclosure provides compounds of formula (I)-(I-8) as otherwise described herein where $R_7$ is unsubstituted or substituted with one $R_{11}$, which is —$NH_2$.

Another embodiment of the disclosure provides compounds of formula (I)-(I-8) as otherwise described herein where $R_2$ is hydrogen or methyl. In certain embodiments of the disclosure, $R_2$ is hydrogen.

One embodiment of the disclosure provides compounds of formula (I)-(I-8) as otherwise described herein where $R_3$ is selected from the group consisting of —$R_8$, —$C(O)R_8$, —$C(O)OR_8$, —$C(O)NH_2$, —$C(O)NHR_8$, and —$S(O)_2R_8$. Another embodiment of the disclosure provides compounds of formula (I)-(I-8) as otherwise described herein where $R_3$ is selected from the group consisting of aryl($C_0$-$C_4$ alkyl) optionally substituted with one or more $R_{13}$, heteroaryl($C_0$-$C_4$ alkyl) optionally substituted with one or more $R_{13}$, heterocyclyl($C_0$-$C_4$ alkyl) optionally substituted with one or more $R_{13}$, cyclyl($C_0$-$C_4$ alkyl) optionally substituted with one or more $R_{13}$, —$C(O)R_8$, —$C(O)OR_8$, —$C(O)NH_2$, —$C(O)NHR_8$, and —$S(O)_2R_8$. Another embodiment of the disclosure provides compounds of formula (I)-(I-8) as otherwise described herein where $R_3$ is selected from the group consisting of aryl($C_0$-$C_4$ alkyl) optionally substituted with one or more $R_{13}$, heteroaryl($C_0$-$C_4$ alkyl) optionally substituted with one or more $R_{13}$, —C(O)$R_8$, —C(O)O$R_8$, —C(O)NH$_2$, —C(O)NH$R_8$, and —S(O)$_2R_8$. Yet another embodiment of the disclosure provides compounds of formula (I)-(I-8) as otherwise described herein where $R_3$ is selected from the group consisting of aryl optionally substituted with one or more $R_{13}$, aryl(methyl) optionally substituted with one or more $R_{13}$, heteroaryl optionally substituted with one or more $R_{13}$, heteroaryl(methyl) optionally substituted with one or more $R_{13}$, —C(O)$R_8$, —C(O)O$R_8$, —C(O)NH$_2$, —C(O)N$R_8R_9$, and —S(O)$_2$—$R_8$. In certain embodiments of the disclosure, $R_3$ is selected from the group consisting of aryl optionally substituted with one or more $R_{13}$, aryl (methyl) optionally substituted with one or more $R_{13}$, heteroaryl optionally substituted with one or more $R_{13}$, —C(O)$R_8$, —C(O)O$R_8$, —C(O)NH$_2$, —C(O)NH$R_8$, and —S(O)$_2R_8$. Another embodiment of the disclosure provides compounds of formula (I)-(I-8) as otherwise described herein where $R_3$ is selected from the group consisting of —C(O)$R_8$, —C(O)O$R_8$, —C(O)NH$_2$, —C(O)N$R_8R_9$, and —S(O)$_2$—$R_8$. In certain embodiments of the disclosure, $R_3$ is selected from the group consisting of —C(O)$R_8$, —C(O)O$R_8$, —C(O)NH$R_8$, and —S(O)$_2R_8$. In certain embodiments of the disclosure, $R_3$ is selected from the group consisting of —C(O)$R_8$, —C(O)O$R_8$, and —C(O)NH$R_8$. In certain embodiments of the disclosure, $R_3$ is selected from the group consisting of —C(O)$R_8$, —C(O)O$R_8$, and —S(O)$_2R_8$. In certain embodiments of the disclosure, $R_3$ is —C(O)$R_8$ or —C(O)O$R_8$.

In certain embodiments of the disclosure, the compounds as otherwise described herein are those where each $R_8$ is independently selected from the group consisting of $C_1$-$C_8$ alkyl optionally substituted with one or more $R_{13}$, aryl($C_0$-$C_1$ alkyl) optionally substituted with one or more $R_{13}$, heteroaryl($C_0$-$C_1$ alkyl) optionally substituted with one or more $R_{13}$, heterocyclyl($C_0$-$C_1$ alkyl) optionally substituted with one or more $R_{13}$, and cyclyl($C_0$-$C_1$ alkyl) optionally substituted with one or more $R_{13}$. In certain embodiments of the disclosure, each $R_8$ is independently selected from the group consisting of $C_1$-$C_6$ alkyl, aryl($C_0$-$C_1$ alkyl) optionally substituted with one or more $R_{13}$, heteroaryl($C_0$-$C_1$ alkyl) optionally substituted with one or more $R_{13}$, and heterocyclyl($C_0$-$C_1$ alkyl) optionally substituted with one or more $R_{13}$. In certain embodiments of the disclosure, each $R_8$ is independently selected from the group consisting of $C_1$-$C_6$ alkyl, aryl optionally substituted with one or more $R_{13}$, heteroaryl optionally substituted with one or more $R_{13}$, heteroaryl(methyl) optionally substituted with one or more $R_{13}$, heterocyclyl optionally substituted with one or more $R_{13}$, and heterocyclyl(methyl) optionally substituted with one or more $R_{13}$. In certain embodiments of the disclosure, each $R_8$ is independently selected from the group consisting of $C_1$—C alkyl, aryl optionally substituted with one or more $R_{13}$, heteroaryl optionally substituted with one or more $R_{13}$, heterocyclyl optionally substituted with one or more $R_{13}$, and heterocyclyl(methyl) optionally substituted with one or more $R_{13}$. In certain embodiments of the disclosure, each $R_8$ is independently selected from the group consisting of $C_1$-$C_4$ alkyl, aryl optionally substituted with one or more $R_{13}$, heteroaryl optionally substituted with one or more $R_{13}$, heterocyclyl optionally substituted with one or more $R_{13}$, and heterocyclyl(methyl) optionally substituted with one or more $R_{13}$. In certain embodiments of the disclosure, each $R_8$ is independently selected from the group consisting of aryl optionally substituted with one or more $R_{13}$, heteroaryl optionally substituted with one or more $R_{13}$, heterocyclyl optionally substituted with one or more $R_{13}$; and heterocyclyl(methyl) optionally substituted with one or more $R_{13}$. In certain embodiments of the disclosure, each $R_3$ is independently selected from the group consisting of aryl optionally substituted with one or more $R_{13}$, heteroaryl optionally substituted with one or more $R_{13}$, and heterocyclyl optionally substituted with one or more $R_{13}$.

In certain embodiments of the disclosure, the compounds as otherwise described herein are those where each $R_{13}$ is independently selected from the group consisting of halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy optionally substituted with one or more $R_{16}$, $C_1$-$C_6$ haloalkoxy, —CONH$_2$, —CONH($C_1$-$C_6$ alkyl), —CON($C_1$-$C_6$ alkyl)$_2$, —CONH—OH, —CO$_2$H, —CO$_2$($C_1$-$C_6$ alkyl), —P(O)(OH)$_2$, —P(O)(O$C_1$-$C_6$ alkyl)$_2$, —P(O)($C_1$-$C_6$ alkyl)$_2$, aryl optionally substituted with one or more $R_{14}$, heteroaryl optionally substituted with one or more $R_{14}$, and heterocyclyl optionally substituted with one or more $R_{14}$; or two $R_{13}$ groups when attached to the same carbon atom form =O. In certain embodiments, $R_{13}$ is independently selected from the group consisting of halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy optionally substituted with one or more $R_{16}$, $C_1$-$C_6$ haloalkoxy, —CONH$_2$, —CONH($C_1$-$C_6$ alkyl), —CON($C_1$-$C_6$ alkyl)$_2$, —CONH—OH, —CO$_2$H, —CO$_2$($C_1$-$C_6$ alkyl), aryl optionally substituted with one or more $R_{14}$, heteroaryl optionally substituted with one or more $R_{14}$, and heterocyclyl optionally substituted with one or more $R_{14}$; or two $R_{13}$ groups when attached to the same carbon atom form =O. In certain embodiments of the disclosure, $R_{13}$ is independently selected from the group consisting of halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy optionally substituted with one or more $R_{16}$, $C_1$-$C_6$ haloalkoxy, —CONH$_2$, —CONH($C_1$-$C_6$ alkyl), —CON($C_1$-$C_6$ alkyl)$_2$, —CONH—OH, —CO$_2$H, and —CO$_2$($C_1$-$C_6$ alkyl). In certain embodiments of the disclosure, $R_{13}$ is independently selected from the group consisting of halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CONH$_2$, —CONH($C_1$-$C_6$ alkyl), —CON($C_1$-$C_6$ alkyl)$_2$, —CO$_2$H, and —CO$_2$($C_1$-$C_6$ alkyl). In certain embodiments of the disclosure, $R_{13}$ is independently selected from the group consisting of halogen, —CN, —CH$_3$, halomethyl, —NH$_2$, —NH(CH$_3$), —N(CH$_3$)$_2$, —OH, methoxy, halomethoxy, —CONH$_2$, —CONH(CH$_3$), —CON(CH$_3$)$_2$, —CO$_2$H, and —CO$_2$(CH$_3$). In certain embodiments of the disclosure, $R_{13}$ is independently selected from the group consisting of halogen, —CN, —CH$_3$, halomethyl, —NH$_2$, —NH(CH$_3$), —N(CH$_3$)$_2$, —OH, methoxy, halomethoxy, —CONH$_2$, and —CO$_2$H.

In certain embodiments of the disclosure, the compounds as otherwise described herein are those where $R_3$ is unsubstituted, or substituted with one or more $R_{11}$ selected from halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CONH$_2$, —CONH($C_1$-$C_6$ alkyl), —CON($C_1$-$C_6$ alkyl)$_2$, —CO$_2$H, and —CO$_2$($C_1$-$C_6$ alkyl). In some embodiments of the disclosure, $R_3$ is unsubstituted, or substituted with one $R_{11}$ selected from halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CONH$_2$, —CONH($C_1$-$C_6$ alkyl), —CON($C_1$-$C_6$ alkyl)$_2$, —CO$_2$H, and —CO$_2$($C_1$-$C_6$ alkyl). In certain embodiments of the disclosure, $R_3$ is unsubstituted, or substituted with one or more $R_{11}$ selected from halogen, —CN, —CH$_3$, halomethyl, —NH$_2$, —NH(CH$_3$), —N(CH$_3$)$_2$, —OH, methoxy, halomethoxy, —CONH$_2$, and —CO$_2$H. In some embodiments of the disclosure, $R_3$ is unsubstituted, or substituted with one $R_{11}$ selected from halogen, —CN, —CH$_3$, halomethyl, —NH$_2$, —NH(CH$_3$), —N(CH$_3$)$_2$, —OH, methoxy, halomethoxy, —CONH$_2$, and —CO$_2$H.

Another embodiment of the disclosure provides compounds of formula (I)-(I-8) as otherwise described herein where each $R_4$ is independently selected from hydrogen and $C_1$-$C_6$ alkyl. In certain embodiments of the disclosure, each $R_4$ is independently selected from hydrogen and methyl. In some embodiments of the disclosure, each $R_4$ is independently hydrogen.

Another embodiment of the disclosure provides compounds of formula (I)-(I-8) as otherwise described herein where each $R_5$ is independently selected from hydrogen and $C_1$-$C_6$ alkyl. In some embodiments of the disclosure, ach $R_5$ is independently selected from hydrogen and methyl. In some embodiments of the disclosure, each $R_5$ is independently hydrogen.

Another embodiment of the disclosure provides compounds of formula (I)-(I-8) as otherwise described herein where each $R_6$ is independently selected from hydrogen and $C_1$-$C_6$ alkyl, or two $R_6$ groups form an oxo group. In some embodiments of the disclosure, each $R_6$ is independently selected from hydrogen and methyl, or two $R_6$ groups form an oxo group. In some embodiments of the disclosure, each $R_6$ is hydrogen, or two $R_6$ groups form an oxo group. In certain embodiments of the disclosure, each $R_6$ is hydrogen. In certain embodiments of the disclosure, two $R_6$ groups form an oxo group.

Another aspect of the disclosure provides compounds of formula (II) as provided above.

In some embodiments, the compounds of formula (II) as otherwise described herein are those wherein q is 1. In one embodiment, the disclosure provides compounds of formula (II) as otherwise described herein where q is 1, and both w and z are 0, e.g., the compounds of formula (II-1):

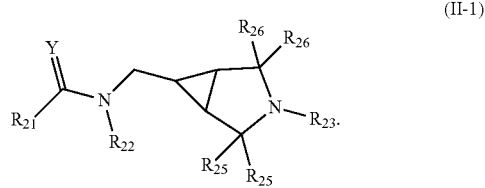

(II-1)

In one embodiment, the disclosure provides compounds of formula (II) as otherwise described herein where q is 1, and both w and z are 1, e.g., the compounds of formula (II-2):

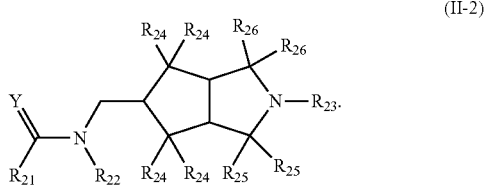

(II-2)

In one embodiment, the disclosure provides compounds of formula (II) as otherwise described herein where q is 1, and w is 2, and z is 1, e.g., the compounds of formula (II-3):

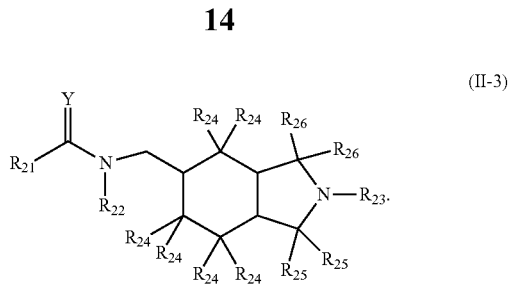

(II-3)

In some embodiments, the compounds of formula (II) as otherwise described herein are those wherein q is 2. In one embodiment, the disclosure provides compounds of formula (II) as otherwise described herein where q is 2, and both w and z are 1. Such compounds are of formula (II-4):

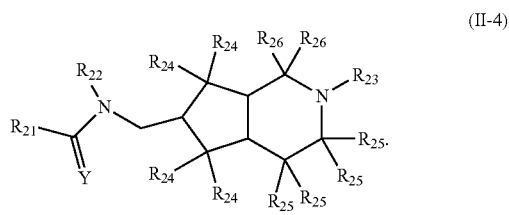

(II-4)

In certain embodiments of the disclosure, the compounds of formula (II)-(II-4) as otherwise described herein are those wherein Y represents O.

Another embodiment of the disclosure provides compounds of formula (II)-(II-4) as otherwise described herein where Y represents N—CN.

One embodiment of the disclosure provides compounds of formula (II)-(II-4) as otherwise described herein where $R_{21}$ is —$R_{27}$ or —NHR$_{27}$.

Another embodiment of the disclosure provides compounds of formula (II)-(II-4) as otherwise described herein where $R_{21}$ is —$R_{25}$.

Another embodiment of the disclosure provides compounds of formula (II)-(II-4) as otherwise described herein where $R_{21}$ is —NHR$_{27}$, wherein $R_{27}$ is $C_1$-$C_6$ alkyl optionally substituted with one or more $R_{30}$, aryl($C_0$-$C_2$ alkyl) optionally substituted with one or more $R_{31}$, aryl($C_2$-$C_3$ alkenyl) optionally substituted with one or more $R_{31}$, heteroaryl($C_0$-$C_2$ alkyl) optionally substituted with one or more $R_{31}$, heteroaryl($C_2$-$C_3$ alkenyl) optionally substituted with one or more $R_{31}$, heterocyclyl($C_0$-$C_2$ alkyl) optionally substituted with one or more $R_{31}$, or cyclyl($C_0$-$C_2$ alkyl) optionally substituted with one or more $R_{31}$. In certain embodiments of the disclosure, are those where $R_{27}$ is $C_1$-$C_6$ alkyl optionally substituted with one or more $R_{30}$, aryl optionally substituted with one or more $R_{31}$, aryl(methyl) optionally substituted with one or more $R_{31}$, heteroaryl optionally substituted with one or more $R_{31}$, heteroaryl(methyl) optionally substituted with one or more $R_{31}$, heterocyclyl optionally substituted with one or more $R_{31}$, or cyclyl optionally substituted with one or more $R_{31}$. In certain embodiments of the disclosure, $R_{27}$ is $C_1$-$C_6$ alkyl, aryl optionally substituted with one or more $R_{31}$, aryl(methyl) optionally substituted with one or more $R_{31}$, heteroaryl optionally substituted with one or more $R_{31}$, heteroaryl(methyl) optionally substituted with one or more $R_{31}$, heterocyclyl optionally substituted with one or more $R_{31}$, or cyclyl optionally substituted with one or more $R_{31}$. In certain embodiments of the disclosure, the compounds of formula (II)-(II-4) as otherwise described herein are those where $R_{27}$ is heteroaryl optionally substituted with one or more $R_{31}$, heteroaryl(methyl) optionally substituted with one or more $R_{31}$, or heterocyclyl optionally substituted with one or more $R_{31}$. In certain embodiments of the disclosure, the compounds of formula (II)-(II-4) as otherwise described herein are those where $R_{27}$ is pyridinyl, 4-pyridinyl(methyl), 3-pyridinyl(methyl), or 2-pyridinyl (methyl), each optionally substituted with one or more $R_{31}$.

In certain embodiments of the disclosure, the compounds of formula (II)-(II-4) as otherwise described herein are those where each $R_{31}$ is independently selected from the group consisting of halogen, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, aryl optionally substituted with one or more $R_{32}$, heteroaryl optionally substituted with one or more $R_{32}$, and heterocyclyl optionally substituted with one or more $R_{32}$. In certain embodiments of the disclosure, the compounds of formula (II)-(II-4) as otherwise described herein are those where each $R_{31}$ is independently selected from the group consisting of halogen, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, and heteroaryl optionally substituted with one or more $R_{32}$. In certain embodiments of the disclosure, the compounds of formula (II)-(II-4) as otherwise described herein are those where each $R_{31}$ is independently selected from the group consisting of halogen, —$NH_2$, —$NH(C_1$-$C_6$ alkyl), —$N(C_1$-$C_6$ alkyl)$_2$, —OH, $C_1$-$C_6$ alkoxy, and $C_1$-$C_6$ haloalkoxy. In certain embodiments of the disclosure, the compounds of formula (II)-(II-4) as otherwise described herein are those where each $R_{31}$ is independently selected from the group consisting of halogen, —$NH_2$, —$NH(C_1$-$C_6$ alkyl), —$N(C_1$-$C_6$ alkyl)$_2$, —OH, and $C_1$-$C_6$ alkoxy. In certain embodiments of the disclosure, each $R_{31}$ is independently selected from the group consisting of halogen, —$NH_2$, —$NH(C_1$-$C_6$ alkyl), and —$N(C_1$-$C_6$ alkyl)$_2$. In certain embodiments of the disclosure, each $R_{31}$ is independently selected from the group consisting of halogen, —$NH_2$, and —OH. In certain embodiments of the disclosure, each $R_{31}$ is independently selected from the group consisting of halogen, and —$NH_2$.

Another embodiment of the disclosure provides compounds of formula (II)-(II-4) as otherwise described herein where $R_{27}$ is unsubstituted or substituted with one $R_{31}$ selected from halogen and —$NH_2$. Other embodiment of the disclosure provides compounds of formula (II)-(II-4) as otherwise described herein where $R_{27}$ is unsubstituted or substituted with one $R_{31}$, which is —$NH_2$.

Another embodiment of the disclosure provides compounds of formula (II)-(II-4) as otherwise described herein where $R_{22}$ is hydrogen or methyl. In certain embodiments of the disclosure, $R_{22}$ is hydrogen.

One embodiment of the disclosure provides compounds of formula (II)-(II-4) as otherwise described herein where $R_{23}$ is selected from the group consisting of —$R_{28}$, —C(O)$R_{28}$, —C(O)O$R_{28}$, —C(O)$NH_2$, —C(O)NH$R_{28}$, and —S(O)$_2R_{28}$. Another embodiment of the disclosure provides compounds of formula (II)-(II-4) as otherwise described herein where $R_{23}$ is selected from the group consisting of aryl($C_0$-$C_4$ alkyl) optionally substituted with one or more $R_{33}$, heteroaryl($C_0$-$C_4$ alkyl) optionally substituted with one or more $R_{33}$, heterocyclyl($C_0$-$C_4$ alkyl) optionally substituted with one or more $R_{33}$, cyclyl($C_0$-$C_4$ alkyl) optionally substituted with one or more $R_{33}$, —C(O)$R_{28}$, —C(O)O$R_{28}$, —C(O)$NH_2$, —C(O)NH$R_{28}$, and —S(O)$_2R_{28}$. Another embodiment of the disclosure provides compounds of formula (II)-(II-4) as otherwise described herein where $R_{23}$ is selected from the group consisting of aryl($C_0$-$C_4$ alkyl) optionally substituted with one or more $R_{33}$, heteroaryl($C_0$-$C_4$ alkyl) optionally substituted with one or more $R_{33}$, —C(O)$R_{28}$, —C(O)O$R_{28}$, —C(O)$NH_2$, —C(O)NH$R_{28}$, and —S(O)$_2R_{28}$. Yet another embodiment of the disclosure provides compounds of formula (II)-(II-4) as otherwise described herein where $R_{23}$ is selected from the group consisting of aryl optionally substituted with one or more $R_{33}$, aryl(methyl) optionally substituted with one or more $R_{33}$, heteroaryl optionally substituted with one or more $R_{33}$, heteroaryl(methyl) optionally substituted with one or more $R_{33}$, —C(O)$R_{28}$, —C(O)O$R_{28}$, —C(O)$NH_2$, —C(O) N$R_{28}R_9$, and —S(O)$_2$—$R_{28}$. In certain embodiments of the disclosure, $R_{23}$ is selected from the group consisting of aryl optionally substituted with one or more $R_{33}$, aryl(methyl) optionally substituted with one or more $R_{33}$, heteroaryl optionally substituted with one or more $R_{33}$, —C(O)$R_{28}$, —C(O)O$R_{28}$, —C(O)$NH_2$, —C(O)NH$R_{28}$, and —S(O)$_2R_{28}$. Another embodiment of the disclosure provides compounds of formula (II)-(II-4) as otherwise described herein where $R_{23}$ is selected from the group consisting of —C(O)$R_{28}$, —C(O)O$R_{28}$, —C(O)$NH_2$, —C(O)N$R_{28}R_9$, and —S(O)$_2$—$R_{28}$. In certain embodiments of the disclosure, $R_{23}$ is selected from the group consisting of —C(O)$R_{28}$, —C(O)O$R_{28}$, —C(O)NH$R_{28}$, and —S(O)$_2R_{28}$. In certain embodiments of the disclosure, $R_{23}$ is selected from the group consisting of —C(O)$R_{28}$, —C(O)O$R_{28}$, and —C(O) NH$R_{28}$. In certain embodiments of the disclosure, $R_{23}$ is selected from the group consisting of —C(O)$R_{28}$, —C(O) O$R_{28}$, and —S(O)$_2R_{28}$. In certain embodiments of the disclosure, $R_{23}$ is —C(O)$R_{28}$ or —C(O)O$R_{28}$.

In certain embodiments of the disclosure, the compounds as otherwise described herein are those where each $R_{28}$ is independently selected from the group consisting of $C_1$-$C_6$ alkyl optionally substituted with one or more $R_{33}$, aryl($C_0$-$C_1$ alkyl) optionally substituted with one or more $R_{33}$, heteroaryl($C_0$-$C_1$ alkyl) optionally substituted with one or more $R_{33}$, heterocyclyl($C_0$-$C_1$ alkyl) optionally substituted with one or more $R_{33}$, and cyclyl($C_0$-$C_1$ alkyl) optionally substituted with one or more $R_{33}$. In certain embodiments of the disclosure, each $R_{28}$ is independently selected from the group consisting of $C_1$-$C_6$ alkyl, aryl($C_0$-$C_1$ alkyl) optionally substituted with one or more $R_{33}$, heteroaryl($C_0$-$C_1$ alkyl) optionally substituted with one or more $R_{33}$, and heterocyclyl($C_0$-$C_1$ alkyl) optionally substituted with one or more $R_{33}$. In certain embodiments of the disclosure, each $R_{28}$ is independently selected from the group consisting of $C_1$-$C_6$ alkyl, aryl optionally substituted with one or more $R_{33}$, heteroaryl optionally substituted with one or more $R_{33}$, heteroaryl(methyl) optionally substituted with one or more $R_{33}$, heterocyclyl optionally substituted with one or more $R_{33}$, and heterocyclyl(methyl) optionally substituted with one or more $R_{33}$. In certain embodiments of the disclosure, each $R_{28}$ is independently selected from the group consisting of $C_1$-$C_6$ alkyl, aryl optionally substituted with one or more $R_{33}$, heteroaryl optionally substituted with one or more $R_{33}$, heterocyclyl optionally substituted with one or more $R_{33}$, and heterocyclyl(methyl) optionally substituted with one or more $R_{33}$. In certain embodiments of the disclosure, each $R_{28}$ is independently selected from the group consisting of $C_1$-$C_4$ alkyl, aryl optionally substituted with one or more $R_{33}$, heteroaryl optionally substituted with one or more $R_{33}$, heterocyclyl optionally substituted with one or more $R_{33}$, and heterocyclyl(methyl) optionally substituted with one or more $R_{33}$. In certain embodiments of the disclosure, each $R_{28}$ is independently selected from the group consisting of aryl optionally substituted with one or more $R_{33}$, heteroaryl optionally substituted with one or more $R_{33}$, heterocyclyl optionally substituted with one or more $R_{33}$; and heterocyclyl(methyl) optionally substituted with one or more $R_{33}$. In certain embodiments of the disclosure, each $R_{28}$ is independently selected from the group consisting of aryl optionally substituted with one or more $R_{33}$, heteroaryl optionally substituted with one or more $R_{33}$, and heterocyclyl optionally substituted with one or more $R_{33}$.

In certain embodiments of the disclosure, the compounds as otherwise described herein are those where $R_{33}$ is independently selected from the group consisting of halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CONH_2$, —CONH($C_1$-$C_6$ alkyl), —CON($C_1$-$C_6$ alkyl)$_2$, —CONH—OH, —$CO_2$H, —$CO_2$($C_1$-$C_6$ alkyl), aryl optionally substituted with one or more $R_{34}$, heteroaryl optionally substituted with one or more $R_{34}$, and heterocyclyl optionally substituted with one or more $R_{34}$; or two $R_{33}$ groups when attached to the same carbon atom form =O. In certain embodiments of the disclosure, $R_{33}$ is independently selected from the group consisting of halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CONH_2$, —CONH($C_1$-$C_6$ alkyl), —CON($C_1$-$C_6$ alkyl)$_2$, —CONH—OH, —$CO_2$H, and —$CO_2$($C_1$-$C_6$ alkyl). In certain embodiments of the disclosure, $R_{33}$ is independently selected from the group consisting of halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CONH_2$, —CONH($C_1$-$C_6$ alkyl), —CON($C_1$-$C_6$ alkyl)$_2$, —$CO_2$H, and —$CO_2$($C_1$-$C_6$ alkyl). In certain embodiments of the disclosure, $R_{33}$ is independently selected from the group consisting of halogen, —CN, —$CH_3$, halomethyl, —$NH_2$, —NH($CH_3$), —N($CH_3$)$_2$, —OH, methoxy, halomethoxy, —$CONH_2$, —CONH($CH_3$), —CON($CH_3$)$_2$, —$CO_2$H, and —$CO_2$($CH_3$). In certain embodiments of the disclosure, $R_{33}$ is independently selected from the group consisting of halogen, —CN, —$CH_3$, halomethyl, —$NH_2$, —NH($CH_3$), —N($CH_3$)$_2$, —OH, methoxy, halomethoxy, —$CONH_2$, and —$CO_2$H.

In certain embodiments of the disclosure, the compounds as otherwise described herein are those where $R_{28}$ is unsubstituted, or substituted with one or more $R_{31}$ selected from halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CONH_2$, —CONH($C_1$-$C_6$ alkyl), —CON($C_1$-$C_6$ alkyl)$_2$, —$CO_2$H, and —$CO_2$($C_1$-$C_6$ alkyl). In some embodiments of the disclosure, $R_{28}$ is unsubstituted, or substituted with one $R_{31}$ selected from halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CONH_2$, —CONH($C_1$-$C_6$ alkyl), —CON($C_1$-$C_6$ alkyl)$_2$, —$CO_2$H, and —$CO_2$($C_1$-$C_6$ alkyl). In certain embodiments of the disclosure, $R_{28}$ is unsubstituted, or substituted with one or more $R_{31}$ selected from halogen, —CN, —$CH_3$, halomethyl, —$NH_2$, —NH($CH_3$), —N($CH_3$)$_2$, —OH, methoxy, halomethoxy, —$CONH_2$, and —$CO_2$H. In some embodiments of the disclosure, $R_{28}$ is unsubstituted, or substituted with one $R_{31}$ selected from halogen, —CN, —$CH_3$, halomethyl, —$NH_2$, —NH($CH_3$), —N($CH_3$)$_2$, —OH, methoxy, halomethoxy, —$CONH_2$, and —$CO_2$H.

Another embodiment of the disclosure provides compounds of formula (II)-(II-4) as otherwise described herein where each $R_{24}$ is independently selected from hydrogen and $C_1$-$C_6$ alkyl. In certain embodiments of the disclosure, each $R_{24}$ is independently selected from hydrogen and methyl. In some embodiments of the disclosure, each $R_{24}$ is independently hydrogen.

Another embodiment of the disclosure provides compounds of formula (II)-(II-4) as otherwise described herein where each $R_{25}$ is independently selected from hydrogen and $C_1$-$C_6$ alkyl. In some embodiments of the disclosure, ach $R_{25}$ is independently selected from hydrogen and methyl. In some embodiments of the disclosure, each $R_{25}$ is independently hydrogen.

Another embodiment of the disclosure provides compounds of formula (II)-(II-4) as otherwise described herein where each $R_{26}$ is independently selected from hydrogen and $C_1$-$C_6$ alkyl, or two $R_{26}$ groups form an oxo group. In some embodiments of the disclosure, each $R_{26}$ is independently selected from hydrogen and methyl, or two $R_{26}$ groups form an oxo group. In some embodiments of the disclosure, each $R_{26}$ is hydrogen, or two $R_{26}$ groups form an oxo group. In certain embodiments of the disclosure, each $R_{26}$ is hydrogen. In certain embodiments of the disclosure, two $R_{26}$ groups form an oxo group.

Therapeutics Applications

The disclosure also provides methods of treating cancer. Such method includes administering to a subject in need of such treatment an effective amount of one or more compounds of the disclosure as described herein (i.e., compounds of formula (I)-(I-8) or (II)-(II-4)) or a pharmaceutical composition of the disclosure as described herein.

Many different cancers can be treated with compounds and compositions of the disclosure. Particularly suitable cancer is a solid tumor. Examples of solid tumors include, but are not limited to, carcinomas, sarcomas, and astrocytomas. In certain embodiments, the cancer is breast cancer, prostate cancer, lung cancer (e.g., small-cell lung carcinoma (SCLC) and non-small-cell lung carcinoma (NSCLC)), gastric cancer, colorectal cancer, cervical cancer, endometrial cancer, ovarian cancer, skin cancer (e.g., basal-cell skin cancer (BCC), squamous-cell skin cancer (SCC), and melanoma), pancreatic cancer, kidney cancer, adrenal gland cancer, sarcoma, thyroid cancer, cholangiocarcinoma, glioblastoma, astrocytoma, oligodendroglioma, high-grade glioma, malignant glioma, glioma, neuroblastoma, leukemia or lymphoma. Suitable cancers also include a hematological malignancy, such as leukemia or lymphoma. In certain embodiments, the cancer is acute myeloid leukemia (AML), chronic myeloid leukemia (CML), acute lymphoblastic leukemia (ALL), chronic lymphocytic leukemia (CLL), or lymphoma.

Accumulating evidence indicates that mutations in canonical metabolic enzymes can promote the development of cancer. Germline mutations in the tricarboxylic acid (TCA) cycle enzyme succinate dehydrogenase give rise to familial paraganglioma and pheochromocytoma, and germline fumarate hydratase mutations result in familial forms of renal cell cancer. More recently, recurrent somatic mutations in the isocitrate dehydrogenase 1 (IDH1) and IDH2 genes have been identified in a large fraction of gliomas, acute myeloid leukemias (AML), angioimmunoblastic T cell lymphomas (AITL), chondrosarcomas, and cholangiocarcinomas. Tateishi et al. (Cancer Cell 28:1-12 (2015)) discovered that IDH1 mutant cancer cells have a profound vulnerability to depletion of the coenzyme NAD+. Mutant IDH1 lowered NAD+ levels by downregulating the NAD+ salvage pathway sensitizing to NAD+ depletion via concomitant NAMPT inhibition. NAD+ depletion activated the intracellular energy sensor AMPK, triggered autophagy, and resulted in cytotoxicity. The inventors have found that, in certain embodiments, the compounds of the disclosure are particularly active in IDH1 mutant cancers. Thus, the methods of the disclosure as described herein include treatment of cancers comprising mutations in IDH1 and/or IDH2.

The MYC gene family (MYC, MYCN and MYCL) consists of potent oncogenes that play critical roles in the pathogenesis of diverse types of human cancers. In glioblastoma (GBM), Myc enhances the self-renewal capacity of glioma stem-like/tumor neurosphere (tumorsphere) cells, and high-level amplification of the MYC and MYCN genes are observed in a subset of GBM. Despite extensive efforts, direct inhibition of the Myc transcription factor has remained a challenge. However, inhibition of the Myc-induced glycolysis can be a selective strategy for Myc-driven GBM. Tateishi et al. (Clin. Cancer Res. 22(17): 4452-4465 (2016)) discovered that cancers genetically driven by MYC are affected by the depletion of the coenzyme NAD+. The inventors have found that, in certain embodiments, the compounds of the disclosure are particularly active in MYC mutant cancers and MYC amplified. Thus, the methods of the disclosure as described herein include treatment of cancers comprising mutations or gene amplifications in MYC, MYCN, and/or MYCL.

The compounds and compositions of the disclosure as described herein may also be administered in combination with one or more secondary therapeutic agents. Thus, in certain embodiment, the method also includes administering to a subject in need of such treatment an effective amount of one or more compounds of the disclosure as described herein (i.e., compounds of formula (I)-(I-8) or (II)-(II-4)) or a pharmaceutical composition of the disclosure as described herein and one or more secondary therapeutic agents. Examples of suitable secondary therapeutic agents include, but are not limited to, temozolomide, camptothecin, doxorubicin, daunorubicin, vincristine, paclitaxel, neocarzinostatin, calicheamicin, cisplatin, carboplatin, oxaliplatin, satraplatin, picoplatin, lurtotecan, annamycin, docetaxel, tamoxifen, epirubicin, methotrexate, vinblastin, vincristin, topotecan, prednisone, prednisolone, chloroquine, hydroxychloroquine, autophagy inhibitors, and abt-737. When administered as a combination, the compounds and compositions of the disclosure as described herein and the secondary therapeutic agents can be formulated as separate compositions that are given simultaneously or sequentially, or the therapeutic agents can be given as a single composition. In certain embodiments, the secondary therapeutic agent may be administered in an amount below its established half maximal inhibitory concentration ($IC_{50}$). For example, the secondary therapeutic agent may be administered in an amount less than 1% of, e.g., less than 10%, or less than 25%, or less than 50%, or less than 75%, or even less than 90% of the inhibitory concentration ($IC_{50}$).

Another aspect of the disclosure provides a method of inhibiting nicotinamide phosphoribosyltransferase (NAMPT), the method including administering one or more compounds of the disclosure as described herein or a pharmaceutical composition of the disclosure as described herein.

Pharmaceutical Compositions

In another aspect, the present disclosure provides compositions comprising one or more of compounds as described above with respect to formula (I)-(I-8) and (II)-(II-4I-8) and an appropriate carrier, solvent, adjuvant, or diluent. The exact nature of the carrier, solvent, adjuvant, or diluent will depend upon the desired use for the composition, and may range from being suitable or acceptable for veterinary uses to being suitable or acceptable for human use. The composition may optionally include one or more secondary therapeutic agents. In certain embodiments, the composition may include one or more secondary anticancer therapeutic agents.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known. For buccal administration, the compositions may take the form of tablets or lozenges formulated in conventional manner. For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethyl sulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective dosages without undue experimentation.

Definitions

The following terms and expressions used herein have the indicated meanings.

Terms used herein may be preceded and/or followed by a single dash, "–", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" (i.e., the attachment is via the last portion of the name) unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, and —$CH_2CH(CH_2CH_3)CH_2$—.

The term "alkylene" refers to a bivalent alkyl group. An "alkylene chain" is a polymethylene group, i.e., —$(CH_2)_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thioxo groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thioxo.

The terms "cyano" and "nitrile" as used herein, mean a —CN group.

The term "cyclyl" or "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thioxo. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thioxo.

The term "halo" or "halogen" as used herein, means —Cl, —Br, —I or —F.

The terms "haloalkyl" and "haloalkoxy" refer to an alkyl or alkoxy group, as the case may be, which is substituted with one or more halogen atoms.

The term "heteroaryl," as used herein, means a monocyclic heteroaryl, a bicyclic ring, or a tricyclic ring system containing at least one heteroaromatic ring. In certain embodiments, the heteroaryl is a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The tricyclic heteroaryl consists of a monocyclic heteroaryl fused to two rings selected from a phenyl, a monocyclic cycloalkyl, a monocyclic cycloalkenyl, a monocyclic heterocyclyl, and a monocyclic heteroaryl. The fused cycloalkyl or heterocyclyl portion of the bicyclic heteroaryl group is optionally substituted with one or two groups which are independently oxo or thioxo. When the bicyclic or tricyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, 2,3-dihydrothieno[3,4-b][1,4]dioxan-5-yl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thioxo.

The terms "heterocyclyl" and "heterocycloalkyl" as used herein, mean a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thioxo. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thioxo.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

The term "thioxo" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Treating" or "treatment" as used herein covers the treatment of a disease or disorder described herein, in a subject, preferably a human, and includes:
  i. inhibiting a disease or disorder, i.e., arresting its development;
  ii. relieving a disease or disorder, i.e., causing regression of the disorder;
  iii. slowing progression of the disorder; and/or
  iv. inhibiting, relieving, ameliorating, or slowing progression of one or more symptoms of the disease or disorder "Subject" refers to a warm blooded animal such as a mammal, preferably a human, or a human child, which is afflicted with, or has the potential to be afflicted with one or more diseases and disorders described herein.

Methods of Preparation

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/I, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formula (I) or (II) can be prepared according to Schemes 1-8, general procedures (below), and/or analogous synthetic procedures. One of skill in the art can adapt the reaction sequences of Schemes 1-8, general procedures, and Examples 1-342 to fit the desired target molecule. Of course, in certain situations one of skill in the art will use different reagents to affect one or more of the individual steps or to use protected versions of certain of the substituents. Additionally, one skilled in the art would recognize that compounds of the disclosure can be synthesized using different routes altogether.

As shown in Scheme 1, compounds of formula (I) can be prepared by reaction of the amine 1 with the appropriate reagents to provide amides, ureas, carbamates and cyanoimine derivatives of the disclosure.

Scheme 1

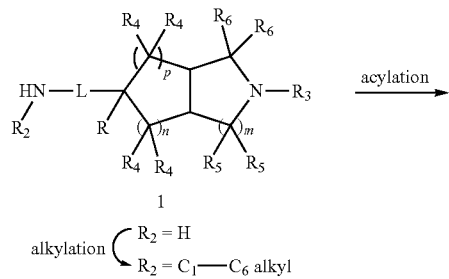

Scheme 2

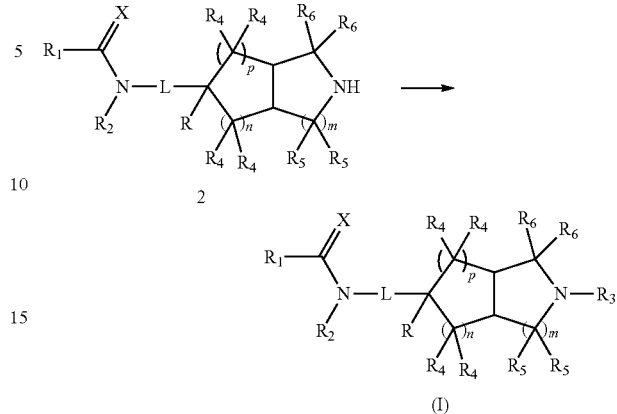

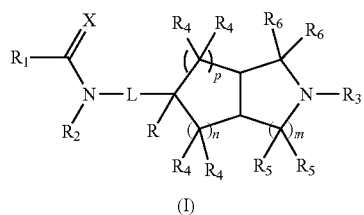

Alternatively, compounds of formula (I), where the $R_3$ group is a protecting group, can be deprotected to provide amines of structure 2 (Scheme 2). Reaction of compounds 2 with the appropriate acylating, arylating, alkylating or sulfonylating reagents can also provide compounds of formula (I).

Intermediates of the structure 1 can be prepared from the appropriately functionalized ketones 3. Derivatives with an ethylene linker group (1a) can arise from complete reduction of the cyanoolefin 4, which can be prepared by olefination of 3. Olefination can also provide intermediates 5 ($Y=CO_2Et$) which can be reduced to the alcohol ($Y=CH_2OH$). Transformation of the alcohol to a leaving group, such as halogen or sulfonate, followed by displacement with cyanide can provide the nitrile ($Y=CH_2CN$). Subsequent reduction can give propylene derivatives 1b. Partial reduction of nitrile 4 can afford aldehyde 6, which can be homologated to provide nitriles 7. Subsequent reduction can lead to butylene derivatives 1c. It is understood that reductions of olefin-containing functional groups can occur in one step or be performed in a sequential manner in multiple steps.

Scheme 3

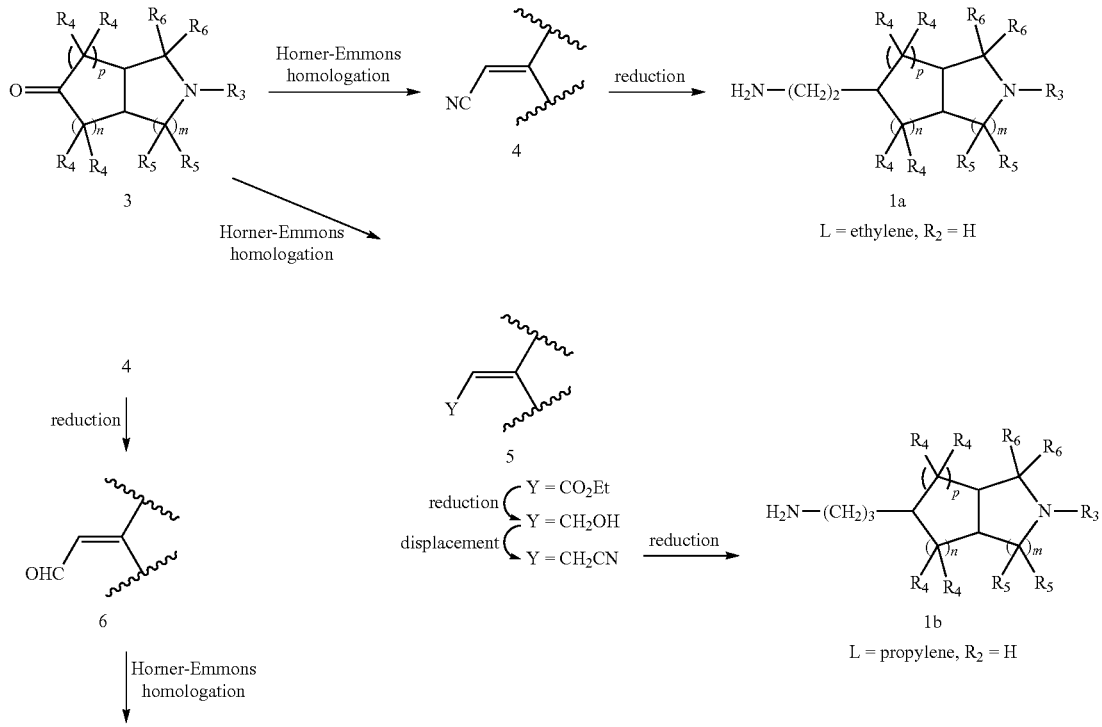

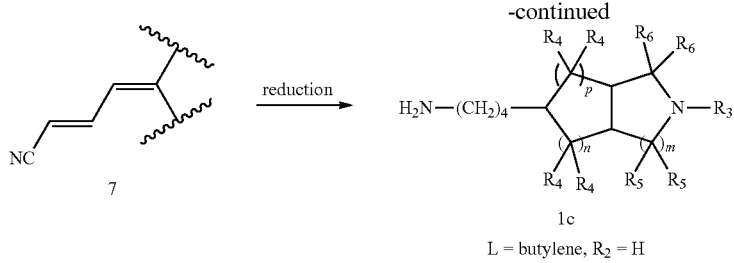

L = butylene, $R_2$ = H

Intermediate ketones of structure 3a, where all $R_4$ groups are hydrogen, can be utilized to assemble intermediates 3, where one or more of the $R_4$ groups are not hydrogen, as shown in Scheme 4. The various reactions illustrated can be performed simultaneously or sequentially to install more than one $R_4$ group. Hydroxy, amino and alkoxy $R_4$ groups can also arise from reaction of the intermediates where $R_4$ is halo. Compounds where $R_4$ is halo can serve as reactive intermediates in the preparation of compounds where $R_4$ is other than halo.

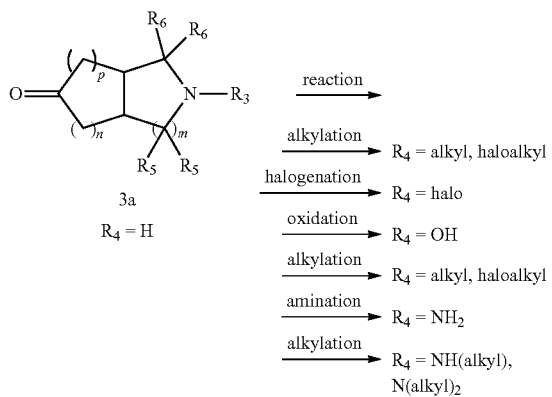

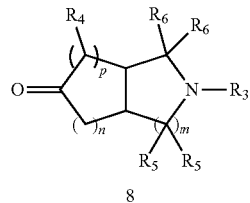

Ketones of structure 3a where a 4-, 5-, or 6-membered ring is fused to the cyclic amine ring can be purchased commercially, where $R_3$ is a protecting group such as BOC or Bn, or can be prepared via methods illustrated in Scheme 5. An appropriate unsaturated cyclic amine 9 can undergo cycloaddition reactions to provide compounds 10 or 17. Transformation of the olefin in 10 to an alcohol, followed by oxidation, can afford cyclohexanones 11. Cyclopentanones 13 can be prepared either by ring opening of 10 followed by cyclization of the resulting diacid, or via cyclization of the appropriately functionalized amines 14 or 15.

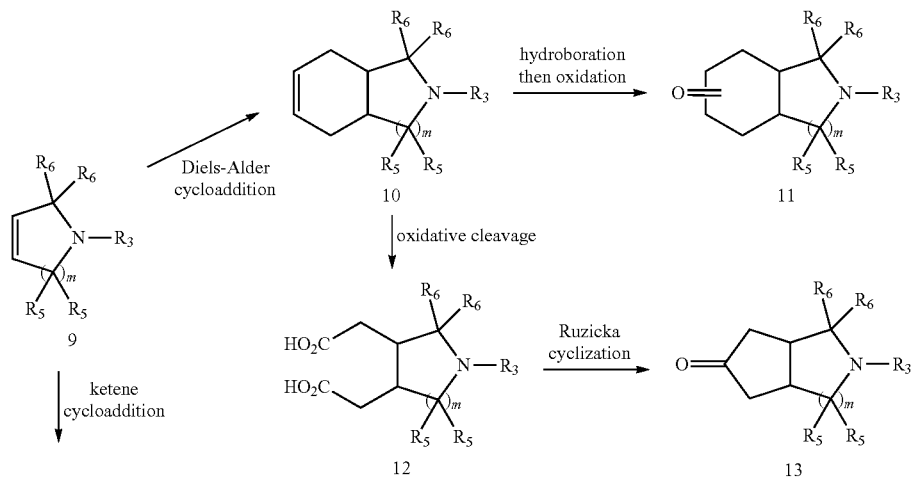

-continued

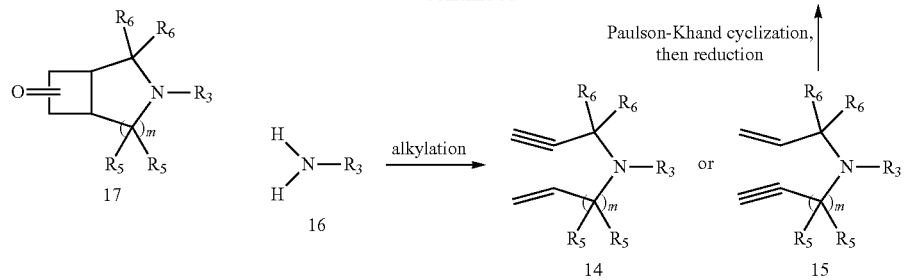

Intermediates where a 3-membered ring is fused to the cyclic amine ring can be purchased commercially, where $R_3$ is a protecting group such as BOC or Bn, or can be prepared via methods illustrated in Scheme 6. Cyclopropanation of the cyclic amines 9 can provide esters 18 ($R'=CO_2Et$), which can be fully reduced to alcohols 19 (X=OH) or partially reduced to aldehydes 18 ($R'=CHO$). Transformation of the alcohol in 19 to the nitrile followed by reduction can afford amines with an ethylene linker. The corresponding propylene- and butylene-containing linker derivatives (20) can be prepared via known homologation methods, as exemplified in Scheme 3.

Scheme 6

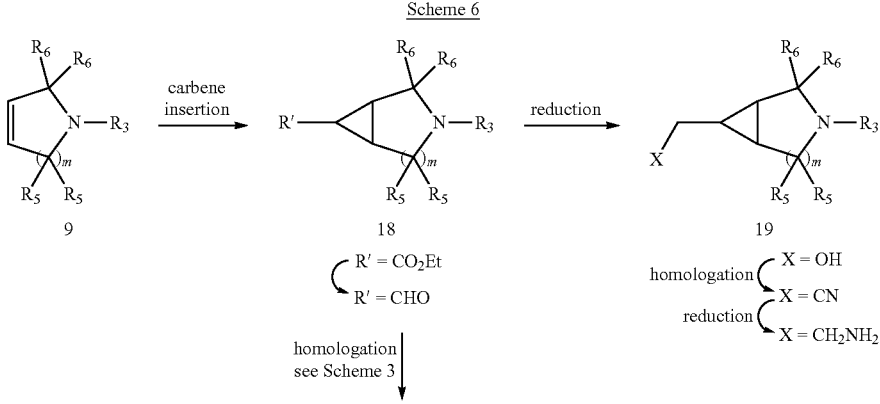

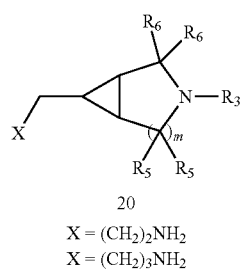

20
X = $(CH_2)_2NH_2$
X = $(CH_2)_3NH_2$

Appropriate intermediates where a 3-membered ring is fused to the cyclic amine ring can also be prepared as shown in Scheme 7. Alcohols 21, prepared via literature methods, can be transformed into the corresponding amines 22, for example, by halogenation or sulfonylation to give a leaving group followed by treatment with an amine. Manipulation of intermediate 22 into the corresponding α-diazoamide 23 followed by a carbene insertion reaction can provide the cyclopropane-fused intermediates 24. Reduction of the nitrile moiety can provide lactams of the disclosure, whereas complete reduction can afford cyclic amines 26.

Scheme 7

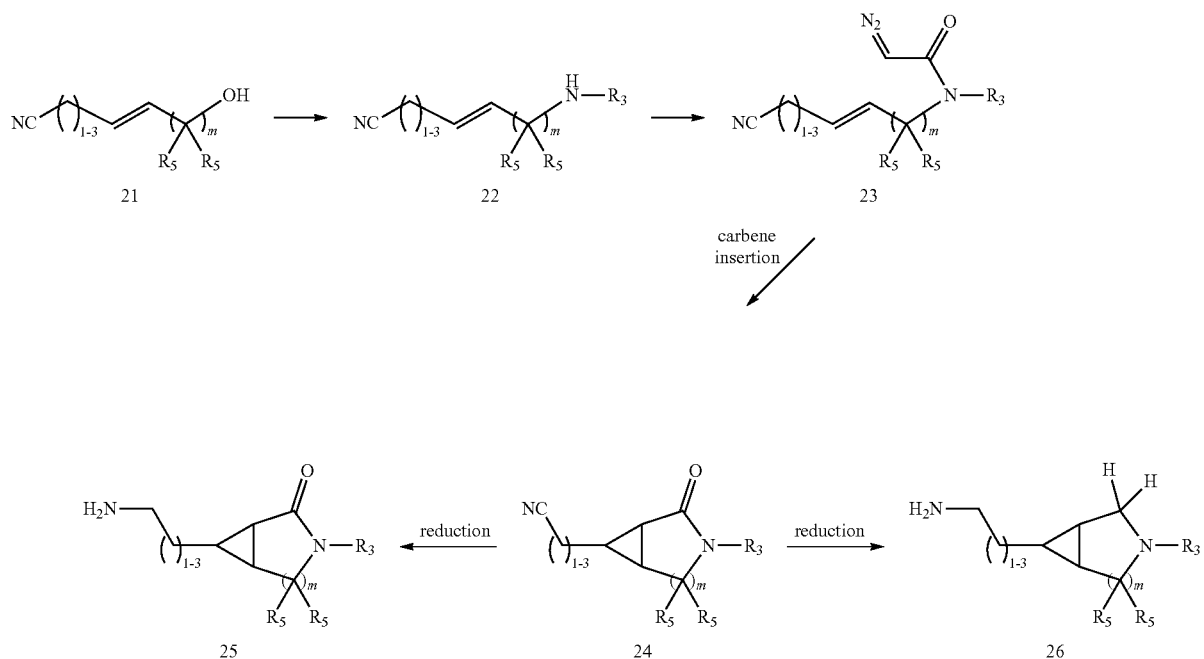

Compounds of formula (II) can be prepared via methods similar to those utilized for the assembly of compounds of formula (I), as shown in Scheme 8. Preparation of the methylene linker-containing amine 33 can be accomplished via two general routes, through either manipulation of the aldehyde 29 or rearrangement of acid 32. Some compounds of formula (II) can be prepared directly from 32.

Scheme 8

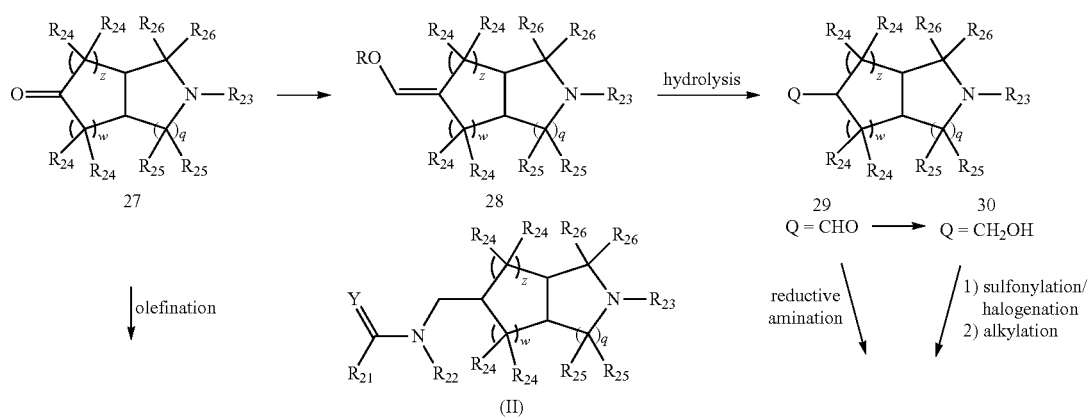

37

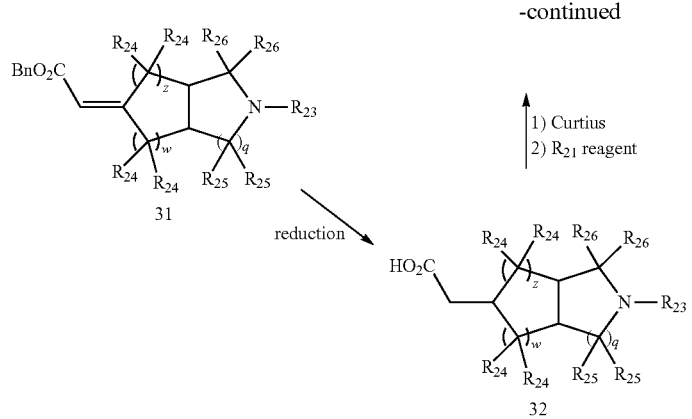

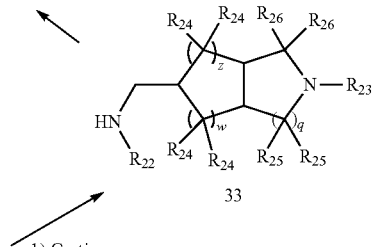

38

-continued

General Procedures and Intermediates

Preparation of Intermediate 1: (1R,5S,6s)-tert-butyl 6-(cyanomethyl)-3-azabicyclo[3.1.0]hexane-3-carboxylate

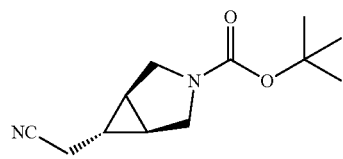 [SMILES: CC(C)(C)OC(=O)N1C[C@@H]2[C@@H](CC#N)[C@@H]2C1]

To a well-stirred solution of (1R,5S,6r)-tert-butyl 6-(hydroxymethyl)-3-azabicyclo[3.1.0]hexane-3-carboxylate (6.0 g, 28.1 mmol) in dichloromethane (250 mL) was added triphenylphosphine (11.7 g, 42.2 mmol) and carbon tetrabromide (14.0 g, 42.2 mmol) portionwise at 0-5° C. The mixture was warmed to 25° C. and stirred for 12 h. Two additional identical reactions on the same scale were performed. The solvent was removed by concentration under vacuum for each reaction batch and the combined residues were purified by silica gel column chromatography (petroleum ether/ethyl acetate, from 100/1 to 10/1) to give 13.5 g (58%) of (1R,5S,6r)-tert-butyl 6-(bromomethyl)-3-azabicyclo[3.1.0]hexane-3-carboxylate as a light yellow oil. MS (ESI) m/z: 176.2/178.2 (M+H-$^t$Bu)$^+$. $^1$H NMR (400 MHz, DMSO-d$_6$): δ 3.64-3.53 (m, 2H), 3.43-3.27 (m, 4H), 1.53-1.52 (m, 2H), 1.43 (s, 9H), 1.17-1.13 (m, 1H).

The (1R,5S,6r)-tert-butyl 6-(bromomethyl)-3-azabicyclo[3.1.0]hexane-3-carboxylate (13.5 g, 48.9 mmol) prepared above was dissolved in N,N-dimethylformamide (150 mL) then sodium cyanide (3.6 g, 73.32 mmol) was added, and the mixture was stirred at 25° C. for 16 h. The mixture was diluted with water (500 mL) and ethyl acetate (200 mL), and the organic layer was extracted with ethyl acetate (100 mL×3). The combined organic layers were washed with brine (150 mL), dried over sodium sulfate, filtered and concentrated under vacuum. The residue was purified by silica gel column chromatography (petroleum ether/ethyl acetate, from 100/1 to 5/1) to give 9.8 g (91%) of Intermediate 1 as a light yellow oil. MS (ESI) m/z: 227.2 (M+H)$^+$. $^1$H NMR (400 MHz, DMSO-d$_6$): δ 3.68 (d, J=10.8 Hz, 1H), 3.60 (d, J=10.8 Hz, 1H), 3.37-3.34 (m, 2H), 2.53-2.33 (m, 2H), 1.54-1.51 (m, 2H), 1.44 (s, 9H), 0.94-0.89 (m, 1H).

Preparation of Intermediate 2: (1R,5S,6s)-tert-butyl 6-(2-aminoethyl)-3-azabicyclo[3.1.0]hexane-3-carboxylate

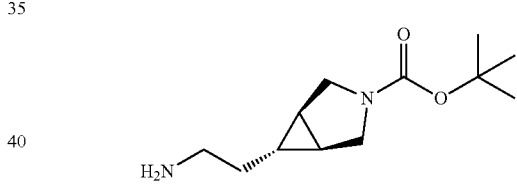

To a solution of methanol (50 mL) was bubbled ammonia at 0° C. for 30 min, and Intermediate 1 (4.5 g, 20.2 mmol) was added to and dissolved in the resulting solution. Raney nickel (1.0 g) was added to the reaction mixture under nitrogen. The suspension was purged with hydrogen three times and stirred at 25° C. under a hydrogen atmosphere (45 psi) for 5 h. The reaction mixture was filtered and the filtrate was concentrated under vacuum to give 5.0 g of crude Intermediate 2 as a light yellow oil. MS (ESI) m/z: 227.3 (M+H)$^+$. $^1$H NMR (400 MHz, DMSO-d$_6$): δ 3.59-3.48 (m, 2H), 3.42-3.41 (m, 2H), 3.32-3.33 (m, 2H), 1.43 (s, 9H), 1.20-1.29 (m, 4H), 0.53-0.50 (m, 1H).

EXAMPLES

The preparation of the compounds of the disclosure is illustrated further by the following examples, which are not to be construed as limiting the disclosure in scope or spirit to the specific procedures and compounds described in them. In all cases, unless otherwise specified, the column chromatography is performed using a silica gel solid phase.

Example 1: (1R,5S,6s)-tert-butyl 6-(2-((E)-3-(pyridin-3-yl)acrylamido)ethyl)-3-azabicyclo[3.1.0]hexane-3-carboxylate

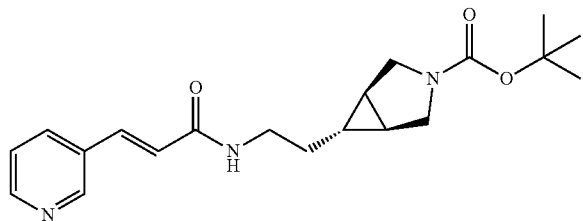

To a mixture of Intermediate 2 (60.0 mg, 0.27 mmol) and (E)-3-(3-pyridyl)prop-2-enoic acid (47.5 mg, 0.32 mmol) in pyridine (4 mL) was added 1-(3-dimethylaminopropyl)-3-ethylcarbodiimide hydrochloride (71.2 mg, 0.37 mmol). The reaction mixture was stirred at 25° C. for 4 h. The reaction mixture was concentration in vacuo, and the residue was diluted with water (15 mL). The solution was extracted with ethyl acetate (10 mL×2) and the combined organic layers were washed with brine (10 mL). The organic layer was dried over sodium sulfate, filtered and concentrated under vacuum. The residue was purified by preparative HPLC (Phenomenex Gemini C18 column (150×25 mm, 5 um); flow rate: 25 mL/min; gradient: 25%-55% B over 12 min; mobile phase A: 0.05% aqueous ammonium hydroxide, mobile phase B: acetonitrile) to give 20.3 mg (21%) of the title compound as a white solid. MS (ESI) m/z: 358.3 (M+H)$^+$. $^1$H NMR (400 MHz, DMSO-d$_6$): δ 8.76 (d, J=1.6 Hz, 1H), 8.55 (d, J=4.8 Hz, 1H), 8.19 (t, J=5.6 Hz, 1H), 7.98 (d, J=8.0 Hz, 1H), 7.47-7.43 (m, 2H), 5.74 (d, J=12.0 Hz, 1H), 3.42-3.41 (m, 2H), 3.27-3.21 (m, 4H), 1.43-1.41 (m, 2H), 1.36 (s, 9H), 1.33-1.33 (m, 2H), 0.51-0.47 (m, 1H).

Examples 2-14

The following compounds were prepared substantially according to the procedures described above:

| Ex. No. | Chemical structure | Chemical name | MS (ESI) m/z (M + H)$^+$ |
|---|---|---|---|
| 2 | 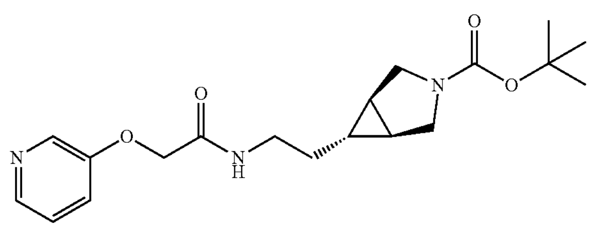 [SMILES: CC(C)(C)OC(=O)N1C[C@@H]2[C@@H](CCNC(=O)COc3cccnc3)[C@@H]2C1] | (1R,5S,6s)-tert-butyl 6-(2-(2-(pyridin-3-yloxy)acetamido)ethyl)-3-azabicyclo[3.1.0]hexane-3-carboxylate | 362.4 |
| 3 | 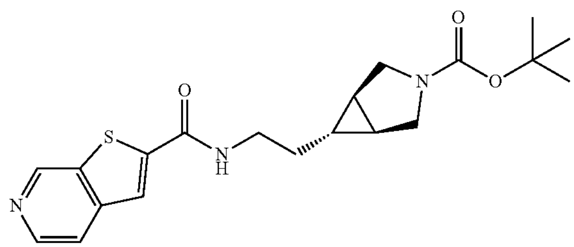 [SMILES: CC(C)(C)OC(=O)N1C[C@@H]2[C@@H](CCNC(=O)c3cc4ccncc4s3)[C@@H]2C1] | (1R,5S,6s)-tert-butyl 6-(2-(thieno[2,3-b]pyridine-2-carboxamido)ethyl)-3-azabicyclo[3.1.0]hexane-3-carboxylate | 388.3 |
| 4 | 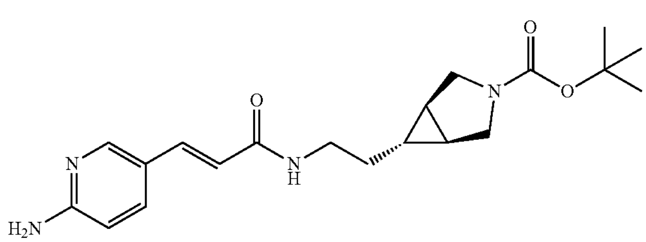 [SMILES: CC(C)(C)OC(=O)N1C[C@@H]2[C@@H](CCNC(=O)/C=C/c3ccc(N)nc3)[C@@H]2C1] | (1R,5S,6s)-tert-butyl 6-(2-((E)-3-(6-aminopyridin-3-yl)acrylamido)ethyl)-3-azabicyclo[3.1.0]hexane-3-carboxylate | 373.3 |
| 5 | 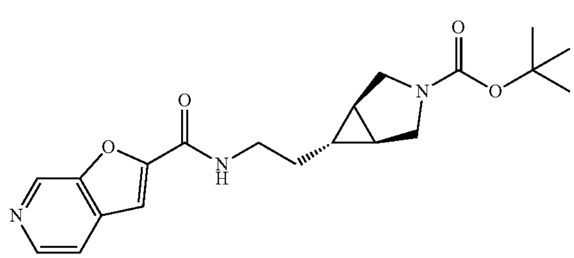 [SMILES: CC(C)(C)OC(=O)N1C[C@@H]2[C@@H](CCNC(=O)c3cc4ccncc4o3)[C@@H]2C1] | (1R,5S,6s)-tert-butyl 6-(2-(furo[2,3-b]pyridine-2-carboxamido)ethyl)-3-azabicyclo[3.1.0]hexane-3-carboxylate | 372.2 |

-continued

| Ex. No. | Chemical structure | Chemical name | MS (ESI) m/z (M + H)+ |
|---|---|---|---|
| 6 | 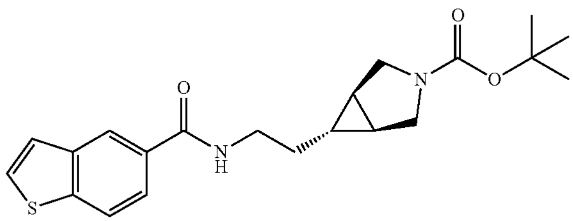 [SMILES: CC(C)(C)OC(=O)N1C[C@@H]2[C@@H](CCNC(=O)c3ccc4sccc4c3)[C@@H]2C1] | (1R,5S,6S)-tert-butyl 6-(2-(benzo[b]thiophene-5-carboxamido)ethyl)-3-azabicyclo[3.1.0]hexane-3-carboxylate | 387.3 |
| 7 | 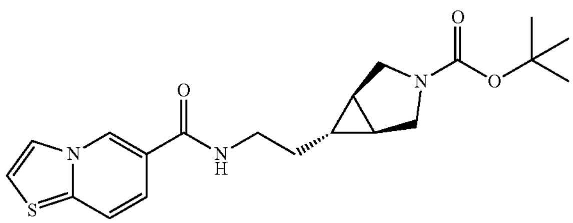 | (1R,5S,6s)-tert-butyl 6-(2-(imidazo[1,2-a]pyridine-6-carboxamido)ethyl)-3-azabicyclo[3.1.0]hexane-3-carboxylate | 371.4 |
| 8 | 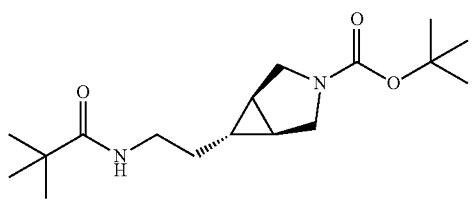 [SMILES: CC(C)(C)OC(=O)N1C[C@@H]2[C@@H](CCNC(=O)C(C)(C)C)[C@@H]2C1] | (1R,5S,6s)-tert-butyl 6-(2-pivalamidoethyl)-3-azabicyclo[3.1.0]hexane-3-carboxylate | 311.4 |
| 9 | 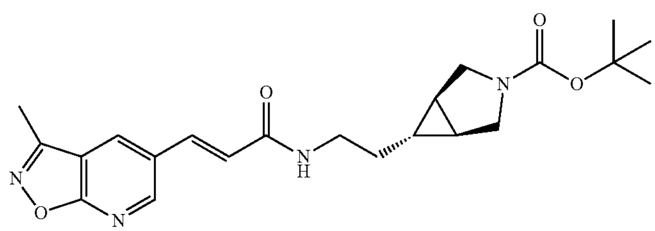 [SMILES: Cc1noc2ncc(/C=C/C(=O)NCC[C@@H]3[C@H]4CN(C(=O)OC(C)(C)C)C[C@@H]34)cc12] | tert-butyl (1R,5S,6s)-6-(2-((E)-3-(3-methylisoxazolo[5,4-b]pyridin-5-yl)acrylamido)ethyl)-3-azabicyclo[3.1.0]hexane-3-carboxylate | 413.3 |
| 10 | 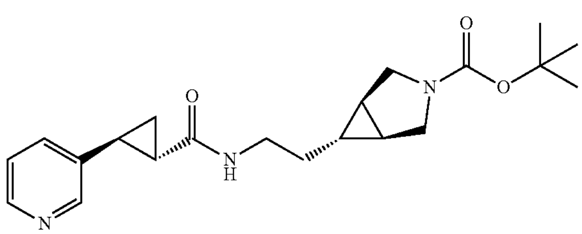 [SMILES: CC(C)(C)OC(=O)N1C[C@@H]2[C@@H](CCNC(=O)[C@H]3C[C@@H]3c3cccnc3)[C@@H]2C1] | (1R,5S,6s)-tert-butyl 6-(2-((1R,2R)-2-(pyridin-3-yl)cyclopropanecarboxamido)ethyl)-3-azabicyclo[3.1.0]hexane-3-carboxylate | 372.4 |
| 11 | 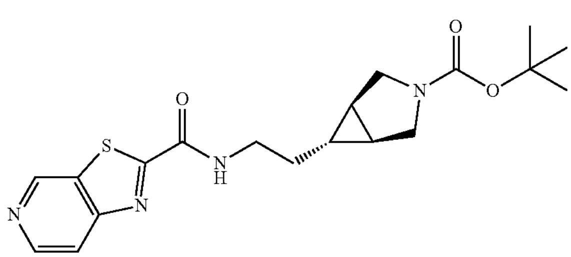 [SMILES: CC(C)(C)OC(=O)N1C[C@@H]2[C@@H](CCNC(=O)c3nc4ccncc4s3)[C@@H]2C1] | (1R,5S,6s)-tert-butyl 6-(2-(thiazolo[5,4-c]pyridine-2-carboxamido)ethyl)-3-azabicyclo[3.1.0]hexane-3-carboxylate | 389.3 |

| Ex. No. | Chemical structure | Chemical name | MS (ESI) m/z (M + H)+ |
|---|---|---|---|
| 12 | 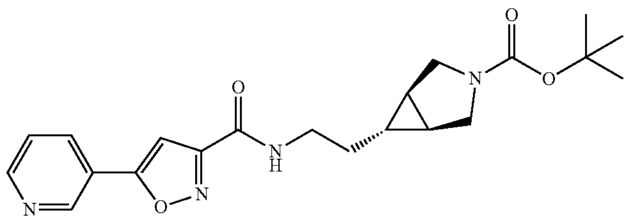 [SMILES: CC(C)(C)OC(=O)N1C[C@@H]2[C@@H](CCNC(=O)c3cc(-c4cccnc4)on3)[C@@H]2C1] | (1R,5S,6s)-tert-butyl 6-(2-(5-(pyridin-3-yl)isoxazole-3-carboxamido)ethyl)-3-azabicyclo[3.1.0]hexane-3-carboxylate | 399.3 |
| 13 | 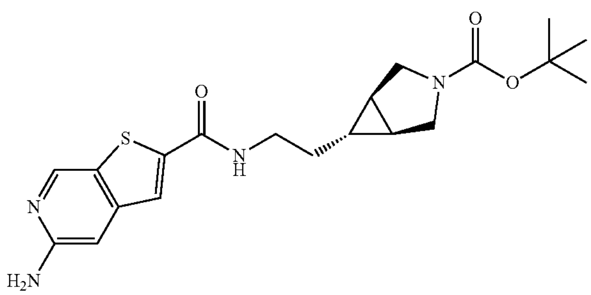 [SMILES: CC(C)(C)OC(=O)N1C[C@@H]2[C@@H](CCNC(=O)c3cc4cc(N)ncc4s3)[C@@H]2C1] | (1R,5S,6s)-tert-butyl 6-(2-(5-aminothieno[2,3-c]pyridine-2-carboxamido)ethyl)-3-azabicyclo[3.1.0]hexane-3-carboxylate | 403.3 |
| 14 | 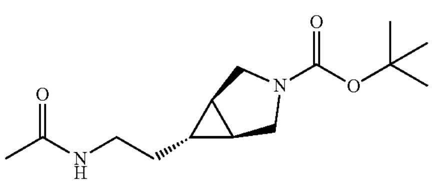 [SMILES: CC(=O)NCC[C@@H]1[C@H]2CN(C(=O)OC(C)(C)C)C[C@@H]12] | (1R,5S,6s)-tert-butyl 6-(2-azetamidoethyl)-3-azabicyclo[3.1.0]hexane-3-carboxylate | 269.4 |

Example 15: (1R,5S,6s)-tert-butyl 6-(2-(isoindoline-2-carboxamido)ethyl)-3-azabicyclo[3.1.0]hexane-3-carboxylate

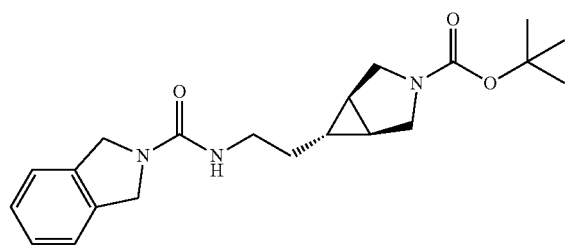 [SMILES: CC(C)(C)OC(=O)N1C[C@@H]2[C@@H](CCNC(=O)N3Cc4ccccc4C3)[C@@H]2C1]

To a mixture of Intermediate 2 (50 mg, 0.22 mmol) in acetonitrile (5 mL) was added pyridine (21.0 mg, 0.27 mmol) and N,N'-disuccinimidyl carbonate (62.3 mg, 0.24 mmol) at 25° C. The mixture was stirred at 25° C. for 14 h before the addition of isoindoline (39.5 mg, 0.33 mmol) and triethylamine (0.11 g, 1.10 mmol). The reaction solution was stirred at 25° C. for another 2 h. The reaction mixture was diluted with water (10 mL) and extracted with ethyl acetate (10 mL×3). The combined organic layers were washed with brine (10 mL) and dried over sodium sulfate. The solution was filtered and the filtrate was concentrated under vacuum. The residue was purified by preparative HPLC (Phenomenex Gemini C18 column (150×25 mm, 5 um); flow rate: 25 mL/min; gradient: 45%-72% B over 10 min; mobile phase A: 0.05% aqueous ammonium hydroxide, mobile phase B: acetonitrile) to give 17.1 mg (21%) of the title compound as a white solid. MS (ESI) m/z: 372.4 (M+H)+. $^1$H NMR (400 MHz, DMSO-$d_6$): δ 7.34-7.28 (m, 4H), 6.35 (d, J=5.6 Hz, 1H), 4.58 (s, 4H), 3.42-3.40 (m, 2H), 3.26-3.23 (m, 2H), 3.17 (m, 2H), 1.41-1.38 (m, 2H), 1.36 (s, 9H), 1.30-1.29 (m, 2H), 0.48-0.44 (m, 1H).

Examples 16-17

The following compounds were prepared substantially according to the procedures described above:

| Ex. No. | Chemical structure | Chemical name | MS (ESI) m/z (M + H)+ |
|---|---|---|---|
| 16 | 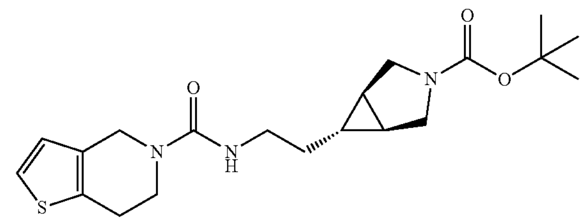 [SMILES: CC(C)(C)OC(=O)N1C[C@@H]2[C@@H](CCNC(=O)N3CCc4sccc4C3)[C@@H]2C1] | (1R,5S,6s)-tert-butyl 6-(2-(4,5,6,7-tetrahydrothieno[3,2-c]pyridine-5-carboxamido)ethyl)-3-azabicyclo[3.1.0]hexane-3-carboxylate | 392.3 |
| 17 | 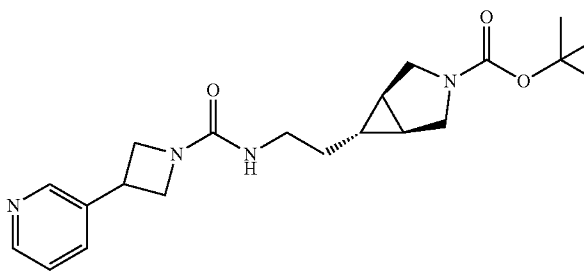 | (1R,5S,6s)-tert-butyl 6-(2-(3-(pyridin-3-yl)azetidine-1-carboxamido)ethyl)-3-azabicyclo[3.1.0]hexane-3-carboxylate | 387.4 |

Example 18: (1R,5S,6s)-tert-butyl 6-(2-((E)-2-cyano-3-(pyridin-4-yl)guanidino)ethyl)-3-azabicyclo[3.1.0]hexane-3-carboxylate

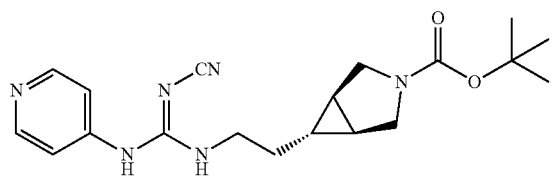 [SMILES: CC(C)(C)OC(=O)N1C[C@@H]2[C@@H](CCN/C(=N\C#N)Nc3ccncc3)[C@@H]2C1]

To a mixture of 3-cyano-2-methyl-1-(4-pyridyl)isothiourea (60 mg, 0.31 mmol) and Intermediate 2 (70.6 mg, 0.31 mmol) in pyridine (2 mL) was added triethylamine (34.7 mg, 0.34 mmol) and 4-dimethylaminopyridine (7.6 mg, 0.06 mmol). The reaction mixture was heated to 80° C. and stirred at that temperature for 12 h. The reaction mixture was cooled to room temperature and concentrated under vacuum. The resulting residue was purified by preparative HPLC (Phenomenex Gemini C18 column (150×25 mm, 5 um); flow rate: 25 mL/min; gradient: 25%-55% B over 12 min; mobile phase A: 0.05% aqueous ammonium hydroxide, mobile phase B: acetonitrile) to afford 30.5 mg (26%) of the title compound as a white solid. MS (ESI) m/z: 371.4 (M+H)+. $^1$H NMR (400 MHz, DMSO-d$_6$): δ 9.38 (br s, 1H), 8.37 (d, J=5.2 Hz, 2H), 7.80 (br s, 1H), 7.22 (br s, 2H), 3.43-3.40 (m, 4H), 3.25-3.21 (m, 2H), 1.50-1.43 (m, 2H), 1.35 (s, 9H), 1.35-1.34 (m, 2H), 0.49-0.44 (m, 1H).

Example 19: (1R,5S,6s)-tert-butyl 6-(2-(3-((pyridin-3-yl)methyl)ureido)ethyl)-3-azabicyclo[3.1.0]hexane-3-carboxylate

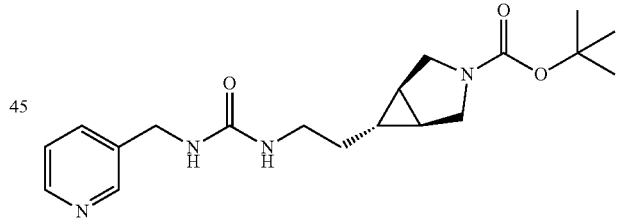

To a solution of (1R,5S,6r)-tert-butyl 6-(hydroxymethyl)-3-azabicyclo[3.1.0]hexane-3-carboxylate (0.6 g, 2.81 mmol) in dichloromethane (30 mL) at 0° C. was added (1,1,1-triacetoxy)-1,1-dihydro-1,2-benziodoxol-3(1H)-one (1.8 g, 4.22 mmol). The mixture was stirred at 25° C. for 12 h. The mixture was washed with saturated potassium carbonate solution (30 mL×2). The organic layer was washed with brine (30 mL×3), dried over sodium sulfate, filtered and concentrated under reduced pressure to afford 0.4 g of crude (1R,5S,6r)-tert-butyl-6-formyl-3-azabicyclo[3.1.0]hexane-3-carboxylate as a colorless oil. MS (ESI) m/z: 156.1 (M+H-$^t$Bu)+. $^1$H NMR (400 MHz, DMSO-d$_6$): δ 9.45 (d, J=4.0 Hz, 1H), 3.74-3.71 (m, 2H), 3.49-3.46 (m, 2H), 2.22-2.21 (m, 2H), 1.84-1.82 (m, 1H), 1.45 (s, 9H).

To a solution of benzyl 2-(dimethoxyphosphoryl)acetate (0.64 g, 2.46 mmol) in tetrahydrofuran (20 mL) was added sodium hydride (0.1 g, 2.84 mmol, 60% in mineral oil). The mixture was stirred at 25° C. for 15 min followed by the addition of (1R,5S,6r)-tert-butyl 6-formyl-3-azabicyclo[3.1.0]hexane-3-carboxylate (0.4 g, 1.89 mmol). The mixture was stirred at 25° C. for 15 min. The reaction was quenched with saturated aqueous ammonium chloride (10 mL) and extracted with ethyl acetate (10 mL×3). The combined organic layers were washed with brine (10 mL×3), dried over sodium sulfate, filtered and concentrated under reduced pressure. The residue was purified by silica gel column chromatography (petroleum ether/ethyl acetate, from 50/1 to 5/1) to give 0.4 g (61%) of (1R,5S,6s)-tert-butyl 6-((E)-3-(benzyloxy)-3-oxoprop-1-en-1-yl)-3-azabicyclo[3.1.0]hexane-3-carboxylate as a colorless oil. MS (ESI) m/z: 366.0 (M+Na)⁺. ¹H NMR (400 MHz, DMSO-d₆): δ 7.38-7.31 (m, 5H), 6.56 (dd, J=10.0 Hz, 15.2 Hz, 1H), 5.89 (d, J=15.6 Hz, 1H), 5.25 (s, 2H), 3.72-3.60 (m, 2H), 3.43-3.42 (m, 2H), 1.77-1.76 (m, 2H), 1.45 (s, 9H), 1.45-1.44 (m, 1H).

To a solution of (1R,5S,6s)-tert-butyl 6-((E)-3-(benzyloxy)-3-oxoprop-1-en-1-yl)-3-azabicyclo[3.1.0]hexane-3-carboxylate (0.53 g, 1.54 mmol) in methanol (20 mL) was added cobalt chloride hexahydrate (2.6 g, 10.8 mmol) and sodium borohydride (0.29 g, 7.7 mmol) at 0° C. The mixture was stirred at 0° C. for 1 h. The reaction was quenched with water (10 mL) and concentrated in vacuo to remove methanol. The resulting residue was extracted with ethyl acetate (20 mL×3), and the combined organic layers were washed with brine (30 mL) and concentrated under vacuum. The residue was purified by silica gel column chromatography (petroleum ether/ethyl acetate, from 50/1 to 5/1) to afford 0.38 g (47%) of (1R,5S,6s)-tert-butyl 6-(3-(benzyloxy)-3-oxopropyl)-3-azabicyclo[3.1.0]hexane-3-carboxylate as a colorless oil. MS (ESI) m/z: 368.0 (M+Na)+.

To a solution of (1R,5S,6s)-tert-butyl 6-(3-(benzyloxy)-3-oxopropyl)-3-azabicyclo[3.1.0]hexane-3-carboxylate (0.4 g, 1.01 mmol) in a mixture of methanol/water (1/1, 10 mL) was added lithium hydroxide hydrate (0.1 g, 0.30 mmol). The mixture was stirred at 60° C. for 2 h. The mixture was diluted with water (10 mL) and extracted with ethyl acetate (5 mL×2). The aqueous phase was adjusted to pH 4 with hydrochloride acid (1 N) and extracted with ethyl acetate (10 mL×3). The combined organic layers were washed with brine (30 mL), dried over sodium sulfate, filtered and concentrated under reduced pressure to give 0.2 g (82%) of 3-((1R,5S,6s)-3-(tert-butoxycarbonyl)-3-azabicyclo[3.1.0]hexan-6-yl)propanoic acid as a light yellow oil. MS (ESI) m/z: 278.2 (M+Na)+.

To a solution of 3-((1R,5S,6s)-3-(tert-butoxycarbonyl)-3-azabicyclo[3.1.0]hexan-6-yl)propanoic acid (100.0 mg, 0.24 mmol) in toluene (1 mL) was added diphenylphosphoryl azide (71.1 mg, 0.26 mmol) and triethylamine (71.3 mg, 0.71 mmol). The mixture was stirred at 80° C. for 3 h, cooled down to 25° C., and 3-pyridylmethanamine (50.8 mg, 0.47 mmol) was added with stirring. The mixture was stirred at 25° C. for an additional 1 h. The mixture was concentrated under reduced pressure, and the resulting residue was purified by preparative HPLC (Phenomenex Gemini C18 column (150×25 mm, 10 um); flow rate: 25 mL/min; gradient: 23%-53% B over 12 min; mobile phase A: 0.05% aqueous ammonium hydroxide, mobile phase B: acetonitrile) to afford 13.7 mg (16%) of the title compound as a colorless oil. MS (ESI) m/z: 361.0 (M+H)⁺. ¹H NMR (400 MHz, DMSO-d₆): δ 8.46 (s, 1H), 8.42 (d, J=4.0 Hz, 1H), 7.63 (d, J=7.6 Hz, 1H), 7.37-7.28 (m, 1H), 6.41 (t, J=6.0 Hz, 1H), 6.00 (t, J=5.6 Hz, 1H), 4.21 (d, J=6.0 Hz, 2H), 3.39 (d, J=5.2 Hz, 2H), 3.27-3.17 (m, 2H), 3.05 (d, J=6.0 Hz, 2H), 1.36 (s, 9H), 1.33-1.23 (m, 4H), 0.45-0.35 (m, 1H).

Example 20: (1R,5S,6s)-tert-butyl 6-(2-(2,3-dihydro-1H-pyrrolo[3,4-c]pyridine-2-carboxamido)ethyl)-3-azabicyclo[3.1.0]hexane-3-carboxylate

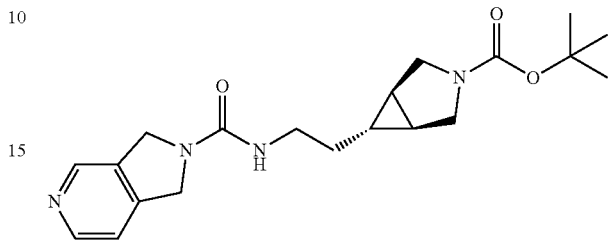

This compound was prepared substantially according to the procedures described above. MS (ESI) m/z: 373.2 (M+H)⁺.

Example 21: (1R,5S,6s)-3-methyloxetan-3-yl 6-(2-((E)-3-(pyridin-3-yl)acrylamido)ethyl)-3-azabicyclo[3.1.0]hexane-3-carboxylate

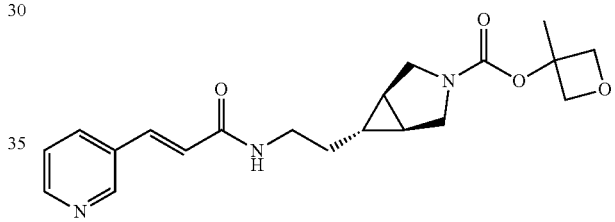

To a solution of the Example 1 compound (180 mg, 0.50 mmol) in dichloromethane (3.0 mL) was added trifluoroacetic acid (770 mg, 6.75 mmol). The mixture was stirred at 25° C. for 0.5 h. The reaction mixture was concentrated under vacuum to give 180 mg of (E)-N-(2-((1R,5S,6s)-3-azabicyclo[3.1.0]hexan-6-yl)ethyl)-3-(pyridin-3-yl)acrylamide as a yellow oil. MS (ESI) m/z: 258.1 (M+H)⁺.

To a solution of oxetan-3-one (2 g, 27.7 mmol) in tetrahydrofuran (60 mL) was added methyllithium (1.6 M in diethyl ether, 34.7 mL) dropwise at −40° C. under an atmosphere of nitrogen. The mixture was warmed to 0° C. and stirred for another 2 h. (4-Nitrophenyl) chloroformate (5.59 g, 27.7 mmol) was added to the resulting solution at 0° C., and the reaction mixture was stirred at 0° C. for an additional 3 h. The reaction was quenched with water (100 mL) and extracted with ethyl acetate (50 mL×3). The combined organic layers were washed with brine (30 mL×3), dried over sodium sulfate, filtered and concentrated under vacuum. The residue was purified by silica gel column chromatography (petroleum ether/ethyl acetate, from 20/1 to 10/1) to give 2.5 g (36%) of (3-methyloxetan-3-yl) (4-nitrophenyl) carbonate as a brown oil. ¹H NMR (400 MHz, CDCl₃): δ 8.31 (d, J=8.8 Hz, 2H), 7.42 (d, J=8.8 Hz, 2H), 4.92 (d, J=7.6 Hz, 2H), 4.59 (d, J=8.2 Hz, 2H), 1.87 (s, 3H).

To a solution of (E)-N-(2-((1R,5S,6s)-3-azabicyclo[3.1.0]hexan-6-yl)ethyl)-3-(pyridin-3-yl)acrylamide (180 mg, 0.70 mmol, TFA salt) in acetonitrile (5 mL) was added triethylamine (142 mg, 1.40 mmol) and (3-methyloxetan-3-yl)

(4-nitrophenyl) carbonate (177 mg, 0.70 mmol). The mixture was stirred at 25° C. for 1 h. The reaction mixture was concentrated under vacuum. The resulting residue was purified by preparative HPLC (Phenomenex Gemini 018 column (150×25 mm, 5 um); flow rate: 25 mL/min; gradient: 12%-42% B over 10 min; mobile phase A: 0.05% aqueous ammonium hydroxide, mobile phase B: acetonitrile) to give 60 mg (23%) of the title compound as a yellow solid. MS (ESI) m/z: 372.4 (M+H)+. 1H NMR (400 MHz, DMSO-d6): δ 8.75 (d, J=2 Hz, 1H), 8.75 (dd, J=1.6 Hz, 4.8 Hz, 1H), 8.20 (t, J=6.0 Hz, 1H), 7.97-7.99 (m, 1H), 7.43-7.48 (m, 2H), 8.75 (d, J=16 Hz, 1H), 4.58 (t, J=7.6 Hz, 2H), 8.20 (d, J=7.2 Hz, 2H), 3.24-3.50 (m, 6H), 1.59 (s, 3H), 1.36-1.45 (m, 4H), 0.51-0.55 (m, 1H).

Examples 22-85

The following compounds were prepared substantially according to the procedures described above:

| Ex. No. | Chemical structure | Chemical name | MS (ESI) m/z (M + H)+ |
|---|---|---|---|
| 22 | 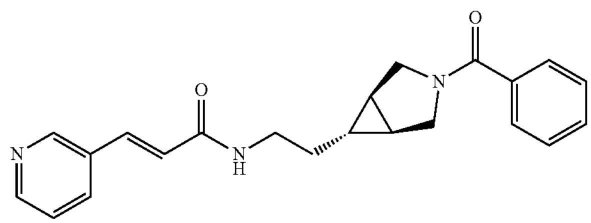 [SMILES: O=C(/C=C/c1cccnc1)NCC[C@@H]1[C@H]2CN(C(=O)c3ccccc3)C[C@@H]12] | (E)-N-(2-((1R,5S,6s)-3-benzoyl-3-azabicyclo[3.1.0]hexan-6-yl)ethyl)-3-(pyridin-3-yl)acrylamide | 362.3 |
| 23 | 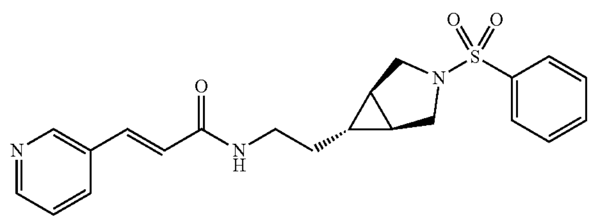 [SMILES: O=C(/C=C/c1cccnc1)NCC[C@@H]1[C@H]2CN(S(=O)(=O)c3ccccc3)C[C@@H]12] | (E)-N-(2-((1R,5S,6s)-3-(phenylsulfonyl)-3-azabicyclo[3.1.0]hexan-6-yl)ethyl)-3-(pyridin-3-yl)acrylamide | 398.2 |
| 24 | 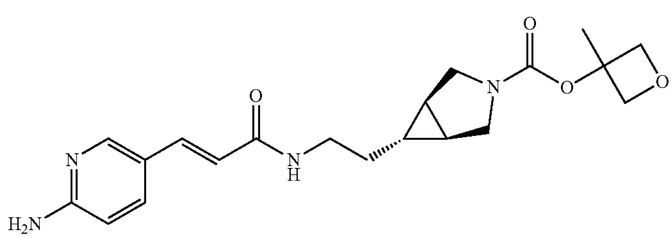 [SMILES: CC1(OC(=O)N2C[C@@H]3[C@@H](CCNC(=O)/C=C/c4ccc(N)nc4)[C@@H]3C2)COC1] | (1R,5S,6s)-3-methyloxetan-3-yl 6-(2-((E)-3-(6-aminopyridin-3-yl)acrylamido)ethyl)-3-azabicyclo[3.1.0]hexane-3-carboxylate | 387.4 |
| 25 | 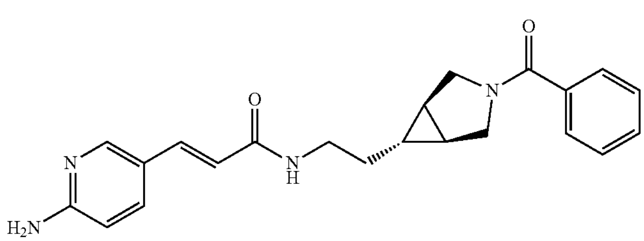 [SMILES: Nc1ccc(/C=C/C(=O)NCC[C@@H]2[C@H]3CN(C(=O)c4ccccc4)C[C@@H]23)cn1] | (E)-3-(6-aminopyridin-3-yl)-N-(2-((1R,5S,6s)-3-benzoyl-3-azabicyclo[3.1.0]hexan-6-yl)ethyl)acrylamide | 377.4 |
| 26 | 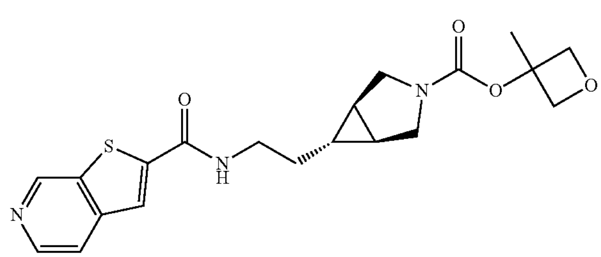 [SMILES: CC1(OC(=O)N2C[C@@H]3[C@@H](CCNC(=O)c4cc5ccncc5s4)[C@@H]3C2)COC1] | (1R,5S,6s)-3-methyloxetan-3-yl 6-(2-(thieno[2,3-c]pyridine-2-carboxamido)ethyl)-3-azabicyclo[3.1.0]hexane-3-carboxylate | 402.4 |

-continued

| Ex. No. | Chemical structure | Chemical name | MS (ESI) m/z (M + H)+ |
|---|---|---|---|
| 27 | 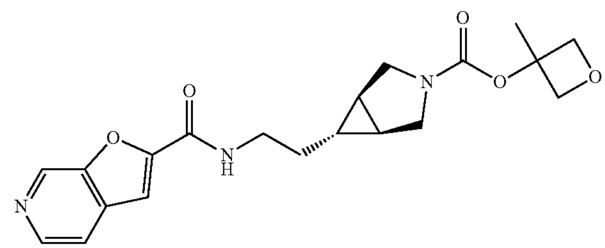 | (1R,5S,6s)-3-methyloxetan-3-yl 6-(2-(furo[2,3-c]pyridine-2-carboxamido)ethyl)-3-azabicyclo[3.1.0]hexane-3-carboxylate | 386.4 |
| 28 | 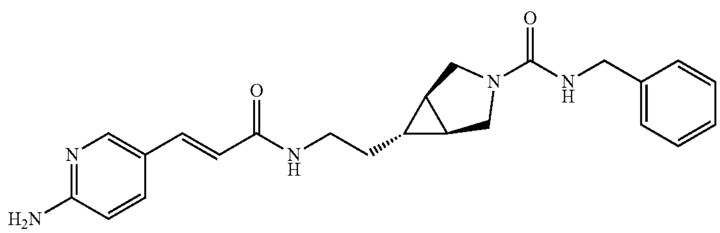 [SMILES: Nc1ccc(/C=C/C(=O)NCC[C@@H]2[C@H]3CN(C(=O)NCc4ccccc4)C[C@@H]23)cn1] | (1R,5S,6s)-6-(2-((E)-3-(6-aminopyridin-3-yl)acrylamido)ethyl)-N-benzyl-3-azabicyclo[3.1.0]hexane-3-carboxamide | 406.5 |
| 29 | 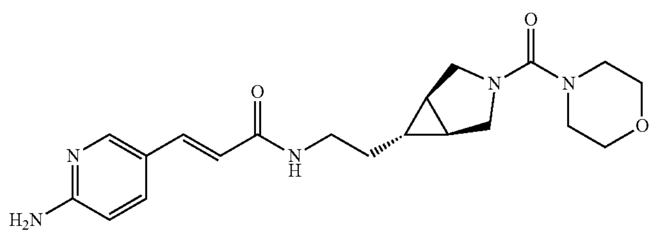 [SMILES: Nc1ccc(/C=C/C(=O)NCC[C@@H]2[C@H]3CN(C(=O)N4CCOCC4)C[C@@H]23)cn1] | (E)-3-(6-aminopyridin-3-yl)-N-(2-((1R,5S,6s)-3-(morpholine-4-carbonyl)-3-azabicyclo[3.1.0]hexan-6-yl)ethyl)acrylamide | 386.4 |
| 30 | 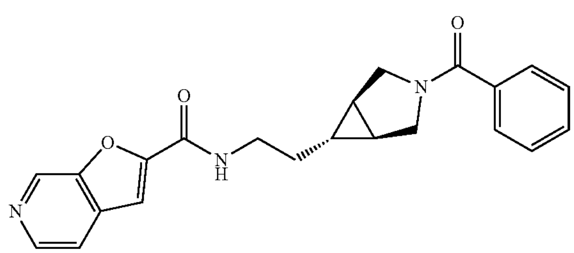 [SMILES: O=C(NCC[C@@H]1[C@H]2CN(C(=O)c3ccccc3)C[C@@H]12)c1cc2ccncc2o1] | N-(2-((1R,5S,6s)-3-benzoyl-3-azabicyclo[3.1.0]hexan-6-yl)ethyl)furo[2,3-c]pyridine-2-carboxamide | 376.4 |
| 31 | 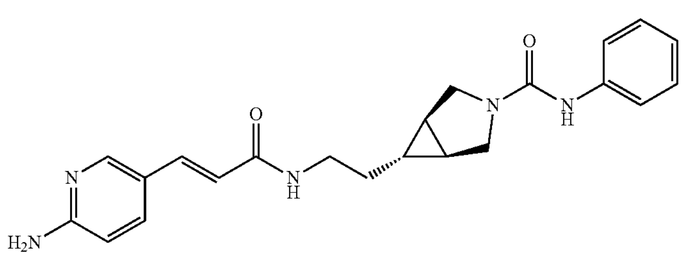 [SMILES: Nc1ccc(/C=C/C(=O)NCC[C@@H]2[C@H]3CN(C(=O)Nc4ccccc4)C[C@@H]23)cn1] | (1R,5S,6s)-6-(2-((E)-3-(6-aminopyridin-3-yl)acrylamido)ethyl)-N-phenyl-3-azabicyclo[3.1.0]hexane-3-carboxamide | 392.4 |
| 32 | 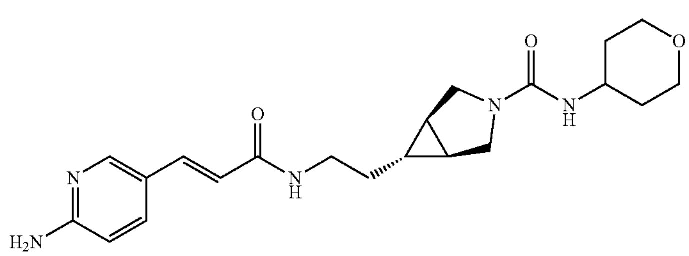 | (1R,5S,6s)-6-(2-((E)-3-(6-aminopyridin-3-yl)acrylamido)ethyl)-N-(tetrahydro-2H-pyran-4-yl)-3-azabicyclo[3.1.0]hexane-3-carboxamide | 400.3 |

-continued

| Ex. No. | Chemical structure | Chemical name | MS (ESI) m/z $(M + H)^+$ |
|---|---|---|---|
| 33 | 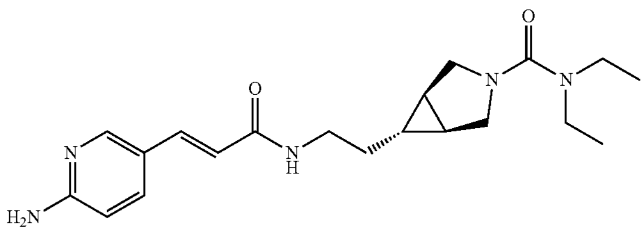 [SMILES: CCN(CC)C(=O)N1C[C@@H]2[C@@H](CCNC(=O)/C=C/c3ccc(N)nc3)[C@@H]2C1] | (1R,5S,6s)-6-(2-((E)-3-(6-aminopyridin-3-yl)acrylamido)ethyl)-N,N-diethyl-3-azabicyclo[3.1.0]hexane-3-carboxamide | 372.4 |
| 34 | 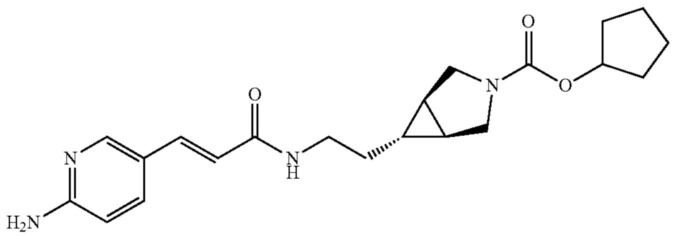 [SMILES: Nc1ccc(/C=C/C(=O)NCC[C@@H]2[C@H]3CN(C(=O)OC4CCCC4)C[C@@H]23)cn1] | (1R,5S,6s)-cyclopentyl 6-(2-((E)-3-(6-aminopyridin-3-yl)acrylamido)ethyl)-3-azabicyclo[3.1.0]hexane-3-carboxylate | 385.4 |
| 35 | 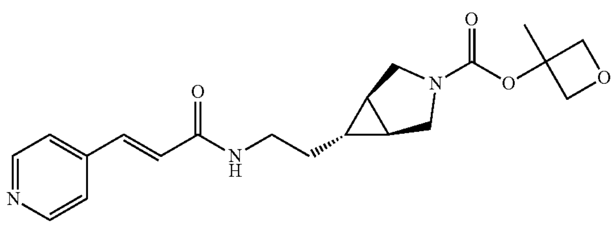 [SMILES: CC1(OC(=O)N2C[C@@H]3[C@@H](CCNC(=O)/C=C/c4ccncc4)[C@@H]3C2)COC1] | (1R,5S,6s)-3-methyloxetan-3-yl 6-(2-((E)-3-(pyridin-4-yl)acrylamido)ethyl)-3-azabicyclo[3.1.0]hexane-3-carboxylate | 372.4 |
| 36 | 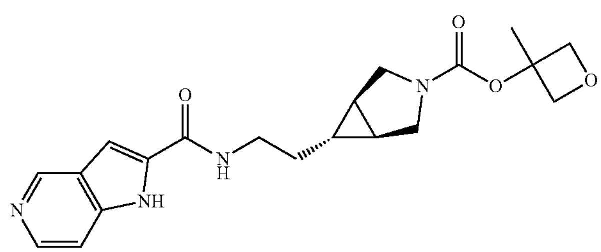 [SMILES: CC1(OC(=O)N2C[C@@H]3[C@@H](CCNC(=O)c4cc5cnccc5[nH]4)[C@@H]3C2)COC1] | (1R,5S,6s)-3-methyloxetan-3-yl 6-(2-(1H-pyrrolo[3,2-c]pyridine-2-carboxamido)ethyl)-3-azabicyclo[3.1.0]hexane-3-carboxylate | 385.4 |
| 37 | 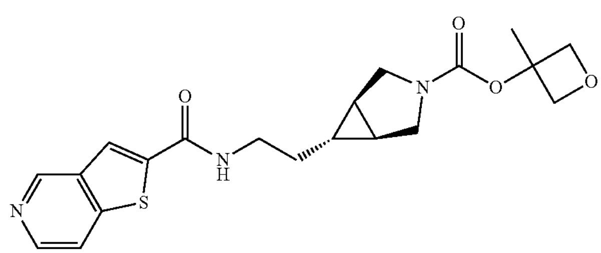 [SMILES: CC1(OC(=O)N2C[C@@H]3[C@@H](CCNC(=O)c4cc5cnccc5s4)[C@@H]3C2)COC1] | (1R,5S,6s)-3-methyloxetan-3-yl 6-(2-(thieno[3,2-c]pyridine-2-carboxamido)ethyl)-3-azabicyclo[3.1.0]hexane-3-carboxylate | 402.3 |
| 38 | 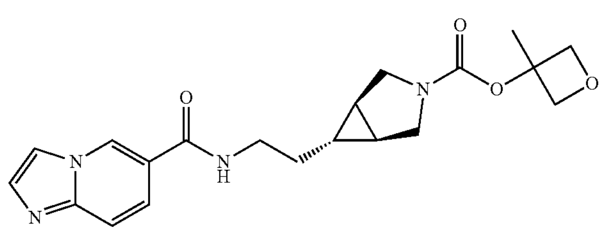 [SMILES: CC1(OC(=O)N2C[C@@H]3[C@@H](CCNC(=O)c4ccc5nccn5c4)[C@@H]3C2)COC1] | (1R,5S,6s)-3-methyloxetan-3-yl 6-(2-(imidazo[1,2-a]pyridine-6-carboxamido)ethyl)-3-azabicyclo[3.1.0]hexane-3-carboxylate | 385.4 |

-continued

| Ex. No. | Chemical structure | Chemical name | MS (ESI) m/z (M + H)+ |
|---|---|---|---|
| 39 | 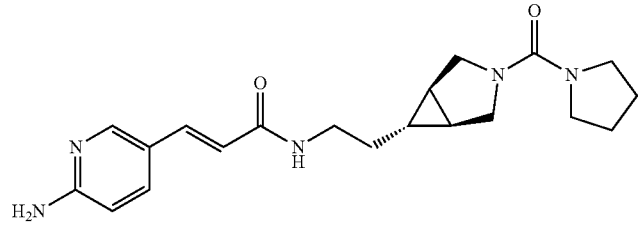 [SMILES: Nc1ccc(/C=C/C(=O)NCC[C@@H]2[C@H]3CN(C(=O)N4CCCC4)C[C@@H]23)cn1] | (E)-3-(6-aminopyridin-3-yl)-N-(2-((1R,5S,6s)-3-(pyrrolidine-1-carbonyl)-3-azabicyclo[3.1.0]hexan-6-yl)ethyl)acrylamide | 370.3 |
| 40 | 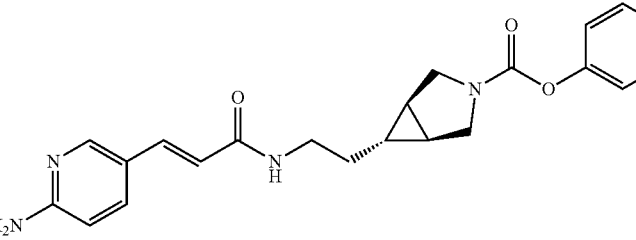 | (1R,5S,6s)-phenyl 6-(2-((E)-3-(6-aminopyridin-3-yl)acrylamido)ethyl)-3-azabicyclo[3.1.0]hexane-3-carboxylate | 393.4 |
| 41 | 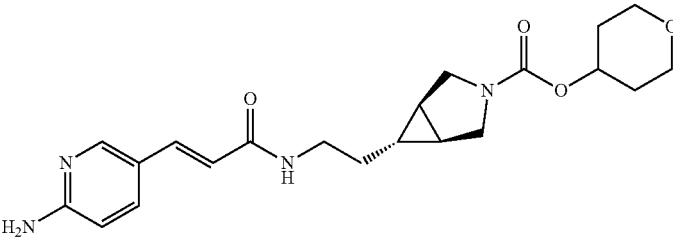 [SMILES: Nc1ccc(/C=C/C(=O)NCC[C@@H]2[C@H]3CN(C(=O)Oc4ccccc4)C[C@@H]23)cn1] | (1R,5S,6s)-tetrahydro-2H-pyran-4-yl 6-(2-((E)-3-(6-aminopyridin-3-yl)acrylamido)ethyl)-3-azabicyclo[3.1.0]hexane-3-carboxylate | 401.4 |
| 42 | 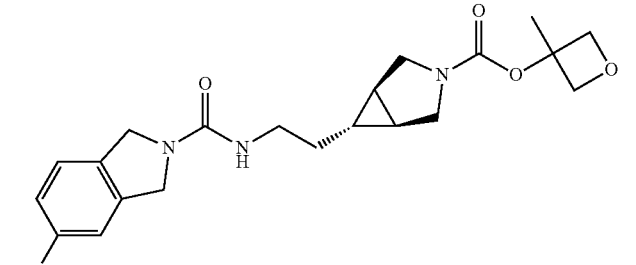 | (1R,5S,6s)-3-methyloxetan-3-yl 6-(2-(5-fluoroisoindoline-2-carboxamido)ethyl)-3-azabicyclo[3.1.0]hexane-3-carboxylate | 404.4 |
| 43 | 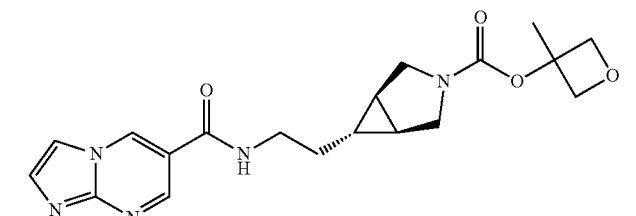 | (1R,5S,6s)-3-methyloxetan-3-yl 6-(2-(imidazo[1,2-a]pyrimidine-6-carboxamido)ethyl)-3-azabicyclo[3.1.0]hexane-3-carboxylate | 386.4 |
| 44 | 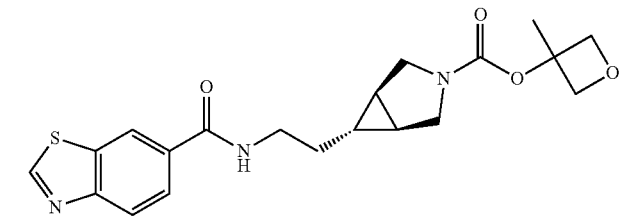 [SMILES: CC1(OC(=O)N2C[C@@H]3[C@@H](CCNC(=O)c4ccc5ncsc5c4)[C@@H]3C2)COC1] | (1R,5S,6s)-3-methyloxetan-3-yl 6-(2-(benzo[d]thiazole-6-carboxamido)ethyl)-3-azabicyclo[3.1.0]hexane-3-carboxylate | 402.3 |

-continued

| Ex. No. | Chemical structure | Chemical name | MS (ESI) m/z (M + H)+ |
|---|---|---|---|
| 45 | 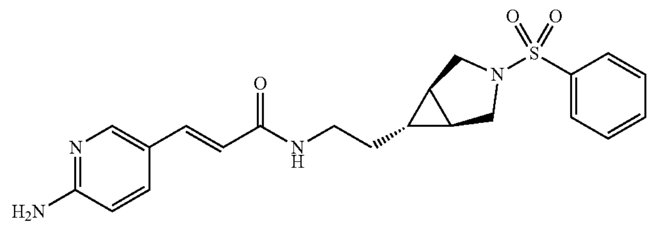 [SMILES: Nc1ccc(/C=C/C(=O)NCC[C@@H]2[C@H]3CN(S(=O)(=O)c4ccccc4)C[C@@H]23)cn1] | (E)-3-(6-aminopyrdiin-3-yl)-N-(2-((1R,5S,6s)-3-(phenylsulfonyl)-3-azabicyclo[3.1.0]hexan-6-yl)ethyl)acrylamide | 413.3 |
| 46 | 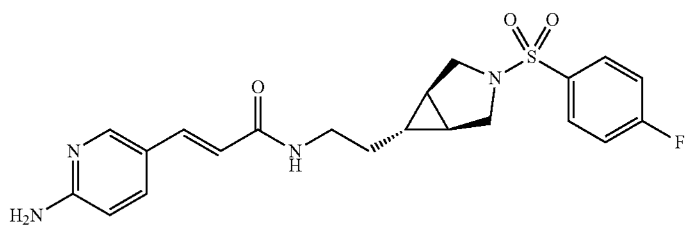 [SMILES: Nc1ccc(/C=C/C(=O)NCC[C@@H]2[C@H]3CN(S(=O)(=O)c4ccc(F)cc4)C[C@@H]23)cn1] | (E)-3-(6-aminopyridin-3-yl)-N-(2-((1R,5S,6s)-3-((4-fluorophenyl)sulfonyl)-3-azabicyclo[3.1.0]hexan-6-yl)ethyl)acrylamide | 431.3 |
| 47 | 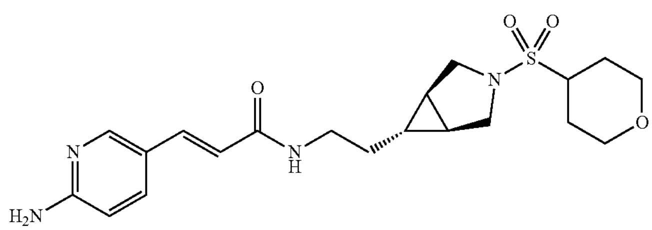 [SMILES: Nc1ccc(/C=C/C(=O)NCC[C@@H]2[C@H]3CN(S(=O)(=O)C4CCOCC4)C[C@@H]23)cn1] | (E)-3-(6-aminopyridin-3-yl)-N-(2-((1R,5S,6s)-3-((tetrahydro-2H-pyran-4-yl)sulfonyl)-3-azabicyclo[3.1.0]hexan-6-yl)ethyl)acrylamide | 421.4 |
| 48 | 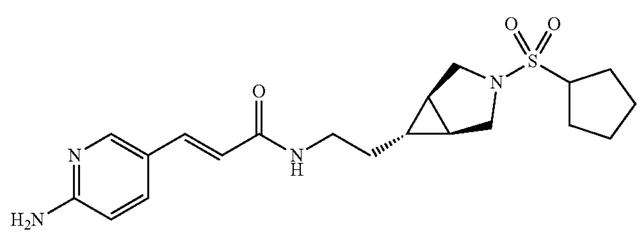 [SMILES: Nc1ccc(/C=C/C(=O)NCC[C@@H]2[C@H]3CN(S(=O)(=O)C4CCCC4)C[C@@H]23)cn1] | (E)-3-(6-aminopyridin-3-yl)-N-(-2 ((1R,5S,6s)-3-(cyclopentylsulfonyl)-3-azabicyclo[3.1.0]hexan-6-yl)ethyl)acrylamide | 405.3 |
| 49 | 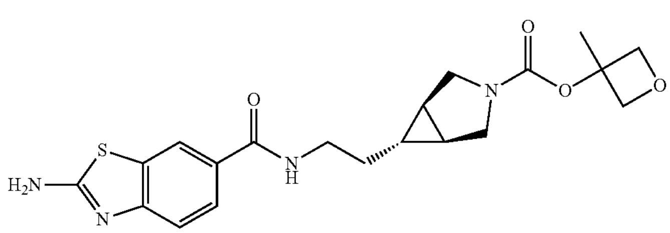 [SMILES: CC1(OC(=O)N2C[C@@H]3[C@@H](CCNC(=O)c4ccc5nc(N)sc5c4)[C@@H]3C2)COC1] | (1R,5S,6s)-3-methyloxetan-3-yl 6-(2-(2-aminobenzo[d]thiazole-6-carboxamido)ethyl)-3-azabicyclo[3.1.0]hexane-3-carboxylate | 417.4 |
| 50 | 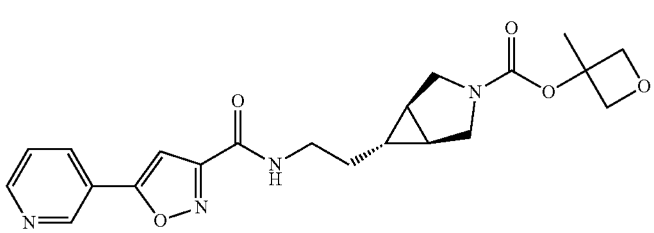 [SMILES: CC1(OC(=O)N2C[C@@H]3[C@@H](CCNC(=O)c4cc(-c5cccnc5)on4)[C@@H]3C2)COC1] | (1R,5S,6s)-3-methyloxetan-3-yl 6-(2-(5-(pyridin-3-yl)isoxazole-3-carboxamido)ethyl)-3-azabicyclo[3.1.0]hexane-3-carboxylate | 413.4 |

| Ex. No. | Chemical structure | Chemical name | MS (ESI) m/z (M + H)+ |
|---|---|---|---|
| 51 | 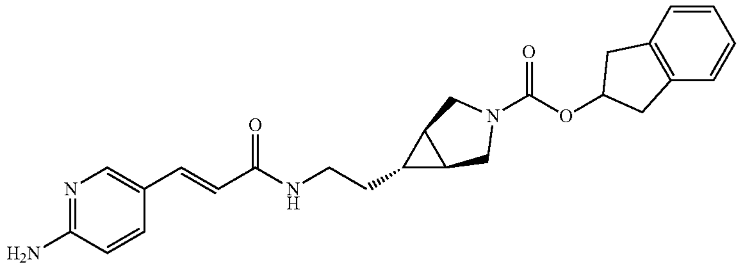 [SMILES: Nc1ccc(/C=C/C(=O)NCC[C@@H]2[C@H]3CN(C(=O)OC4Cc5ccccc5C4)C[C@@H]23)cn1] | (1R,5S,6s)-2,3-dihydro-1H-inden-2-yl 6-(2-((E)-3-(6-aminopyridin-3-yl)acrylamido)ethyl)-3-azabicyclo[3.1.0]hexane-3-carboxylate | 433.4 |
| 52 | 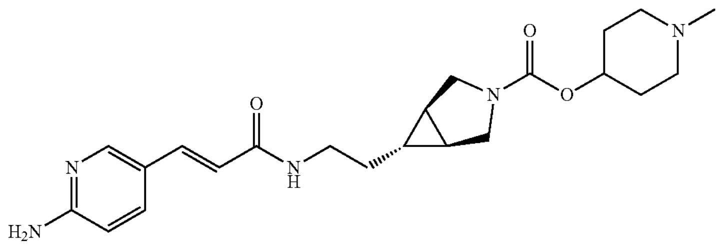 [SMILES: CN1CCC(OC(=O)N2C[C@@H]3[C@@H](CCNC(=O)/C=C/c4ccc(N)nc4)[C@@H]3C2)CC1] | (1R,5S,6s)-(1-methylpiperidin)-4-yl 6-(2-((E)-3-(6-aminopyridin-3-yl)acrylamido)ethyl)-3-azabicyclo[3.1.0]hexane-3-carboxylate | 414.4 |
| 53 | 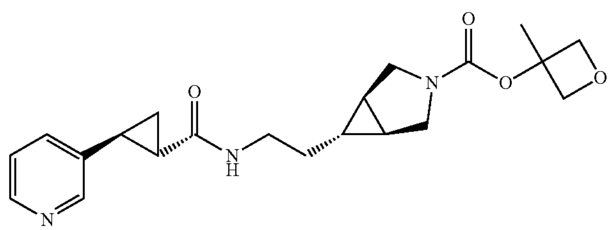 | (1R,5S,6s)-3-methyloxetan-3-yl 6-(2-((1S,2S)-2-(pyridin-3-yl)cyclopropanecarboxamido)ethyl)-3-azabicyclo[3.1.0]hexane-3-carboxylate and (1R,5S,6s)-3-methyloxetan-3-yl 6-(2-((1R,2R)-2-(pyridin-3-yl)cyclopropanecarboxamido)ethyl)-3-azabicyclo[3.1.0]hexane-3-carboxylate | 386.4 |
| 54 | 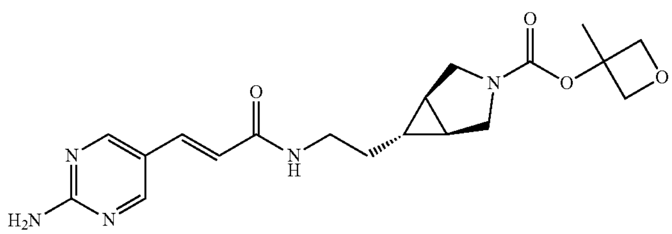 | (1R,5S,6s)-3-methyloxetan-3-yl 6-(2-((E)-3-(2-aminopyrimidin-5-yl)acrylamido)ethyl)-3-azabicyclo[3.1.0]hexane-3-carboxylate | 388.4 |
| 55 | 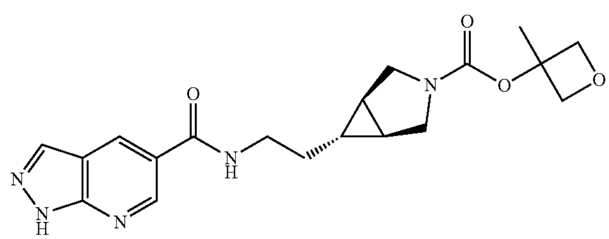 [SMILES: CC1(OC(=O)N2C[C@@H]3[C@@H](CCNC(=O)c4cnc5[nH]ncc5c4)[C@@H]3C2)COC1] | (1R,5S,6s)-3-methyloxetan-3-yl 6-(2-(1H-pyrazolo[3,4-b]pyridine-5-carboxamido)ethyl)-3-azabicyclo[3.1.0]hexane-3-carboxylate | 386.4 |
| 56 | 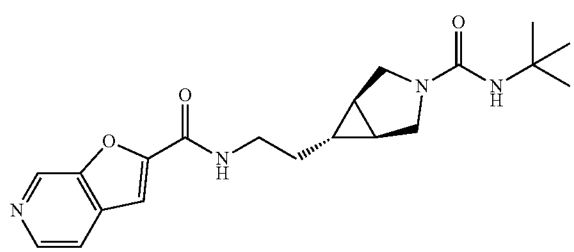 [SMILES: CC(C)(C)NC(=O)N1C[C@@H]2[C@@H](CCNC(=O)c3cc4ccncc4o3)[C@@H]2C1] | N-(2-((1R,5S,6s)-3-(tert-butylcarbamoyl)-3-azabicyclo[3.1.0]hexan-6-yl)ethyl)furo[2,3-c]pyridine-2-carboxamide | 371.4 |

-continued

| Ex. No. | Chemical structure | Chemical name | MS (ESI) m/z (M + H)+ |
|---|---|---|---|
| 57 | 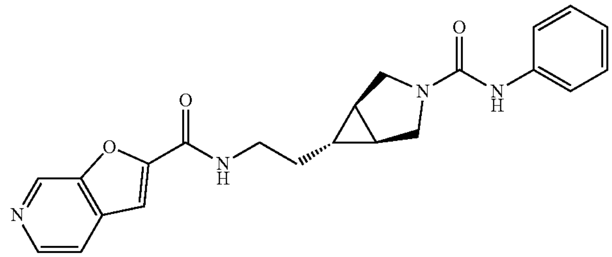 [SMILES: O=C(NCC[C@@H]1[C@H]2CN(C(=O)Nc3ccccc3)C[C@@H]12)c1cc2ccncc2o1] | N-(2-((1R,5S,6s)-3-(phenylcarbamoyl)-3-azabicyclo[3.1.0]hexan-6-yl)ethyl)furo[2,3-c]pyridine-2-carboxamide | 391.4 |
| 58 | 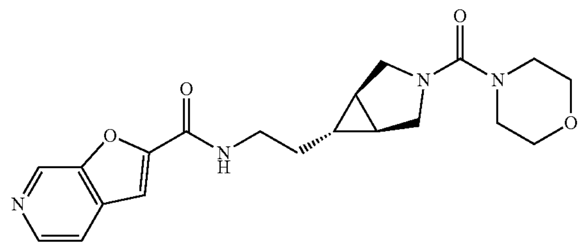 [SMILES: O=C(NCC[C@@H]1[C@H]2CN(C(=O)N3CCOCC3)C[C@@H]12)c1cc2ccncc2o1] | N-(2-((1R,5S,6s)-3-(morpholine-4-carbonyl)-3-azabicyclo[3.1.0]hexan-6-yl)ethyl)furo[2,3-c]pyridine-2-carboxamide | 385.4 |
| 59 | 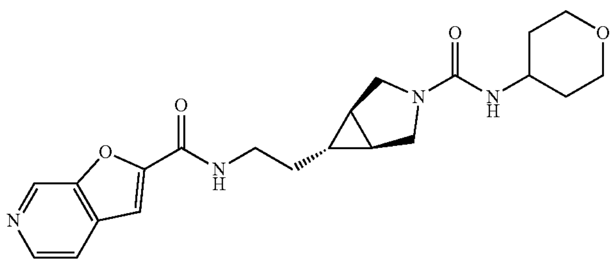 [SMILES: O=C(NCC[C@@H]1[C@H]2CN(C(=O)NC3CCOCC3)C[C@@H]12)c1cc2ccncc2o1] | N-(2-((1R,5S,6s)-3-((tetrahydro-2H-pyran-4-yl)carbamoyl)-3-azabicyclo[3.1.0]hexan-6-yl)ethyl)furo[2,3-c]pyridine-2-carboxamide | 399.3 |
| 60 | 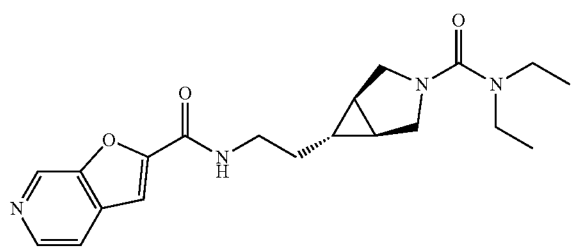 [SMILES: CCN(CC)C(=O)N1C[C@@H]2[C@@H](CCNC(=O)c3cc4ccncc4o3)[C@@H]2C1] | N-(2-((1R,5S,6s)-3-(diethylcarbamoyl)-3-azabicyclo[3.1.0]hexan-6-yl)ethyl)furo[2,3-c]pyridine-2-carboxamide | 371.4 |
| 61 | 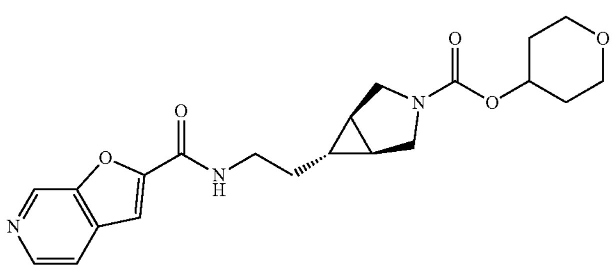 | (1R,5S,6s)-3-tetrahydro-2H-pyran-4-yl 6-(2-(furo[2,3-c]pyridine-2-carboxamido)ethyl)-3-azabicyclo[3.1.0]hexane-3-carboxylate | 400.3 |
| 62 | 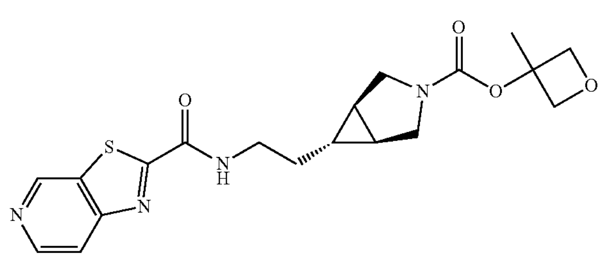 [SMILES: CC1(OC(=O)N2C[C@@H]3[C@@H](CCNC(=O)c4nc5ccncc5s4)[C@@H]3C2)COC1] | (1R,5S,6s)-3-methyloxetan-3-yl 6-(2-(thiazolo[5,4-c]pyridine-2-carboxamido)ethyl)-3-azabicyclo[3.1.0]hexane-3-carboxylate | 403.3 |

-continued

| Ex. No. | Chemical structure | Chemical name | MS (ESI) m/z (M + H)+ |
|---|---|---|---|
| 63 | 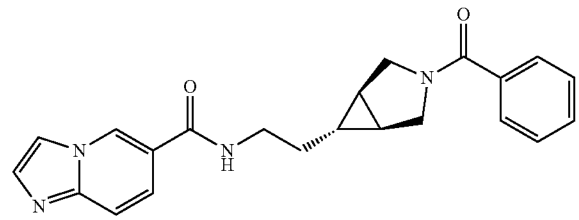 [SMILES: O=C(NCC[C@@H]1[C@H]2CN(C(=O)c3ccccc3)C[C@@H]12)c1ccc2nccn2c1] | N-(2-((1R,5S,6s)-3-benzoyl-3-azabicyclo[3.1.0]hexan-6-yl)ethyl)imidazo[1,2-a]pyridine-6-carboxamide | 375.3 |
| 64 | 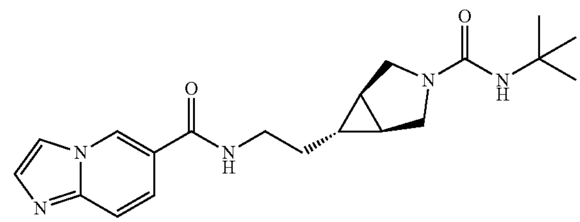 [SMILES: CC(C)(C)NC(=O)N1C[C@@H]2[C@@H](CCNC(=O)c3ccc4nccn4c3)[C@@H]2C1] | N-(2-((1R,5S,6s)-3-(tert-butylcarbamoyl)-3-azabicyclo[3.1.0]hexan-6-yl)ethyl)imidazo[1,2-a]pyridine-6-carboxamide | 370.4 |
| 65 | 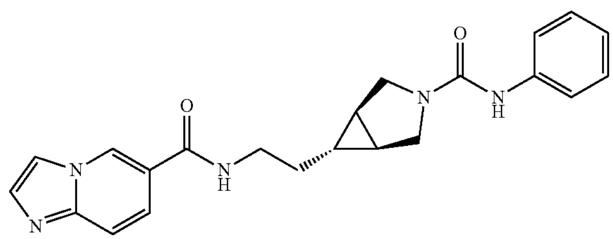 [SMILES: O=C(NCC[C@@H]1[C@H]2CN(C(=O)Nc3ccccc3)C[C@@H]12)c1ccc2nccn2c1] | N-(2-((1R,5S,6s)-3-(phenylcarbamoyl)-3-azabicyclo[3.1.0]hexan-6-yl)ethyl)imidazo[1,2-a]pyridine-6-carboxamide | 390.4 |
| 66 | 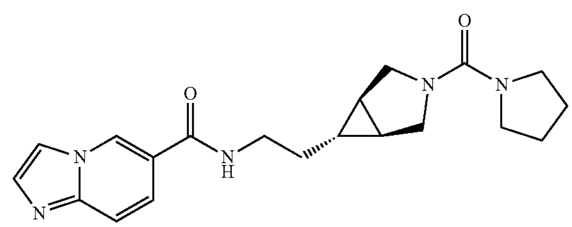 [SMILES: O=C(NCC[C@@H]1[C@H]2CN(C(=O)N3CCCC3)C[C@@H]12)c1ccc2nccn2c1] | N-(2-((1R,5S,6s)-3-(pyrrolidine-1-carbonyl)-3-azabicyclo[3.1.0]hexan-6-yl)ethyl)imidazo[1,2-a]pyridine-6-carboxamide | 368.4 |
| 67 | 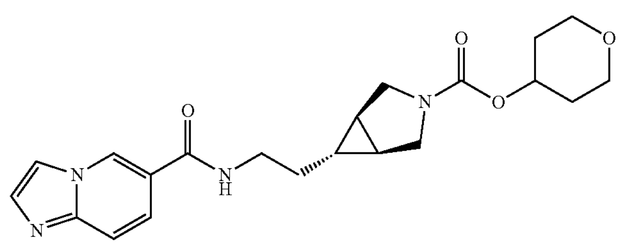 [SMILES: O=C(NCC[C@@H]1[C@H]2CN(C(=O)OC3CCOCC3)C[C@@H]12)c1ccc2nccn2c1] | (1R,5S,6s)-tetrahydro-2H-pyran-4-yl 6-(2-(imidazo[1,2-a]pyridine-6-carboxamido)ethyl)-3-azabicyclo[3.1.0]hexane-3-carboxylate | 399.3 |
| 68 | 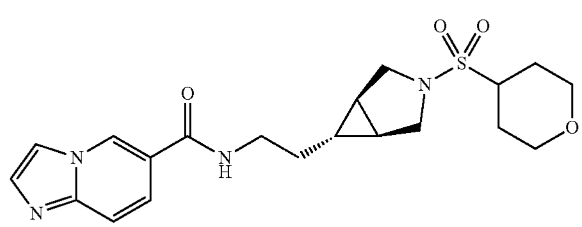 [SMILES: O=C(NCC[C@@H]1[C@H]2CN(S(=O)(=O)C3CCOCC3)C[C@@H]12)c1ccc2nccn2c1] | N-(2-((1R,5S,6s)-3-((tetrahydro-2H-pyran-4-yl)sulfonyl)-3-azabicyclo[3.1.0]hexan-6-yl)ethyl)imidazo[1,2-a]pyridine-6-carboxamide | 419.3 |

-continued

| Ex. No. | Chemical structure | Chemical name | MS (ESI) m/z (M + H)+ |
|---|---|---|---|
| 69 | 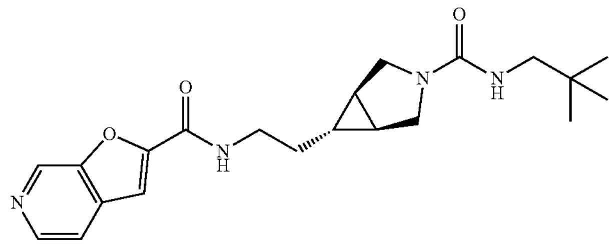 [SMILES: CC(C)(C)CNC(=O)N1C[C@@H]2[C@@H](CCNC(=O)c3cc4ccncc4o3)[C@@H]2C1] | N-(2-((1R,5S,6s)-3-(neopentylcarbamoyl)-3-azabicyclo[3.1.0]hexan-6-yl)ethyl)furo[2,3-c]pyridine-2-carboxamide | 385.4 |
| 70 | 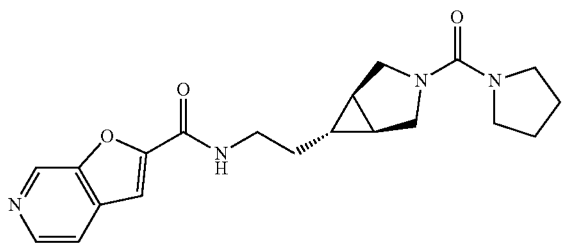 [SMILES: O=C(NCC[C@@H]1[C@H]2CN(C(=O)N3CCCC3)C[C@@H]12)c1cc2ccncc2o1] | N-(2-((1R,5S,6s)-3-(pyrrolidine-1-carbonyl)-3-azabicyclo[3.1.0]hexan-6-yl)ethyl)furo[2,3-c]pyridine-2-carboxamide | 369.3 |
| 71 | 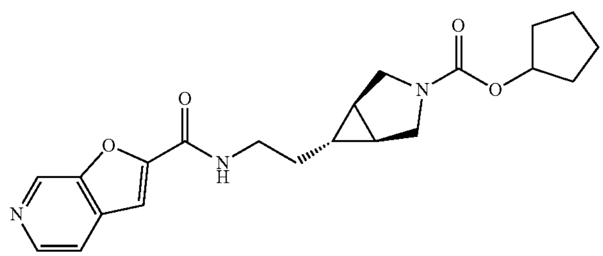 [SMILES: O=C(NCC[C@@H]1[C@H]2CN(C(=O)OC3CCCC3)C[C@@H]12)c1cc2ccncc2o1] | (1R,5S,6s)-(cyclopentyl) 6-(2-(furo[2,3-c]pyridine-2-carboxamido)ethyl)-3-azabicyclo[3.1.0]hexane-3-carboxylate | 384.4 |
| 72 | 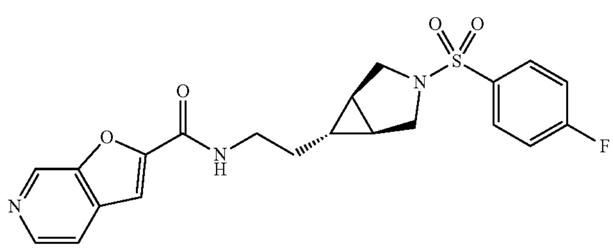 [SMILES: O=C(NCC[C@@H]1[C@H]2CN(S(=O)(=O)c3ccc(F)cc3)C[C@@H]12)c1cc2ccncc2o1] | N-(2-((1R,5S,6s)-3-((4-fluorophenyl)sulfonyl)-3-azabicyclo[3.1.0]hexan-6-yl)ethyl)furo[2,3-c]pyridine-2-carboxamide | 430.3 |
| 73 | 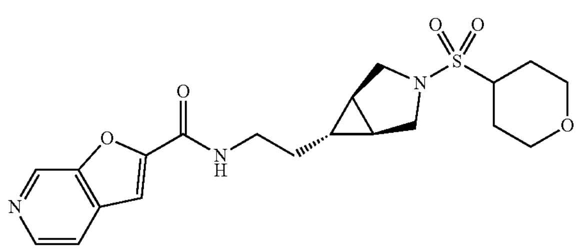 [SMILES: O=C(NCC[C@@H]1[C@H]2CN(S(=O)(=O)C3CCOCC3)C[C@@H]12)c1cc2ccncc2o1] | N-(2-((1R,5S,6s)-3-((tetrahydro-2H-pyran-4-yl)sulfonyl)-3-azabicyclo[3.1.0]hexan-6-yl)ethyl)furo[2,3-c]pyridine-2-carboxamide | 420.3 |
| 74 | 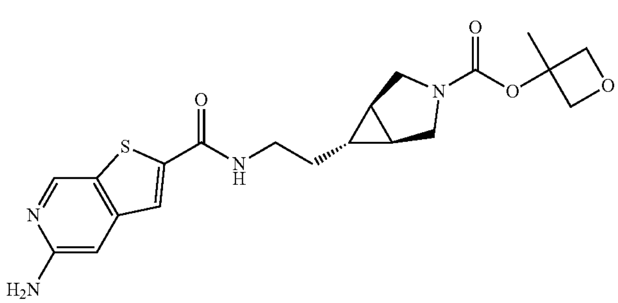 [SMILES: CC1(OC(=O)N2C[C@@H]3[C@@H](CCNC(=O)c4cc5cc(N)ncc5s4)[C@@H]3C2)COC1] | (1R,5S,6s)-3-methyloxetan-3-yl 6-(2-(5-aminothieno[2,3-c]pyridine-2-carboxamido)ethyl)-3-azabicyclo[3.1.0]hexane-3-carboxylate | 417.3 |

| Ex. No. | Chemical structure | Chemical name | MS (ESI) m/z (M + H)+ |
|---|---|---|---|
| 75 | 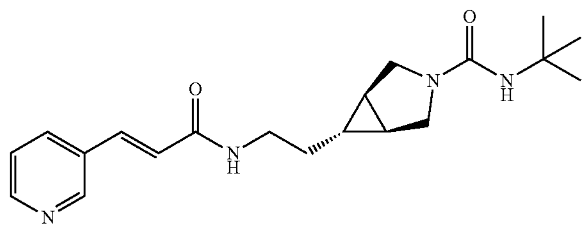 [SMILES: CC(C)(C)NC(=O)N1C[C@@H]2[C@@H](CCNC(=O)/C=C/c3cccnc3)[C@@H]2C1] | (1R,5S,6s)-N-(tert-butyl)-6-(2-((E)-3-(pyridin-3-yl)acrylamido)ethyl)-3-azabicyclo[3.1.0]hexane-3-carboxamide | 357.4 |
| 76 | 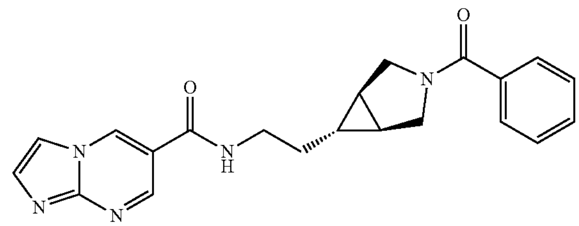 [SMILES: O=C(NCC[C@@H]1[C@H]2CN(C(=O)c3ccccc3)C[C@@H]12)c1cnc2nccn2c1] | N-(2-((1R,5S,6s)-3-benzoyl-3-azabicyclo[3.1.0]hexan-6-yl)ethyl)imidazo[1,2-a]pyrimidine-6-carboxamide | 376.3 |
| 77 | 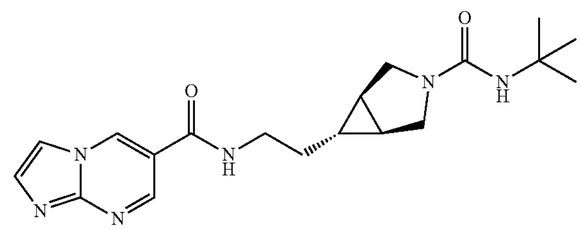 [SMILES: CC(C)(C)NC(=O)N1C[C@@H]2[C@@H](CCNC(=O)c3cnc4nccn4c3)[C@@H]2C1] | N-(2-((1R,5S,6s)-3-(tert-butylcarbamoyl)-3-azabicyclo[3.1.0]hexan-6-yl)ethyl)imidazo[1,2-a]pyrimidine-6-carboxamide | 371.4 |
| 78 | 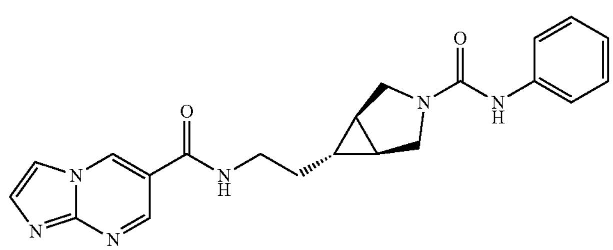 [SMILES: O=C(NCC[C@@H]1[C@H]2CN(C(=O)Nc3ccccc3)C[C@@H]12)c1cnc2nccn2c1] | N-(2-((1R,5S,6s)-3-(phenylcarbamoyl)-3-azabicyclo[3.1.0]hexan-6-yl)ethyl)imidazo[1,2-a]pyrimidine-6-carboxamide | 391.3 |
| 79 | 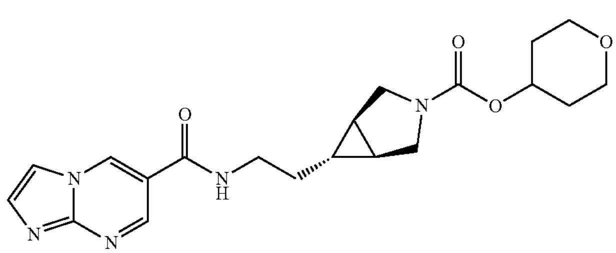 [SMILES: O=C(NCC[C@@H]1[C@H]2CN(C(=O)OC3CCOCC3)C[C@@H]12)c1cnc2nccn2c1] | (1R,5S,6s)-tetrahydro-2H-pyran-4-yl 6-(2-(imidazo[1,2-a]pyrimidine-6-carboxamido)ethyl)-3-azabicyclo[3.1.0]hexane-3-carboxylate | 400.3 |
| 80 | 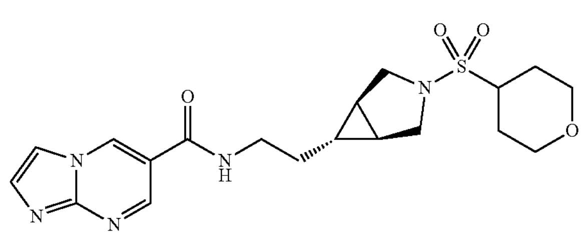 [SMILES: O=C(NCC[C@@H]1[C@H]2CN(S(=O)(=O)C3CCOCC3)C[C@@H]12)c1cnc2nccn2c1] | N-(2-((1R,5S,6s)-3-((tetrahydro-2H-pyran-4-yl)sulfonyl)-3-azabicyclo[3.1.0]hexan-6-yl)ethyl)imidazo[1,2-a]pyrimidine-6-carboxamide | 420.3 |

-continued

| Ex. No. | Chemical structure | Chemical name | MS (ESI) m/z (M + H)+ |
|---|---|---|---|
| 81 | 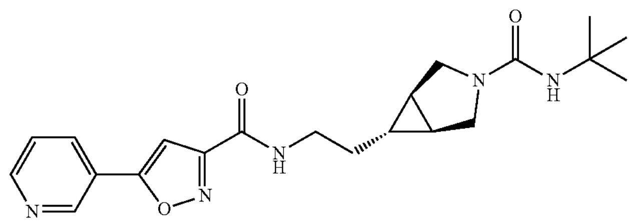 [SMILES: CC(C)(C)NC(=O)N1C[C@@H]2[C@@H](CCNC(=O)c3cc(-c4cccnc4)on3)[C@@H]2C1] | N-(2-(((1R,5S,6s)-3-(tert-butylcarbamoyl)-3-azabicyclo[3.1.0]hexan-6-yl)ethyl)-5-(pyridin-3-yl)isoxazole-3-carboxamide | 398.4 |
| 82 | 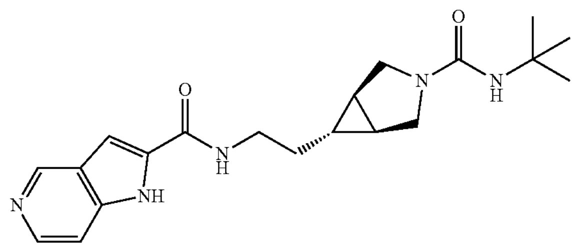 [SMILES: CC(C)(C)NC(=O)N1C[C@@H]2[C@@H](CCNC(=O)c3cc4cnccc4[nH]3)[C@@H]2C1] | N(2-(((1R,5S,6s)-3-(tert-butylcarbamoyl)-3-azabicyclo[3.1.0]hexan-6-yl)ethyl)-1H-pyrrolo[3,2-c]pyridine-2-carboxamide | 370.4 |
| 83 | 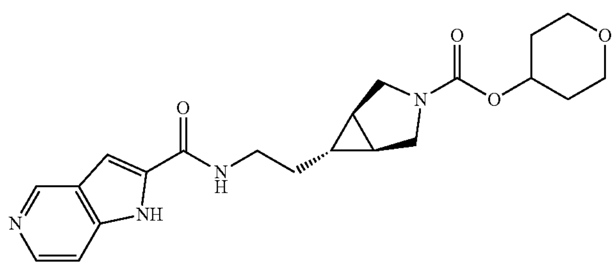 [SMILES: O=C(NCC[C@@H]1[C@H]2CN(C(=O)OC3CCOCC3)C[C@@H]12)c1cc2cnccc2[nH]1] | (1R,5S,6s)-tetrahydro-2H-pyran-4-yl 6-(2-(1H-pyrrolo[3,2-c]pyridine-2-carboxamido)ethyl)-3-azabicyclo[3.1.0]hexane-3-carboxylate | 399.3 |
| 84 | 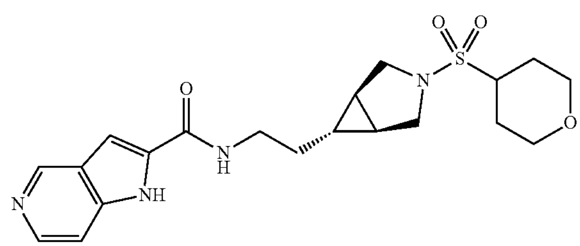 [SMILES: O=C(NCC[C@@H]1[C@H]2CN(S(=O)(=O)C3CCOCC3)C[C@@H]12)c1cc2cnccc2[nH]1] | N-(2-(((1R,5S,6s)-3-((tetrahydro-2H-pyran-4-yl)sulfonyl)-3-azabicyclo[3.1.0]hexan-6-yl)ethyl)-1H-pyrrolo[3,2-c]pyridine-2-carboxamide | 419.3 |
| 85 | 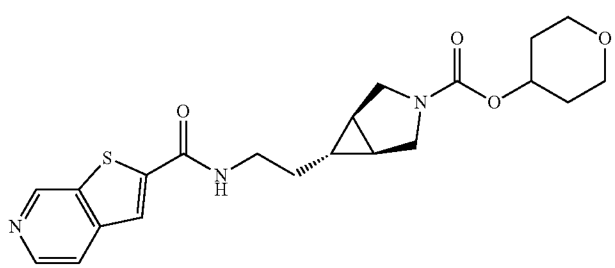 | (1R,5S,6s)-tetrahydro-2H-pyran-4-yl 6-(2-(thieno[2,3-c]pyridine-2-carboxamido)ethyl)-3-azabicyclo[3.1.0]hexane-3-carboxylate | 416.3 |

Example 86: (E)-3-(6-aminopyridin-3-yl)-N-(2-((1R,5S,6s)-3-(4-fluorobenzoyl)-3-azabicyclo[3.1.0]hexan-6-yl)ethyl)acrylamide

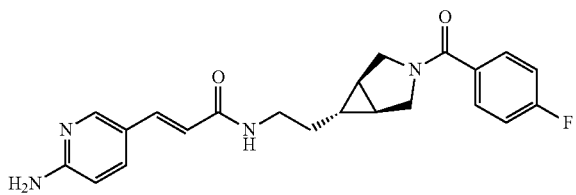 [SMILES: Nc1ccc(/C=C/C(=O)NCC[C@@H]2[C@H]3CN(C(=O)c4ccc(F)cc4)C[C@@H]23)cn1]

To a solution of the Example 4 compound (1.4 g, 3.6 mmol) in dichloromethane (30 mL) was added trifluoroacetic acid (4.1 g, 35.7 mmol). The reaction mixture was stirred at 20° C. for 2 h. The mixture was concentrated under vacuum to afford 1.5 g of crude (E)-N-(2-((1R,5S,6s)-3-azabicyclo[3.1.0]hexan-6-yl)ethyl)-3-(6-aminopyridin-3-yl)acrylamide as a brown oil. MS (ESI) m/z: 273.2 (M+H)$^+$.

To a solution of 4-fluorobenzoic acid (13.1 mg, 0.093 umol) in pyridine (5 mL) was added 1-(3-dimethylaminopropyl)-3-ethylcarbodiimide hydrochloride (19.4 mg, 0.10 mmol) The mixture was stirred at 25° C. for 15 min, and (E)-N-(2-((1R,5S,6s)-3-azabicyclo[3.1.0]hexan-6-yl)ethyl)-3-(6-aminopyridin-3-yl)acrylamide (30 mg, 0.078 mmol, TFA salt) was added. The mixture was stirred at 25° C. for 1 h. The mixture was concentrated under vacuum to give a residue. Two additional identical reactions were performed on the same scale. The combined residues from the three batches were purified by preparative HPLC (Phenomenex Gemini C18 column (150×25 mm, 10 um); flow rate: 25 mL/min; gradient: 25%-46% B over 12 min; mobile phase A: 0.05% aqueous ammonium hydroxide, mobile phase B: acetonitrile) to give 20.2 mg (26%) of the title compound as a white solid. MS (ESI) m/z: 395.4 (M+H)$^+$. $^1$H NMR (400 MHz, DMSO-$d_6$): δ 8.03 (d, J=0.8 Hz, 1H), 7.90-7.85 (m, 1H), 7.59-7.54 (m, 1H), 7.51-7.47 (m, 2H), 7.24-7.21 (m, 2H), 6.45 (d, J=8.8 Hz, 1H), 6.31 (d, J=15.6 Hz, 1H), 3.91 (d, J=12 Hz, 1H), 3.64-3.60 (m, 1H), 3.37-3.34 (m, 2H), 3.21-3.18 (m, 2H), 1.41-1.36 (m, 4H), 0.53-0.49 (m, 11H).

Examples 87-116

The following compounds were prepared substantially according to the procedures described above:

| Ex. No. | Chemical structure | Chemical name | MS (ESI) m/z (M + H)$^+$ |
|---|---|---|---|
| 87 | 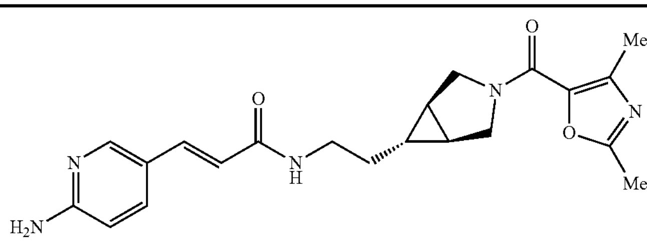 | (E)-3-(6-aminopyridin-3-yl)-N-(2-((1R,5S,6s)-3-(2,4-dimethyloxazole-5-carbonyl)-3-azabicyclo[3.1.0]hexan-6-yl)ethyl)acrylamide | 396.4 |
| 88 | 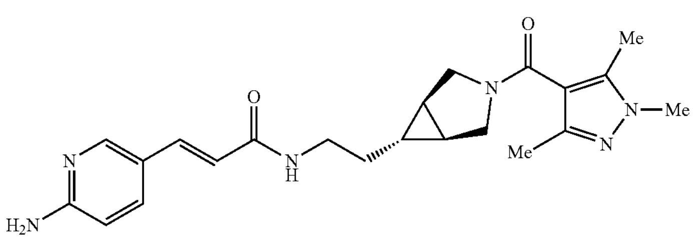 [SMILES: Cc1nn(C)c(C)c1C(=O)N1C[C@@H]2[C@@H](CCNC(=O)/C=C/c3ccc(N)nc3)[C@@H]2C1] | (E)-3-(6-aminopyridin-3-yl)-N-(2-((1R,5S,6s)-3-(1,3,5-trimethyl-1H-pyrazole-4-carbonyl)-3-azabicyclo[3.1.0]hexan-6-yl)ethyl)acrylamide | 409.4 |
| 89 | 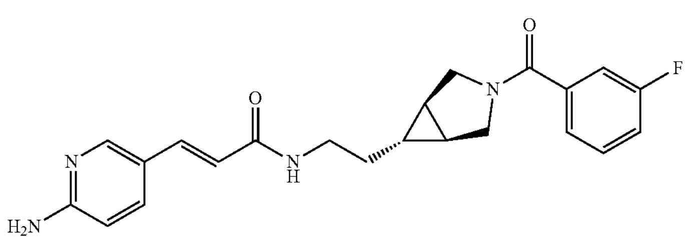 [SMILES: Nc1ccc(/C=C/C(=O)NCC[C@@H]2[C@H]3CN(C(=O)c4cccc(F)c4)C[C@@H]23)cn1] | (E)-3-(6-aminopyridin-3-yl)-N-(2-((1R,5S,6s)-3-(3-fluorobenzoyl)-3-azabicyclo[3.1.0]hexan-6-yl)ethyl)acrylamide | 395.4 |
| 90 | 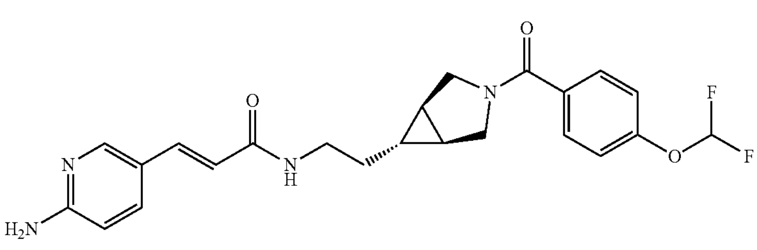 [SMILES: Nc1ccc(/C=C/C(=O)NCC[C@@H]2[C@H]3CN(C(=O)c4ccc(OC(F)F)cc4)C[C@@H]23)cn1] | (E)-3-(6-aminopyridin-3-yl)-N-(2-((1R,5S,6s)-3-(4-(difluoromethoxy)benzoyl)-3-azabicyclo[3.1.0]hexan-6-yl)ethyl)acrylamide | 443.4 |

-continued

| Ex. No. | Chemical structure | Chemical name | MS (ESI) m/z (M + H)+ |
|---|---|---|---|
| 91 | 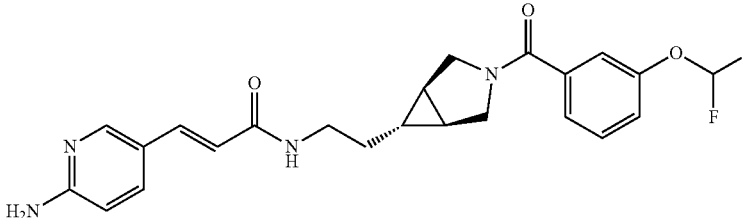 | (E)-3-(6-aminopyridin-3-yl)-N-(2-((1R,5S,6s)-3-(3-(difluoromethoxy)benzoyl)-3-azabicyclo[3.1.0]hexan-6-yl)ethyl)acrylamide | 443.4 |
| 92 | 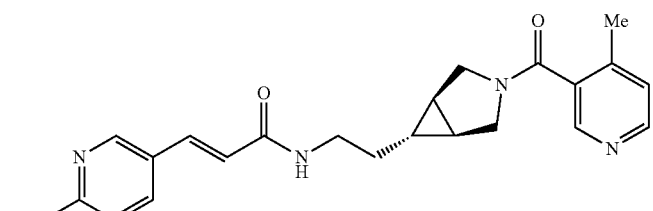 | (E)-3-(6-aminopyridin-3-yl)-N-(2-((1R,5S,6s)-3-(4-methylnicotinoyl)-3-azabicyclo[3.1.0]hexan-6-yl)ethyl)acrylamide | 392.4 |
| 93 | 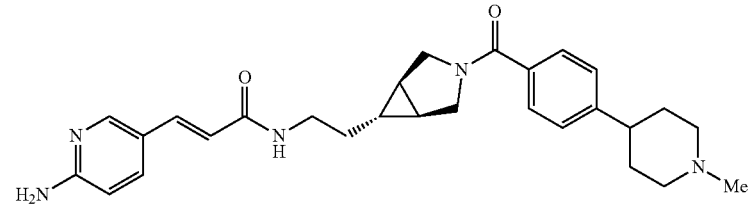 [SMILES: CN1CCC(c2ccc(C(=O)N3C[C@@H]4[C@@H](CCNC(=O)/C=C/c5ccc(N)nc5)[C@@H]4C3)cc2)CC1] | (E)-3-(6-aminopyridin-3-yl)-N-(2-((1R,5S,6s)-3-(4-(1-methylpiperidin-4-yl)benzoyl)-3-azabicyclo[3.1.0]hexan-6-yl)ethyl)acrylamide | 474.5 |
| 94 | 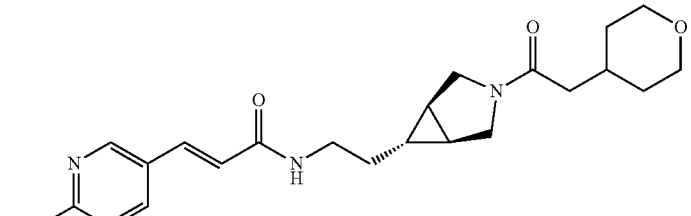 | (E)-3-(6-aminopyridin-3-yl)-N-(2-((1R,5S,6s)-3-(2-(tetrahydro-2H-pyran-4-yl)acetyl)-3-azabicyclo[3.1.0]hexan-6-yl)ethyl)acrylamide | 399.5 |
| 95 | 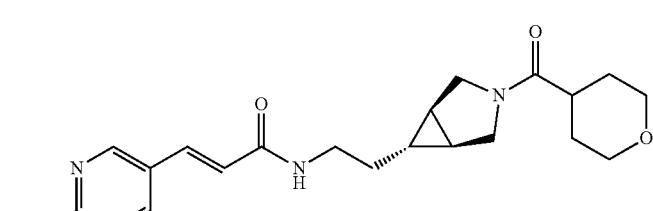 | (E)-3-(6-aminopyridin-3-yl)-N-(2-((1R,5S,6s)-3-(tetrahydro-2H-pyran-4-carbonyl)-3-azabicyclo[3.1.0]hexan-6-yl)ethyl)acrylamide | 385.4 |
| 96 | 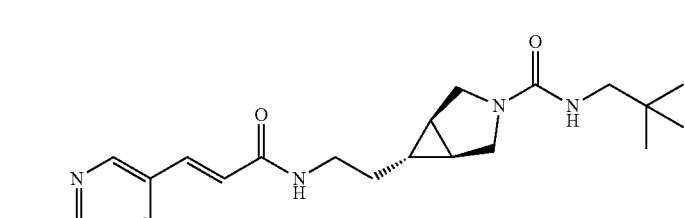 | (1R,5S,6s)-6-(2-((E)-3-(6-aminopyridin-3-yl)acrylamido)ethyl)-N-neopentyl-3-azabicyclo[3.1.0]hexane-3-carboxamide | 386.5 |

-continued

| Ex. No. | Chemical structure | Chemical name | MS (ESI) m/z (M + H)+ |
|---|---|---|---|
| 97 | 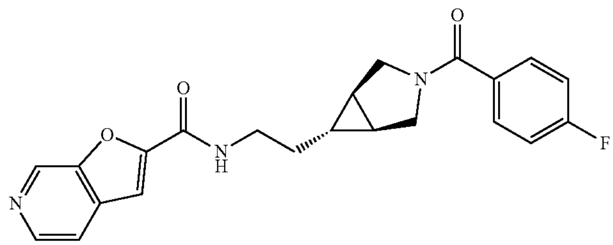 [SMILES: O=C(NCC[C@@H]1[C@H]2CN(C(=O)c3ccc(F)cc3)C[C@@H]12)c1cc2ccncc2o1] | N-(2-((1R,5S,6s)-3-(4-fluorobenzoyl)-3-azabicyclo[3.1.0]hexan-6-yl)ethyl)furo[2,3-c]pyridine-2-carboxamide | 394.4 |
| 98 | 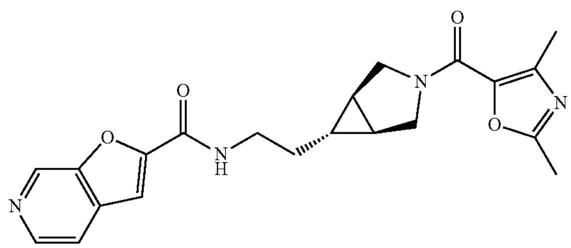 [SMILES: Cc1nc(C)c(C(=O)N2C[C@@H]3[C@@H](CCNC(=O)c4cc5ccncc5o4)[C@@H]3C2)o1] | N-(2-((1R,5S,6s)-3-(2,4-dimethyloxazole-5-carbonyl)-3-azabicyclo[3.1.0]hexan-6-yl)ethyl)furo[2,3-c]pyridine-2-carboxamide | 395.3 |
| 99 | 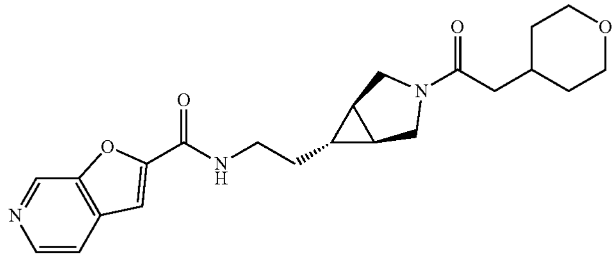 | N-(2-((1R,5S,6s)-3-(2-(tetrahydro-2H-pyran-4-yl)acetyl)-3-azabicyclo[3.1.0]hexan-6-yl)ethyl)furo[2,3-c]pyridine-2-carboxamide | 398.4 |
| 100 | 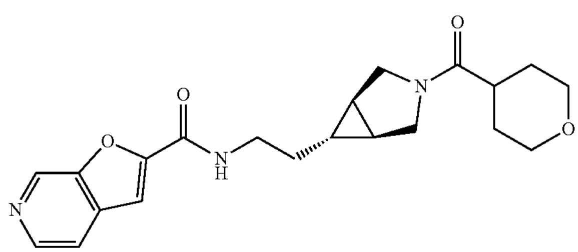 [SMILES: O=C(NCC[C@@H]1[C@H]2CN(C(=O)C3CCOCC3)C[C@@H]12)c1cc2ccncc2o1] | N-(2-((1R,5S,6s)-3-(tetrahydro-2H-pyran-4-carbonyl)-3-azabicyclo[3.1.0]hexan-6-yl)ethyl)furo[2,3-c]pyridine-2-carboxamide | 384.4 |
| 101 | 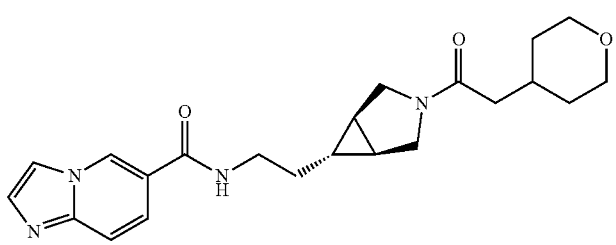 | N-(2-((1R,5S,6s)-3-(2-(tetrahydro-2H-pyran-4-yl)acetyl)-3-azabicyclo[3.1.0]hexan-6-yl)ethyl)imidazo[1,2-a]pyridine-6-carboxamide | 397.4 |
| 102 | 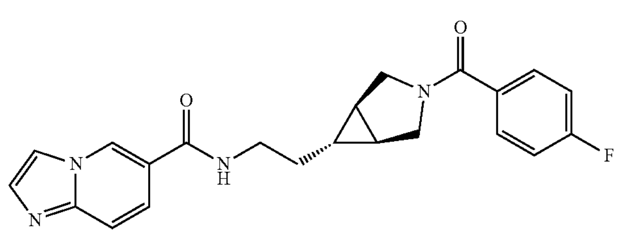 [SMILES: O=C(NCC[C@@H]1[C@H]2CN(C(=O)c3ccc(F)cc3)C[C@@H]12)c1ccc2nccn2c1] | N-(2-((1R,5S,6s)-3-(4-fluorobenzoyl)-3-azabicyclo[3.1.0]hexan-6-yl)ethyl)imidazo[1,2-a]pyridine-6-carboxamide | 393.3 |

-continued

| Ex. No. | Chemical name | MS (ESI) m/z (M + H)+ |
|---|---|---|
| 103 | N-(2-((1R,5S,6s)-3-(2,4-dimethyloxazole-5-carbonyl)-3-azabicyclo[3.1.0]hexan-6-yl)ethyl)imidazo[1,2-a]pyridine-6-carboxamide | 394.3 |
| 104 | (E)-3-(pyridin-3-yl)-N-(((1R,5S,6s)-3-(2-(tetrahydro-2H-pyran-4-yl)acetyl)-3-azabicyclo[3.1.0]hexan-6-yl)methyl)acrylamide | 384.4 |
| 105 | (E)-N-(2-((1R,5S,6s)-3-(2,4-dimethyloxazole-5-carbonyl)-3-azabicyclo[3.1.0]hexan-6-yl)ethyl)-3-(pyridin-3-yl)acrylamide | 381.4 |
| 106 | N-(2-((1R,5S,6s)-3-(2-(tetrahydro-2H-pyran-4-yl)acetyl)-3-azabicyclo[3.1.0]hexan-6-yl)ethyl)imidazo[1,2-a]pyrimidine-6-carboxamide | 398.2 |
| 107 | N-(2-((1R,5S,6s)-3-(4-fluorobenzoyl)-3-azabicyclo[3.1.0]hexan-6-yl)ethyl)imidazo[1,2-a]pyrimidine-6-carboxamide | 394.3 |
| 108 | N-(2-((1R,5S,6s)-3-(2,4-dimethyloxazole-5-carbonyl)-3-azabicyclo[3.1.0]hexan-6-yl)ethyl)imidazo[1,2-a]pyrimidine-6-carboxamide | 395.3 |

| Ex. No. | Chemical structure | Chemical name | MS (ESI) m/z (M + H)+ |
|---|---|---|---|
| 109 | 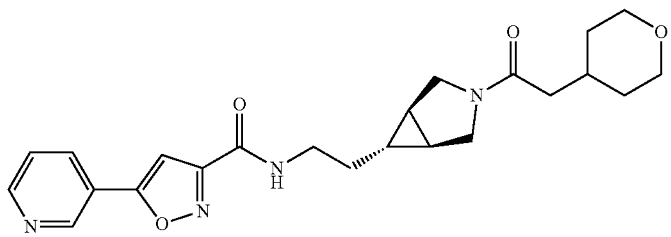 [SMILES: O=C(NCC[C@@H]1[C@H]2CN(C(=O)CC3CCOCC3)C[C@@H]12)c1cc(-c2cccnc2)on1] | 5-(pyridin-3-yl)-N-(2-((1R,5S,6s)-3-(2-(tetrahydro-2H-pyran-4-yl)acetyl)-3-azabicyclo[3.1.0]hexan-6-yl)ethyl)isoxazole-3-carboxamide | 425.4 |
| 110 | 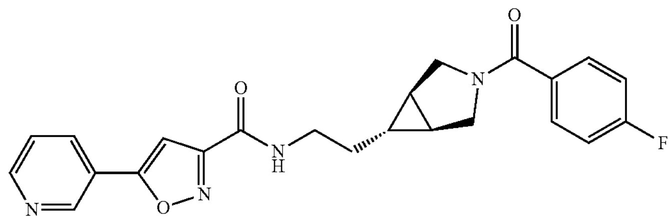 [SMILES: O=C(NCC[C@@H]1[C@H]2CN(C(=O)c3ccc(F)cc3)C[C@@H]12)c1cc(-c2cccnc2)on1] | N-(2-((1R,5S,6s)-3-(4-fluorobenzoyl)-3-azabicyclo[3.1.0]hexan-6-yl)ethyl)-5-(pyridin-3-yl)isoxazole-3-carboxamide | 421.3 |
| 111 | 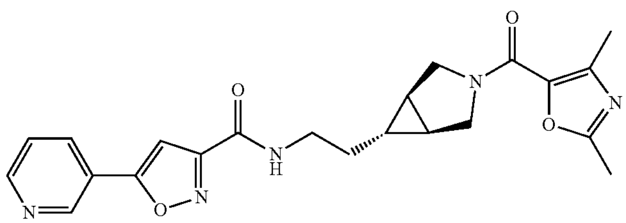 [SMILES: Cc1nc(C)c(C(=O)N2C[C@@H]3[C@@H](CCNC(=O)c4cc(-c5cccnc5)on4)[C@@H]3C2)o1] | N-(2-((1R,5S,6s)-3-(2,4-dimethyloxazole-5-carbonyl)-3-azabicyclo[3.1.0]hexan-6-yl)ethyl)-5-(pyridin-3-yl)isoxazole-3-carboxamide | 422.3 |
| 112 | 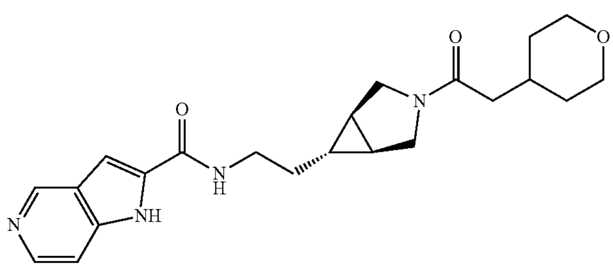 [SMILES: O=C(NCC[C@@H]1[C@H]2CN(C(=O)CC3CCOCC3)C[C@@H]12)c1cc2cnccc2[nH]1] | N-(2-((1R,5S,6s)-3-(2-(tetrahydro-2H-pyran-4-yl)acetyl)-3-azabicyclo[3.1.0]hexan-6-yl)ethyl)-1H-pyrrolo[3,2-c]pyridine-2-carboxamide | 397.1 |
| 113 | 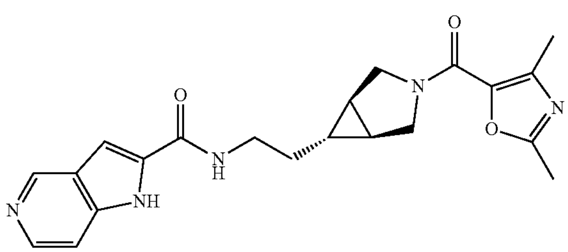 [SMILES: Cc1nc(C)c(C(=O)N2C[C@@H]3[C@@H](CCNC(=O)c4cc5cnccc5[nH]4)[C@@H]3C2)o1] | N-(2-((1R,5S,6s)-3-(2,4-dimethyloxazole-5-carbonyl)-3-azabicyclo[3.1.0]hexan-6-yl)ethyl)-1H-pyrrolo[3,2-c]pyridine-2-carboxamide | 394.2 |
| 114 | 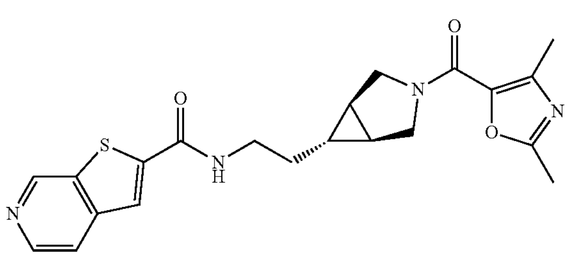 | N-(2-((1R,5S,6s)-3-(2,4-dimethyloxazole-5-carbonyl)-3-azabicyclo[3.1.0]hexan-6-yl)ethyl)thieno[2,3-c]pyridine-2-carboxamide | 411.4 |

| Ex. No. | Chemical structure | Chemical name | MS (ESI) m/z (M + H)+ |
|---|---|---|---|
| 115 | 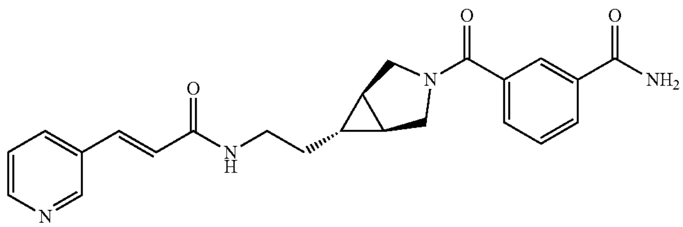 [SMILES: NC(=O)c1cccc(C(=O)N2C[C@@H]3[C@@H](CCNC(=O)/C=C/c4cccnc4)[C@@H]3C2)c1] | 3-((1R,5S,6s)-6-(2-((E)-3-(pyridin-3-yl)acrylamido)ethyl)-3-azabicyclo[3.1.0]hexane-3-carbonyl)benzamide | 405.4 |
| 116 | 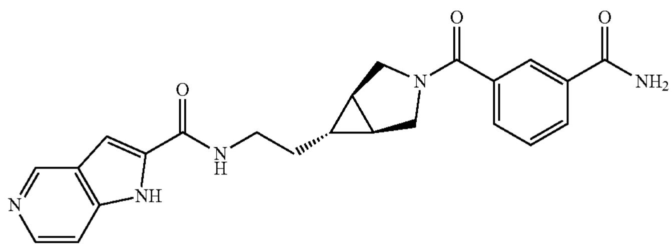 [SMILES: NC(=O)c1cccc(C(=O)N2C[C@@H]3[C@@H](CCNC(=O)c4cc5cnccc5[nH]4)[C@@H]3C2)c1] | N-(2-((1R,5S,6s)-3-(3-carbamoylbenzoyl)-3-azabicyclo[3.1.0]hexan-6-yl)ethyl)-1H-pyrrolo[3,2-c]pyridine-2-carboxamide | 418.2 |

Example 117: (E)-N-(2-((1R,5S,6s)-3-phenyl-3-azabicyclo[3.1.0]hexan-6-yl)ethyl)-3-(pyridin-3-yl)acrylamide

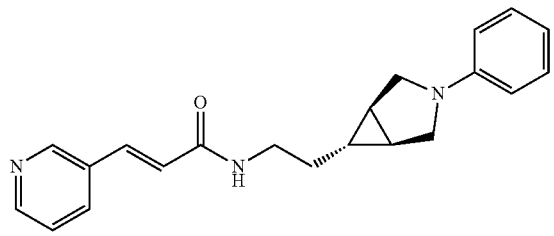 [SMILES: O=C(/C=C/c1cccnc1)NCC[C@@H]1[C@H]2CN(c3ccccc3)C[C@@H]12]

To a stirred suspension of (E)-N-(2-((1R,5S,6s)-3-azabicyclo[3.1.0]hexan-6-yl)ethyl)-3-(pyridin-3-yl)acrylamide (0.15 g, 0.40 mmol, TFA salt) and cesium carbonate (395 mg, 1.21 mmol) in toluene (10 mL) was added tris(dibenzylideneacetone)dipalladium (36.9 mg, 0.40 mmol), 2,2'-bis(diphenylphosphino)-1,1'-binaphthyl (50.3 mg, 0.81 mmol) and bromobenzene (95.1 mg, 0.61 mmol) at 20° C. The reaction was heated at 100° C. under an atmosphere of nitrogen for 10 h. The reaction mixture was cooled to 25° C. and diluted with water (10 mL). The solution was extracted with ethyl acetate (15 mL×3) and the combined organic layers were washed with brine (50 mL). The organic layer was concentrated under vacuum to afford a residue. The residue was purified by preparative HPLC (Phenomenex Gemini C18 column (150×25 mm, 10 um); flow rate: 25 mL/min; gradient: 25%-55% B over 9 min; mobile phase A: 0.1% aqueous trifluoroacetic acid, mobile phase B: acetonitrile) to give 80 mg (43%) of the title compound as a light yellow solid. MS (ESI) m/z: 334.4 (M+H)+. $^1$H NMR (400 MHz, DMSO-$d_6$): δ 8.89 (s, 1H), 8.67 (d, J=5.0 Hz, 1H), 8.26 (d, J=6.0 Hz, 2H), 7.68 (dd, J=5.2, 7.8 Hz, 1H), 7.51 (d, J=16.0 Hz, 1H), 7.12 (t, J=7.8 Hz, 2H), 6.81 (d, J=16.0 Hz, 1H), 6.59 (t, J=7.2 Hz, 1H), 6.50 (d, J=8.0 Hz, 2H), 3.48 (d, J=9.2 Hz, 2H), 3.29 (q, J=6.4 Hz, 2H), 3.13 (d, J=8.4 Hz, 2H), 1.52 (s, 2H), 1.45 (q, J=6.8 Hz, 2H), 0.70 (tt, J=3.2, 6.8 Hz, 1H).

Examples 118-161

The following compounds were prepared substantially according to the procedures described above:

| Ex. No. | Chemical structure | Chemical name | MS (ESI) m/z (M + H)+ |
|---|---|---|---|
| 118 | 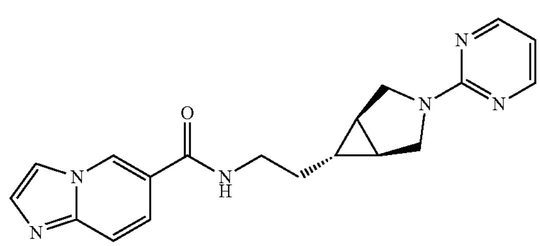 [SMILES: O=C(NCC[C@@H]1[C@H]2CN(c3ncccn3)C[C@@H]12)c1ccc2nccn2c1] | N-(2-((1R,5S,6s)-3-(pyrimidin-2-yl)-3-azabicyclo[3.1.0]hexan-6-yl)ethyl)imidazo[1,2-a]pyridine-6-carboxamide | 349.3 |

| Ex. No. | Chemical structure | Chemical name | MS (ESI) m/z (M + H)+ |
|---|---|---|---|
| 119 | 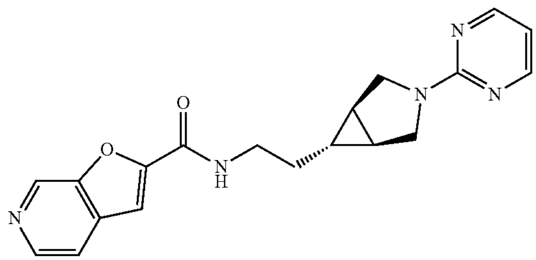 | N-(2-((1R,5S,6s)-3-(pyrimidin-2-yl)-3-azabicyclo[3.1.0]hexan-6-yl)ethyl)furo[2,3-c]pyridine-2-carboxamide | 350.3 |
| 120 | 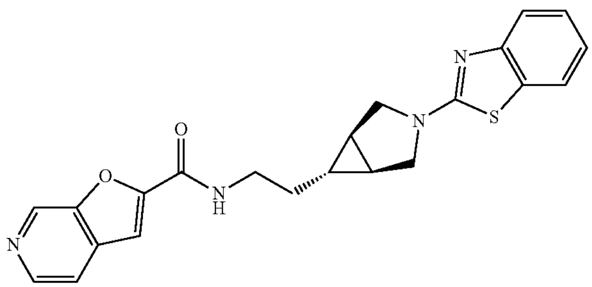 [SMILES: O=C(NCC[C@@H]1[C@H]2CN(c3nc4ccccc4s3)C[C@@H]12)c1cc2ccncc2o1] | N-(2-((1R,5S,6s)-3-(benzo[d]thiazol-2-yl)-3-azabicyclo[3.1.0]hexan-6-yl)ethyl)furo[2,3-c]pyridine-2-carboxamide | 405.3 |
| 121 | 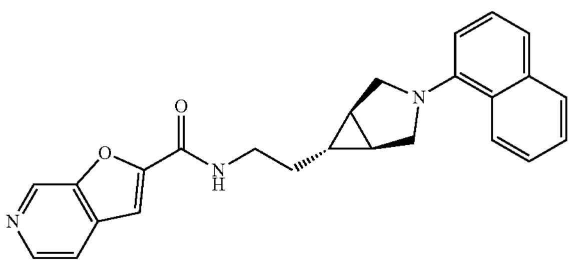 [SMILES: O=C(NCC[C@@H]1[C@H]2CN(c3cccc4ccccc34)C[C@@H]12)c1cc2ccncc2o1] | N-(2-((1R,5S,6s)-3-(naphthalen-1-yl)-3-azabicyclo[3.1.0]hexan-6-yl)ethyl)furo[2,3-c]pyridine-2-carboxamide | 398.3 |
| 122 | 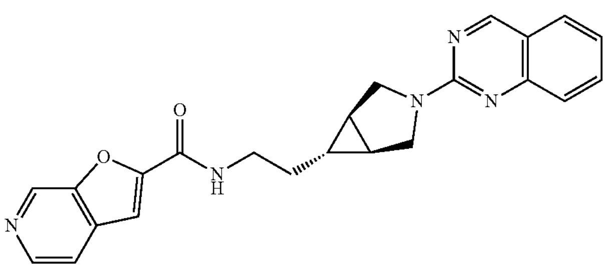 [SMILES: O=C(NCC[C@@H]1[C@H]2CN(c3ncc4ccccc4n3)C[C@@H]12)c1cc2ccncc2o1] | N-(2-((1R,5S,6s)-3-(quinazolin-2-yl)-3-azabicyclo[3.1.0]hexan-6-yl)ethyl)furo[2,3-c]pyridine-2-carboxamide | 400.3 |
| 123 | 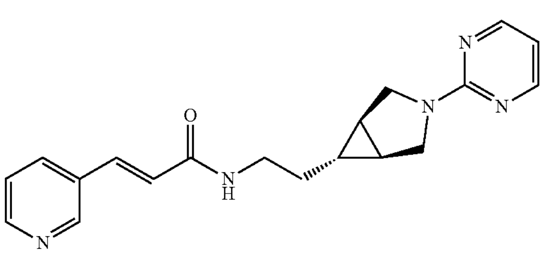 [SMILES: O=C(/C=C/c1cccnc1)NCC[C@@H]1[C@H]2CN(c3ncccn3)C[C@@H]12] | (E)-3-(pyridin-3-yl)-N-(2-((1R,5S,6s)-3-(pyrimidin-2-yl)-3-azabicyclo[3.1.0]hexan-6-yl)ethyl)acrylamide | 336.3 |

-continued

| Ex. No. | Chemical structure | Chemical name | MS (ESI) m/z (M + H)+ |
|---|---|---|---|
| 124 | 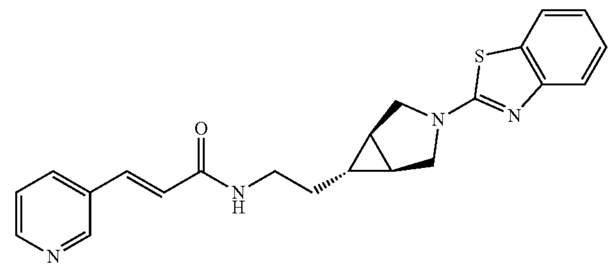 [SMILES: O=C(/C=C/c1cccnc1)NCC[C@@H]1[C@H]2CN(c3nc4ccccc4s3)C[C@@H]12] | (E)-N-(2-((1R,5S,6s)-3-(benzo[d]thiazol-2-yl)-3-azabicyclo[3.1.0]hexan-6-yl)ethyl)-3-(pyridin-3-yl)acrylamide | 391.3 |
| 125 | 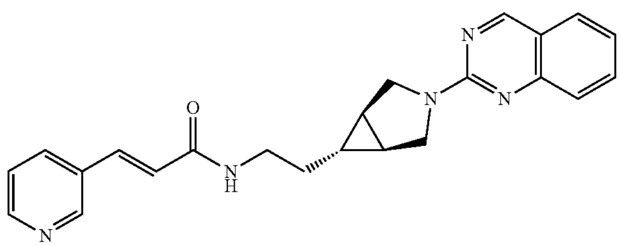 [SMILES: O=C(/C=C/c1cccnc1)NCC[C@@H]1[C@H]2CN(c3ncc4ccccc4n3)C[C@@H]12] | (E)-3-(pyridin-3-yl)-N-(2-((1R,5S,6s)-3-(quinazolin-2-yl)-3-azabicyclo[3.1.0]hexan-6-yl)ethyl)acrylamide | 386.3 |
| 126 | 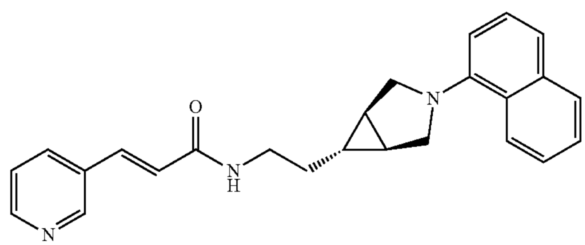 | (E)-N-(2-((1R,5S,6s)-3-(naphthalen-1-yl)-3-azabicyclo[3.1.0]hexan-6-yl)ethyl)-3-(pyridin-3-yl)acrylamide | 384.4 |
| 127 | 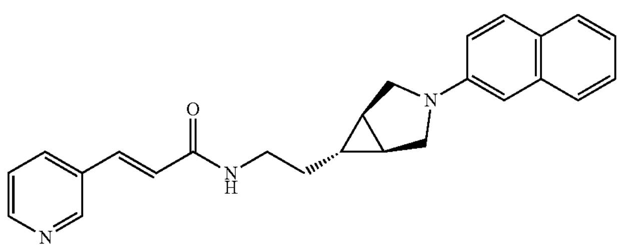 [SMILES: O=C(/C=C/c1cccnc1)NCC[C@@H]1[C@H]2CN(c3ccc4ccccc4c3)C[C@@H]12] | (E)-N-(2-((1R,5S,6s)-3-(naphthalen-2-yl)-3-azabicyclo[3.1.0]hexan-6-yl)ethyl)-3-(pyridin-3-yl)acrylamide | 384.4 |
| 128 | 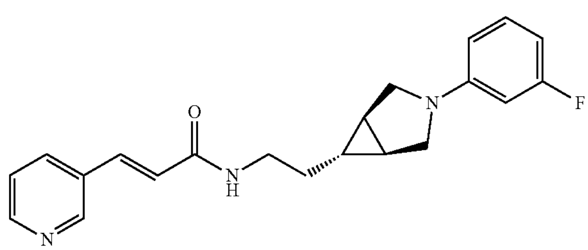 [SMILES: O=C(/C=C/c1cccnc1)NCC[C@@H]1[C@H]2CN(c3cccc(F)c3)C[C@@H]12] | (E)-N-(2-((1R,5S,6s)-3-(3-fluorophenyl)-3-azabicyclo[3.1.0]hexan-6-yl)ethyl)-3-(pyridin-3-yl)acrylamide | 352.3 |
| 129 | 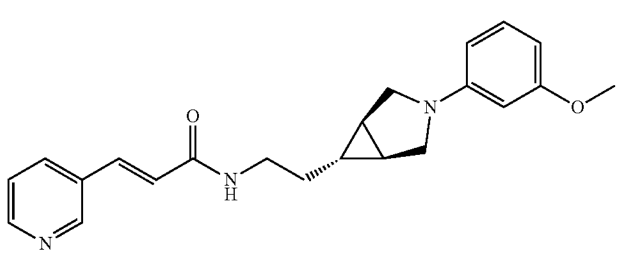 [SMILES: COc1cccc(N2C[C@@H]3[C@@H](CCNC(=O)/C=C/c4cccnc4)[C@@H]3C2)c1] | (E)-N-(2-((1R,5S,6s)-3-(3-methoxyphenyl)-3-azabicyclo[3.1.0]hexan-6-yl)ethyl)-3-(pyridin-3-yl)acrylamide | 364.4 |

| Ex. No. | Chemical structure | Chemical name | MS (ESI) m/z (M + H)+ |
|---|---|---|---|
| 130 | 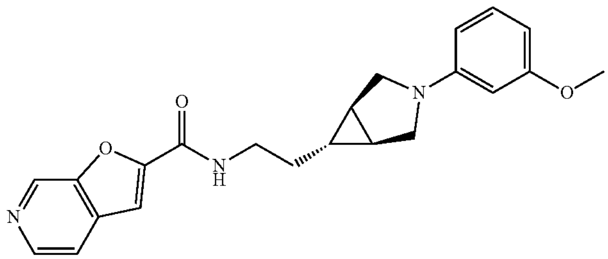 [SMILES: COc1cccc(N2C[C@@H]3[C@@H](CCNC(=O)c4cc5ccncc5o4)[C@@H]3C2)c1] | N-(2-((1R,5S,6s)-3-(3-methoxyphenyl)-3-azabicyclo[3.1.0]hexan-6-yl)ethyl)furo[2,3-c]pyridine-2-carboxamide | 378.3 |
| 131 | 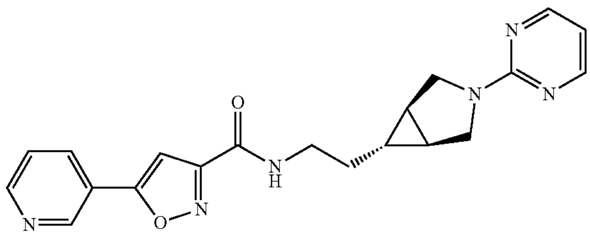 [SMILES: O=C(NCC[C@@H]1[C@H]2CN(c3ncccn3)C[C@@H]12)c1cc(-c2cccnc2)on1] | 5-(pyridin-3-yl)-N-(2-((1R,5S,6s)-3-(pyrimidin-2-yl)-3-azabicyclo[3.1.0]hexan-6-yl)ethyl)isoxazole-3-carboxamide | 377.3 |
| 132 | 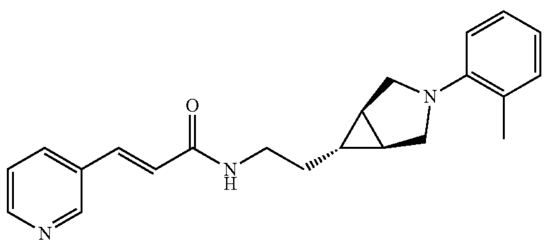 [SMILES: Cc1ccccc1N1C[C@@H]2[C@@H](CCNC(=O)/C=C/c3cccnc3)[C@@H]2C1] | (E)-3-(pyridin-3-yl)-N-(2-((1R,5S,6s)-3-(o-tolyl)-3-azabicyclo[3.1.0]hexan-6-yl)ethyl)acrylamide | 348.3 |
| 133 | 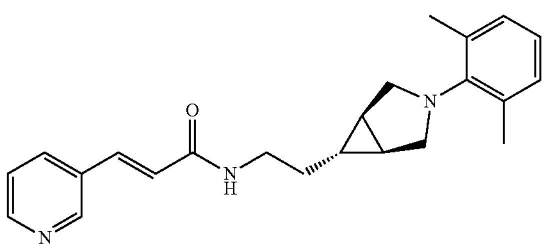 [SMILES: Cc1cccc(C)c1N1C[C@@H]2[C@@H](CCNC(=O)/C=C/c3cccnc3)[C@@H]2C1] | (E)-N-(2-((1R,5S,6s)-3-(2,6-dimethylphenyl)-3-azabicyclo[3.1.0]hexan-6-yl)ethyl)-3-(pyridin-3-yl)acrylamide | 362.3 |
| 134 | 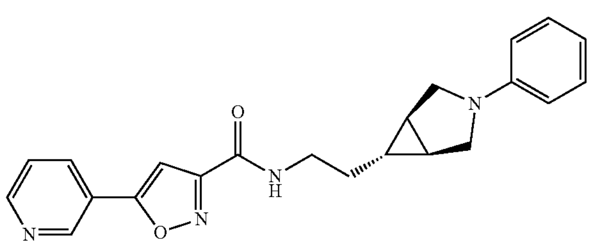 [SMILES: O=C(NCC[C@@H]1[C@H]2CN(c3ccccc3)C[C@@H]12)c1cc(-c2cccnc2)on1] | N-(2-((1R,5S,6s)-3-phenyl-3-azabicyclo[3.1.0]hexan-6-yl)ethyl)-5-(pyridin-3-yl)isoxazole-3-carboxamide | 375.3 |
| 135 | 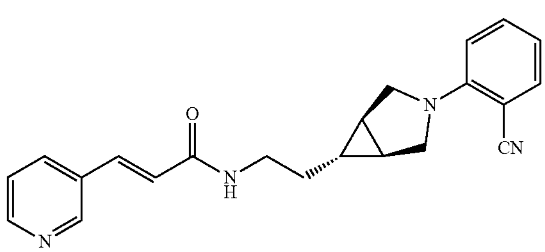 | (E)-N-(2-((1R,5S,6s)-3-(2-cyanophenyl)-3-azabicyclo[3.1.0]hexan-6-yl)ethyl)-3-(pyridin-3-yl)acrylamide | 359.4 |

-continued

| Ex. No. | Chemical structure | Chemical name | MS (ESI) m/z (M + H)+ |
|---|---|---|---|
| 136 | 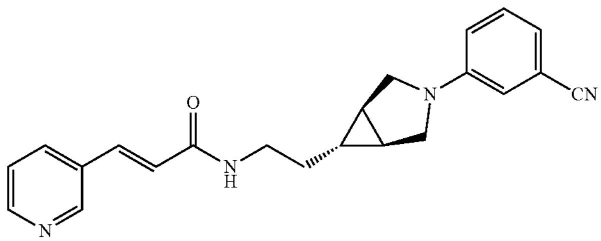 [SMILES: N#Cc1cccc(N2C[C@@H]3[C@@H](CCNC(=O)/C=C/c4cccnc4)[C@@H]3C2)c1] | (E)-N-(2-((1R,5S,6s)-3-(3-cyanophenyl)-3-azabicyclo[3.1.0]hexan-6-yl)ethyl)-3-(pyridin-3-yl)acrylamide | 359.4 |
| 137 | 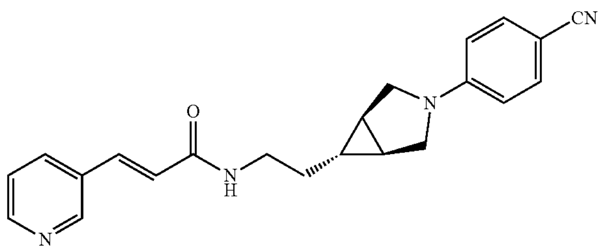 [SMILES: N#Cc1ccc(N2C[C@@H]3[C@@H](CCNC(=O)/C=C/c4cccnc4)[C@@H]3C2)cc1] | (E)-N-(2-((1R,5S,6s)-3-(4-cyanophenyl)-3-azabicyclo[3.1.0]hexan-6-yl)ethyl)-3-(pyridin-3-yl)acrylamide | 359.4 |
| 138 | 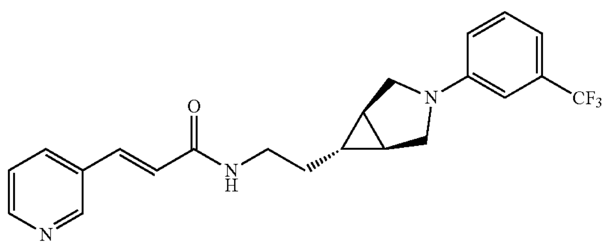 [SMILES: O=C(/C=C/c1cccnc1)NCC[C@@H]1[C@H]2CN(c3cccc(C(F)(F)F)c3)C[C@@H]12] | (E)-3-(pyridin-3-yl)-N-(2-((1R,5S,6s)-3-(3-(trifluoromethyl)phenyl)-3-azabicyclo[3.1.0]hexan-6-yl)ethyl)acrylamide | 402.4 |
| 139 | 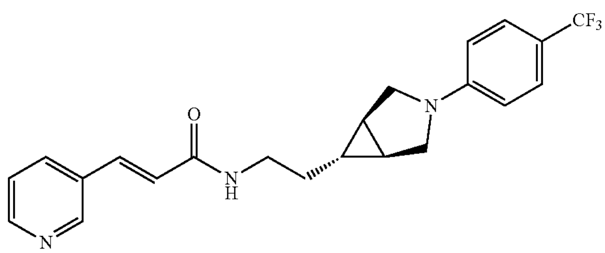 [SMILES: O=C(/C=C/c1cccnc1)NCC[C@@H]1[C@H]2CN(c3ccc(C(F)(F)F)cc3)C[C@@H]12] | (E)-3-(pyridin-3-yl)-N-(2-((1R,5S,6s)-3-(4-(trifluoromethyl)phenyl)-3-azabicyclo[3.1.0]hexan-6-yl)ethyl)acrylamide | 402.3 |
| 140 | 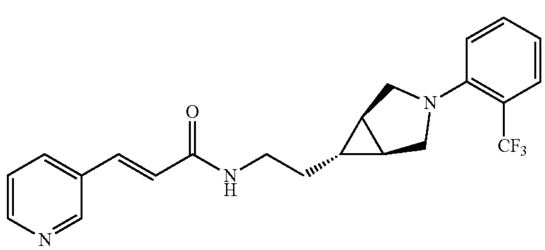 | (E)-3-(pyridin-3-yl)-N-(2-((1R,5S,6S)-3-(2-(trifluoromethyl)phenyl)-3-azabicyclo[3.1.0]hexan-6-yl)ethyl)acrylamide | 402.3 |
| 141 | 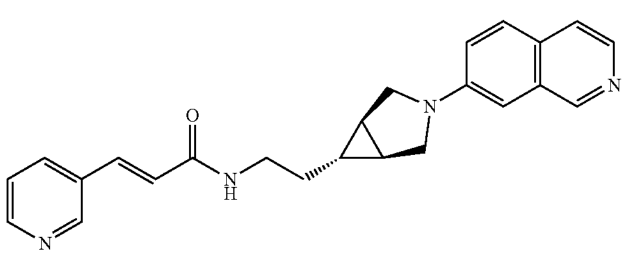 [SMILES: O=C(/C=C/c1cccnc1)NCC[C@@H]1[C@H]2CN(c3ccc4ccncc4c3)C[C@@H]12] | (E)-N-(2-((1R,5S,6s)-3-(isoquinolin-7-yl)-3-azabicyclo[3.1.0]hexan-6-yl)ethyl)-3-(pyridin-3-yl)acrylamide | 385.4 |

-continued

| Ex. No. | Chemical structure | Chemical name | MS (ESI) m/z $(M + H)^+$ |
|---|---|---|---|
| 142 | 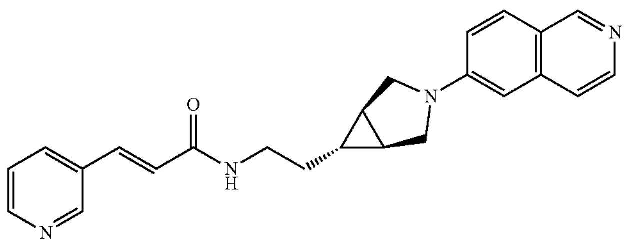 [SMILES: O=C(/C=C/c1cccnc1)NCC[C@@H]1[C@H]2CN(c3ccc4cnccc4c3)C[C@@H]12] | (E)-N-(2-((1R,5S,6s)-3-(isoquinolin-6-yl)-3-azabicyclo[3.1.0]hexan-6-yl)ethyl)-3-(pyridin-3-yl)acrylamide | 385.4 |
| 143 | 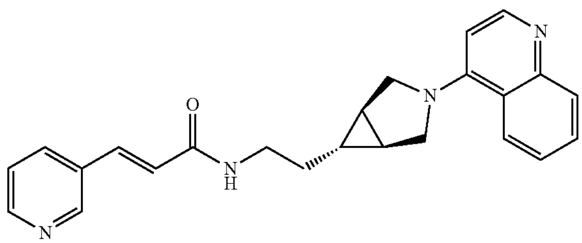 [SMILES: O=C(/C=C/c1cccnc1)NCC[C@@H]1[C@H]2CN(c3ccnc4ccccc34)C[C@@H]12] | (E)-3-(pyridin-3-yl)-N-(2-((1R,5S,6s)-3-(quinolin-4-yl)-3-azabicyclo[3.1.0]hexan-6-yl)ethyl)acrylamide | 385.3 |
| 144 | 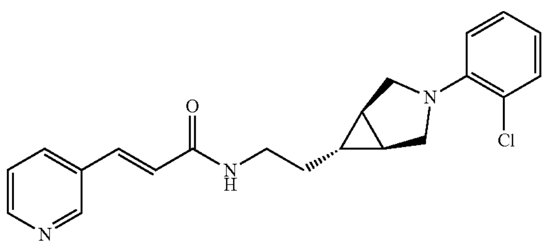 | (E)-N-(2-((1R,5S,6s)-3-(2-chlorphenyl)-3-azabicyclo[3.1.0]hexan-6-yl)ethyl)-3-(pyridin-3-yl)acrylamide | 368.2 |
| 145 | 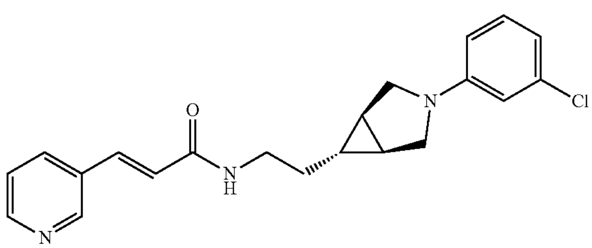 [SMILES: O=C(/C=C/c1cccnc1)NCC[C@@H]1[C@H]2CN(c3cccc(Cl)c3)C[C@@H]12] | (E)-N-(2-((1R,5S,6s)-3-(3-chlorophenyl)-3-azabicyclo[3.1.0]hexan-6-yl)ethyl)-3-(pyridin-3-yl)acrylamide | 368.2 |
| 146 | 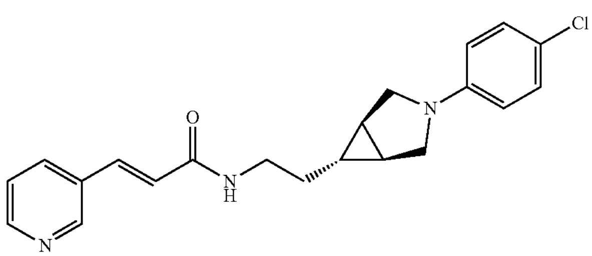 [SMILES: O=C(/C=C/c1cccnc1)NCC[C@@H]1[C@H]2CN(c3ccc(Cl)cc3)C[C@@H]12] | (E)-N-(2-((1R,5S,6s)-3-(4-chlorophenyl)-3-azabicyclo[3.1.0]hexan-6-yl)ethyl)-3-(pyridin-3-yl)acrylamide | 368.2 |
| 147 | 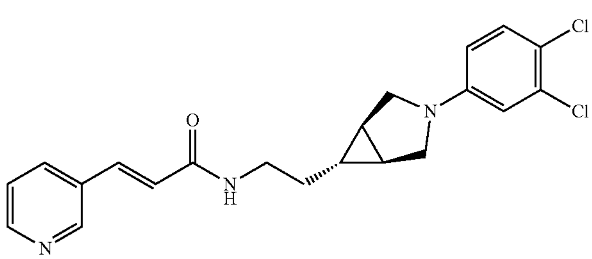 [SMILES: O=C(/C=C/c1cccnc1)NCC[C@@H]1[C@H]2CN(c3ccc(Cl)c(Cl)c3)C[C@@H]12] | (E)-N-(2-((1R,5S,6s)-3-(3,4-dichlorophenyl)-3-azabicyclo[3.1.0]hexan-6-yl)ethyl)-3-(pyridin-3-yl)acrylamide | 402.2 |

| Ex. No. | Chemical structure | Chemical name | MS (ESI) m/z (M + H)+ |
|---|---|---|---|
| 148 | 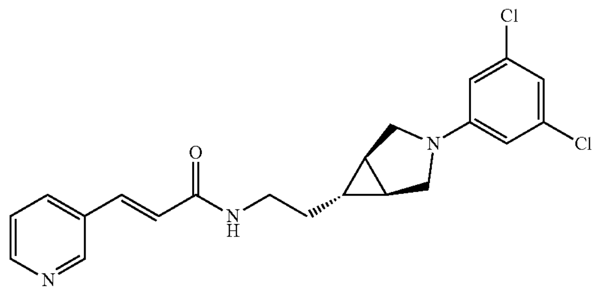 [SMILES: O=C(/C=C/c1cccnc1)NCC[C@@H]1[C@H]2CN(c3cc(Cl)cc(Cl)c3)C[C@@H]12] | (E)-N-(2-((1R,5S,6s)-3-(3,5-dichlorophenyl)-3-azabicyclo[3.1.0]hexan-6-yl)ethyl)-3-(pyridin-3-yl)acrylamide | 402.2 |
| 149 | 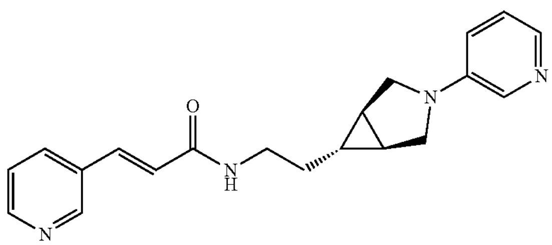 [SMILES: O=C(/C=C/c1cccnc1)NCC[C@@H]1[C@H]2CN(c3cccnc3)C[C@@H]12] | (E)-3-(pyridin-3-yl)-N-(2-((1R,5S,6s)-3-(pyridin-3-yl)-3-azabicyclo[3.1.0]hexan-6-yl)ethyl)acrylamide | 335.2 |
| 150 | 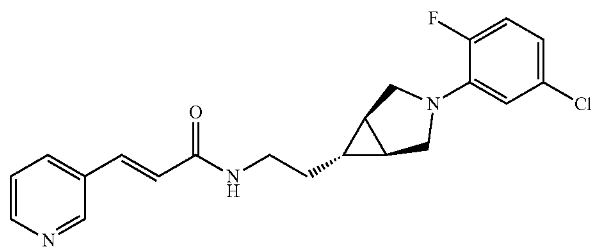 [SMILES: O=C(/C=C/c1cccnc1)NCC[C@@H]1[C@H]2CN(c3cc(Cl)ccc3F)C[C@@H]12] | (E)-N-(2-((1R,5S,6s)-3-(5-chloro-2-flurophenyl)-3-azabicyclo[3.1.0]hexan-6-yl)ethyl)-3-(pyridin-3-yl)acrylamide | 386.2 |
| 151 | 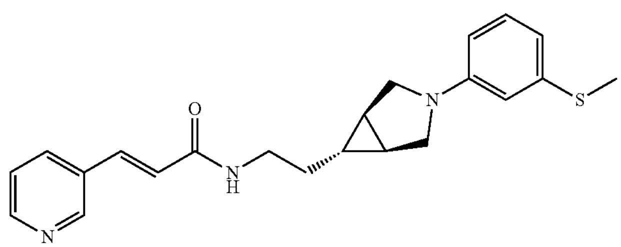 [SMILES: CSc1cccc(N2C[C@@H]3[C@@H](CCNC(=O)/C=C/c4cccnc4)[C@@H]3C2)c1] | (E)-N-(2-((1R,5S,6s)-3-(3-(methylthio)phenyl)-3-azabicyclo[3.1.0]hexan-6-yl)ethyl)-3-(pyridin-3-yl)acrylamide | 380.3 |
| 152 | 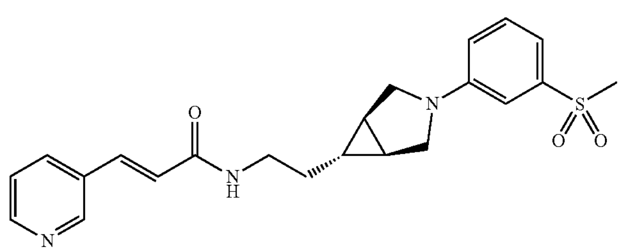 [SMILES: CS(=O)(=O)c1cccc(N2C[C@@H]3[C@@H](CCNC(=O)/C=C/c4cccnc4)[C@@H]3C2)c1] | (E)-N-(2-((1R,5S,6s)-3-(3-(methylsulfonyl)phenyl)-3-azabicyclo[3.1.0]hexan-6-yl)ethyl)-3-(pyridin-3-yl)acrylamide | 412.2 |
| 153 | 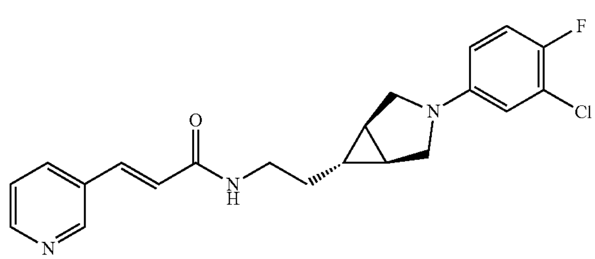 [SMILES: O=C(/C=C/c1cccnc1)NCC[C@@H]1[C@H]2CN(c3ccc(F)c(Cl)c3)C[C@@H]12] | (E)-N-(2-((1R,5S,6s)-3-(3-chloro-4-fluorophenyl)-3-azabicyclo[3.1.0]hexan-6-yl)ethyl)-3-(pyridin-3-yl)acrylamide | 386.2 |

-continued

| Ex. No. | Chemical structure | Chemical name | MS (ESI) m/z (M + H)+ |
|---|---|---|---|
| 154 | 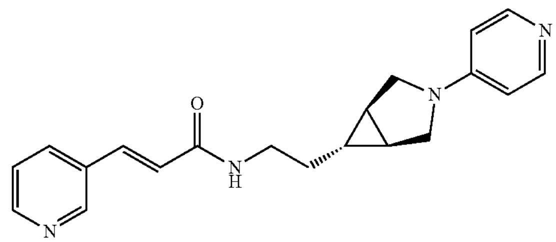 | (E)-3-(pyridin-3-yl)-N-(2-((1R,5S,6s)-3-(pyridin-4-yl)-3-azabicyclo[3.1.0]hexan-6-yl)ethyl)acrylamide | 335.1 |
| 155 | 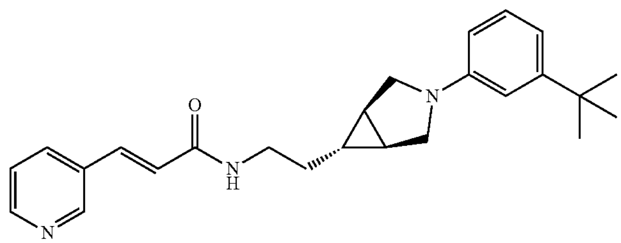 [SMILES: CC(C)(C)c1cccc(N2C[C@@H]3[C@@H](CCNC(=O)/C=C/c4cccnc4)[C@@H]3C2)c1] | (E)-N-(2-((1R,5S,6s)-3-(3-(tert-butyl)phenyl)-3-azabicyclo[3.1.0]hexan-6-yl)ethyl)-3-(pyridin-3-yl)acrylamide | 390.3 |
| 156 | 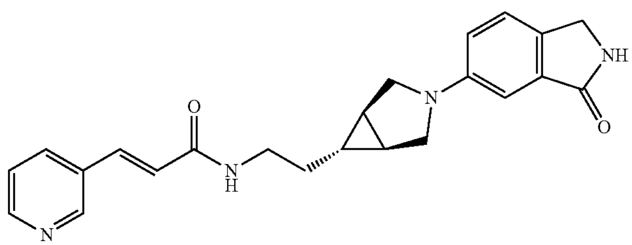 [SMILES: O=C(/C=C/c1cccnc1)NCC[C@@H]1[C@H]2CN(c3ccc4c(c3)C(=O)NC4)C[C@@H]12] | (E)-N-(2-((1R,5S,6s)-3-(3-oxoisoindolin-5-yl)-3-azabicyclo[3.1.0]hexan-6-yl)ethyl)-3-(pyridin-3-yl)acrylamide | 389.3 |
| 157 | 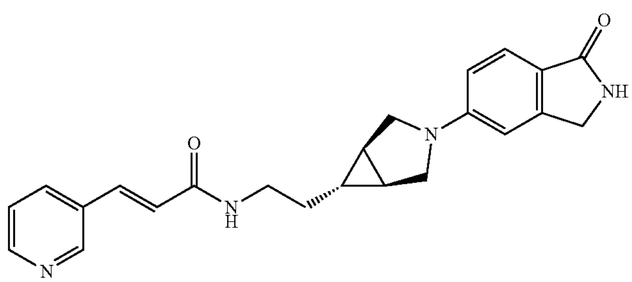 [SMILES: O=C(/C=C/c1cccnc1)NCC[C@@H]1[C@H]2CN(c3ccc4c(c3)CNC4=O)C[C@@H]12] | (E)-N-(2-((1R,5S,6s)-3-(1-oxoisoindolin-5-yl)-3-azabicyclo[3.1.0]hexan-6-yl)ethyl)-3-(pyridin-3-yl)acrylamide | 389.3 |
| 158 | 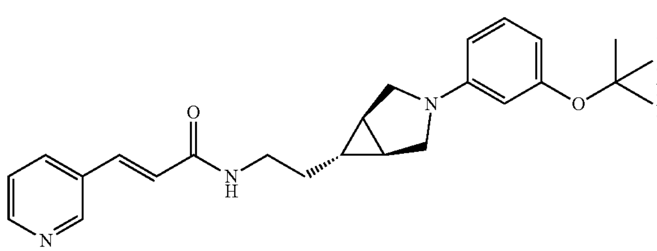 | (E)-N-(2-((1R,5S,6s)-3-(3-(tert-butoxy)phenyl)-3-azabicyclo[3.1.0]hexan-6-yl)ethyl)-3-(pyridin-3-yl)acrylamide | 406.3 |
| 159 | 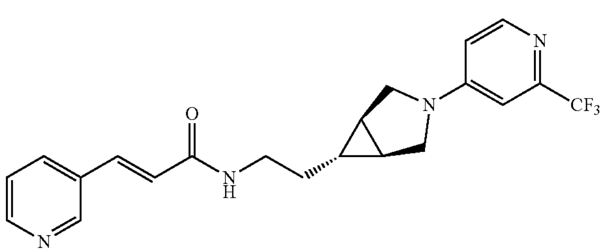 [SMILES: O=C(/C=C/c1cccnc1)NCC[C@@H]1[C@H]2CN(c3ccnc(C(F)(F)F)c3)C[C@@H]12] | (E)-3-(pyridin-3-yl)-N-(2-((1R,5S,6s)-3-(2-(trifluoromethyl)pyridin-4-yl)-3-azabicyclo[3.1.0]hexan-6-yl)ethyl)acrylamide | 403.2 |

| Ex. No. | Chemical structure | Chemical name | MS (ESI) m/z (M + H)+ |
|---|---|---|---|
| 160 | 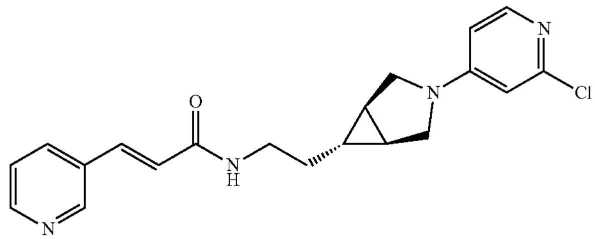 [SMILES: O=C(/C=C/c1cccnc1)NCC[C@@H]1[C@H]2CN(c3ccnc(Cl)c3)C[C@@H]12] | (E)-N-(2-((1R,5S,6s)-3-(2-chloropyridin-4-yl)-3-azabicyclo[3.1.0]hexan-6-yl)ethyl)-3-(pyridin-3-yl)acrylamide | 369.1 |
| 161 | 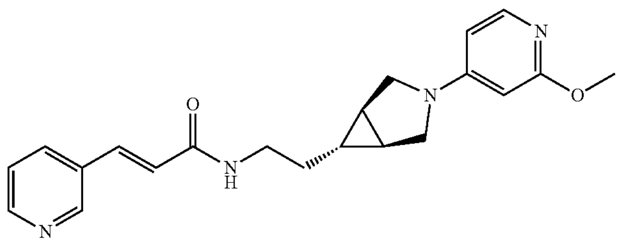 [SMILES: COc1cc(N2C[C@@H]3[C@@H](CCNC(=O)/C=C/c4cccnc4)[C@@H]3C2)ccn1] | (E)-N-(2-((1R,5S,6S)-3-(2-methoxypyridin-4-yl)-3-azabicyclo[3.1.0]hexan-6-yl)ethyl)-3-(pyridin-3-yl)acrylamide | 365.3 |

Example 162: (E)-3-(pyridin-3-yl)-N-(2-((1R,5S,6s)-3-(5-(trifluoromethyl)pyrimidin-2-yl)-3-azabicyclo[3.1.0]hexan-6-yl)ethyl)acrylamide

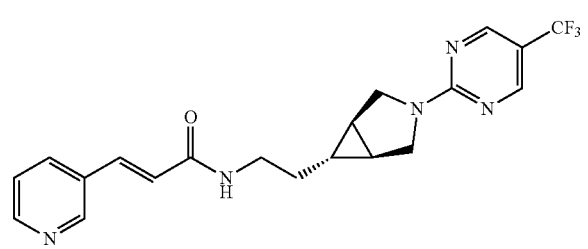 [SMILES: O=C(/C=C/c1cccnc1)NCC[C@@H]1[C@H]2CN(c3ncc(C(F)(F)F)cn3)C[C@@H]12]

To a suspension of (E)-N-(2-((1R,5S,6s)-3-azabicyclo[3.1.0]hexan-6-yl)ethyl)-3-(pyridin-3-yl)acrylamide (50 mg, 0.14 mmol, TFA salt) in N,N-dimethylformamide (2 mL) was added cesium carbonate (132 mg, 0.40 mmol) and 2-chloro-5-(trifluoromethyl)pyrimidine (24.6 mg, 0.14 mmol). The mixture was heated to 100° C. and stirred for 2 h. The reaction mixture was cooled to room temperature, filtered, concentrated under reduced pressure and purified by preparative HPLC (Phenomenex Gemini C18 column (150× 30 mm, 5 um); flow rate: 25 mL/min; gradient: 27%-47% B over 8 min; mobile phase A: 0.1% aqueous trifluoroacetic acid, mobile phase B: acetonitrile) to give 19.3 mg (26%) of the title compound as a yellow solid. MS (ESI) m/z: 404.3 (M+H)+. $^1$H NMR (400 MHz, DMSO-$d_6$): δ 8.82 (d, J=1.6 Hz, 1H), 8.66 (s, 2H), 8.60 (dd, J=1.2, 4.8 Hz, 1H), 8.23 (t, J=5.6 Hz, 1H), 8.11 (d, J=8.0 Hz, 1H), 7.55 (dd, J=4.8, 8.0 Hz, 1H), 7.47 (d, J=16.0 Hz, 1H), 6.76 (d, J=16.0 Hz, 1H), 3.82 (d, J=11.6 Hz, 2H), 3.54 (d, J=11.6 Hz, 2H), 3.28 (q, J=6.4 Hz, 2H), 1.55 (s, 2H), 1.46 (q, J=6.8 Hz, 2H), 0.59 (tt, J=3.2, 6.8 Hz, 1H).

Examples 163-177

The following compounds were prepared substantially according to the procedures described above:

| Ex. No. | Chemical structure | Chemical name | MS (ESI) m/z (M + H)+ |
|---|---|---|---|
| 163 | 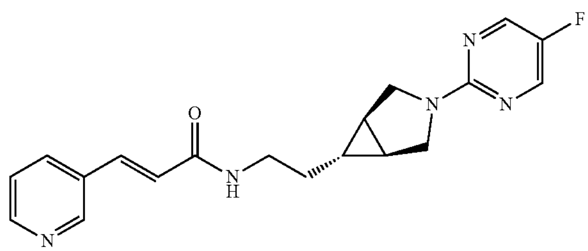 [SMILES: O=C(/C=C/c1cccnc1)NCC[C@@H]1[C@H]2CN(c3ncc(F)cn3)C[C@@H]12] | (E)-N-(2-((1R,5S,6s)-3-(5-fluoropyrimidin-2-yl)-3-azabicyclo[3.1.0]hexan-6-yl)ethyl)-3-(pyridin-3-yl)acrylamide | 354.3 |

-continued

| Ex. No. | Chemical structure | Chemical name | MS (ESI) m/z (M + H)+ |
|---|---|---|---|
| 164 | 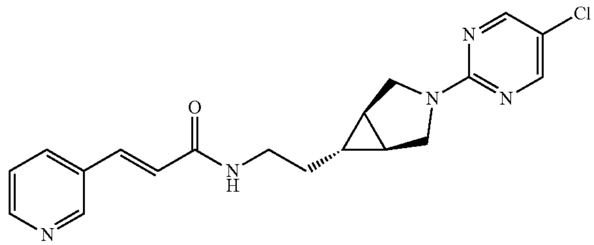 [SMILES: O=C(/C=C/c1cccnc1)NCC[C@@H]1[C@H]2CN(c3ncc(Cl)cn3)C[C@@H]12] | (E)-N-(2-((1R,5S,6s)-3-(5-chloropyrimidin-2-yl)-3-azabicyclo[3.1.0]hexan-6-yl)ethyl)-3-(pyridin-3-yl)acrylamide | 370.3 |
| 165 | 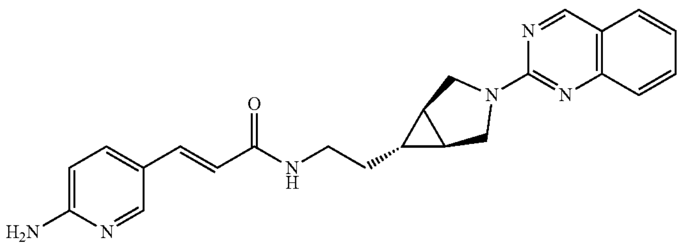 [SMILES: Nc1ccc(/C=C/C(=O)NCC[C@@H]2[C@H]3CN(c4ncc5ccccc5n4)C[C@@H]23)cn1] | (E)-3-(6-aminopyridin-3-yl)-N-(2-((1R,5S,6s)-3-(quinazolin-2-yl)-3-azabicyclo[3.1.0]hexan-6-yl)ethyl)acrylamide | 401.4 |
| 166 | 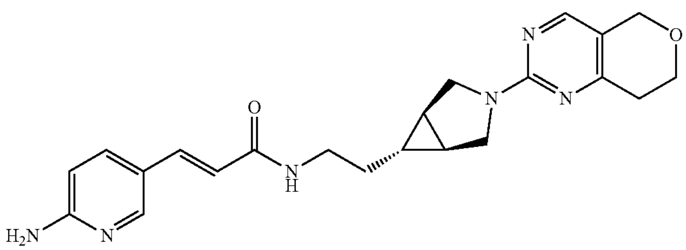 [SMILES: Nc1ccc(/C=C/C(=O)NCC[C@@H]2[C@H]3CN(c4ncc5c(n4)CCOC5)C[C@@H]23)cn1] | (E)-N-(2-((1R,5S,6s)-3-(7,8-dihydro-5H-pyrano[4,3-d]pyrimidin-2-yl)-3-azabicyclo[3.1.0]hexan-6-yl)ethyl)-3-(pyridin-3-yl)acrylamide | 392.4 |
| 167 | 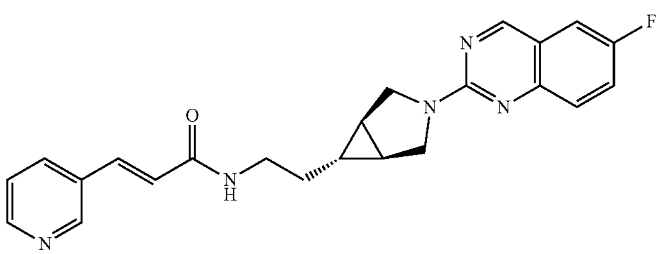 [SMILES: O=C(/C=C/c1cccnc1)NCC[C@@H]1[C@H]2CN(c3ncc4cc(F)ccc4n3)C[C@@H]12] | (E)-N-(2-((1R,5S,6s)-3-(6-fluoroquinazolin-2-yl)-3-azabicyclo[3.1.0]hexan-6-yl)ethyl)-3-(pyridin-3-yl)acrylamide | 404.3 |
| 168 | 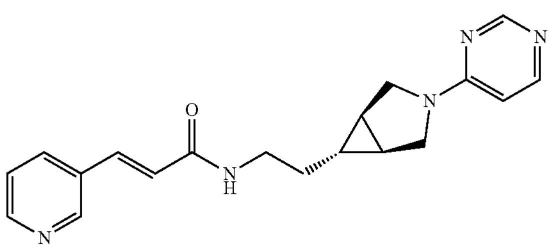 | (E)-3-(pyridin-3-yl)-N-(2-((1R,5S,6s)-3-(pyrimidin-4-yl)-3-azabicyclo[3.1.0]hexan-6-yl)ethyl)acrylamide | 336.2 |
| 169 | 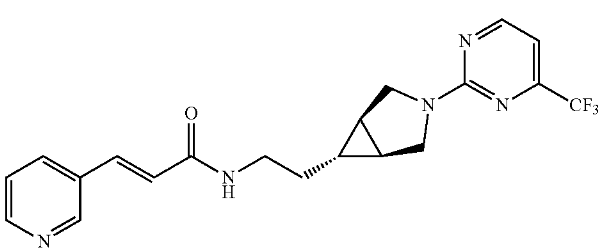 [SMILES: O=C(/C=C/c1cccnc1)NCC[C@@H]1[C@H]2CN(c3nccc(C(F)(F)F)n3)C[C@@H]12] | (E)-3-(pyridin-3-yl)-N-(2-((1R,5S,6s)-3-(4-(trifluoromethyl)pyrimidin-2-yl)-3-azabicyclo[3.1.0]hexan-6-yl)ethyl)acrylamide | 404.3 |

-continued

| Ex. No. | Chemical structure | Chemical name | MS (ESI) m/z (M + H)+ |
|---|---|---|---|
| 170 | 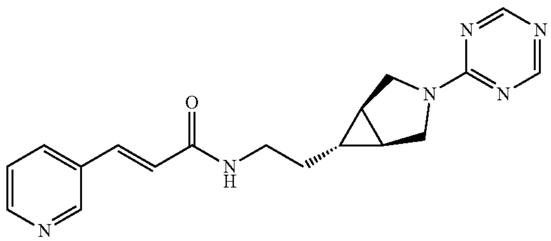 [SMILES: O=C(/C=C/c1cccnc1)NCC[C@@H]1[C@H]2CN(c3ncncn3)C[C@@H]12] | (E)-N-(2-((1R,5S,6s)-3-(1,3,5-triazin-2-yl)-3-azabicyclo[3.1.0]hexan-6-yl)ethyl)-3-(pyridin-3-yl)acrylamide | 337.4 |
| 171 | 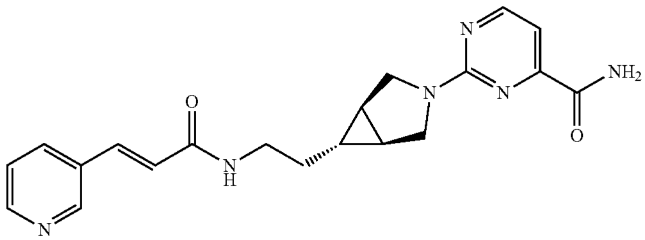 [SMILES: NC(=O)c1ccnc(N2C[C@@H]3[C@@H](CCNC(=O)/C=C/c4cccnc4)[C@@H]3C2)n1] | 2-((1R,5S,6s)-6-(2-((E)-3-(pyridin-3-yl)acrylamido)ethyl)-3-azabicyclo[3.1.0]hexan-3-yl)pyrimidine-4-carboxamide | 379.3 |
| 172 | 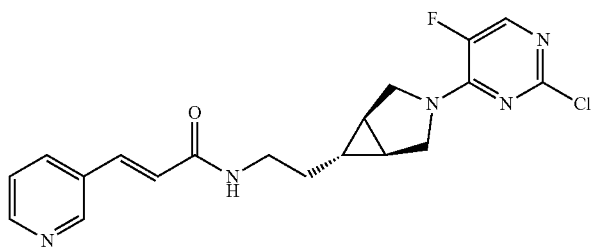 | (E)-N-(2-((1R,5S,6s)-3-(2-chloro-5-fluoropyrimidin-4-yl)-3-azabicyclo[3.1.0]hexan-6-yl)ethyl)-3-(pyridin-3-yl)acrylamide | 388.3 |
| 173 | 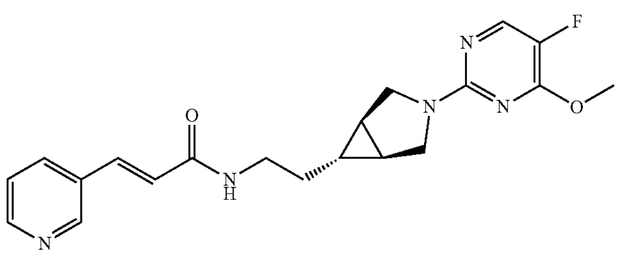 [SMILES: COc1nc(N2C[C@@H]3[C@@H](CCNC(=O)/C=C/c4cccnc4)[C@@H]3C2)ncc1F] | (E)-N-(2-((1R,5S,6s)-3-(5-fluoro-4-methoxypyrimidin-2-yl)-3-azabicyclo[3.1.0]hexan-6-yl)ethyl)-3-(pyridin-3-yl)acrylamide | 384.3 |
| 174 | 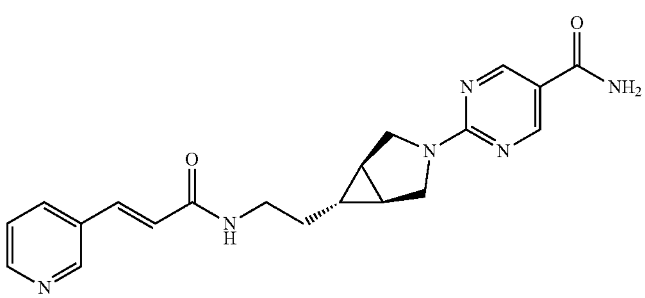 [SMILES: NC(=O)c1cnc(N2C[C@@H]3[C@@H](CCNC(=O)/C=C/c4cccnc4)[C@@H]3C2)nc1] | 2-((1R,5S,6s)-6-(2-((E)-3-(pyridin-3-yl)acrylamido)ethyl)-3-azabicyclo[3.1.0]hexan-3-yl)pyrimidine-5-carboxamide | 379.3 |
| 175 | 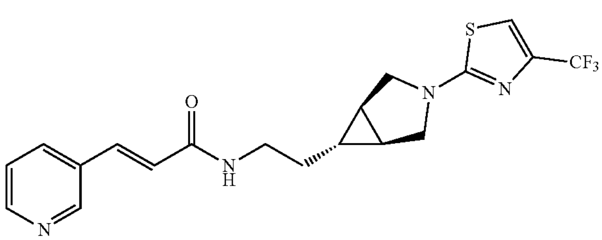 [SMILES: O=C(/C=C/c1cccnc1)NCC[C@@H]1[C@H]2CN(c3nc(C(F)(F)F)cs3)C[C@@H]12] | (E)-3-(pyridin-3-yl)-N-(2-((1R,5S,6s)-3-(4-(trifluoromethyl)thiazol-2-yl)-3-azabicyclo[3.1.0]hexan-6-yl)ethyl)acrylamide | 409.3 |

| Ex. No. | Chemical structure | Chemical name | MS (ESI) m/z (M + H)+ |
|---|---|---|---|
| 176 | 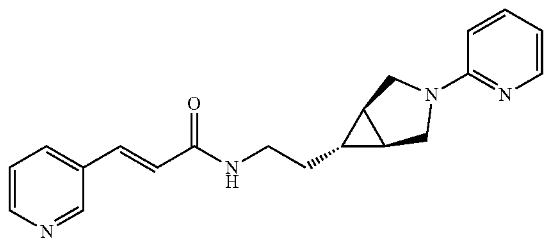 [SMILES: O=C(/C=C/c1cccnc1)NCC[C@@H]1[C@H]2CN(c3ccccn3)C[C@@H]12] | (E)-N-(2-((1R,5S,6s)-3-(pyridin-2-yl)-3-azabicyclo[3.1.0]hexan-6-yl)ethyl)-3-(pyridin-3-yl)acrylamide | 335.1 |
| 177 | 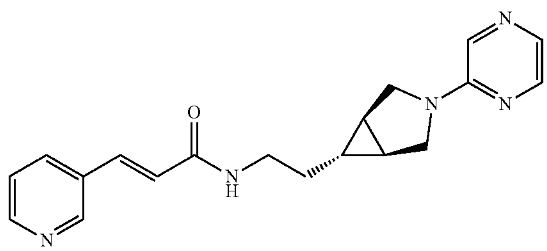 [SMILES: O=C(/C=C/c1cccnc1)NCC[C@@H]1[C@H]2CN(c3cnccn3)C[C@@H]12] | (E)-N-(2-((1R,5S,6s)-3-(pyrazin-2-yl)-3-azabicyclo[3.1.0]hexan-6-yl)ethyl)-3-(pyridin-3-yl)acrylamide | 336.4 |

Example 178: 3-((1R,5S,6s)-6-(2-((E)-3-(6-aminopyridin-3-yl)acrylamido)ethyl)-3-azabicyclo[3.1.0]hexane-3-carbonyl)benzoic acid

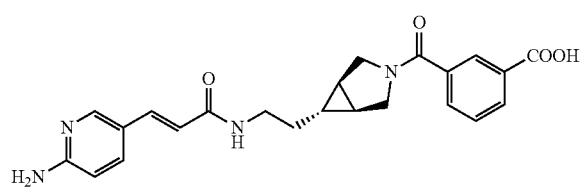 [SMILES: Nc1ccc(/C=C/C(=O)NCC[C@@H]2[C@H]3CN(C(=O)c4cccc(C(=O)O)c4)C[C@@H]23)cn1]

To a solution of 3-methoxycarbonylbenzoic acid (51.3 mg, 0.28 mmol) in pyridine (5 mL) was added 1-(3-dimethylaminopropyl)-3-ethylcarbodiimide hydrochloride (64.5 mg, 0.34 mmol). The mixture was stirred at 25° C. for 15 min, and to the resulting solution was added (E)-N-(2-((1R, 5S,6s)-3-azabicyclo[3.1.0]hexan-6-yl)ethyl)-3-(6-aminopyridin-3-yl)acrylamide (100 mg, 0.26 mmol) at 25° C. The reaction mixture was stirred for another 1 h. The reaction was concentrated under vacuum and diluted with 1 N hydrochloric acid (1 mL), water (15 mL) and ethyl acetate (20 mL). The aqueous layer was washed with ethyl acetate (10 mL×2), and the combined aqueous layers were concentrated under vacuum to give 100 mg of crude methyl 3-((1R,5S,6s)-6-(2-((E)-3-(6-aminopyridin-3-yl)acrylamido)ethyl)-3-azabicyclo[3.1.0]hexane-3-carbonyl)benzoate as a yellow oil as the HCl salt. MS (ESI) m/z: 435.4 (M+H)+.

To a solution of methyl 3-((1R,5S,6s)-6-(2-((E)-3-(6-aminopyridin-3-yl)acrylamido)ethyl)-3-azabicyclo[3.1.0] hexane-3-carbonyl)benzoate hydrochloride (100 mg, 0.21 mmol) in methanol (5 mL) and water (5 mL) was added lithium hydroxide monohydrate (28.8 mg, 0.67 mmol) at 20° C. The reaction mixture was stirred at 20° C. for 2 h. The solution was adjusted to pH 4-5 with 1 N aqueous hydrochloric acid and concentrated under vacuum. The residue was purified by preparative HPLC (Phenomenex Gemini C18 column (150×25 mm, 10 um); flow rate: 25 mL/min; gradient: 10%-40% B over 9 min; mobile phase A: 0.1% aqueous trifluoroacetic acid, mobile phase B: acetonitrile) to afford 25 mg (22%) of the title compound as a yellow solid. MS (ESI) m/z: 421.4 (M+H)+. 1H NMR (400 MHz, DMSO-d6): δ 8.25-8.05 (m, 3H), 8.04-7.91 (m, 4H), 7.69 (d, J=7.8 Hz, 1H), 7.60-7.49 (m, 1H), 7.32 (d, J=15.6 Hz, 1H), 6.93 (d, J=9.2 Hz, 1H), 6.48 (d, J=15.6 Hz, 1H), 3.94 (d, J=12.0 Hz, 1H), 3.64 (dd, J=4.0, 10.4 Hz, 1H), 3.26-3.15 (m, 4H), 1.46-1.32 (m, 4H), 0.56-0.52 (m, 1H).

Examples 179-183

The following compounds were prepared substantially according to the procedures described above:

| Ex. No. | Chemical structure | Chemical name | MS (ESI) m/z (M + H)+ |
|---|---|---|---|
| 179 | 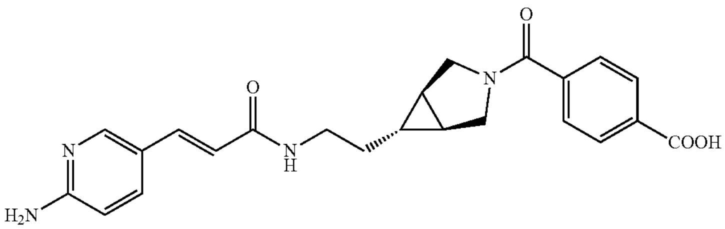 [SMILES: Nc1ccc(/C=C/C(=O)NCC[C@@H]2[C@H]3CN(C(=O)c4ccc(C(=O)O)cc4)C[C@@H]23)cn1] | 4-((1R,5S,6s)-6-(2-((E)-3-(6-aminopyridin-3-yl)acrylamido)ethyl)-3-azabicyclo[3.1.0]hexane-3-carbonyl)benzoic acid | 421.4 |
| 180 | 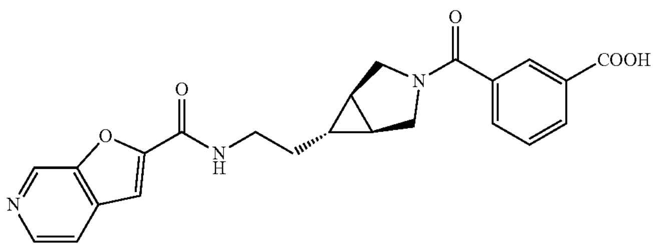 [SMILES: O=C(O)c1cccc(C(=O)N2C[C@@H]3[C@@H](CCNC(=O)c4cc5ccncc5o4)[C@@H]3C2)c1] | 3-((1R,5S,6s)-6-(2-(furo[2,3-c]pyridine-2-carboxamido)ethyl)-3-azabicyclo[3.1.0]hexane-3-carbonyl)benzoic acid | 420.4 |
| 181 | 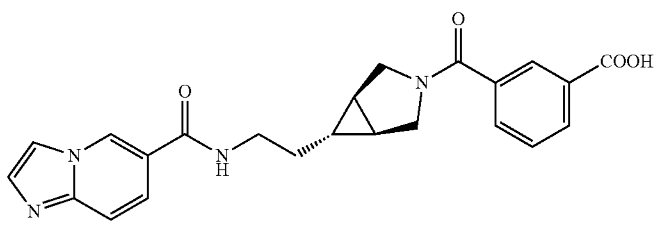 [SMILES: O=C(O)c1cccc(C(=O)N2C[C@@H]3[C@@H](CCNC(=O)c4ccc5nccn5c4)[C@@H]3C2)c1] | 3-((1R,5S,6s)-6-(2-(imidazo[1,2-a]pyridine-6-carboxamido)ethyl)-3-azabicyclo[3.1.0]hexane-3-carbonyl)benzoic acid | 419.3 |
| 182 | 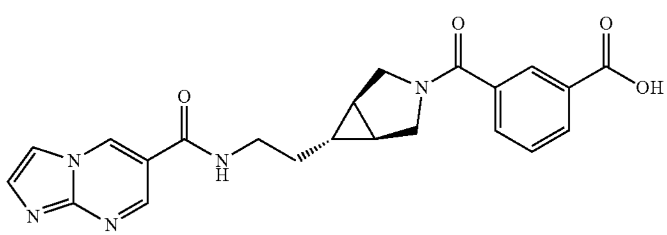 [SMILES: O=C(O)c1cccc(C(=O)N2C[C@@H]3[C@@H](CCNC(=O)c4cnc5nccn5c4)[C@@H]3C2)c1] | 3-((1R,5S,6s)-6-(2-(imidazo[1,2-a]pyrimidine-6-carboxamido)ethyl)-3-azabicyclo[3.1.0]hexane-3-carbonyl)benzoic acid | 420.1 |
| 183 | 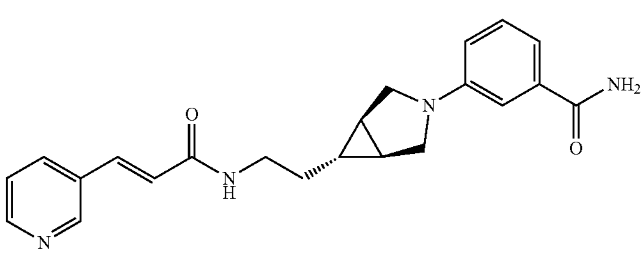 [SMILES: NC(=O)c1cccc(N2C[C@@H]3[C@@H](CCNC(=O)/C=C/c4cccnc4)[C@@H]3C2)c1] | 3-((1R,5S,6s)-6-(2-((E)-3-(pyridin-3-yl)acrylamido)ethyl)-3-azabicyclo[3.1.0]hexan-3-yl)benzamide | 377.3 |

Example 184: (E)-N-(2-((1R,5S,6s)-3-(3-acetamidophenyl)-3-azabicyclo[3.1.0]hexan-6-yl)ethyl)-3-(pyridin-3-yl)acrylamide

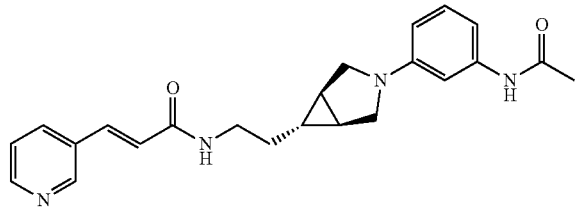 [SMILES: CC(=O)Nc1cccc(N2C[C@@H]3[C@@H](CCNC(=O)/C=C/c4cccnc4)[C@@H]3C2)c1]

To a solution of (E)-N-(2-((1R,5S,6s)-3-azabicyclo[3.1.0]hexan-6-yl)ethyl)-3-(pyridin-3-yl)acrylamide (200 mg, 0.54 mmol, TFA salt) in N,N-dimethylformamide (5 mL) was added cesium carbonate (526 mg, 1.62 mmol) and 1-fluoro-3-nitrobenzene (91.2 mg, 0.65 mmol) at 25° C. The mixture was heated to 100° C. and stirred for 48 h under an atmosphere of nitrogen. The reaction mixture was filtered and the filtrate was concentrated under vacuum to give a residue. The residue was purified by silica gel column chromatography (petroleum ether/ethyl ester, from 1/1 to 0/1) to give 80 mg (39%) of (E)-N-(2-((1R,5S,6s)-3-(3-nitrophenyl)-3-azabicyclo[3.1.0]hexan-6-yl)ethyl)-3-(pyridin-3-yl)acrylamide as a yellow solid. MS (ESI) m/z: 379.2 (M+H)$^+$. $^1$H NMR (400 MHz, DMSO-d$_6$): δ 8.74 (d, J=1.8 Hz, 1H), 8.53 (dd, J=1.6, 4.8 Hz, 1H), 8.22-8.16 (m, 1H), 8.19 (t, J=5.6 Hz, 1H), 7.97 (J=1.8, 7.9 Hz, 1H), 7.49-7.35 (m, 4H), 7.23-7.17 (m, 1H), 6.94 (td, J=2.0, 7.4 Hz, 1H), 6.73 (d, J=15.8 Hz, 1H), 3.56-3.48 (m, 4H), 3.29-3.27 (m, 2H), 1.58 (s, 2H), 1.46 (q, J=6.8 Hz, 2H), 0.68 (td, J=3.6, 6.8 Hz, 1H).

To a solution of (E)-N-(2-((1R,5S,6s)-3-(3-nitrophenyl)-3-azabicyclo[3.1.0]hexan-6-yl)ethyl)-3-(pyridin-3-yl)acrylamide (50 mg, 0.13 mmol) in methanol (3 mL) was added sodium sulfide nonahydrate (63 mg, 0.26 mmol). The mixture was stirred at 90° C. for 1 h. The reaction mixture was filtered and the filtrate was concentrated under vacuum to give 50 mg of crude (E)-N-(2-((1R,5S,6s)-3-(3-aminophenyl)-3-azabicyclo[3.1.0]hexan-6-yl)ethyl)-3-(pyridin-3-yl)acrylamide as a yellow solid. MS (ESI) m/z: 349.1 (M+H)$^+$.

To a solution of (E)-N-(2-((1R,5S,6s)-3-(3-aminophenyl)-3-azabicyclo[3.1.0]hexan-6-yl)ethyl)-3-(pyridin-3-yl)acrylamide (30 mg, 0.08 mmol) in dichloromethane (1 mL) was added triethylamine (17.4 mg, 0.17 mmol) and acetyl chloride (10.1 mg, 0.13 mmol). The mixture was stirred at 25° C. for 15 min. The reaction mixture was concentrated under vacuum and purified by preparative HPLC (Phenomenex Gemini C18 column (150×25 mm, 5 um); flow rate: 25 mL/min; gradient: 12%-42% B over 9 min; mobile phase A: 0.1% aqueous trifluoroacetic acid, mobile phase B: acetonitrile) to give 9.3 mg (21%) of the title compound as a yellow solid. MS (ESI) m/z: 391.3 (M+H)$^+$. $^1$H NMR (400 MHz, DMSO-d$_6$): δ 9.68 (s, 1H), 8.78 (s, 1H), 8.57 (d, J=4.8 Hz, 1H), 8.23 (t, J=5.6 Hz, 1H), 8.06 (d, J=8.0 Hz, 1H), 7.50 (dd, J=4.8, 8.0 Hz, 1H), 7.46 (d, J=16.0 Hz, 1H), 7.03-6.96 (m, 1H), 6.84-6.78 (m, 2H), 6.74 (d, J=16.0 Hz, 1H), 6.21-6.15 (m, 1H), 3.30-3.23 (m, 4H), 3.11 (d, J=8.4 Hz, 2H), 1.98 (s, 3H), 1.50 (s, 2H), 1.43 (q, J=6.8 Hz, 2H), 0.72-0.62 (m, 1H).

Example 185: (E)-N-(2-((1R,5S,6s)-3-(3-(methylsulfonamido)phenyl)-3-azabicyclo[3.1.0]hexan-6-yl)ethyl)-3-(pyridin-3-yl)acrylamide

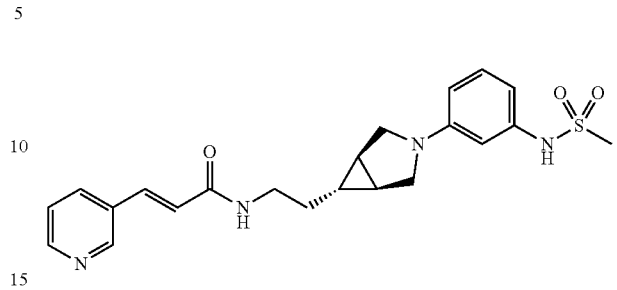

This compound was prepared substantially according to the procedures described above. MS (ESI) m/z: 427.2 (M+H)$^+$.

Example 186: 4-((1R,5S,6s)-6-(2-((E)-3-(pyridin-3-yl)acrylamido)ethyl)-3-azabicyclo[3.1.0]hexan-3-yl)benzamide

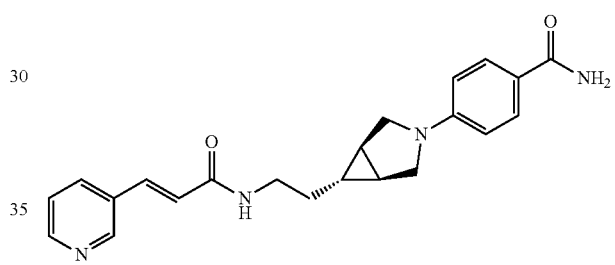

To a solution of (E)-N-(2-((1R,5S,6s)-3-azabicyclo[3.1.0]hexan-6-yl)ethyl)-3-(pyridin-3-yl)acrylamide (100 mg, 0.27 mmol, TFA salt) in N,N-dimethylformamide (3 mL) was added cesium carbonate (175 mg, 0.54 mmol) and 4-fluorobenzonitrile (48.9 mg, 0.40 mmol). The mixture was stirred at 100° C. for 6 h. The reaction mixture was filtered and concentrated under vacuum to give 120 mg of crude (E)-N-(2-((1R,5S,6s)-3-(4-cyanophenyl)-3-azabicyclo[3.1.0]hexan-6-yl)ethyl)-3-(pyridin-3-yl)acrylamide as a white solid. MS (ESI) m/z: 359.2 (M+H)$^+$.

A solution of (E)-N-(2-((1R,5S,6s)-3-(4-cyanophenyl)-3-azabicyclo[3.1.0]hexan-6-yl)ethyl)-3-(pyridin-3-yl)acrylamide (120 mg, 0.33 mmol) in concentrated hydrochloric acid (2.04 g, 20.1 mmol) was stirred at 50° C. for 2 h. The reaction mixture was concentrated under vacuum and purified by preparative HPLC (Phenomenex Gemini C18 column (150×25 mm, 10 um); flow rate: 25 mL/min; gradient: 20%-40% B over 7 min; mobile phase A: 0.1% aqueous trifluoroacetic acid, mobile phase B: acetonitrile) to afford 28.5 mg (17%) of the title compound as an off-white solid. MS (ESI) m/z: 377.4 (M+H)$^+$. $^1$H NMR (400 MHz, DMSO-d$_6$): δ 8.86 (d, J=1.6 Hz, 1H), 8.64 (dd, J=1.6, 5.2 Hz, 1H), 8.26 (t, J=5.6 Hz, 1H), 8.18 (d, J=8.0 Hz, 1H), 7.70 (d, J=8.8 Hz, 2H), 7.62 (dd, J=4.8, 8.0 Hz, 2H), 7.50 (d, J=16.0 Hz, 1H), 6.90 (s, 1H), 6.79 (d, J=16.0 Hz, 1H), 6.50 (d, J=8.8 Hz, 2H), 3.52 (d, J=9.6 Hz, 2H), 3.36-3.18 (m, 4H), 1.56 (s, 2H), 1.46 (q, J=6.8 Hz, 2H), 0.72-0.62 (m, 1H).

Example 187: (E)-N-(2-((1R,5S,6s)-3-(5-fluoro-4-hydroxypyrimidin-2-yl)-3-azabicyclo[3.1.0]hexan-6-yl)ethyl)-3-(pyridin-3-yl)acrylamide

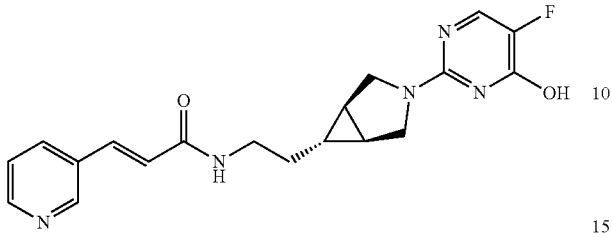

A solution of the Example 173 compound (700 mg, 1.69 mmol) in hydrochloric acid (6M, 8 mL) was stirred at 80° C. for 12 h. The reaction mixture was cooled to room temperature, concentrated under vacuum and purified by preparative HPLC (Phenomenex Gemini C18 column (150×25 mm, 10 um); flow rate: 25 mL/min; gradient: 0%-20% B over 9 min; mobile phase A: 0.1% aqueous trifluoroacetic acid, mobile phase B: acetonitrile) to afford 41 mg (62%) of the title compound as a yellow solid. MS (ESI) m/z: 370.2 (M+H)$^+$. $^1$H NMR (400 MHz, DMSO-d$_6$): δ 8.87 (d, J=2.0 Hz, 1H), 8.65 (dd, J=1.6, 4.8 Hz, 1H), 8.31-8.17 (m, 2H), 7.72 (d, J=4.0 Hz, 1H), 7.65 (dd, J=5.2, 8.0 Hz, 1H), 7.50 (d, J=16.0 Hz, 1H), 6.79 (d, J=16.0 Hz, 1H), 3.64 (d, J=10.6 Hz, 2H), 3.41 (d, J=10.6 Hz, 2H), 3.26 (q, J=6.4 Hz, 2H), 1.51 (s, 2H), 1.43 (q, J=6.8 Hz, 2H), 0.63-0.50 (m, 1H).

Example 188: (E)-N-(2-((1R,5S,6s)-3-(4-chloro-5-fluoropyrimidin-2-yl)-3-azabicyclo[3.1.0]hexan-6-yl)ethyl)-3-(pyridin-3-yl)acrylamide

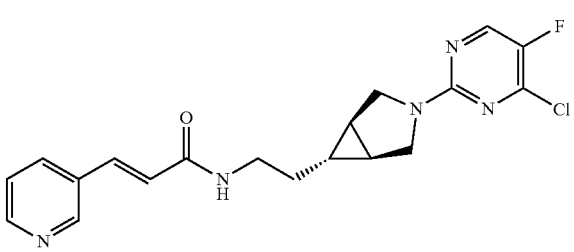 [SMILES: O=C(/C=C/c1cccnc1)NCC[C@@H]1[C@H]2CN(c3ncc(F)c(Cl)n3)C[C@@H]12]

A solution of the Example 187 compound (100 mg, 0.25 mmol) in phosphorus oxychloride (4.71 g, 30.7 mmol) was stirred at 80° C. for 1 h. The reaction mixture was quenched with water (20 mL) and the resulting solution was adjusted to pH 7 with saturated aqueous sodium bicarbonate solution. The solution was extracted with ethyl acetate (15 mL×3). The combined organic layers were washed with brine (15 mL), dried over sodium sulfate and concentrated under vacuum. The residue was purified by preparative TLC (silica gel, ethyl acetate/MeOH=10/1) to afford 5.5 mg (5%) of the title compound as an off-white solid. MS (ESI) m/z: 388.3 (M+H)$^+$. $^1$H NMR (400 MHz, DMSO-d$_6$): δ 8.81 (s, 1H), 8.60 (d, J=4.8 Hz, 1H), 8.56 (s, 1H), 8.25 (t, J=5.6 Hz, 1H), 8.03 (d, J=8.0 Hz, 1H), 7.55-7.45 (m, 2H), 6.79 (d, J=16.0 Hz, 1H), 3.78-3.75 (m, 2H), 3.55-3.51 (m, 2H), 3.35-3.30 (m, 2H), 1.57 (s, 2H), 1.54-1.45 (m, 2H), 0.71-0.59 (m, 1H).

Example 189: (E)-3-(6-aminopyridin-3-yl)-N-(2-((1R,5S,6s)-3-(pyrimidin-2-yl)-3-azabicyclo[3.1.0]hexan-6-yl)ethyl)acrylamide

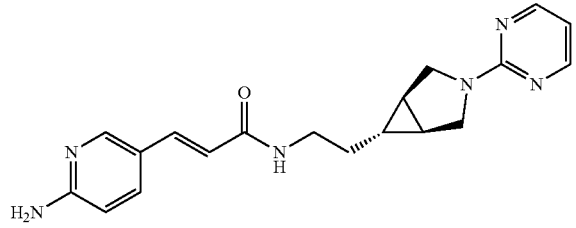

To a solution of Intermediate 1 (150 mg, 0.67 mol) in dichloromethane (5 mL) was added trifluoroacetic acid (2.31 g, 24.2 mmol) at 20° C. The reaction mixture was stirred at 20° C. for 12 h. The solution was concentrated under vacuum to give 150 mg of crude 2-((1R,5S,6s)-3-azabicyclo[3.1.0]hexan-6-yl)acetonitrile as a light yellow oil. MS (ESI) m/z: 123.3 (M+H)$^+$.

To a solution of 2-((1R,5S,6s)-3-azabicyclo[3.1.0]hexan-6-yl)acetonitrile (150 mg, 0.64 mmol, as TFA salt) in toluene (10 mL) was added cesium carbonate (827 mg, 2.54 mmol) at 25° C. The mixture was stirred at 25° C. for 0.5 h followed by the addition of 2,2'-bis(diphenyl phosphino)-1,1'-binaphthyl (40 mg, 0.060 mmol), tris(dibenzylideneacetone)-dipalladium (29 mg, 0.030 mmol) and 2-bromopyrimidine (111 mg, 0.70 mmol) under an atmosphere of nitrogen. The mixture was heated to 100° C. and stirred for 10 h. The reaction was quenched with saturated aqueous ammonium chloride (0.5 mL) and concentrated under vacuum. The resulting residue was diluted with water (15 mL) and ethyl acetate (20 mL), and the aqueous layer was extracted with ethyl acetate (10 mL×2). The combined organic layers were washed with brine (10 mL), dried over sodium sulfate and concentrated under vacuum. The resulting crude product was purified by silica gel column chromatography (petroleum ether/ethyl acetate, from 20/1 to 5/1) to give 70 mg (55%) of 2-((1R,5S,6s)-3-(pyrimidin-2-yl)-3-azabicyclo[3.1.0]hexan-6-yl)acetonitrile as a colorless oil. MS (ESI) m/z: 201.3 (M+H)$^+$.

Ammonia gas was bubbled through methanol (5 mL) at 0° C. for 30 min, and 2-((1R,5S,6s)-3-(pyrimidin-2-yl)-3-azabicyclo[3.1.0]hexan-6-yl)acetonitrile (60 mg, 0.30 mmol) was added to the solution. Raney nickel (0.1 g) was added to the reaction mixture under an atmosphere of nitrogen. The suspension was purged with hydrogen gas three times and stirred at 25° C. under a hydrogen atmosphere (15 psi) for 12 h. The reaction mixture was filtered and the filtrate was concentrated under vacuum to give 40 mg of crude 2-((1R,5S,6s)-3-(pyrimidin-2-yl)-3-azabicyclo[3.1.0]hexan-6-yl)ethanamine as a colorless oil. MS (ESI) m/z: 205.4 (M+H)$^+$.

To a solution of (E)-3-(6-amino-3-pyridyl)prop-2-enoic acid (38.6 mg, 0.24 mmol) in pyridine (3 mL) was added 1-(3-dimethylaminopropyl)-3-ethylcarbodiimide hydrochloride (45.1 mg, 0.24 mmol). The mixture was stirred at 25° C. for 15 min. 2-((1R,5S,6s)-3-(Pyrimidin-2-yl)-3-azabicyclo[3.1.0]hexan-6-yl)ethanamine (40.0 mg, 0.20 mmol) was added and the solution was stirred at 25° C. for 3 h. The reaction mixture was concentrated under vacuum, and the resulting residue was purified by preparative HPLC (Phenomenex Gemini C18 column (150×25 mm, 10 um); flow rate: 25 mL/min; gradient: 11%-41% B over 10 min;

mobile phase A: 0.05% aqueous ammonium hydroxide, mobile phase B: acetonitrile) to give 24 mg (34%) of the title compound as a yellow solid. MS (ESI) m/z: 351.4 (M+H)$^+$.
$^1$H NMR (400 MHz, DMSO-d$_6$): δ 8.30 (d, J=4.8 Hz, 1H), 8.05 (d, J=2.0 Hz, 1H), 7.98-7.93 (m, 1H), 7.59-7.56 (dd, J=2.4 Hz, 4.8 Hz, 1H), 7.25 (d, J=11.6 Hz, 1H), 6.59 (t, J=4.8 Hz, 1H), 6.45 (d, J=8.8 Hz, 1H), 6.39 (s, 2H), 6.34 (d, J=11.6 Hz, 1H), 3.77-3.72 (m, 2H), 3.44-3.42 (m, 2H), 3.21-3.16 (m, 2H), 1.49-1.47 (m, 2H), 1.43-1.41 (m, 2H), 0.59-0.51 (m, 1H).

Examples 190-204

The following compounds were prepared substantially according to the procedures described above:

| Ex. No. | Chemical structure | Chemical name | MS (ESI) m/z (M + H)$^+$ |
|---|---|---|---|
| 190 | 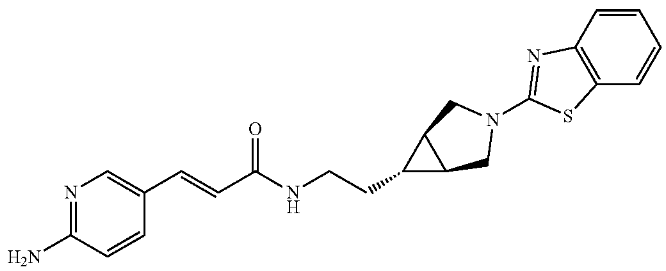 [SMILES: Nc1ccc(/C=C/C(=O)NCC[C@@H]2[C@H]3CN(c4nc5ccccc5s4)C[C@@H]23)cn1] | (E)-3-(6-aminopyridin-3-yl)-N-(2-((1R,5S,6s)-3-(benzo[d]thiazol-2-yl)-3-azabicyclo[3.1.0]hexan-6-yl)ethyl)acrylamide | 406.3 |
| 191 | 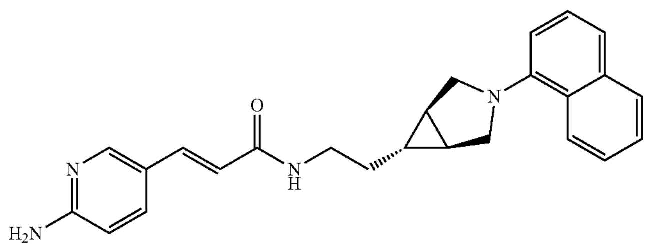 [SMILES: Nc1ccc(/C=C/C(=O)NCC[C@@H]2[C@H]3CN(c4cccc5ccccc45)C[C@@H]23)cn1] | (E)-3-(6-aminopyridin-3-yl)-N-(2-((1R,5S,6s)-3-(naphthalen-1-yl)-3-azabicyclo[3.1.0]hexan-6-yl)ethyl)acrylamide | 399.4 |
| 192 | 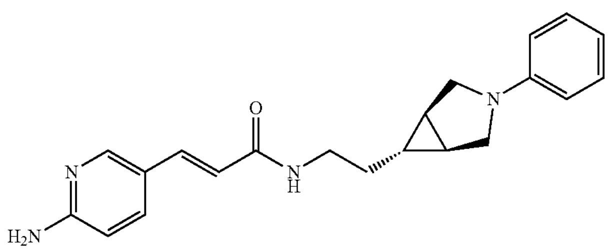 [SMILES: Nc1ccc(/C=C/C(=O)NCC[C@@H]2[C@H]3CN(c4ccccc4)C[C@@H]23)cn1] | (E)-3-(6-aminopyridin-3-yl)-N-(2-((1R,5S,6s)-3-phenyl-3-azabicyclo[3.1.0]hexan-6-yl)ethyl)acrylamide | 349.4 |
| 193 | 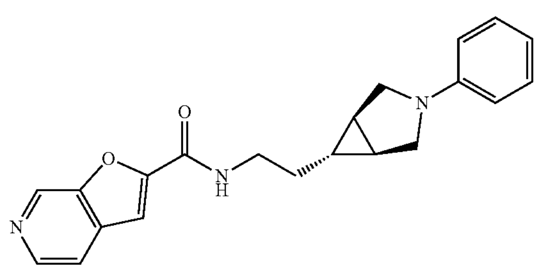 [SMILES: O=C(NCC[C@@H]1[C@H]2CN(c3ccccc3)C[C@@H]12)c1cc2ccncc2o1] | N-(2-((1R,5S,6s)-3-phenyl-3-azabicyclo[3.1.0]hexan-6-yl)ethyl)furo[2,3-c]pyridine-2-carboxamide | 348.3 |
| 194 | 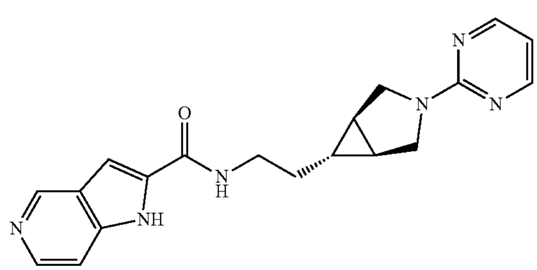 [SMILES: O=C(NCC[C@@H]1[C@H]2CN(c3ncccn3)C[C@@H]12)c1cc2cnccc2[nH]1] | N-(2-((1R,5S,6s)-3-(pyrimidin-2-yl)-3-azabicyclo[3.1.0]hexan-6-yl)ethyl)-1H-pyrrolo[3,2-c]pyridine-2-carboxamide | 349.3 |

-continued

| Ex. No. | Chemical structure | Chemical name | MS (ESI) m/z (M + H)+ |
|---|---|---|---|
| 195 | 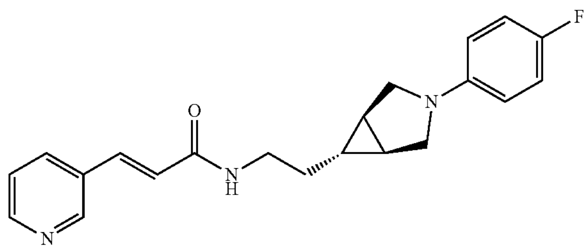 [SMILES: O=C(/C=C/c1cccnc1)NCC[C@@H]1[C@H]2CN(c3ccc(F)cc3)C[C@@H]12] | (E)-N-(2-((1R,5S,6s)-3-(4-fluorophenyl)-3-azabicyclo[3.1.0]hexan-6-yl)ethyl)-3-(pyridin-3-yl)acrylamide | 352.3 |
| 196 | 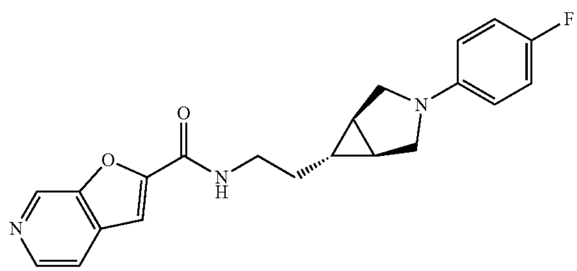 [SMILES: O=C(NCC[C@@H]1[C@H]2CN(c3ccc(F)cc3)C[C@@H]12)c1cc2ccncc2o1] | N-(2-((1R,5S,6s)-3-(4-fluorophenyl)-3-azabicyclo[3.1.0]hexan-6-yl)ethyl)furo[2,3-c]pyridine-2-carboxamide | 366.3 |
| 197 | 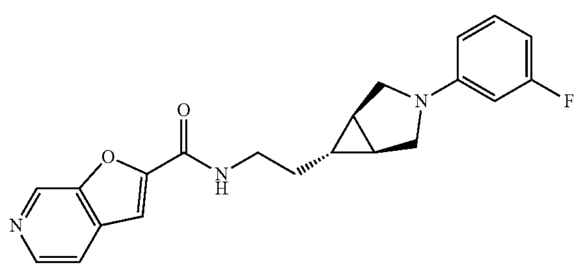 [SMILES: O=C(NCC[C@@H]1[C@H]2CN(c3cccc(F)c3)C[C@@H]12)c1cc2ccncc2o1] | N-(2-((1R,5S,6s)-3-(3-fluorophenyl)-3-azabicyclo[3.1.0]hexan-6-yl)ethyl)furo[2,3-c]pyridine-2-carboxamide | 366.3 |
| 198 | 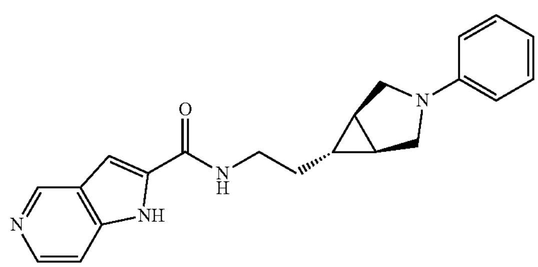 [SMILES: O=C(NCC[C@@H]1[C@H]2CN(c3ccccc3)C[C@@H]12)c1cc2cnccc2[nH]1] | N-(2-((1R,5S,6s)-3-phenyl-3-azabicyclo[3.1.0]hexan-6-yl)ethyl)-1H-pyrrolo[3,2-c]pyridine-2-carboxamide | 347.3 |
| 199 | 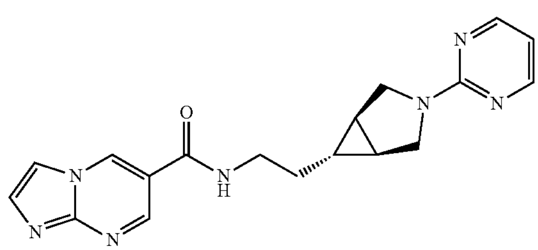 [SMILES: O=C(NCC[C@@H]1[C@H]2CN(c3ncccn3)C[C@@H]12)c1cnc2nccn2c1] | N-(2-((1R,5S,6s)-3-(pyrimidin-2-yl)-3-azabicyclo[3.1.0]hexan-6-yl)ethyl)imidazo[1,2-a]pyrimidine-6-carboxamide | 350.3 |

-continued

| Ex. No. | Chemical structure | Chemical name | MS (ESI) m/z (M + H)+ |
|---|---|---|---|
| 200 | 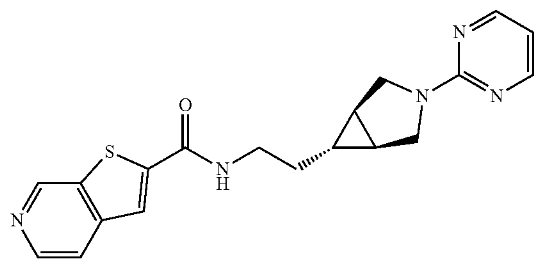 [SMILES: O=C(NCC[C@@H]1[C@H]2CN(c3ncccn3)C[C@@H]12)c1cc2ccncc2s1] | N-(2-((1R,5S,6s)-3-(pyrimidin-2-yl)-3-azabicyclo[3.1.0]hexan-6-yl)ethyl)thieno[2,3-c]pyridine-2-carboxamide | 366.3 |
| 201 | 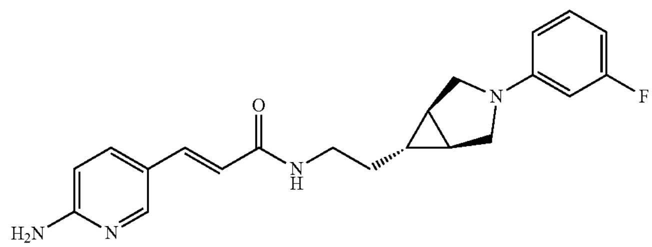 [SMILES: Nc1ccc(/C=C/C(=O)NCC[C@@H]2[C@H]3CN(c4cccc(F)c4)C[C@@H]23)cn1] | (E)-3-(6-aminopyridin-3-yl)-N-(2-((1R,5S,6s)-3-(3-fluorophenyl)-3-azabicyclo[3.1.0]hexan-6-yl)ethyl)acrylamide | 367.4 |
| 202 | 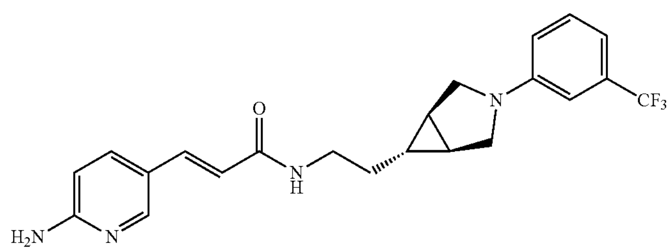 [SMILES: Nc1ccc(/C=C/C(=O)NCC[C@@H]2[C@H]3CN(c4cccc(C(F)(F)F)c4)C[C@@H]23)cn1] | (E)-3-(6-aminopyridin-3-yl)-N-(2-((1R,5S,6s)-3-(3-(trifluoromethyl)phenyl)-3-azabicyclo[3.1.0]hexan-6-yl)ethyl)acrylamide | 417.4 |
| 203 | 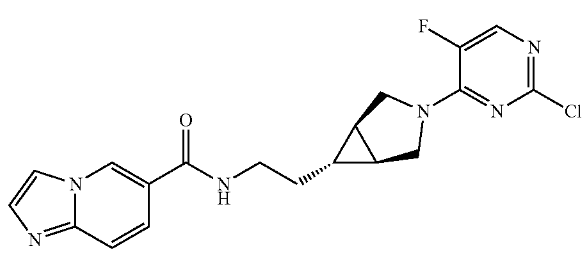 [SMILES: O=C(NCC[C@@H]1[C@H]2CN(c3nc(Cl)ncc3F)C[C@@H]12)c1ccc2nccn2c1] | N-(2-((1R,5S,6s)-3-(2-chloro-5-fluoropyrimidin-4-yl)-3-azabicyclo[3.1.0]hexan-6-yl)ethyl)imidazo[1,2-a]pyridine-6-carboxamide | 401.0 |
| 204 | 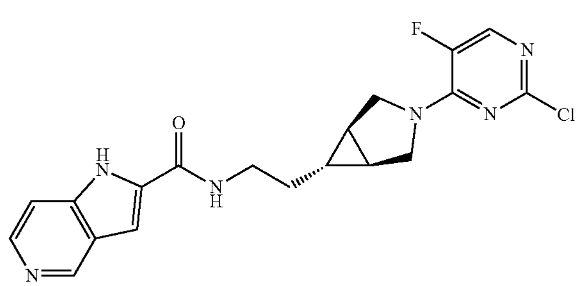 [SMILES: O=C(NCC[C@@H]1[C@H]2CN(c3nc(Cl)ncc3F)C[C@@H]12)c1cc2cnccc2[nH]1] | N-(2-((1R,5S,6s)-3-(2-chloro-5-fluoropyrimidin-4-yl)-3-azabicyclo[3.1.0]hexan-6-yl)ethyl)-1H-pyrrolo[3,2-c]pyridine-2-carboxamide | 401.1 |

Example 205: (E)-N-(2-((1R,5S,6s)-3-(2-chloro-5-fluoropyrimidin-4-yl)-3-azabicyclo[3.1.0]hexan-6-yl)ethyl)-3-(6-chloropyridin-3-yl)acrylamide

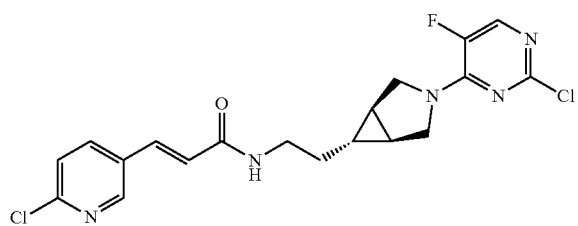 [SMILES: O=C(/C=C/c1ccc(Cl)nc1)NCC[C@@H]1[C@H]2CN(c3nc(Cl)ncc3F)C[C@@H]12]

To a solution of 2-((1R,5S,6s)-3-azabicyclo[3.1.0]hexan-6-yl)acetonitrile (1.0 g, 4.23 mmol, TFA salt) in 1,4-dioxane (15 mL) was added diisopropylethylamine (1.09 g, 8.47 mmol), and 2,4-dichloro-5-fluoropyrimidine (706 mg, 4.23 mmol). The reaction mixture was stirred at 60° C. for 2 h. The reaction mixture was cooled to room temperature, concentrated under vacuum, and the resulting residue was purified by silica gel column chromatography (petroleum ether/ethyl acetate, from 1/0 to 3/1) to give 600 mg (55%) of 2-((1R,5S,6s)-3-(2-chloro-5-fluoropyrimidin-4-yl)-3-azabicyclo[3.1.0]hexan-6-yl)acetonitrile as a white solid. MS (ESI) m/z: 252.8 (M+H)⁺.

To a solution of 2-((1R,5S,6s)-3-(2-chloro-5-fluoropyrimidin-4-yl)-3-azabicyclo[3.1.0]hexan-6-yl)acetonitrile (300 mg, 1.16 mmol) in ethanol (8 mL) at 0° C. was added nickel chloride (151 mg, 1.16 mmol) and sodium borohydride (132 mg, 3.49 mmol). The reaction mixture was warmed to and stirred at 25° C. for 2 h. The resulting suspension was filtered and concentrated under vacuum. The resulting residue was diluted with ethyl acetate (15 mL), washed with water (10 mL) and brine (20 mL×2), dried over sodium sulfate and concentrated under vacuum to give 180 mg of crude 2-((1R,5S,6s)-3-(2-chloro-5-fluoropyrimidin-4-yl)-3-azabicyclo[3.1.0]hexan-6-yl)ethanamine as a light yellow oil. MS (ESI) m/z: 257.1 (M+H)⁺

To a solution of (E)-3-(6-chloro-3-pyridyl)prop-2-enoic acid (39.3 mg, 0.21 mmol) in pyridine (3 mL) was added 1-(3-dimethylaminopropyl)-3-ethylcarbodiimide hydrochloride (41.1 mg, 0.21 mmol). The mixture was stirred at 25° C. for 15 min and 2-((1R,5S,6s)-3-(2-chloro-5-fluoropyrimidin-4-yl)-3-azabicyclo[3.1.0]hexan-6-yl)ethanamine (50 mg, 0.19 mmol) was added. The mixture was stirred at 25° C. for 1 h and then concentrated under vacuum to afford a residue. The residue was diluted with ethyl acetate (15 mL), washed with water (10 mL) and brine (10 mL×2), dried over sodium sulfate and concentrated under vacuum. The resulting residue was purified by preparative HPLC (Phenomenex Gemini C18 column (150×25 mm, 5 um); flow rate: 25 mL/min; gradient: 40%-70% B over 9 min; mobile phase A: 0.1% aqueous trifluoroacetate, mobile phase B: acetonitrile) to give 19.8 mg (23%) of the title compound as a white solid. MS (ESI) m/z: 422.0 (M+H)⁺. ¹H NMR (400 MHz, DMSO-d₆): δ 8.60 (d, J=2.4 Hz, 1H), 8.23 (d, J=6.0 Hz, 1H), 8.11 (d, J=6.4 Hz, 1H), 8.04 (d, J=8.8 Hz, 1H), 7.57 (d, J=8.4 Hz, 1H), 7.51 (d, J=16.0 Hz, 1H), 6.74 (d, J=16.0 Hz, 1H), 3.86-3.84 (m, 2H), 3.70-3.60 (m, 2H), 3.29-3.24 (m, 2H), 1.55-1.53 (m, 2H), 1.45-1.42 (m, 2H), 0.64-0.52 (m, 1H).

Examples 206-224

The following compounds were prepared substantially according to the procedures described above:

| Ex. No. | Chemical structure | Chemical name | MS (ESI) m/z (M + H)⁺ |
|---|---|---|---|
| 206 | 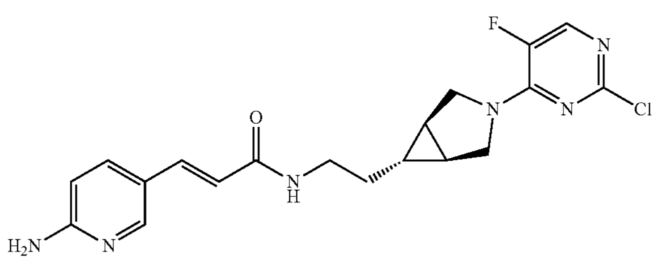 [SMILES: Nc1ccc(/C=C/C(=O)NCC[C@@H]2[C@H]3CN(c4nc(Cl)ncc4F)C[C@@H]23)cn1] | (E)-3-(6-aminopyridin-3-yl)-N-(2-((1R,5S,6s)-3-(2-chloro-5-fluoropyrimidin-4-yl)-3-azabicyclo[3.1.0]hexan-6-yl)ethyl)acrylamide | 403.0 |
| 207 | 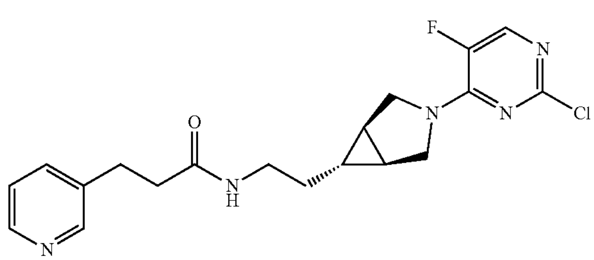 [SMILES: O=C(CCc1cccnc1)NCC[C@@H]1[C@H]2CN(c3nc(Cl)ncc3F)C[C@@H]12] | N-(2-((1R,5S,6s)-3-(2-chloro-5-fluoropyrimidin-4-yl)-3-azabicyclo[3.1.0]hexan-6-yl)ethyl)-3-(pyridin-3-yl)propanamide | 390.2 |

| Ex. No. | Chemical structure | Chemical name | MS (ESI) m/z (M + H)+ |
|---|---|---|---|
| 208 | 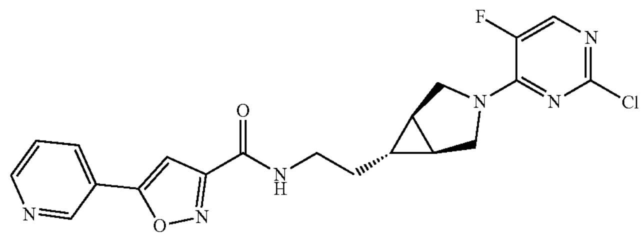 [SMILES: O=C(NCC[C@@H]1[C@H]2CN(c3nc(Cl)ncc3F)C[C@@H]12)c1cc(-c2cccnc2)on1] | N-(2-((1R,5S,6s)-3-(2-chloro-5-fluoropyrimidin-4-yl)-3-azabicyclo[3.1.0]hexan-6-yl)ethyl)-5-(pyridin-3-yl)isoxazole-3-carboxamide | 429.2 |
| 209 | 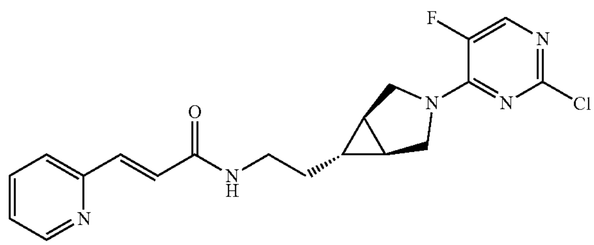 | (E)-N-(2-((1R,5S,6s)-3-(2-chloro-5-fluoropyrimidin-4-yl)-3-azabicyclo[3.1.0]hexan-6-yl)ethyl)-3-(pyridin-2-yl)acrylamide | 388.0 |
| 210 | 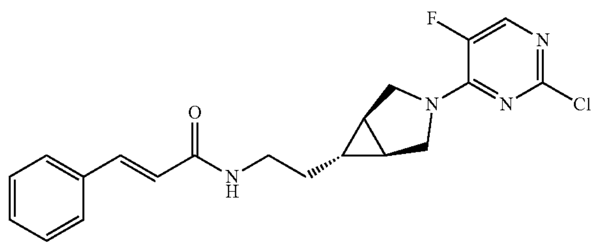 [SMILES: O=C(/C=C/c1ccccc1)NCC[C@@H]1[C@H]2CN(c3nc(Cl)ncc3F)C[C@@H]12] | N-(2-((1R,5S,6s)-3-(2-chloro-5-fluoropyrimidin-4-yl)-3-azabicyclo[3.1.0]hexan-6-yl)ethyl)cinnamamide | 387.2 |
| 211 | 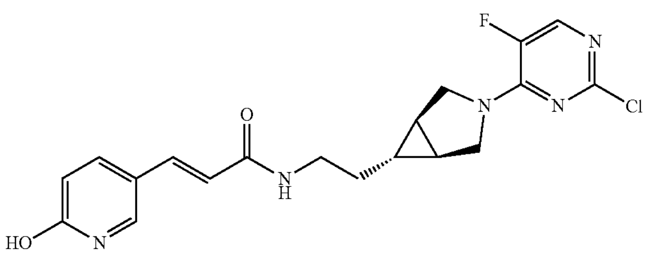 [SMILES: O=C(/C=C/c1ccc(O)nc1)NCC[C@@H]1[C@H]2CN(c3nc(Cl)ncc3F)C[C@@H]12] | (E)-N-(2-((1R,5S,6s)-3-(2-chloro-5-fluoropyrimidin-4-yl)-3-azabicyclo[3.1.0]hexan-6-yl)ethyl)-3-(6-hydroxypyridin-3-yl)acrylamide | 404.2 |
| 212 | 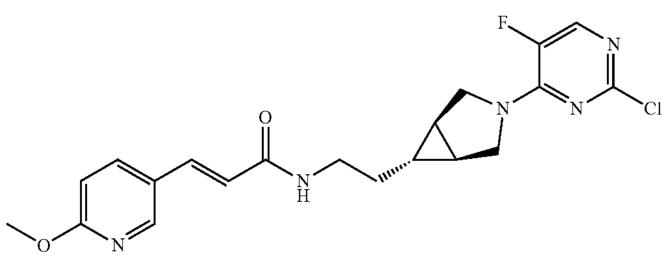 [SMILES: COc1ccc(/C=C/C(=O)NCC[C@@H]2[C@H]3CN(c4nc(Cl)ncc4F)C[C@@H]23)cn1] | (E)-N-(2-((1R,5S,6s)-3-(2-chloro-5-fluoropyrimidin-4-yl)-3-azabicyclo[3.1.0]hexan-6-yl)ethyl)-3-(6-methoxypyridin-3-yl)acrylamide | 418.2 |
| 213 | 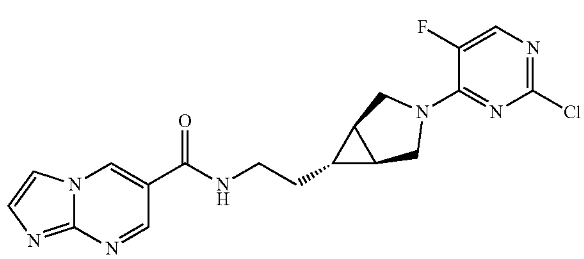 [SMILES: O=C(NCC[C@@H]1[C@H]2CN(c3nc(Cl)ncc3F)C[C@@H]12)c1cnc2nccn2c1] | N-(2-((1R,5S,6s)-3-(2-chloro-5-fluoropyrimidin-4-yl)-3-azabicyclo[3.1.0]hexan-6-yl)ethyl)imidazo[1,2-a]pyrimidine-6-carboxamide | 402.1 |

-continued

| Ex. No. | Chemical structure | Chemical name | MS (ESI) m/z (M + H)+ |
|---|---|---|---|
| 214 | 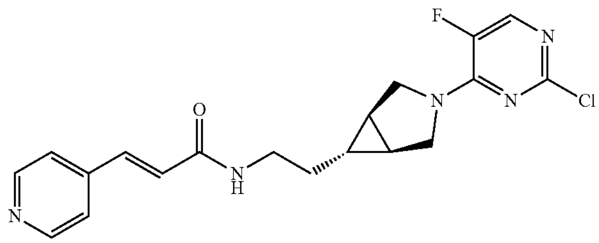 [SMILES: O=C(/C=C/c1ccncc1)NCC[C@@H]1[C@H]2CN(c3nc(Cl)ncc3F)C[C@@H]12] | (E)-N-(2-((1R,5S,6s)-3-(2-chloro-5-fluoropyrimidin-4-yl)-3-azabicyclo[3.1.0]hexan-6-yl)ethyl)-3-(pyridin-4-yl)acrylamide | 388.3 |
| 215 | 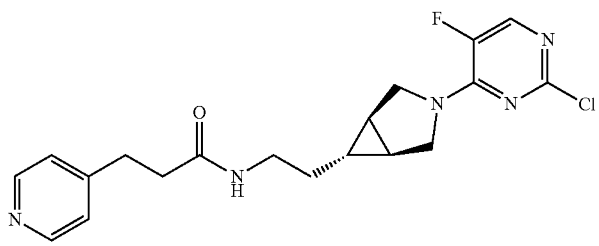 [SMILES: O=C(CCc1ccncc1)NCC[C@@H]1[C@H]2CN(c3nc(Cl)ncc3F)C[C@@H]12] | N-(2-((1R,5S,6s)-3-(2-chloro-5-fluoropyrimidin-4-yl)-3-azabicyclo[3.1.0]hexan-6-yl)ethyl)-3-(pyridin-4-yl)propanamide | 390.2 |
| 216 | 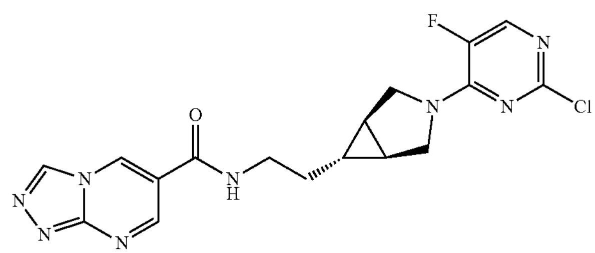 [SMILES: O=C(NCC[C@@H]1[C@H]2CN(c3nc(Cl)ncc3F)C[C@@H]12)c1cnc2nncn2c1] | N-(2-((1R,5S,6s)-3-(2-chloro-5-fluoropyrimidin-4-yl)-3-azabicyclo[3.1.0]hexan-6-yl)ethyl)-[1,2,4]triazolo[4,3-a]pyridine-6-carboxamide | 402.2 |
| 217 | 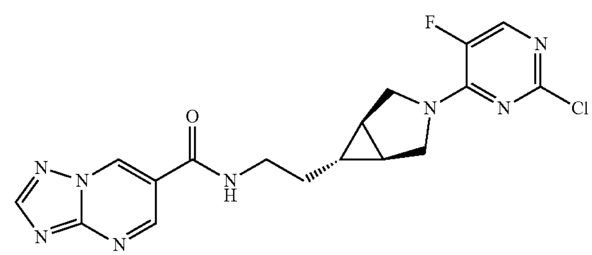 [SMILES: O=C(NCC[C@@H]1[C@H]2CN(c3nc(Cl)ncc3F)C[C@@H]12)c1cnc2ncnn2c1] | N-(2-((1R,5S,6s)-3-(2-chloro-5-fluoropyrimidin-4-yl)-3-azabicyclo[3.1.0]hexan-6-yl)ethyl)-[1,2,4]triazolo[1,5-a]pyridine-6-carboxamide | 402.2 |
| 218 | 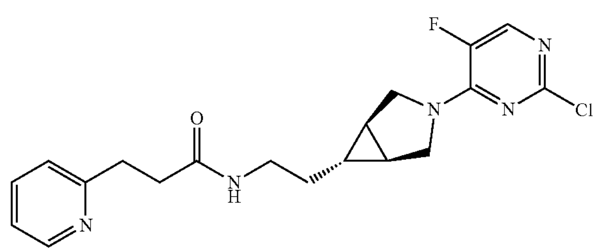 [SMILES: O=C(CCc1ccccn1)NCC[C@@H]1[C@H]2CN(c3nc(Cl)ncc3F)C[C@@H]12] | N-(2-((1R,5S,6s)-3-(2-chloro-5-fluoropyrimidin-4-yl)-3-azabicyclo[3.1.0]hexan-6-yl)ethyl)-3-(pyridin-2-yl)propanamide | 390.2 |
| 219 | 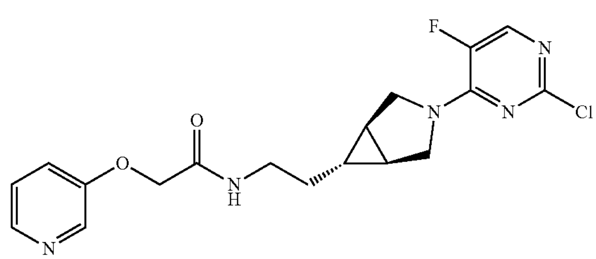 [SMILES: O=C(COc1cccnc1)NCC[C@@H]1[C@H]2CN(c3nc(Cl)ncc3F)C[C@@H]12] | N-(2-((1R,5S,6s)-3-(2-chloro-5-fluoropyrimidin-4-yl)-3-azabicyclo[3.1.0]hexan-6-yl)ethyl)-2-(pyridin-3-yloxy)acetamide | 392.2 |

-continued

| Ex. No. | Chemical structure | Chemical name | MS (ESI) m/z (M + H)+ |
|---|---|---|---|
| 220 | 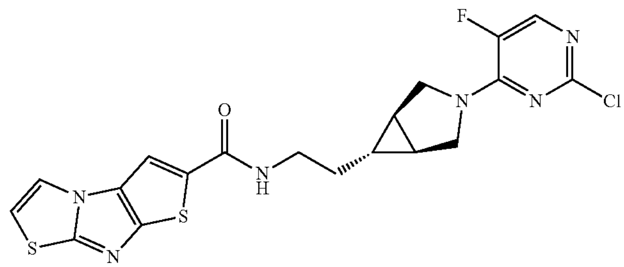 [SMILES: O=C(NCC[C@@H]1[C@H]2CN(c3nc(Cl)ncc3F)C[C@@H]12)c1cc2c(nc3sccn32)s1] | N-(2-((1R,5S,6s)-3-(2-chloro-5-fluoropyrimidin-4-yl)-3-azabicyclo[3.1.0]hexan-6-yl)ethyl)thieno[2',3':4,5]imidazo[2,1-b]thiazole-2-carboxamide | 463.0 |
| 221 | 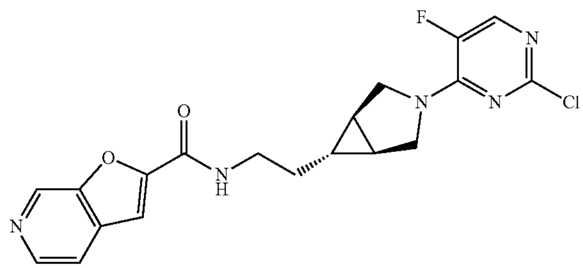 | N-(2-((1R,5S,6s)-3-(2-chloro-5-fluoropyrimidin-4-yl)-3-azabicyclo[3.1.0]hexan-6-yl)ethyl)furo[2,3-c]pyridine-2-carboxamide | 402.2 |
| 222 | 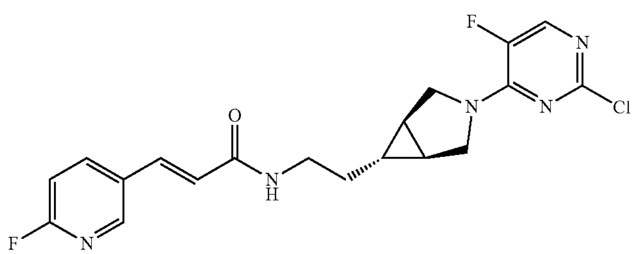 [SMILES: O=C(/C=C/c1ccc(F)nc1)NCC[C@@H]1[C@H]2CN(c3nc(Cl)ncc3F)C[C@@H]12] | (E)-N-(2-((1R,5S,6s)-3-(2-chloro-5-fluoropyrimidin-4-yl)-3-azabicyclo[3.1.0]hexan-6-yl)ethyl)-3-(6-fluoropyridin-3-yl)acrylamide | 406.2 |
| 223 | 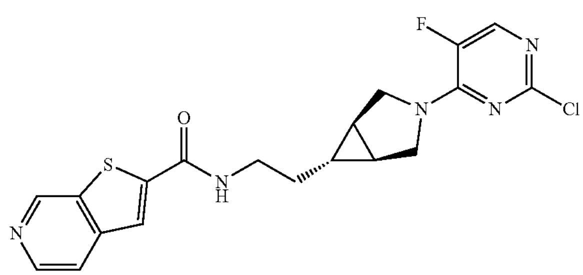 [SMILES: O=C(NCC[C@@H]1[C@H]2CN(c3nc(Cl)ncc3F)C[C@@H]12)c1cc2ccncc2s1] | N-(2-((1R,5S,6s)-3-(2-chloro-5-fluoropyrimidin-4-yl)-3-azabicyclo[3.1.0]hexan-6-yl)ethyl)thieno[2,3-c]pyridine-2-carboxamide | 418.1 |
| 224 | 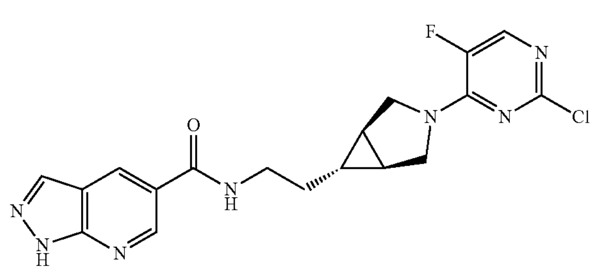 [SMILES: O=C(NCC[C@@H]1[C@H]2CN(c3nc(Cl)ncc3F)C[C@@H]12)c1cnc2[nH]ncc2c1] | N-(2-((1R,5S,6s)-3-(2-chloro-5-fluoropyrimidin-4-yl)-3-azabicyclo[3.1.0]hexan-6-yl)ethyl)-1H-pyrazolo[3,4-b]pyridine-5-carboxamide | 402.2 |

Example 225: N-(2-((1R,5S,6s)-3-(2-chloro-5-fluoropyrimidin-4-yl)-3-azabicyclo[3.1.0]hexan-6-yl)ethyl)isoindoline-2-carboxamide

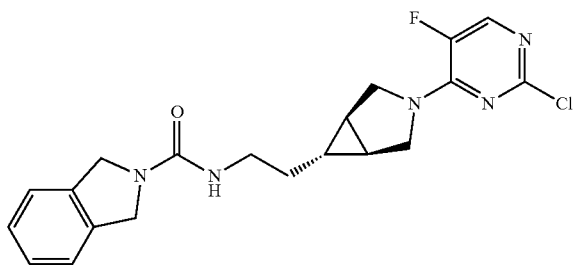 [SMILES: O=C(NCC[C@@H]1[C@H]2CN(c3nc(Cl)ncc3F)C[C@@H]12)N1Cc2ccccc2C1]

To a solution of 2-((1R,5S,6s)-3-(2-chloro-5-fluoropyrimidin-4-yl)-3-azabicyclo[3.1.0]hexan-6-yl)ethanamine (50 mg, 0.19 mmol) in acetonitrile (3 mL) was added bis(2,5-dioxopyrrolidin-1-yl) carbonate (52.3 mg, 0.20 mmol) and triethylamine (20.7 mg, 0.20 mmol). The mixture was stirred at 25° C. for 1 h. Isoindoline (23.2 mg, 0.195 mmol) was added to the resulting mixture and the reaction mixture was stirred at 25° C. for 12 h. The suspension was filtered and the filtrate was concentrated under vacuum. The residue was purified by preparative HPLC (Phenomenex Gemini C18 column (150×25 mm, 5 um); flow rate: 25 mL/min; gradient: 40%-70% B over 9 min; mobile phase A: 0.1% aqueous trifluoroacetic acid, mobile phase B: acetonitrile) to give 19.4 mg (19%) of the title compound as a white solid. MS (ESI) m/z: 402.1 (M+H)+. 1H NMR (400 MHz, DMSO-d6): δ 8.09 (d, J=4.4 Hz, 1H), 7.37-7.27 (m, 4H), 6.35 (s, 1H), 4.58 (s, 4H), 3.87-3.84 (m, 2H), 3.64-3.63 (m, 2H), 3.18-3.16 (m, 2H), 1.53-1.50 (m, 2H), 1.45-1.40 (m, 2H), 0.53-0.58 (m, 1H).

Examples 226-227

The following compounds were prepared substantially according to the procedures described above:

| Ex. No. | Chemical structure | Chemical name | MS (ESI) m/z (M + H)+ |
|---|---|---|---|
| 226 | 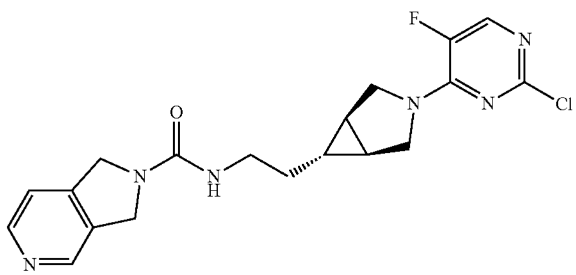 [SMILES: O=C(NCC[C@@H]1[C@H]2CN(c3nc(Cl)ncc3F)C[C@@H]12)N1Cc2ccncc2C1] | N-(2-((1R,5S,6s)-3-(2-chloro-5-fluoropyrimidin-4-yl)-3-azabicyclo[3.1.0]hexan-6-yl)ethyl)-1H-pyrrolo[3,4-c]pyridine-2(3H)-carboxamide | 403.2 |
| 227 | 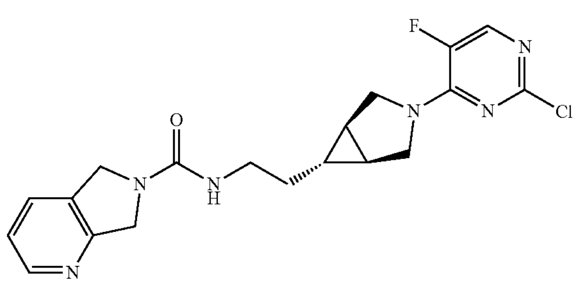 | N-(2-((1R,5S,6s)-3-(2-chloro-5-fluoropyrimidin-4-yl)-3-azabicyclo[3.1.0]hexan-6-yl)ethyl)-5H-pyrrolo[3,4-b]pyridine-6(7H)-carboxamide | 403.2 |

Example 228: (E)-1-(2-((1R,5S,6s)-3-benzoyl-3-azabicyclo[3.1.0]hexan-6-yl)ethyl)-2-cyano-3-(pyridin-4-yl)guanidine

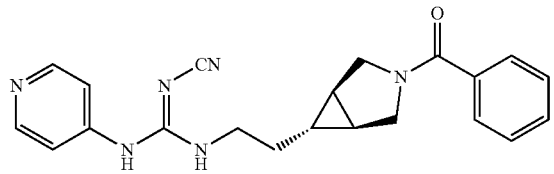 [SMILES: N#C/N=C(\NCC[C@@H]1[C@H]2CN(C(=O)c3ccccc3)C[C@@H]12)Nc1ccncc1]

To a solution of the Example 18 compound (110 mg, 0.30 mmol) in 1,4-dioxane (10 mL) was added a hydrogen chloride/1,4-dioxane solution (4 M, 1 mL) at 0° C. The mixture was stirred at 0° C. for 1 h. The mixture was concentrated under vacuum to obtain 170 mg of crude (E)-1-(2-((1R,5S,6s)-3-azabicyclo[3.1.0]hexan-6-yl)ethyl)-2-cyano-3-(pyridin-4-yl)guanidine as the HCl salt as a yellow solid. MS (ESI) m/z: 271.4 (M+H)$^+$.

To a solution of (E)-1-(2-((1R,5S,6s)-3-azabicyclo[3.1.0]hexan-6-yl)ethyl)-2-cyano-3-(pyridin-4-yl)guanidine (70 mg, 0.23 mmol, HCl salt) in dichloromethane (2 mL) was added N,N-diisopropylethylamine (147 mg, 1.14 mmol). The mixture was stirred at 25° C. for 0.5 h. Benzoyl chloride (38 mg, 0.27 mmol) was added to the reaction mixture dropwise at 0° C. The cooling bath was removed and the mixture was stirred at 25° C. for 0.5 h. The mixture was concentrated under vacuum. An identical reaction was performed on a similar scale (100 mg of starting amine). The resulting residues from the two batches were combined and purified by preparative HPLC (Phenomenex Gemini C18 column (150×25 mm, 5 um); flow rate: 25 mL/min; gradient: 10%-40% B over 10 min; mobile phase A: 0.05% aqueous ammonium hydroxide, mobile phase B: acetonitrile) to give 20.1 mg (10%) of the title compound as a white solid. MS (ESI) m/z: 375.4 (M+H)$^+$. $^1$H NMR (400 MHz, DMSO-d$_6$): δ 9.34 (s, 1H), 8.33 (d, J=5.6 Hz, 2H), 7.71 (s, 1H), 7.41-7.44 (m, 5H), 7.17 (s, 2H), 3.95 (d, J=11.6 Hz, 1H), 3.62 (dd, J=4.0 Hz, 10.4 Hz, 1H), 3.8 (d, J=4.0 Hz, 2H), 3.31 (s, 2H), 1.45-1.54 (m, 1H), 1.37-1.43 (m, 3H), 0.49-0.52 (m, 1H).

Example 229: (1R,5S,6s)-3-methyloxetan-3-yl 6-(2-((E)-2-cyano-3-(pyridin-4-yl)guanidino)ethyl)-3-azabicyclo[3.1.0]hexane-3-carboxylate

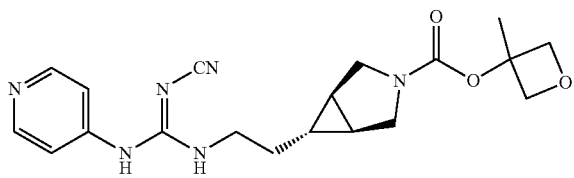 [SMILES: CC1(OC(=O)N2C[C@@H]3[C@@H](CCN/C(=N\C#N)Nc4ccncc4)[C@@H]3C2)COC1]

This compound was prepared substantially according to the procedures described above. MS (ESI) m/z: 385.4 (M+H)$^+$.

Example 230: (1R,5S,6s)-3-methyloxetan-3-yl 6-(2-(isoindoline-2-carboxamido)ethyl)-3-azabicyclo[3.1.0]hexane-3-carboxylate

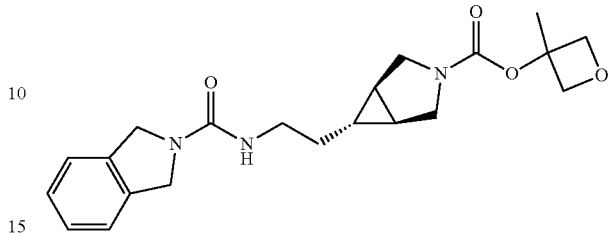

To a solution of the Example 15 compound (150 mg, 0.40 mmol) in dichloromethane (3 mL) was added trifluoroacetic acid (770 mg, 6.75 mmol). The mixture was stirred at 20° C. for 1 h. The reaction mixture was concentrated under vacuum to provide 150 mg of crude N-(2-((1R,5S,6s)-3-azabicyclo[3.1.0]hexan-6-yl)ethyl)isoindoline-2-carboxamide as a light yellow oil. MS (ESI) m/z: 272.4 (M+H)$^+$.

To a solution of N-(2-((1R,5S,6s)-3-azabicyclo[3.1.0]hexan-6-yl)ethyl)isoindoline-2-carboxamide (150 mg, 0.39 mmol, TFA salt) in acetonitrile (3 mL) was added N,N-diisopropylethylamine (100 mg, 0.78 mmol) and 3-methyloxetan-3-yl(4-nitrophenyl) carbonate (99 mg, 0.39 mmol). The reaction mixture was stirred at 20° C. for 1 h. The mixture was concentrated under vacuum to give a residue. The resulting residue was purified by preparative HPLC (Phenomenex Gemini C18 column (150×25 mm, 5 um); flow rate: 25 mL/min; gradient: 25%-49% B over 10 min; mobile phase A: 0.05% aqueous ammonium hydroxide, mobile phase B: acetonitrile) to give 33 mg (22%) of the title compound as an off-white solid. MS (ESI) m/z: 386.4 (M+H)$^+$. $^1$H NMR (400 MHz, DMSO-d$_6$): δ 7.27-7.34 (m, 4H), 6.36 (t, J=4.6 Hz, 1H), 4.58 (t, J=7.6 Hz, 6H), 4.35 (d, J=7.2 Hz 1H), 3.46 (dd, J=10.8 Hz, 16.0 Hz, 2H), 3.29 (d, J=4.0 Hz, 2H), 3.15 (dd, J=2.4 Hz, 4.8 Hz, 2H), 1.59 (s, 3H), 1.32-1.43 (m, 4H), 0.48-0.52 (m, 1H).

Example 231: (1R,5S,6s)-tert-butyl 6-((5-(pyridin-3-yl)isoxazole-3-carboxamido)methyl)-3-azabicyclo[3.1.0]hexane-3-carboxylate

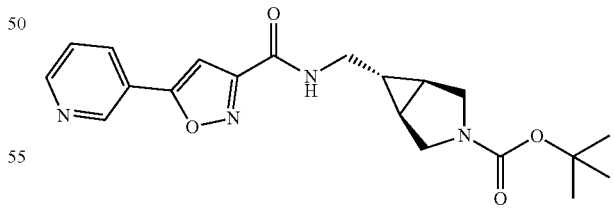

To 25-28% aqueous ammonium hydroxide (15 mL) was added (1R,5S,6r)-tert-butyl 6-(bromomethyl)-3-azabicyclo[3.1.0]hexane-3-carboxylate (100 mg, 0.36 mmol) in a sealed tube. The mixture was heated at 100° C. for 12 h. The mixture was cooled to room temperature and concentrated under vacuum to afford 80 mg of crude (1R,5S,6s)-tert-butyl 6-(aminomethyl)-3-azabicyclo[3.1.0]hexane-3-carboxylate as a yellow oil, which was used without purification. MS (ESI) m/z: 213.4 (M+H)$^+$.

To a solution of 1-(pyridin-3-yl)ethanone (5 g, 41.3 mmol, 4.5 mL) and diethyl oxalate (6.03 g, 41.3 mmol, 5.6 mL) in tetrahydrofuran (150 mL) was added slowly to a solution of freshly prepared sodium methoxide (49.5 mmol, 2.68 g) in methanol (30 mL) at 0° C. The reaction mixture was stirred at 0° C. for 1 h. The solid was filtered, washed with tetrahydrofuran (200 mL) and dried under vacuum. The resulting sodium salt was dissolved in water (100 mL) and the solution was acidified with 10% acetic acid to pH 3-4 at 0° C. The precipitate obtained was filtered and washed with water. The solids are dried under vacuum to give 6.5 g (76%) of methyl 2,4-dioxo-4-(pyridin-3-yl)butanoate as a light yellow solid. MS (ESI) m/z: 208.1 (M+H)$^+$.

To a solution of methyl 2,4-dioxo-4-(pyridin-3-yl)butanoate (1.5 g, 7.24 mmol) in ethanol (30 mL) was added hydroxylamine hydrochloride (503 mg, 7.24 mmol). The mixture was stirred at 80° C. for 5 h. The reaction mixture was concentrated under vacuum to give 1.5 g of crude (Z)-methyl 2-(hydroxyimino)-4-oxo-4-(pyridin-3-yl)butanoate as the HCl salt as a white solid. MS (ESI) m/z: 223.1 (M+H)$^+$. $^1$H NMR (400 MHz, DMSO-d$_6$): δ 8.94 (d, J=1.8 Hz, 1H), 8.90-8.85 (m, 1H), 8.52 (td, J=1.6, 8.2 Hz, 1H), 7.98 (dd, J=5.6, 8.2 Hz, 1H), 4.36 (s, 1H), 3.84 (s, 3H), 3.64 (d, J=18.6 Hz, 1H), 3.42 (d, J=18.6 Hz, 1H).

A solution of (Z)-methyl 2-(hydroxyimino)-4-oxo-4-(pyridin-3-yl)butanoate (500 mg, 1.93 mmol, HCl salt) in formic acid (10 mL) was stirred at 100° C. for 12 h. The reaction mixture was concentrated under vacuum to give 0.45 g of crude methyl 5-(pyridin-3-yl)isoxazole-3-carboxylate as a light yellow solid. MS (ESI) m/z: 205.2 (M+H)$^+$.

To a solution of 5-(pyridin-3-yl)isoxazole-3-carboxylate (450 mg, 2.2 mmol) in methanol (5 mL) was added aqueous lithium hydroxide (2 M, 2.2 mL). The mixture was stirred at 20° C. for 1 h. The reaction mixture was adjusted to pH 6-7 by addition of 2 M hydrochloric acid, and allowing the white solid to precipitate. After filtration, the solid was dried under vacuum to afford 0.4 g of 5-(pyridin-3-yl)isoxazole-3-carboxylic acid as a light yellow solid. MS (ESI) m/z: 191.1 (M+H)$^+$. $^1$H NMR (400 MHz, DMSO-d$_6$): δ 14.17 (s, 1H), 9.17 (d, J=1.6 Hz, 1H), 8.72 (dd, J=1.4, 4.8 Hz, 1H), 8.34 (td, J=1.8, 8.0 Hz, 1H), 7.64-7.55 (m, 2H).

To a solution of 5-(pyridin-3-yl)isoxazole-3-carboxylic acid (71.7 mg, 0.38 mmol) in pyridine (3 mL) was added 1-(3-dimethylaminopropyl)-3-ethylcarbodiimide hydrochloride (86.7 mg, 0.45 mmol) and 1-hydroxybenzotriazole (50.9 mg, 0.38 mmol). The mixture was stirred at 25° C. for 30 min. (1R,5S,6s)-tert-Butyl 6-(aminomethyl)-3-azabicyclo[3.1.0]hexane-3-carboxylate (80 mg, 0.38 mmol) was added into the mixture. The mixture was stirred at 25° C. for 30 min. The mixture was concentrated under vacuum to give a residue. The resulting residue was purified by preparative HPLC (Phenomenex Gemini C18 column (150×25 mm, 5 um); flow rate: 25 mL/min; gradient: 30%-57% B over 10 min; mobile phase A: 0.05% aqueous ammonium hydroxide, mobile phase B: acetonitrile) to give 28 mg (19%) of the title compound as a white solid. MS (ESI) m/z: 407.1 (M+Na)$^+$. $^1$H NMR (400 MHz, DMSO-d$_6$): δ 9.16 (dd, J=0.6, 2.2 Hz, 1H), 8.98 (t, J=5.6 Hz, 1H), 8.72 (dd, J=1.6, 5.0 Hz, 1H), 8.33 (td, J=1.8, 8.2 Hz, 1H), 7.61 (ddd, J=0.8, 5.0, 8.0 Hz, 1H), 7.53 (s, 1H), 3.43 (d, J=11.0 Hz, 2H), 3.27 (d, J=12.2 Hz, 2H), 3.22-3.18 (m, 2H), 1.53 (s, 2H), 1.37 (s, 9H), 0.80 (td, J=3.4, 6.8 Hz, 1H).

Examples 232-236

The following compounds were prepared substantially according to the procedures described above:

| Ex. No. | Chemical structure | Chemical name | MS (ESI) m/z (M + H)$^+$ |
|---|---|---|---|
| 232 | 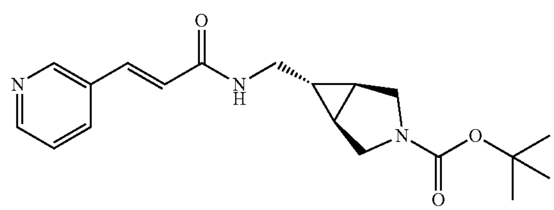 [SMILES: CC(C)(C)OC(=O)N1C[C@@H]2[C@@H](CNC(=O)/C=C/c3cccnc3)[C@@H]2C1] | (1R,5S,6s)-tert-butyl 6-(((E)-3-(pyridin-3-yl)acrylamido)methyl)-3-azabicyclo[3.1.0]hexane-3-carboxylate | 344.4 |
| 233 | 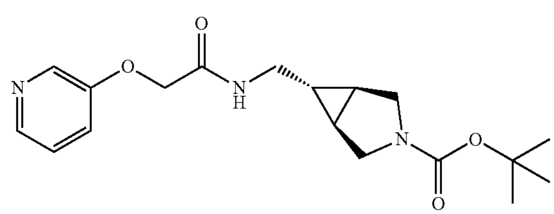 [SMILES: CC(C)(C)OC(=O)N1C[C@@H]2[C@@H](CNC(=O)COc3cccnc3)[C@@H]2C1] | (1R,5S,6s)-tert-butyl 6-((2-(pyridin-3-yloxy)acetamido)methyl)-3-azabicyclo[3.1.0]hexane-3-carboxylate | 348.4 |
| 234 | 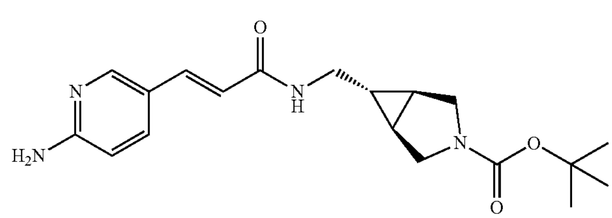 [SMILES: CC(C)(C)OC(=O)N1C[C@@H]2[C@@H](CNC(=O)/C=C/c3ccc(N)nc3)[C@@H]2C1] | (1R,5S,6s)-tert-butyl 6-(((E)-3-(6-aminopyridin-3-yl)acrylamido)methyl)-3-azabicyclo[3.1.0]hexane-3-carboxylate | 359.4 |

| Ex. No. | Chemical structure | Chemical name | MS (ESI) m/z (M + H)+ |
|---|---|---|---|
| 235 | 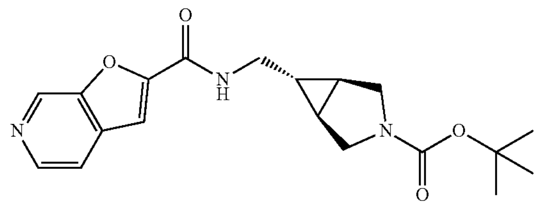 [SMILES: CC(C)(C)OC(=O)N1C[C@@H]2[C@@H](CNC(=O)c3cc4ccncc4o3)[C@@H]2C1] | (1R,5S,6s)-tert-butyl 6-((furo[2,3-c]pyridine-2-carboxamido)methyl)-3-azabicyclo[3.1.0]hexane-3-carboxylate | 358.4 |
| 236 | 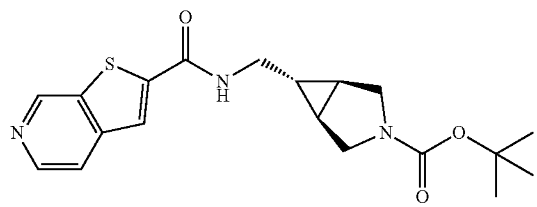 [SMILES: CC(C)(C)OC(=O)N1C[C@@H]2[C@@H](CNC(=O)c3cc4ccncc4s3)[C@@H]2C1] | (1R,5S,6s)-tert-butyl 6-((thieno[2,3-c]pyridine-2-carboxamido)methyl)-3-azabicyclo[3.1.0]hexane-3-carboxylate | 374.3 |

Example 237: (E)-N-(((1R,5S,6s)-3-benzoyl-3-azabicyclo[3.1.0]hexan-6-yl)methyl)-3-(pyridin-3-yl)acrylamide

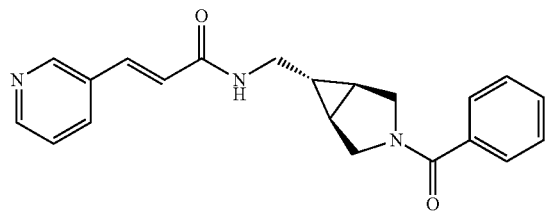 [SMILES: O=C(/C=C/c1cccnc1)NC[C@@H]1[C@H]2CN(C(=O)c3ccccc3)C[C@@H]12]

To a solution of the Example 232 compound (101 mg, 0.26 mmol) in dichloromethane (5 mL) was added trifluoroacetic acid (1.54 g, 13.5 mmol, 1 mL) at 0° C. The mixture was stirred at 0° C. for 30 min. The mixture was concentrated under vacuum to afford 110 mg of crude (E)-N-((1R,5S,6r)-3-azabicyclo[3.1.0]hexan-6-ylmethyl)-3-(pyridin-3-yl)acrylamide as the TFA salt. MS (ESI) m/z: 244.4 (M+H)+.

To a solution of (E)-N-((1R,5S,6r)-3-azabicyclo[3.1.0]hexan-6-ylmethyl)-3-(pyridin-3-yl)acrylamide (40 mg, 0.11 mmol, TFA salt) in pyridine (3 mL) was added N,N-diisopropylethylamine (57.9 mg, 0.45 mmol). The mixture was stirred at 25° C. for 20 min. Benzoyl chloride (15.7 mg, 0.12 mmol) was added to the mixture dropwise at 0° C. The mixture was stirred at 25° C. for 30 min. The mixture was concentrated under vacuum to give a yellow residue. The resulting residue was purified by preparative HPLC (Phenomenex Gemini C18 column (150×25 mm, 10 um); flow rate: 25 mL/min; gradient: 16%-36% B over 8 min; mobile phase A: 0.1% aqueous trifluoroacetic acid, mobile phase B: acetonitrile) to give 26 mg (49%) of the title compound as a yellow solid. MS (ESI) m/z: 348.3 (M+H)+. $^1$H NMR (400 MHz, DMSO-$d_6$): δ 8.78 (d, J=1.8 Hz, 1H), 8.60-8.53 (m, 1H), 8.27 (t, J=5.2 Hz, 1H), 8.04 (d, J=8.1 Hz, 1H), 7.54-7.38 (m, 7H), 6.72 (d, J=15.9 Hz, 1H), 3.97 (d, J=11.7 Hz, 1H), 3.64 (dd, J=4.0, 10.3 Hz, 1H), 3.32-3.31 (m, 2H), 3.14-3.08 (m, 2H), 1.59-1.47 (m, 2H), 0.77-0.69 (m, 1H).

Examples 238-240

The following compounds were prepared substantially according to the procedures described above:

| Ex. No. | Chemical structure | Chemical name | MS (ESI) m/z (M + H)+ |
|---|---|---|---|
| 238 | 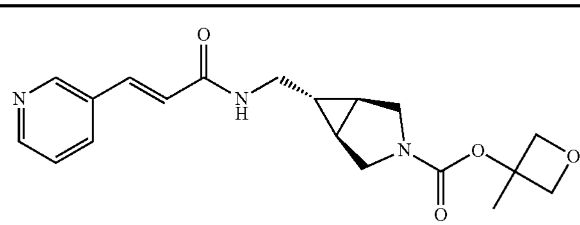 | (1R,5S,6s)-3-methyloxetan-3-yl 6-(((E)-3-(pyridin-3-yl)acrylamido)methyl)-3-azabicyclo[3.1.0]hexane-3-carboxylate | 358.4 |

| Ex. No. | Chemical structure | Chemical name | MS (ESI) m/z (M + H)+ |
|---|---|---|---|
| 239 | 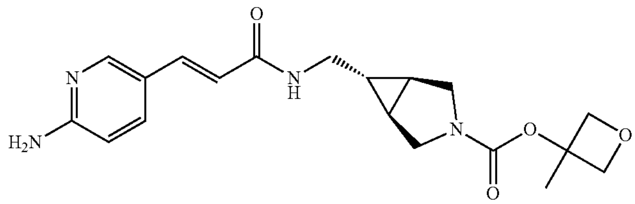 [SMILES: CC1(OC(=O)N2C[C@@H]3[C@@H](CNC(=O)/C=C/c4ccc(N)nc4)[C@@H]3C2)COC1] | (1R,5S,6s)-3-methyloxetan-3-yl 6-(((E)-3-(6-aminopyridin-3-yl)acrylamido)methyl)-3-azabicyclo[3.1.0]hexane-3-carboxylate | 373.4 |
| 240 | 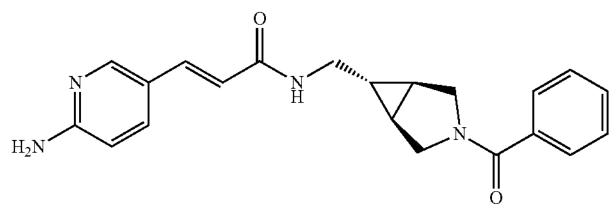 [SMILES: Nc1ccc(/C=C/C(=O)NC[C@@H]2[C@H]3CN(C(=O)c4ccccc4)C[C@@H]23)cn1] | (E)-3-(6-aminopyridin-3-yl)-N-(((1R,5S,6s)-3-benzoyl-3-azabicyclo[3.1.0]hexan-6-yl)methyl)acrylamide | 363.3 |

Example 241: (1R,5S,6s)-tert-butyl 6-((1-((E)-3-(6-aminopyridin-3-yl)acrylamido)cyclopropyl)methyl)-3-azabicyclo[3.1.0]hexane-3-carboxylate

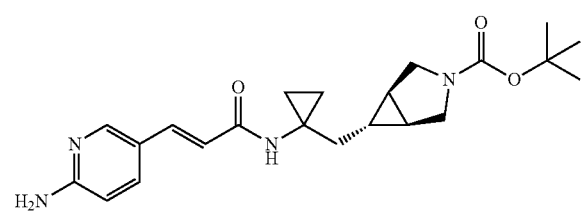 [SMILES: CC(C)(C)OC(=O)N1C[C@@H]2[C@H](C1)[C@H]2CC1(NC(=O)/C=C/c2ccc(N)nc2)CC1]

To a solution of Intermediate 1 (200 mg, 0.90 mmol) and titanium isopropoxide (281 mg, 0.99 mmol) in ethyl ether (10 mL) at −78° C. was added ethylmagnesium bromide (3 M in ether, 0.66 mL) dropwise. The suspension was stirred at −78° C. for 0.5 h and warmed to 20° C. and stirred for 1 h. The mixture was cooled to 0° C., and boron trifluoride diethyl etherate (532 mg, 1.80 mmol) was added to the resulting solution. The reaction mixture was stirred at 20° C. for another 1 h. The reaction mixture was adjusted to pH 5 with 1 M hydrochloric acid at 0° C. and stirred for 0.5 h. The solution was adjusted to pH 10 with 1 M aqueous sodium hydroxide. The mixture was extracted with diethyl ether (10 mL×3). The combined organic layers were dried over anhydrous sodium sulfate and concentrated under vacuum to give 150 mg of crude (1R,5S,6s)-tert-butyl 6-((1-aminocyclopropyl)methyl)-3-azabicyclo[3.1.0]hexane-3-carboxylate as a light-yellow oil. MS (ESI) m/z: 253.4 (M+H)+.

To a solution of (1R,5S,6s)-tert-butyl 6-((1-aminocyclopropyl)methyl)-3-azabicyclo[3.1.0]hexane-3-carboxylate (150 mg, 0.59 mmol) and (E)-3-(6-aminopyridin-3-yl)acrylic acid (97.6 mg, 0.59 mmol) in pyridine (3 mL) was added 1-(3-dimethylaminopropyl)-3-ethylcarbodiimide hydrochloride (125 mg, 0.65 mmol). The mixture was stirred at 20° C. for 1 h. The reaction mixture was concentrated under vacuum to afford a residue. The resulting residue was purified by preparative HPLC ((Phenomenex Gemini C18 column (150×25 mm, 5 um); flow rate: 25 mL/min; gradient: 30%-54% B over 10 min; mobile phase A: 0.05% aqueous ammonium hydroxide, mobile phase B: acetonitrile) to give 38.4 mg (16%) of the title compound as a yellow solid. MS (ESI) m/z: 399.4 (M+H)+. 1H NMR (400 MHz, DMSO-d6): δ 8.19 (s, 1H), 8.04 (s, 1H), 7.55 (d, J=8.8 Hz, 1H), 7.23 (d, J=16.0 Hz, 1H), 6.46 (d, J=8.8 Hz, 1H), 6.39 (s, 2H), 6.28 (d, J=15.6 Hz, 1H), 3.42-3.40 (m, 2H), 3.24-3.18 (m, 2H), 1.52-1.44 (m, 2H), 1.36 (s, 9H), 1.24 (s, 2H), 0.61 (s, 4H), 0.49-0.46 (m, 1H).

Example 242: (1R,5S,6s)-tert-butyl 6-((1-((E)-3-(pyridin-3-yl)acrylamido)cyclopropyl)methyl)-3-azabicyclo[3.1.0]hexane-3-carboxylate

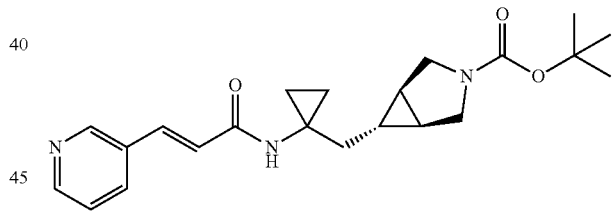

This compound was prepared substantially according to the procedures described above. MS (ESI) m/z: 384.4 (M+H)+.

Example 243: (E)-N-(2-((1R,5S,6s)-3-benzyl-3-azabicyclo[3.1.0]hexan-6-yl)ethyl)-3-(pyridin-3-yl)acrylamide

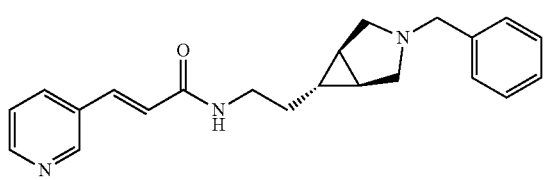 [SMILES: O=C(/C=C/c1cccnc1)NCC[C@@H]1[C@H]2CN(Cc3ccccc3)C[C@@H]12]

To a solution of the Example 1 compound (1.8 g, 5.04 mmol) in dichloromethane (25 mL) was added trifluoroacetic acid (7.7 g, 6.75 mmol, 5.0 mL). The mixture was stirred at 25° C. for 0.5 h. The reaction mixture was concentrated under vacuum to give 1.9 g of crude (E)-N-(2-((1R,5S,6s)-3-azabicyclo[3.1.0]hexan-6-yl)ethyl)-3-(pyridin-3-yl)acrylamide as a yellow oil. MS (ESI) m/z: 258.1 (M+H)+.

To a solution of (E)-N-(2-((1R,5S,6s)-3-azabicyclo[3.1.0]hexan-6-yl)ethyl)-3-(pyridin-3-yl)acrylamide (100 mg, 0.27 mmol, TFA salt) and benzaldehyde (42.9 mg, 0.40 mmol) in methanol (3 mL) was added triethylamine (54.5 mg, 0.54 mmol) and then sodium cyanoborohydride (25.4 mg, 0.40 mmol). The mixture was stirred at 25° C. for 2 h. The reaction mixture was concentrated under vacuum and diluted with ethyl acetate (15 mL). The solution was washed with brine (10 mL×2), dried over sodium sulfate and concentrated under reduced pressure. The residue was purified by prep-HPLC ((Phenomenex Waters Xbridge C18 column (150×25 mm, 5 um); flow rate: 25 mL/min; gradient: 30%-60% B over 10 min; mobile phase A: 0.05% aqueous ammonium hydroxide, mobile phase B: acetonitrile) to give 15 mg (16%) of the title compound as an off-white solid. MS (ESI) m/z: 348.2 (M+H)+. 1H NMR (400 MHz, DMSO-d6): δ 8.75 (d, J=2.0 Hz, 1H), 8.55 (d, J=4.8 Hz, 1H), 8.17 (t, J=6.0 Hz, 1H), 7.97 (d, J=8.0 Hz, 1H), 7.29-7.27 (m, 2H), 7.25-7.22 (m, 5H), 3.54 (s, 2H), 3.24-3.19 (m, 2H), 2.88-2.86 (m, 2H), 2.29-2.27 (m, 2H), 1.36-1.30 (m, 2H), 1.18-1.16 (m, 2H), 1.13-1.10 (m, 1H).

Examples 244-251

The following compounds were prepared substantially according to the procedures described above:

| Ex. No. | Chemical structure | Chemical name | MS (ESI) m/z (M + H)+ |
|---|---|---|---|
| 244 | 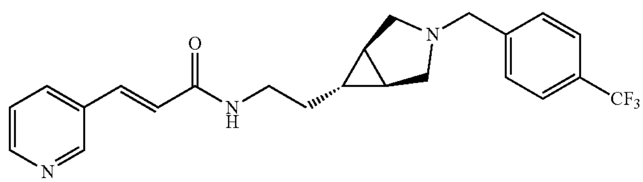 [SMILES: O=C(/C=C/c1cccnc1)NCC[C@@H]1[C@H]2CN(Cc3ccc(C(F)(F)F)cc3)C[C@@H]12] | (E)-3-(pyridin-3-yl)-N-(2-((1R,5S,6s)-3-(4-(trifluoromethyl)benzyl)-3-azabicyclo[3.1.0]hexan-6-yl)ethyl)acrylamide | 416.3 |
| 245 | 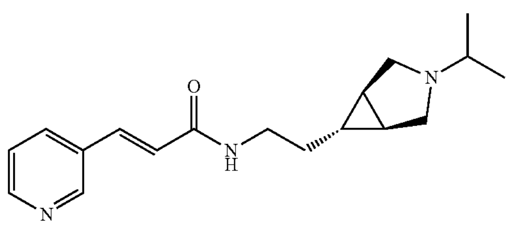 [SMILES: CC(C)N1C[C@@H]2[C@@H](CCNC(=O)/C=C/c3cccnc3)[C@@H]2C1] | (E)-N-(2-((1R,5S,6s)-3-isopropyl-3-azabicyclo[3.1.0]hexan-6-yl)ethyl)-3-(pyridin-3-yl)acrylamide | 300.4 |
| 246 | 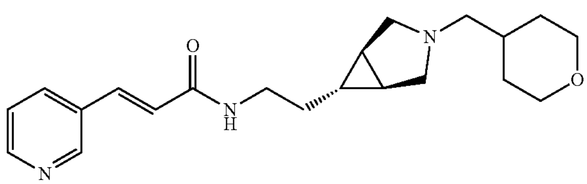 [SMILES: O=C(/C=C/c1cccnc1)NCC[C@@H]1[C@H]2CN(CC3CCOCC3)C[C@@H]12] | (E)-3-(pyridin-3-yl)-N-(2-((1R,5S,6s)-3-((tetrahydro-2H-pyran-4-yl)methyl)-3-azabicyclo[3.1.0]hexan-6-yl)ethyl)acrylamide | 356.4 |
| 247 | 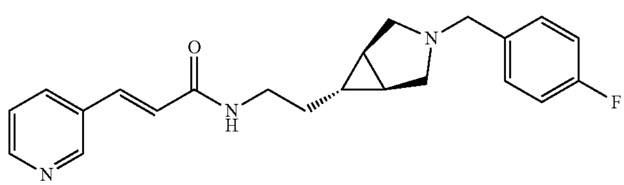 [SMILES: O=C(/C=C/c1cccnc1)NCC[C@@H]1[C@H]2CN(Cc3ccc(F)cc3)C[C@@H]12] | (E)-N-(2-((1R,5S,6s)-3-(4-fluorobenzyl)-3-azabicyclo[3.1.0]hexan-6-yl)ethyl)-3-(pyridin-3-yl)acrylamide | 366.2 |
| 248 | 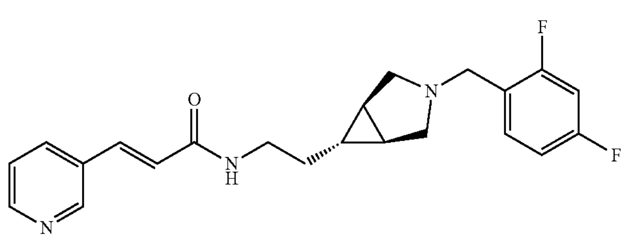 [SMILES: O=C(/C=C/c1cccnc1)NCC[C@@H]1[C@H]2CN(Cc3ccc(F)cc3F)C[C@@H]12] | (E)-N-(2-((1R,5S,6s)-3-(2,4-difluorobenzyl)-3-azabicyclo[3.1.0]hexan-6-yl)ethyl)-3-(pyridin-3-yl)acrylamide | 384.2 |

| Ex. No. | Chemical structure | Chemical name | MS (ESI) m/z (M + H)+ |
|---|---|---|---|
| 249 | 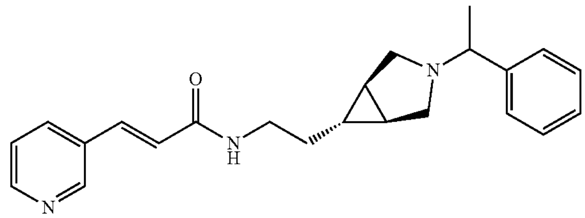 [SMILES: CC(c1ccccc1)N1C[C@@H]2[C@@H](CCNC(=O)/C=C/c3cccnc3)[C@@H]2C1] | (E)-N-(2-((1R,5S,6s)-3-(1-phenylethyl)-3-azabicyclo[3.1.0]hexan-6-yl)ethyl)-3-(pyridin-3-yl)acrylamide | 362.2 |
| 250 | 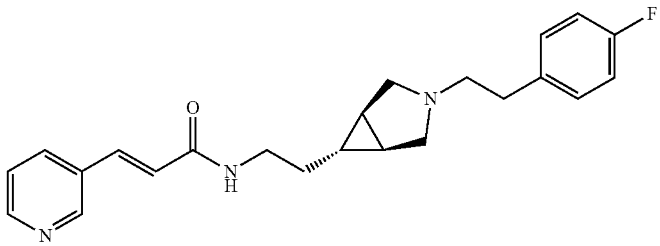 [SMILES: O=C(/C=C/c1cccnc1)NCC[C@@H]1[C@H]2CN(CCc3ccc(F)cc3)C[C@@H]12] | (E)-N-(2-((1R,5S,6s)-3-(4-fluorophenethyl)-3-azabicyclo[3.1.0]hexan-6-yl)ethyl)-3-(pyridin-3-yl)acrylamide | 380.1 |
| 251 | 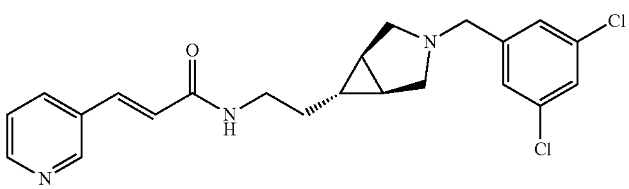 [SMILES: O=C(/C=C/c1cccnc1)NCC[C@@H]1[C@H]2CN(Cc3cc(Cl)cc(Cl)c3)C[C@@H]12] | (E)-N-(2-((1R,5S,6s)-3-(3,5-dichlorobenzyl)-3-azabicyclo[3.1.0]hexan-6-yl)ethyl)-3-(pyridin-3-yl)acrylamide | 416.2 |

Example 252: (1R,5S,6r)-tert-butyl 6-(2-((E)-3-(6-aminopyridin-3-yl)acrylamido)-1-hydroxyethyl)-3-azabicyclo[3.1.0]hexane-3-carboxylate

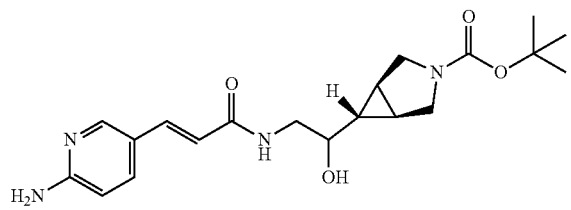 [SMILES: CC(C)(C)OC(=O)N1C[C@@H]2[C@H](C1)[C@H]2C(O)CNC(=O)/C=C/c1ccc(N)nc1]

To a solution of (1R,5S,6r)-tert-butyl 6-(hydroxymethyl)-3-azabicyclo[3.1.0]hexane-3-carboxylate (1.1 g, 5.16 mmol) in dichlormethane (10 mL) was added sodium bicarbonate (2.17 g, 25.8 mmol) and (1,1,1-triacetoxy)-1,1-dihydro-1,2-benziodoxol-3(1H)-one (3.28 g, 7.74 mmol). The mixture was stirred at 25° C. for 12 h. The suspension was filtered and concentrated to give a residue. The residue was purified by silica gel column chromatography (petroleum ether/ethyl acetate, from 20/1 to 5/1) to give 900 mg (83%) of (1R,5S,6r)-tert-butyl 6-formyl-3-azabicyclo[3.1.0]hexane-3-carboxylate as a colorless oil.

To a solution of (1R,5S,6r)-tert-butyl 6-formyl-3-azabicyclo[3.1.0]hexane-3-carboxylate (600 mg, 2.84 mmol) in methanol (10 mL) and water (10 mL) at 0° C. was added sodium cyanide (278 mg, 5.68 mmol). Acetic acid (341 mg, 5.68 mmol) was added and the reaction mixture was warmed to 25° C. and stirred for 48 h. The reaction was diluted with water (15 mL) and extracted with ethyl acetate (10 mL×3). The combined extracts were washed with brine (20 mL), dried over sodium sulfate and concentrated under vacuum to give a residue. The residue was purified by silica gel column chromatography (petroleum ether/ethyl acetate, from 20/1 to 5/1) to give 400 mg (59%) of (1R,5S,6r)-tert-butyl 6-(cyano(hydroxy)methyl)-3-azabicyclo[3.1.0]hexane-3-carboxylate as a white solid. $^1$H NMR (400 MHz, CDCl$_3$): δ 4.39-4.19 (m, 1H), 3.70-3.48 (m, 2H), 3.54-3.29 (m, 2H), 1.68 (s, 2H), 1.37 (s, 9H), 1.18-1.09 (m, 1H).

To a solution of (1R,5S,6r)-tert-butyl 6-(cyano(hydroxy)methyl)-3-azabicyclo[3.1.0]hexane-3-carboxylate (20 mg, 0.08 mmol) in tetrahydrofuran (2 mL) at 0° C. was added lithium aluminum hydride (6.37 mg, 0.17 mmol). The cooling bath was removed and the mixture was stirred at 25° C. for 1 h. The reaction was quenched with saturated aqueous ammonium chloride solution (0.5 mL) and diluted with water (10 mL). The resulting suspension was extracted with EtOAc (10 mL×3), and the combined organic layers were washed with brine (20 mL), dried over sodium sulfate, filtered and concentrated under vacuum. Four additional identical reactions on the same scale were performed. The resulting products from all five batches were combined to give 130 mg of (1R,5S,6r)-tert-butyl 6-(-2-amino-1-hydroxyethyl)-3-azabicyclo[3.1.0]hexane-3-carboxylate as a colorless oil. MS (ESI) m/z: 485.6 (2M+H)$^+$.

A mixture of (1R,5S,6r)-tert-butyl 6-(2-amino-1-hydroxyethyl)-3-azabicyclo[3.1.0]hexane-3-carboxylate (50 mg, 0.21 mmol), (E)-3-(6-aminopyridin-3-yl)acrylic acid (33.9 mg, 0.21 mmol) and 1-(3-dimethylaminopropyl)-3-ethylcarbodiimide hydrochloride (47.5 mg, 0.25 mmol) in pyridine (2 mL) was stirred at 25° C. for 10 h. The reaction was concentrated under vacuum and diluted with water (15 mL). The suspension was extracted with ethyl acetate (10 mL×3). The combined organic layers were washed with brine (20 mL), dried over sodium sulfate and concentrated under vacuum to give a residue. The residue was purified by preparative HPLC (Phenomenex Gemini C18 column (150× 25 mm, 10 um); flow rate: 25 mL/min; gradient: 20%-50% B over 11 min; mobile phase A: 0.05% aqueous ammonium bicarbonate, mobile phase B: acetonitrile) to give 18.5 mg (11%) of the title compound as a yellow solid. MS (ESI) m/z: 389.4 (M+H)+. 1H NMR (400 MHz, DMSO-d6): δ 8.05 (d, J=1.8 Hz, 1H), 7.92 (t, J=5.6 Hz, 1H), 7.64-7.53 (m, 1H), 7.26 (d, J=16.0 Hz, 1H), 6.51-6.33 (m, 4H), 4.84 (s, 1H), 3.29-3.09 (m, 7H), 1.49 (s, 1H), 1.41 (d, J=4.4 Hz, 1H), 1.38-1.35 (m, 9H), 0.55-5.52 (m, 1H).

Example 253: (1R,5S,6r)-tert-butyl 6-(1-hydroxy-2-((E)-3-(pyridin-3-yl)acrylamido)ethyl)-3-azabicyclo[3.1.0]hexane-3-carboxylate

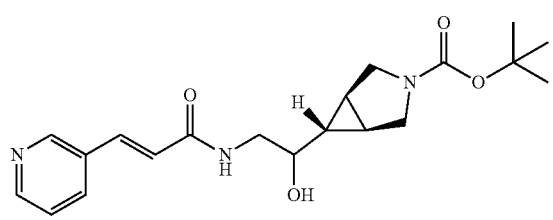 [SMILES: CC(C)(C)OC(=O)N1C[C@@H]2[C@H](C1)[C@H]2C(O)CNC(=O)/C=C/c1cccnc1]

This compound was prepared substantially according to the procedures described above. MS (ESI) m/z: 374.4 (M+H)+.

Example 254: (1R,5S,6r)-tert-butyl 6-(2-((E)-3-(6-aminopyridin-3-yl)acrylamido)-1-fluoroethyl)-3-azabicyclo[3.1.0]hexane-3-carboxylate

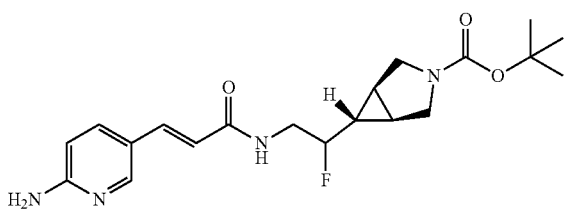 [SMILES: CC(C)(C)OC(=O)N1C[C@@H]2[C@H](C1)[C@H]2C(F)CNC(=O)/C=C/c1ccc(N)nc1]

To a solution of (1R,5S,6r)-tert-butyl 6-(2-((E)-3-(6-aminopyridin-3-yl)acrylamido)-1-hydroxyethyl)-3-azabicyclo[3.1.0]hexane-3-carboxylate (30 mg, 0.07 mmol) in dichloromethane (1 mL) at 0° C. was added diethylaminosulfur trifluoride (18.7 mg, 0.12 mmol). The reaction mixture was stirred at 25° C. for 0.5 h. The mixture was concentrated under vacuum and diluted with water (15 mL). The resulting suspension was extracted with ethyl acetate (10 mL×3), and the combined organic layers were washed with brine (20 mL), dried over sodium sulfate and concentrated under vacuum to give a residue. The residue was purified by preparative HPLC (Phenomenex Gemini C18 column (150× 25 mm, 10 um); flow rate: 25 mL/min; gradient: 22%-52% B over 10 min; mobile phase A: 0.05% aqueous ammonium hydroxide, mobile phase B: acetonitrile to give 3.5 mg (11%) of the title compound as a white solid. MS (ESI) m/z: 391.4 (M+H)+. 1H NMR (400 MHz, DMSO-d6): δ 8.17 (s, 1H), 8.05 (s, 1H), 7.57 (d, J=2.0 Hz, 1H), 7.29 (d, J=16.0 Hz, 1H), 6.46 (d, J=8.8 Hz, 1H), 6.43-6.37 (m, 3H), 4.21-3.96 (m, 1H), 3.46-3.43 (m, 6H), 1.70-1.67 (m, 1H), 1.56-1.53 (m, 1H), 1.35 (s, 9H), 0.83-0.81 (m, 1H).

Example 255: (1R,5S,6r)-tert-butyl 6-(1-fluoro-2-((E)-3-(pyridin-3-yl)acrylamido)ethyl)-3-azabicyclo[3.1.0]hexane-3-carboxylate

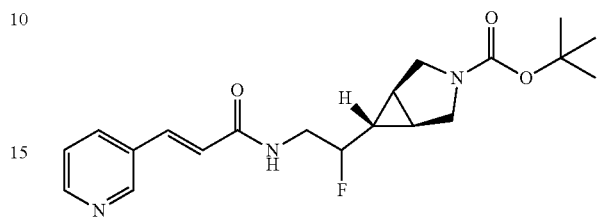

This compound was prepared substantially according to the procedures described above. MS (ESI) m/z: 376.4 (M+H)+.

Example 256: A racemic mixture of (E)-N-(2-((1R,5S,6S)-2-oxo-3-phenyl-3-azabicyclo[3.1.0]hexan-6-yl)ethyl)-3-(pyridin-3-yl)acrylamide and (E)-N-(2-((1S,5R,6R)-2-oxo-3-phenyl-3-azabicyclo[3.1.0]hexan-6-yl)ethyl)-3-(pyridin-3-yl)acrylamide

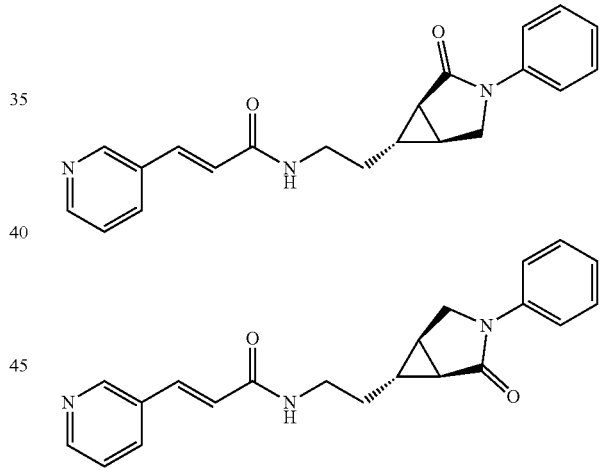

To a solution of 1-phenyl-1H-pyrrole-2,5-dione (3.6 g, 20.8 mmol) in toluene (100 mL) was added ethyl (dimethylsulfuranylidene)acetate (3.8 g, 25.7 mmol) [prepared according to the procedure in Org. Process. Res. Dev. 2014, 1527] in toluene (20 mL) at 100° C. under an atmosphere of nitrogen. The resulting solution was stirred at 100° C. for 2 h. The reaction was concentrated under vacuum and purified by silica gel column chromatography (petroleum ether/ethyl acetate, from 1/10 to 1/3) to give 1.6 g (30%) of (1R,5S,6r)-ethyl 2,4-dioxo-3-phenyl-3-azabicyclo[3.1.0]hexane-6-carboxylate as an off-white solid. MS (ESI) m/z: 260.3 (M+H)+. 1H NMR (400 MHz, CDCl3): δ 7.49-7.42 (m, 2H), 7.42-7.36 (m, 1H), 7.23-7.17 (m, 2H), 4.25 (q, J=7.2 Hz, 2H), 3.05 (d, J=2.8 Hz, 2H), 2.61 (t, J=2.8 Hz, 1H), 1.33 (t, J=7.2 Hz, 3H).

To a solution of ethyl (1R,5S,6r)-ethyl 2,4-dioxo-3-phenyl-3-azabicyclo[3.1.0]hexane-6-carboxylate (1.6 g, 6.17 mmol) and cerium chloride (0.30 g, 1.23 mmol) in water (0.5 mL) and tetrahydrofuran (20 mL) was added sodium borohydride (0.35 g, 9.26 mmol) at 0° C. The mixture was stirred at 0° C. for 30 min. The reaction was quenched with aqueous saturated ammonium chloride (20 mL) and extracted with ethyl acetate (20 mL×4). The combined organic layers were dried over anhydrous sodium sulfate and concentrated under vacuum to give 1.32 g of a crude racemic mixture of (1R,2R,5S,6S)-ethyl 2-hydroxy-4-oxo-3-phenyl-3-azabicyclo[3.1.0]hexane-6-carboxylate and (1 S,2S,5R,6R)-ethyl 2-hydroxy-4-oxo-3-phenyl-3-azabicyclo[3.1.0]hexane-6-carboxylate as a light yellow oil. MS (ESI) m/z: 262.0 (M+H)$^+$.

To a solution of a mixture of (1R,2R,5S,6S)-ethyl 2-hydroxy-4-oxo-3-phenyl-3-azabicyclo[3.1.0]hexane-6-carboxylate and (1 S,2S,5R,6R)-ethyl 2-hydroxy-4-oxo-3-phenyl-3-azabicyclo[3.1.0]hexane-6-carboxylate (1.3 g, 4.98 mmol) in chloroform (15 mL) was added triethylsilane (1.4 g, 12.3 mmol, 2.0 mL) and trifluoroacetic acid (8.5 g, 74.5 mmol, 5.5 mL). The mixture was stirred at 20° C. for 10 h under an atmosphere of nitrogen. The reaction was concentrated under vacuum and diluted with water (10 mL). The resulting suspension was extracted with ethyl acetate (10 mL×3). The combined organic layers were concentrated under vacuum to give a residue. The residue was purified by silica gel column chromatography (petroleum ether/ethyl acetate, from 1/10 to 1/3) to give 0.98 g of a crude racemic mixture of (1S,5R,6S)-ethyl 2-oxo-3-phenyl-3-azabicyclo[3.1.0]hexane-6-carboxylate and (1R,5S,6R)-ethyl 2-oxo-3-phenyl-3-azabicyclo[3.1.0]hexane-6-carboxylate as a off-white solid. MS (ESI) m/z: 246.1 (M+H)$^+$. $^1$H NMR (400 MHz, CDCl$_3$): δ 7.55-7.49 (m, 2H), 7.42-7.33 (m, 2H), 7.19-7.12 (m, 1H), 4.25-4.08 (m, 3H), 3.86 (d, J=10.8 Hz, 1H), 2.67-2.61 (m, 1H), 2.53 (dt, J=2.8, 6.0 Hz, 1H), 1.95 (t, J=2.8 Hz, 1H), 1.29 (t, J=7.2 Hz, 3H).

To a suspension of lithium aluminum hydride (197 mg, 5.2 mmol) in tetrahydrofuran (15 mL) at 0° C. was added a solution of a mixture of (1S,5R,6S)-ethyl 2-oxo-3-phenyl-3-azabicyclo[3.1.0]hexane-6-carboxylate and (1R,5S,6R)-ethyl 2-oxo-3-phenyl-3-azabicyclo[3.1.0]hexane-6-carboxylate (0.98 g, 4.01 mmol) in tetrahydrofuran (3 mL) dropwise. The reaction mixture was stirred at 0° C. for 30 min. The reaction mixture was quenched with water (0.2 mL), and 15% aqueous NaOH solution (0.2 mL) was added, followed by additional water (0.6 mL). The mixture was stirred for 30 min and sodium sulfate (10 g) was added. The suspension was stirred for 30 min. The resulting mixture was filtered and concentrated in vacuo to afford 700 mg of a crude racemic mixture of (1S,5S,6S)-6-(hydroxymethyl)-3-phenyl-3-azabicyclo[3.1.0]hexan-2-one and (1R,5R,6R)-6-(hydroxymethyl)-3-phenyl-3-azabicyclo[3.1.0]hexan-2-one as a light yellow oil. MS (ESI) m/z: 204.3 (M+H)$^+$.

To a solution of a mixture of (1S,5S,6S)-6-(hydroxymethyl)-3-phenyl-3-azabicyclo[3.1.0]hexan-2-one and (1R,5R,6R)-6-(hydroxymethyl)-3-phenyl-3-azabicyclo[3.1.0]hexan-2-one (0.7 g, 3.44 mmol) and carbon tetrabromide (1.71 g, 5.17 mmol) in dichloromethane (15 mL) was added triphenylphosphine (1.36 g, 5.17 mmol) under an atmosphere of nitrogen. The reaction was stirred at 20° C. for 10 h and concentrated under vacuum. The residue was purified by silica gel column chromatography (petroleum ether/ethyl acetate, from 1/10 to 1/1) to give 0.31 g (35%) of a racemic mixture of (1S,5R,6S)-6-(bromomethyl)-3-phenyl-3-azabicyclo[3.1.0]hexan-2-one and 1R,5S,6R)-6-(bromomethyl)-3-phenyl-3-azabicyclo[3.1.0]hexan-2-one as a light yellow solid. MS (ESI) m/z: 266.2, 268.2 (M+H)$^+$. $^1$H NMR (400 MHz, CDCl$_3$): δ 7.51 (d, J=8.8 Hz, 2H), 7.40-7.33 (m, 2H), 7.19-7.12 (m, 1H), 4.11 (dd, J=6.0, 10.4 Hz, 1H), 3.85 (d, J=10.4 Hz, 1H), 2.82 (dd, J=4.8, 17.2 Hz, 1H), 2.43 (dd, J=7.2, 17.2 Hz, 1H), 2.22-2.15 (m, 1H), 2.11-2.08 (m, 1H), 1.49-1.44 (m, 1H).

To a solution of a mixture of (1S,5R,6S)-6-(bromomethyl)-3-phenyl-3-azabicyclo[3.1.0]hexan-2-one and (1R,5S,6R)-6-(bromomethyl)-3-phenyl-3-azabicyclo[3.1.0]hexan-2-one (0.3 g, 1.13 mmol) in N,N-dimethylformamide (3 mL) was added sodium cyanide (82.9 mg, 1.69 mmol). The resulting suspension was stirred at 20° C. for 10 h. The reaction mixture was diluted with water (30 mL) and extracted with ethyl acetate (20 mL×3). The combined organic layers were washed with brine (50 mL), dried over anhydrous sodium sulfate and concentrated under vacuum. The residue was purified by silica gel column chromatography (petroleum ether/ethyl acetate, from 1/5 to 1/1) to give 0.20 g (46%) of a mixture of 2-((1R,5S,6S)-2-oxo-3-phenyl-3-azabicyclo[3.1.0]hexan-6-yl)acetonitrile and 2-((1S,5R,6R)-2-oxo-3-phenyl-3-azabicyclo[3.1.0]hexan-6-yl)acetonitrile as a light yellow solid. MS (ESI) m/z: 213.3 (M+H)$^+$. $^1$H NMR (400 MHz, CDCl$_3$): δ 7.58-7.55 (m, 2H), 7.38 (t, J=8.0 Hz, 2H), 7.20-7.14 (m, 1H), 4.22-4.08 (m, 1H), 3.87 (d, J=10.4 Hz, 1H), 2.84 (dd, J=4.8, 17.2 Hz, 1H), 2.44 (dd, J=6.8, 17.2 Hz, 1H), 2.23-2.20 (m, 1H), 2.13-2.09 (m, 1H), 1.50-1.47 (m, 1H).

Ammonia was bubbled through a solution of methanol (10 mL) at 0° C. for 30 min, and a mixture of 2-((1R,5S,6S)-2-oxo-3-phenyl-3-azabicyclo[3.1.0]hexan-6-yl)acetonitrile and 2-((1R,5S,6S)-2-oxo-3-phenyl-3-azabicyclo[3.1.0]hexan-6-yl)acetonitrile (0.1 g, 0.47 mmol) was added to and dissolved in the resulting solution. Raney nickel (0.12 g) was added to the reaction mixture, degassed with hydrogen three times and stirred at 20° C. under an atmosphere of hydrogen (15 psi) for 10 h. The reaction mixture was filtered and the filtrate was concentrated under vacuum to give 85 mg of a crude racemic mixture of (1R,5S,6S)-6-(2-aminoethyl)-3-phenyl-3-azabicyclo[3.1.0]hexan-2-one and (1S,5R,6R)-6-(2-aminoethyl)-3-phenyl-3-azabicyclo[3.1.0]hexan-2-one as a light green oil. MS (ESI) m/z: 217.3 (M+H)$^+$.

To a solution of (E)-3-(pyridin-3-yl)acrylic acid (64.8 mg, 0.43 mmol) and 1-(3-dimethylaminopropyl)-3-ethylcarbodiimide hydrochloride (87.2 mg, 0.45 mmol) in pyridine (3.0 mL) was added a mixture of (1R,5S,6S)-6-(2-aminoethyl)-3-phenyl-3-azabicyclo[3.1.0]hexan-2-one and (1S,5R,6R)-6-(2-aminoethyl)-3-phenyl-3-azabicyclo[3.1.0]hexan-2-one (85 mg, 0.39 mol). The mixture was stirred at 20° C. for 1 h. The reaction was concentrated under vacuum to give a residue. The residue was diluted with water (5 mL) and extracted with ethyl acetate (5 mL×3). The combined organic layers were concentrated under vacuum and purified by preparative HPLC (Phenomenex Gemini C18 column (150×25 mm, 10 um); flow rate: 25 mL/min; gradient: 10%-37% B over 10 min; mobile phase A: 0.1% aqueous trifluoroacetic acid, mobile phase B: acetonitrile) to give 30.1 mg (16%) of a mixture of the title compounds as a light yellow solid. MS (ESI) m/z: 348.3 (M+H)$^+$. $^1$H NMR (400 MHz, DMSO-d$_6$): δ 8.80 (s, 1H), 8.59 (d, J=4.8 Hz, 1H), 8.28 (t, J=5.2 Hz, 1H), 8.07 (d, J=7.2 Hz, 1H), 7.59-7.54 (m, 2H), 7.52 (d, J=6.4 Hz, 1H), 7.48 (d, J=16.0 Hz, 1H), 7.33 (t, J=8.0 Hz, 2H), 7.08 (t, J=7.2 Hz, 1H), 6.76 (d, J=16.0 Hz, 1H), 4.02 (dd, J=5.2, 10.4 Hz, 1H), 3.76-3.74 (m, 1H), 3.36-3.28 (m, 2H), 1.95-1.89 (m, 2H), 1.57-1.40 (m, 1H), 1.18-1.14 (m, 1H).

A racemic mixture of (E)-N-(2-((1R,5S,6S)-2-oxo-3-phenyl-3-azabicyclo[3.1.0]hexan-6-yl)ethyl)-3-(pyridin-3-yl)acrylamide and (E)-N-(2-((1R,5S,6S)-2-oxo-3-phenyl-3- azabicyclo[3.1.0]hexan-6-yl)ethyl)-3-(pyridin-3-yl) acrylamide (14.1 mg, 0.03 mmol, TFA salt) was purified by SFC (DAICEL CHIRALPAK AS column (250×30 mm, 10 um); flow rate: 60 mL/min; gradient: isocratic 30% B over 14 min; mobile phase A: supercritical fluid $CO_2$, mobile phase B: 0.1% aqueous ammonium hydroxide in methanol) to give 3.5 mg (33%) of one isomer (isomer A; $R_t$=7.1 min; % ee=>99.9%) as an off-white solid and 2.5 (23%) mg of the other isomer (isomer B; $R_t$=9.0 min; % ee=94.9%) as an off-white solid. MS [isomer A] (ESI) m/z: 348.4 $(M+H)^+$. MS [isomer B] (ESI) m/z: 348.4 $(M+H)^+$.

Examples 257-263

The following compounds were prepared substantially according to the procedures described above:

| Ex. No. | Chemical structure | Chemical name | MS (ESI) m/z $(M + H)^+$ |
|---|---|---|---|
| 257 | | (E)-N-(2-((1R,5S,6S)-3-benzyl-2-oxo-3-azabicyclo[3.1.0]hexan-6-yl)ethyl)-3-(pyridin-3-yl)acrylamide and (E)-N-(2-((1S,5R,6R)-3-benzyl-2-oxo-3-azabicyclo[3.1.0]hexan-6-yl)ethyl)-3-(pyridin-3-yl)acrylamide | 362.4 |
| 258 | | (E)-3-(6-aminopyridin-3-yl)-N-(2-((1R,5S,6S)-3-benzyl-2-oxo-3-azabicyclo[3.1.0]hexan-6-yl)ethyl)acrylamide and (E)-3-(6-aminopyridin-3-yl)-N-(2-((1S,5R,6R)-3-benzyl-2-oxo-3-azabicyclo[3.1.0]hexan-6-yl)ethyl)acrylamide | 377.4 |
| 259 | | (E)-3-(6-aminopyridin-3-yl)-N-(2-((1S,5R,6R)-2-oxo-3-phenyl-3-azabicyclo[3.1.0]hexan-6-yl)ethyl)acrylamide and (E)-3-(6-aminopyridin-3-yl)-N-(2-((1R,5S,6S)-2-oxo-3-phenyl-3-azabicyclo[3.1.0]hexan-6-yl)ethyl)acrylamide | 363.3 |

| Ex. No. | Chemical structure | Chemical name | MS (ESI) m/z (M + H)+ |
|---|---|---|---|
| 260 | | N-(2-((1R,5S,6S)-2-oxo-3-phenyl-3-azabicyclo[3.1.0]hexan-6-yl)ethyl)furo[2,3-c]pyridine-2-carboxamide and N-(2-((1S,5R,6R)-2-oxo-3-phenyl-3-azabicyclo[3.1.0]hexan-6-yl)ethyl)furo[2,3-c]pyridine-2-carboxamide | 362.3 |
| 261 | | N-(2-((1R,5S,6S)-2-oxo-3-phenyl-3-azabicyclo[3.1.0]hexan-6-yl)ethyl)-5-(pyridin-3-yl)isoxazole-3-carboxamide/N-(2-((1S,5R,6R)-2-oxo-3-phenyl-3-azabicyclo[3.1.0]hexan-6-yl)ethyl)-5-(pyridin-3-yl)isoxazole-3-carboxamide | 389.3 |
| 262 | | (E)-N-(2-((1R,5S,6S)-2-oxo-3-(3-(trifluoromethyl)phenyl)-3-azabicyclo[3.1.0]hexan-6-yl)ethyl)-3-(pyridin-3-yl)acrylamide and (E)-N-(2-((1S,5R,6R)-2-oxo-3-(3-(trifluoromethyl)phenyl)-3-azabicyclo[3.1.0]hexan-6-yl)ethyl)-3-(pyridin-3-yl)acrylamide | 416.2 |

| Ex. No. | Chemical structure | Chemical name | MS (ESI) m/z (M + H)+ |
|---|---|---|---|
| 263 | 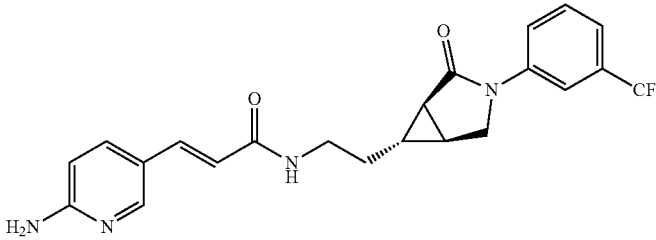 | (E)-3-(6-aminopyridin-3-yl)-N-(2-((1R,5S,6S)-2-oxo-3-(3-(trifluoromethyl)phenyl)-3-azabicyclo[3.1.0]hexan-6-yl)ethyl)acrylamide and (E)-3-(6-aminopyridin-3-yl)-N-(2-((1S,5R,6R)-2-oxo-3-(3-(trifluoromethyl)phenyl)-3-azabicyclo[3.1.0]hexan-6-yl)ethyl)acrylamide | 431.3 |

Example 264: A racemic mixture of (E)-N-(2-((1R,5S,6S)-3-(4-fluorophenyl)-2-oxo-3-azabicyclo[3.1.0]hexan-6-yl)ethyl)-3-(pyridin-3-yl)acrylamide and (E)-N-(2-((1S,5R,6R)-3-(4-fluorophenyl)-2-oxo-3-azabicyclo[3.1.0]hexan-6-yl)ethyl)-3-(pyridin-3-yl)acrylamide

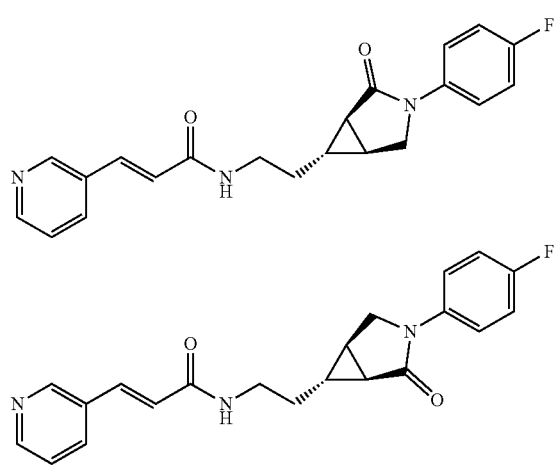

To a solution of (E)-5-hydroxypent-3-enenitrile (1 g, 10.3 mmol) [prepared according to the procedure in U.S. Pat. No. 6,051,699] in dichloromethane (40 mL) at 0° C. was added triphenylphosphine (4.05 g, 15.5 mmol) followed by carbon tetrabromide (5.12 g, 15.5 mmol). The mixture was stirred at 15° C. for 24 h. The mixture was concentrated to give a residue. The residue was purified by silica gel column chromatography (petroleum ether/ethyl acetate, from 20/1 to 10/1) to give 1.2 g (73%) of (E)-5-bromopent-3-enenitrile as a yellow oil. $^1$H NMR (400 MHz, CDCl$_3$): δ 6.10 (ttd, J=1.8, 7.4, 15.2 Hz, 1H), 5.77-5.66 (m, 1H), 3.96 (dd, J=1.0, 7.4 Hz, 2H), 3.20-3.15 (m, 2H).

To a solution of (E)-5-bromopent-3-enenitrile (1.5 g, 9.37 mmol) in N,N-dimethylformamide (10 mL) was added potassium carbonate (2.59 g, 18.8 mmol) and 4-fluoroaniline (1.25 g, 11.3 mmol, 1.1 mL). The mixture was stirred at 15° C. for 1 h, filtered and the filtrate was concentrated to give a residue. The residue was purified by silica gel column chromatography (petroleum ether/ethyl acetate, from 15/1 to 5/1) to give 1.1 g (58%) of (E)-5-((4-fluorophenyl)amino)pent-3-enenitrile as a yellow oil. MS (ESI) m/z: 191.3 (M+H)$^+$. $^1$H NMR (400 MHz, CDCl$_3$): δ 6.92-6.84 (m, 2H), 6.60-6.48 (m, 2H), 5.97 (ttd, J=1.6, 5.2, 15.4 Hz, 1H), 5.69-5.56 (m, 1H), 3.77 (qd, J=1.6, 5.2 Hz, 2H), 3.11 (qd, J=1.6, 5.2 Hz, 2H).

To a solution of (E)-5-((4-fluorophenyl)amino)pent-3-enenitrile (1.0 g, 5.26 mmol) and (E)-2-(2-tosylhydrazono)acetyl chloride (4.11 g, 15.8 mmol) [prepared according to the procedure in *Bioorg. Med. Chem. Lett.* 2001, 3179] in dichloromethane (50 mL) at 0° C. under an atmosphere of nitrogen was added N,N-dimethylaniline (3.19 g, 26.3 mmol, 3.3 mL). The mixture was stirred at 0° C. for 15 min and triethylamine (5.32 g, 52.6 mmol, 7.3 mL) was added dropwise. The reaction mixture was stirred at 0° C. for 15 min, then at 15° C. for 15 min. Saturated aqueous citric acid (100 mL) was added to the mixture and the organic layer was concentrated under vacuum to give a residue. The residue was purified by silica gel column chromatography (petroleum ether/ethyl acetate, from 10/1 to 5/1) to give 0.7 g (52%) of (E)-N-(4-cyanobut-2-en-1-yl)-2-diazo-N-(4-fluorophenyl)acetamide as a yellow oil. MS (ESI) m/z: 259.2 (M+H)$^+$.

A solution of (E)-N-(4-cyanobut-2-en-1-yl)-2-diazo-N-(4-fluorophenyl)acetamide (700 mg, 2.71 mmol) in dichloromethane (5 mL) was added dropwise into a solution of dirhodium(II) tetrakis(methyl 2-pyrrolidone-carboxylate) complex (100 mg, 0.13 mmol) [prepared according to the procedure in *J. Am. Chem. Soc.* 1993, 9968] in dichloromethane (5 mL). The mixture was stirred at 55° C. for 12 h under an atmosphere of nitrogen and concentrated to give a residue. The residue was purified by silica gel column chromatography (petroleum ether/ethyl acetate, from 10/1 to 2/1) to give 150 mg (24%) of a mixture of 2-((1R,5S,6S)-3-(4-fluorophenyl)-2-oxo-3-azabicyclo[3.1.0]hexan-6-yl)

acetonitrile and 2-((1S,5R,6R)-3-(4-fluorophenyl)-2-oxo-3-azabicyclo[3.1.0]hexan-6-yl)acetonitrile as a yellow oil. $^1$H NMR (400 MHz, CDCl$_3$) δ 7.51-7.43 (m, 2H), 7.09-7.00 (m, 2H), 4.07 (dd, J=5.8, 10.3 Hz, 1H), 3.82 (dd, J=1.2, 10.2 Hz, 1H), 2.81 (dd, J=5.0, 17.4 Hz, 1H), 2.49-2.36 (m, 1H), 2.19 (td, J=2.2, 6.4 Hz, 1H), 2.10 (dt, J=3.6, 6.4 Hz, 1H), 1.46 (dt, J=3.2, 7.4 Hz, 1H).

To a solution of 2-((1R,5S,6S)-3-(4-fluorophenyl)-2-oxo-3-azabicyclo[3.1.0]hexan-6-yl)acetonitrile and 2-((1S,5R,6R)-3-(4-fluorophenyl)-2-oxo-3-azabicyclo[3.1.0]hexan-6-yl)acetonitrile (150 mg, 0.65 mmol) in methanol (5 mL) under a nitrogen atmosphere was added Raney nickel (25.0 mg, 0.30 mmol). The suspension was degassed under vacuum and purged with hydrogen several times. The reaction mixture was stirred under an atmosphere of hydrogen (15 psi) at 20° C. for 5 h. The suspension was filtered through a Celite pad, and the filtrate was concentrated under vacuum to give 140 mg (92%) of a mixture of (1R,5S,6S)-6-(2-aminoethyl)-3-(4-fluorophenyl)-3-azabicyclo[3.1.0]hexan-2-one and (1S,5R,6R)-6-(2-aminoethyl)-3-(4-fluorophenyl)-3-azabicyclo[3.1.0]hexan-2-one as a yellow oil. MS (ESI) m/z: 235.2 (M+H)$^+$.

To a solution of (E)-3-(pyridin-3-yl)acrylic acid (20 mg, 0.13 mmol) in pyridine (1 mL) was added 1-(3-dimethylaminopropyl)-3-ethylcarbodiimide hydrochloride (31 mg, 0.16 mmol) and a mixture of (1R,5S,6S)-6-(2-aminoethyl)-3-(4-fluorophenyl)-3-azabicyclo[3.1.0]hexan-2-one and (1S,5R,6R)-6-(2-aminoethyl)-3-(4-fluorophenyl)-3-azabicyclo[3.1.0]hexan-2-one (31 mg, 0.13 mmol). The mixture was stirred at 15° C. for 2 h. The mixture was concentrated under vacuum to give a residue. The reaction and workup were repeated on an identical scale. The resulting combined residues were purified by preparative HPLC (Phenomenex Gemini C18 column (150×25 mm, 5 um); flow rate: 25 mL/min; gradient: 18%-48% B over 9 min; mobile phase A: 0.1% aqueous trifluoroacetic acid, mobile phase B: acetonitrile) to give 20 mg (19%) of a mixture of the title compounds as a yellow oil. MS (ESI) m/z: 366.2 (M+H)$^+$. $^1$H NMR (400 MHz, DMSO-d$_6$): δ 8.83 (d, J=1.8 Hz, 1H), 8.68-8.56 (m, 1H), 8.30 (t, J=5.6 Hz, 1H), 8.14 (d, J=8.0 Hz, 1H), 7.63-7.54 (m, 3H), 7.49 (d, J=16.0 Hz, 1H), 7.22-7.12 (m, 2H), 6.77 (d, J=16.0 Hz, 1H), 4.00 (dd, J=5.4, 10.0 Hz, 1H), 3.73 (d, J=10.0 Hz, 1H), 3.39-3.25 (m, 2H), 1.98-1.88 (m, 2H), 1.65-1.42 (m, 2H), 1.22-1.11 (m, 1H).

Examples 265-266

The following compounds were prepared substantially according to the procedures described above:

| Ex. No. | Chemical structure | Chemical name | MS (ESI) m/z (M + H)$^+$ |
|---|---|---|---|
| 265 | 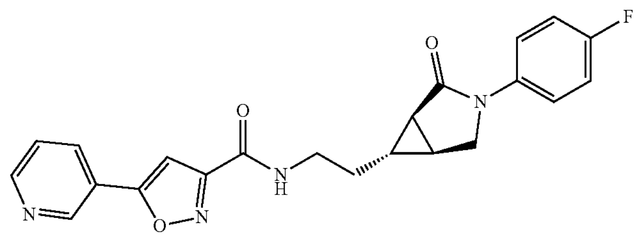 [SMILES: O=C(NCC[C@H]1[C@@H]2CN(c3ccc(F)cc3)C(=O)[C@H]12)c1cc(-c2cccnc2)on1] | N-(2-((1R,5S,6S)-3-(4-fluorophenyl)-2-oxo-3-azabicyclo[3.1.0]hexan-6-yl)ethyl)-5-(pyridin-3-yl)isoxazole-3-carboxamide and N-(2-((1S,5R,6R)-3-(4-fluorophenyl)-2-oxo-3-azabicyclo[3.1.0]hexan-6-yl)ethyl)-5-(pyridin-3-yl)isoxazole-3-carboxamide | 407.2 |
| 266 | 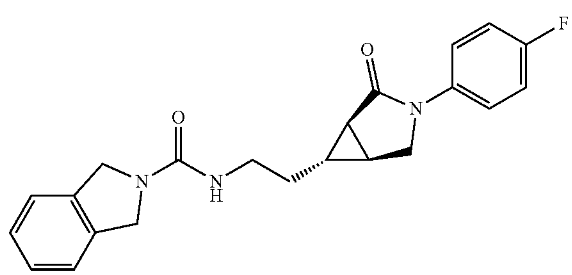 [SMILES: O=C(NCC[C@H]1[C@@H]2CN(c3ccc(F)cc3)C(=O)[C@H]12)N1Cc2ccccc2C1] | N-(2-((1R,5S,6S)-3-(4-fluorophenyl)-2-oxo-3-azabicyclo[3.1.0]hexan-6-yl)ethyl)isoindoline-2-carboxamide and N-(2-((1S,5R,6R)-3-(4-fluorophenyl)-2-oxo-3-azabicyclo[3.1.0]hexan-6-yl)ethyl)isoindoline-2-carboxamide | 380.2 |

| Ex. No. | Chemical structure | Chemical name | MS (ESI) m/z (M + H)+ |
|---|---|---|---|

Example 267: tert-butyl (3aR,5r,6aS)-5-((2,3-dihydro-1H-pyrrolo[3,4-c]pyridine-2-carboxamido)methyl)hexahydrocyclopenta[c]pyrrole-2(1H)-carboxylate To a solution of benzyl 2-(dimethoxyphosphoryl)acetate (824 mg, 3.19 mmol) in tetrahydrofuran (4 mL) was added sodium hydride (128 mg, 3.19 mmol, 60% in mineral oil). The mixture was stirred at 20° C. for 15 min. A solution of tert-butyl 5-oxohexahydrocyclopenta[c]pyrrole-2(1H)-carboxylate (600 mg, 2.66 mmol) in tetrahydrofuran (1 mL) was added to the resulting solution. The reaction mixture was stirred at 20° C. for 1 h. The mixture was quenched with saturated aqueous ammonium chloride (20 mL), and the mixture was extracted with ethyl acetate (30 mL×3). The combined organic layers were washed with water (30 mL) and brine (30 mL), dried over anhydrous sodium sulfate and concentrated under vacuum. The residue was purified by silica gel column chromatography (petroleum ether/ethyl acetate, from 10/1 to 6/1) to give 820 mg (81%) of tert-butyl 5-(2-(benzyloxy)-2-oxoethylidene)hexahydrocyclopenta[c]pyrrole-2(1H)-carboxylate as a colorless oil. MS (ESI) m/z: 302.3 (M+H)+. $^1$H NMR (400 MHz, CDCl$_3$): δ 7.38-7.32 (m, 5H), 5.89 (s, 1H), 3.55 (d, J=6.4 Hz, 2H), 3.22-3.07 (m, 3H), 2.78-2.71 (m, 4H), 2.45 (d, J=14.8 Hz, 1H), 1.61 (s, 2H), 1.46 (s, 9H).

To a solution of tert-butyl 5-(2-(benzyloxy)-2-oxoethylidene)-hexahydrocyclopenta[c]pyrrole-2(1H)-carboxylate (300 mg, 0.84 mmol) in ethyl acetate (20 mL) was added palladium (60 mg, 10% on carbon). The mixture was purged with hydrogen three times and stirred at 20° C. under an atmosphere of hydrogen (15 psi) for 16 h. The reaction mixture was filtered and the filtrate was concentrated under vacuum to give 220 mg (97%) of crude 2-((3aR,5r,6aS)-2-(tert-butoxycarbonyl)octahydrocyclopenta[c]pyrrol-5-yl)acetic acid as an white solid. MS (ESI) m/z: 214.1 (M+H)+.

To a solution of 2-((3aR,5r,6aS)-2-(tert-butoxycarbonyl)octahydrocyclopenta[c]pyrrol-5-yl)acetic acid (100 mg, 0.37 mmol) in toluene (10 mL) was added diphenyl phosphoryl azide (153 mg, 0.56 mmol). The reaction mixture was heated to 70° C. and stirred for 16 h. The mixture was cooled to 20° C., and 2,3-dihydro-1H-pyrrolo[3,4-c]pyridine dihydrochloride (143 mg, 0.74 mmol) was added to the resulting solution. The mixture was stirred for 1 h at 20° C. The reaction was concentrated under vacuum, diluted with water (20 mL) and extracted with ethyl acetate (20 mL×3). The combined organic layers were washed with brine (30 mL), dried over anhydrous sodium sulfate and concentrated under vacuum. The obtained residue was purified by preparative HPLC (Phenomenex Gemini C18 column (150×25 mm, 10 um); flow rate: 25 mL/min; gradient: 20%-50% B over 12 min; mobile phase A: 0.05% aqueous ammonium hydroxide, mobile phase B: acetonitrile) to give 58.6 mg (41%) of the title compound as a white solid. MS (ESI) m/z: 387.2 (M+H)+. $^1$H NMR (400 MHz, DMSO-d$_6$): δ 8.56 (s, 1H), 8.47 (d, J=5.2 Hz, 1H), 7.39 (d, J=4.8 Hz, 1H), 6.42 (t, J=5.2 Hz, 1H), 4.61 (d, J=5.6 Hz, 4H), 3.45-3.41 (m, 1H), 3.11 (d, J=5.6 Hz, 4H), 3.08-3.00 (m, 1H), 2.14-1.98 (m, 1H), 1.96-1.92 (m, 2H), 1.52-1.36 (m, 1H), 1.36 (s, 10H), 1.08-1.03 (m, 2H).

Examples 268-272

The following compounds were prepared substantially according to the procedures described above:

| Ex. No. | Chemical structure | Chemical name | MS (ESI) m/z (M + H)+ |
|---|---|---|---|
| 268 | 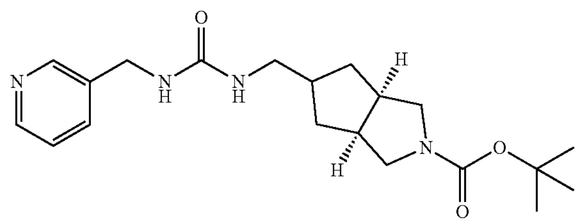 [SMILES: CC(C)(C)OC(=O)N1C[C@H]2CC(CNC(=O)NCc3cccnc3)C[C@H]2C1] | tert-butyl 5-((3-(pyridin-3-ylmethyl)ureido)methyl)hexahydrocyclopenta[c]pyrrole-2(1H)-carboxylate | 375.2 |
| 269 | 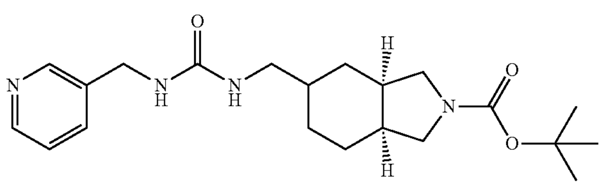 [SMILES: CC(C)(C)OC(=O)N1C[C@H]2CCC(CNC(=O)NCc3cccnc3)C[C@H]2C1] | tert-butyl 5-((3-(pyridin-3-ylmethyl)ureido)methyl)hexahydro-1H-isoindole-2(3H)-carboxylate | 389.1 |
| 270 | 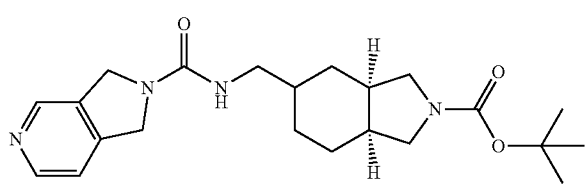 [SMILES: CC(C)(C)OC(=O)N1C[C@H]2CCC(CNC(=O)N3Cc4ccncc4C3)C[C@H]2C1] | tert-butyl 5-((2,3-dihydro-1H-pyrrolo[3,4-c]pyridine-2-carboxamido)methyl)hexahydro-1H-isoindole-2(3H)-carboxylate | 401.2 |
| 271 | 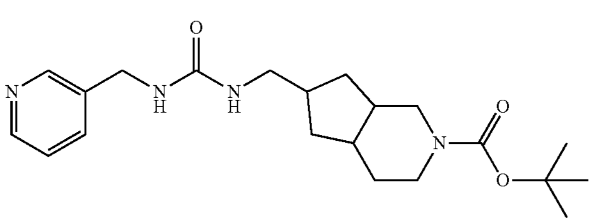 [SMILES: CC(C)(C)OC(=O)N1CCC2CC(CNC(=O)NCc3cccnc3)CC2C1] | tert-butyl 6-((3-(pyridin-3-ylmethyl)ureido)methyl)hexahydro-1H-cyclopenta[c]pyridine-2(3H)-carboxylate | 389.3 |
| 272 | 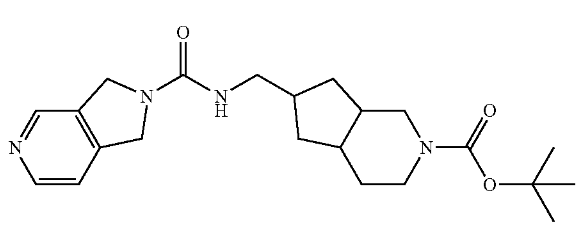 [SMILES: CC(C)(C)OC(=O)N1CCC2CC(CNC(=O)N3Cc4ccncc4C3)CC2C1] | tert-butyl 6-((2,3-dihydro-1H-pyrrolo[3,4-c]pyridine-2-carboxamido)methyl)hexahydro-1H-cyclopenta[c]pyridine-2(3H)-carboxylate | 401.2 |

Example 273: (3aR,5s,6aS)-tert-butyl 5-((2,3-di-hydro-1H-pyrrolo[3,4-c]pyridine-2-carboxamido)methyl)hexahydrocyclopenta[c]pyrrole-2(1H)-carboxylate

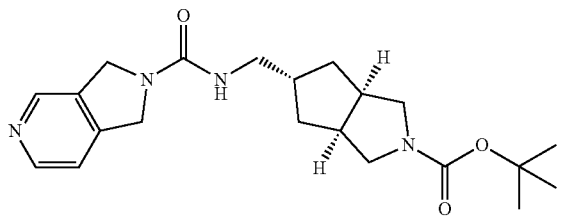 [SMILES: CC(C)(C)OC(=O)N1C[C@H]2C[C@H](CNC(=O)N3Cc4ccncc4C3)C[C@H]2C1]

To a solution of tert-butyl 5-oxohexahydrocyclopenta[c]pyrrole-2(1H)-carboxylate (500 mg, 2.22 mmol) in methanol (10 mL) at 0° C. was added sodium borohydride (336 mg, 8.88 mmol). The reaction mixture was stirred at 25° C. for 0.5 h. The resulting suspension was quenched with aqueous saturated ammonium chloride (10 mL) and extracted with dichloromethane (10 mL×3). The combined organic layers were washed with brine (10 mL×3), dried over anhydrous sodium sulfate and concentrated under vacuum to give 480 mg of crude (3aR,5r,6aS)-tert-butyl 5-hydroxyhexahydrocyclopenta[c]pyrrole-2(1H)-carboxylate as a yellow oil. $^1$H NMR (400 MHz, DMSO-$d_6$): δ4.35-4.25 (m, 1H), 3.56-3.45 (m, 2H), 3.38-3.26 (m, 2H), 2.66-2.55 (m, 2H), 2.23-2.13 (m, 1H), 2.08-2.03 (m, 1H), 1.84-1.81 (m, 1H), 1.47-1.43 (m, 11H).

To a solution of (3aR,5r,6aS)-tert-butyl 5-hydroxyhexahydrocyclopenta[c]pyrrole-2(1H)-carboxylate (370 mg, 1.63 mmol) in dichloromethane (10 mL) at 0° C. was added triethylamine (329 mg, 3.26 mmol) and methanesulfonyl chloride (242 mg, 2.12 mmol, 0.16 mL). The mixture was stirred at 25° C. for 0.5 h. The reaction solution was washed with aqueous saturated sodium bicarbonate (10 mL×3). The organic layer was dried over anhydrous sodium sulfate and concentrated under vacuum. The resulting residue was diluted with dimethylsulfoxide (10 mL) and sodium cyanide (321 mg, 6.55 mmol) was added. The reaction mixture was stirred at 80° C. for 1 h. The solution was cooled to 25° C., diluted with ethyl acetate (30 mL) and washed with water (20 mL×3). The organic layer was concentrated under vacuum. The resulting residue was purified by silica gel column chromatography (petroleum ether/ethyl acetate, from 50/1 to 2/1) to give 150 mg (48%) of (3aR,5s,6aS)-tert-butyl 5-cyanohexahydrocyclopenta[c]pyrrole-2(1H)-carboxylate as an off-white solid. $^1$H NMR (400 MHz, DMSO-$d_6$): δ 3.46 (dd, J=8.4, 11.2 Hz, 2H), 3.23-3.12 (m, 1H), 2.99 (dd, J=4.4, 11.6 Hz, 2H), 2.80-2.77 (m, 2H), 2.04-1.93 (m, 2H), 1.92-1.82 (m, 2H), 1.39 (s, 9H).

To a solution of (3aR,5s,6aS)-tert-butyl 5-cyanohexahydrocyclopenta[c]pyrrole-2(1H)-carboxylate (120 mg, 0.50 mmol) in ethyl alcohol (2 mL) was added sodium hydroxide (80 mg, 2.00 mmol). Raney nickel (104 mg) was added to the mixture under an atmosphere of nitrogen. The suspension was purged with hydrogen three times and stirred under an atmosphere of hydrogen (50 psi) at 25° C. for 3 h. The reaction mixture was filtered and the filtrate was concentrated under vacuum to afford 100 mg of crude (3aR,5s,6aS)-tert-butyl 5-(aminomethyl)hexahydrocyclopenta[c]pyrrole-2(1H)-carboxylate as a yellow oil. MS (ESI) m/z: 241.4 (M+H)$^+$. $^1$H NMR (400 MHz, DMSO-$d_6$): δ 3.49-3.42 (m, 4H), 2.99-2.91 (m, 2H), 2.69-2.54 (m, 2H), 2.06-1.95 (m, 1H), 1.56-1.48 (m, 2H), 1.48-1.39 (m, 2H), 1.38 (s, 9H).

To a solution of (3aR,5s,6aS)-tert-butyl 5-(aminomethyl)hexahydrocyclopenta[c]pyrrole-2(1H)-carboxylate (100 mg, 0.41 mmol) in acetonitrile (2 mL) was added pyridine (39 mg, 0.50 mmol) and di(succinimido) carbonate (117 mg, 0.46 mmol). The mixture was stirred at 25° C. for 1 h. 2,3-dihydro-1H-pyrrolo[3,4-c]pyridine hydrochloride (98 mg, 0.62 mmol) and triethylamine (211 mg, 2.08 mmol) were added to the reaction mixture. The reaction mixture was stirred at 25° C. for 1 h. The resulting solution was concentrated under vacuum. The resulting residue was purified by preparative HPLC (Phenomenex Gemini C18 column (150×25 mm, 5 um); flow rate: 25 mL/min; gradient: 23%-49% B over 12 min; mobile phase A: 0.05% aqueous ammonium hydroxide, mobile phase B: acetonitrile) to give 21 mg (13%) of the title compound as a yellow oil. MS (ESI) m/z: 409.2 (M+H)$^+$. $^1$H NMR (400 MHz, DMSO-$d_6$): δ 8.56 (s, 1H), 8.46 (d, J=5.2 Hz, 1H), 7.38 (d, J=5.2 Hz, 1H), 6.41 (t, J=5.6 Hz, 1H), 4.61 (d, J=4.8 Hz, 4H), 3.48-3.39 (m, 2H), 3.05-2.93 (m, 4H), 2.67-2.64 (m, 2H), 2.30-2.18 (m, 1H), 1.58-1.43 (m, 4H), 1.37 (s, 9H).

Example 274: (3aR,5r,6aS)-tert-butyl 5-(2-((E)-3-(pyridin-3 yl)acrylamido)ethyl)hexahydrocyclopenta[c]pyrrole-2(1H)-carboxylate

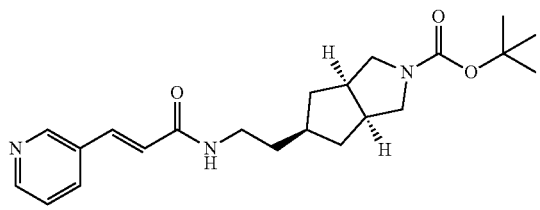 [SMILES: CC(C)(C)OC(=O)N1C[C@H]2C[C@@H](CCNC(=O)/C=C/c3cccnc3)C[C@H]2C1]

To a solution of diethyl (cyanomethyl)phosphonate (608 mg, 3.33 mmol, 0.55 mL) in N,N-dimethylformamide (10 mL) was added sodium hydride (178 mg, 4.44 mmol, 60% in mineral oil) at 0° C. The mixture was stirred at 0° C. for 0.5 h. tert-Butyl 5-oxohexahydrocyclopenta[c]pyrrole-2(1H)-carboxylate (515 mg, 2.22 mmol) was added to the resulting mixture. The suspension was warmed to 25° C. and stirred for 2.5 h. The suspension was quenched with water (30 mL) and the mixture was extracted with ethyl acetate (15 mL×3). The combined organic layers were washed with brine (20 mL), dried over anhydrous sodium sulfate and concentrated under vacuum. The residue was purified by silica gel column chromatography (petroleum ether/ethyl acetate, from 1/0 to 2/1) to give 110 mg (20%) of tert-butyl 5-(cyanomethylene)hexahydrocyclopenta[c]pyrrole-2(1H)-carboxylate as a yellow oil. MS (ESI) m/z: 193.1 (M+H-t-Bu)$^+$. $^1$H NMR (400 MHz, CDCl$_3$) δ 5.32-5.26 (m, 1H), 3.68-3.62 (m, 2H), 3.24-2.72 (m, 6H), 2.67-2.54 (m, 1H), 2.48-2.38 (m, 1H), 1.45 (d, J=3.2 Hz, 1H).

Ammonia was bubbled through a solution of methanol (15 mL) at 0° C. for 30 min, and tert-butyl 5-(cyanomethylene)hexahydrocyclopenta[c]pyrrole-2(1H)-carboxylate (110 mg, 0.44 mmol) was added to and dissolved in the resulting solution. Raney nickel (50 mg) was added into the reaction mixture under an atmosphere of nitrogen. The suspension was purged with hydrogen three times and stirred at 25° C. under an atmosphere of hydrogen (45 psi) for 12 h. The reaction mixture was filtered and the filtrate was concentrated under vacuum to give 105 mg of crude (3aR,5r,6aS)-tert-butyl 5-(2-aminoethyl)hexahydrocyclopenta[c]pyrrole-2(1H)-carboxylate as a light yellow oil. MS (ESI) m/z: 255.4 (M+H)⁺.

A solution of (3aR,5r,6aS)-tert-butyl 5-(2-aminoethyl)hexahydrocyclopenta[c]pyrrole-2(1H)-carboxylate (100 mg, 0.39 mmol), 1-ethyl-(3-(3-dimethylamino)propyl)-carbodiimide hydrochloride (106 mg, 0.55 mmol) and (E)-3-(pyridin-3-yl)acrylic acid (76 mg, 0.51 mmol) in pyridine (3 mL) was stirred at 25° C. for 1 h. The reaction mixture was concentrated and the resulting residue was purified by preparative HPLC (Phenomenex Gemini 150×25 mm, 10 um; flow rate: 25 mL/min; gradient: 30%-60% B over 12 min; mobile phase A: water (0.05% aqueous ammonium hydroxide, mobile phase B: acetonitrile) to give 30.0 mg (20%) of the title compound as an off-white solid. MS (ESI) m/z: 386.4 (M+H)⁺. ¹H NMR (400 MHz, DMSO-d₆) δ 8.74 (d, J=4.0 Hz, 1H), 8.55-8.53 (dd, J=3.2 Hz 4.8 Hz 1H), 7.95-7.93 (m, 1H), 7.92 (s, 1H), 7.46-7.40 (m, 2H), 6.70 (d, J=15.6 Hz, 1H), 3.39-3.35 (m, 2H), 3.22-3.20 (m, 2H), 3.15-3.12 (m, 2H), 2.57-2.56 (m, 2H), 2.09-2.06 (m, 2H), 1.97-1.86 (m, 1H), 1.60-1.54 (m, 2H), 1.40 (d, J=6.8 Hz, 1H), 0.99-0.97 (m, 1H).

Example 275: (3aR,5r,6aS)-tert-butyl 5-(2-(2-(pyridin-3-yloxy)acetamido)ethyl)hexahydrocyclopenta[c]pyrrole-2(1H)-carboxylate

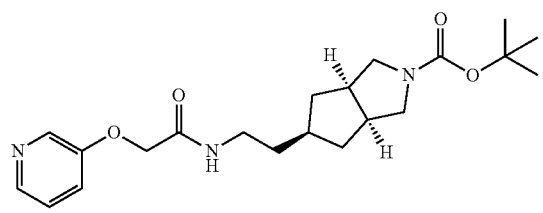 [SMILES: CC(C)(C)OC(=O)N1C[C@H]2C[C@@H](CCNC(=O)COc3cccnc3)C[C@H]2C1]

This compound was prepared substantially according to the procedures described above. MS (ESI) m/z: 390.3 (M+H)⁺.

Example 276: (E)-N-(2-((1R,5S,6s)-3-benzhydryl-3-azabicyclo[3.1.0]hexan-6-yl)ethyl)-3-(pyridin-3-yl)acrylamide

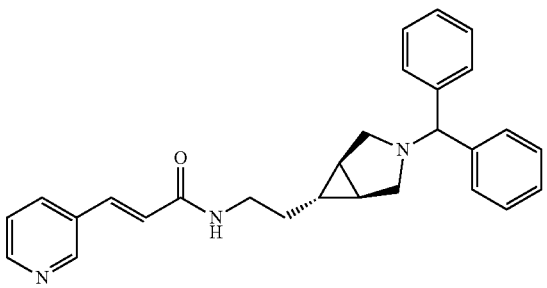 [SMILES: O=C(/C=C/c1cccnc1)NCC[C@@H]1[C@H]2CN(C(c3ccccc3)c3ccccc3)C[C@@H]12]

To a solution of (E)-N-(2-((1R,5S,6s)-3-azabicyclo[3.1.0]hexan-6-yl)ethyl)-3-(pyridin-3-yl)acrylamide (70 mg, 0.27 mmol, TFA salt) and benzhydryl chloride (52 mg, 0.26 mmol) in acetonitrile (3 mL) was added potassium carbonate (58 mg, 0.42 mmol) and sodium iodide (41 mg, 0.27 mmol). The mixture was stirred at 60° C. for 3 h. The reaction mixture was diluted with water (10 mL) and extracted with ethyl acetate (10 mL×3). The combined organic layers were washed with brine (10 mL) and concentrated. The crude product was purified by preparative HPLC (Phenomenex Gemini C18 column (150×25 mm, 10 um); flow rate: 25 mL/min; gradient: 8%-38% B over 10 min; mobile phase A: 0.1% aqueous trifluoroacetic acid, mobile phase B: acetonitrile) to give 20 mg (96%) of the title compound as the TFA salt as a light yellow gum. MS (ESI) m/z: 424.2 (M+H)⁺. ¹H NMR (400 MHz, DMSO-d₆): δ 11.39-11.16 (m, 0.5H), 10.08 (br s, 0.5H), 8.76 (s, 1H), 8.57 (dd, J=1.2, 4.8 Hz, 1H), 8.20 (t, J=5.6 Hz, 1H), 7.99 (d, J=8.0 Hz, 1H), 7.67-7.57 (m, 3H), 7.55-7.31 (m, 8H), 6.71 (d, J=16.0 Hz, 1H), 5.74-5.52 (m, 1H), 3.55 (br s, 1H), 3.27-3.16 (m, 4H), 2.91-2.78 (m, 1H), 1.81-1.61 (m, 2H), 1.40 (br d, J=6.4 Hz, 2H), 1.26-1.09 (m, 1H).

Example 277: (E)-N-(2-((1R,5S,6s)-3-(5-fluoro-2-morpholinopyrimidin-4-yl)-3-azabicyclo[3.1.0]hexan-6-yl)ethyl)-3-(pyridin-3-yl)acrylamide

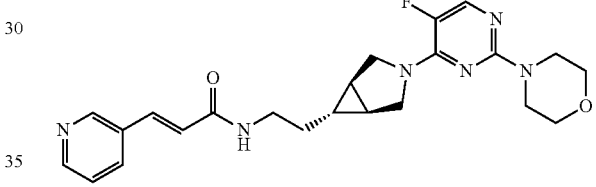

To a sealed tube equipped with a magnetic stir bar was added the Example 172 compound (70 mg, 0.16 mmol, HCl salt) and 1-methylpyrrolidin-2-one (2 mL), follow by N,N-diisopropylethylamine (82 mg, 0.64 mmol, 0.11 mL) and morpholine (210 mg, 0.79 mmol, 0.21 mL). The mixture was heated to 110° C. and stirred for 12 h. The mixture was cooled to room temperature and quenched by slow addition of water (5 mL). The resulting mixture was transferred to a separatory funnel and the aqueous layer was extracted with ethyl acetate (10 mL×3). The combined organic layers were washed with brine (5 mL), dried over anhydrous sodium sulfate, filtered, and concentrated under reduced pressure to afford a brown oily residue. The resulting residue was purified by preparative HPLC (Phenomenex Gemini C18 column (150×25 mm, 10 um); flow rate: 25 mL/min; gradient: 4%-34% B over 10 min; mobile phase A: 0.1% aqueous trifluoroacetic acid, mobile phase B: acetonitrile) to give 43 mg (62%) of the title compound as the TFA salt as a yellow gum. MS (ESI) m/z: 439.3 (M+H)⁺. ¹H NMR (400 MHz, DMSO-d₆): δ 8.83 (s, 1H), 8.62 (d, J=4.8 Hz, 1H), 8.27 (t, J=5.6 Hz, 1H), 8.15 (d, J=8.0 Hz, 1H), 8.03 (d, J=6.8 Hz, 1H), 7.59 (dd, J=5.2, 8.0 Hz, 1H), 7.48 (d, J=16.0 Hz, 1H), 6.78 (d, J=16.0 Hz, 1H), 3.91 (dd, J=2.8, 12.0 Hz, 2H), 3.83-3.54 (m, 10H), 3.27 (q, J=6.4 Hz, 2H), 1.55 (s, 2H), 1.44 (q, J=6.8 Hz, 2H), 0.60 (td, J=3.6, 6.8 Hz, 1H).

Example 278: (E)-N-(2-((1R,5S,6s)-3-(2-(cyclopentyloxy)-5-fluoropyrimidin-4-yl)-3-azabicyclo[3.1.0]hexan-6-yl)ethyl)-3-(pyridin-3-yl)acrylamide

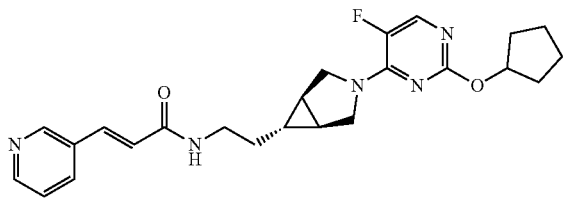 [SMILES: O=C(/C=C/c1cccnc1)NCC[C@@H]1[C@H]2CN(c3nc(OC4CCCC4)ncc3F)C[C@@H]12]

To a 50 mL round-bottom flask equipped with a magnetic stir bar was added sodium hydride (51 mg, 1.27 mmol, 60% dispersion in mineral oil) followed by the addition of N,N-dimethylacetamide (3 mL). The mixture was cooled to 0° C. Cyclopentanol (110 mg, 1.27 mmol, 0.12 mL) was then added dropwise. The mixture was warmed to 25° C. and stirred for 0.5 h. The mixture was cooled to 0° C., and a solution of the Example 172 compound (70 mg, 0.16 mmol, HCl salt) in N,N-dimethylacetamide (0.3 mL) was added dropwise. The resulting mixture was heated to 100° C. and stirred for 12 h under an atmosphere of nitrogen. The reaction mixture was cooled to room temperature and quenched by slow addition of water (10 mL). The resulting mixture was transferred to a separatory funnel, and the aqueous layer was extracted with ethyl acetate (10 mL×3). The combined organic layers were washed with brine (10 mL), dried over anhydrous sodium sulfate, filtered, and concentrated under reduced pressure to afford a residue as a yellow oil. The resulting residue was purified by preparative HPLC (Phenomenex Gemini C18 column (150×25 mm, 5 um); flow rate: 25 mL/min; gradient: 8%-38% B over 9 min; mobile phase A: 0.075% aqueous trifluoroacetic acid, mobile phase B: acetonitrile) to give 23 mg (26%) of the title compound as the TFA salt as a yellow gum. MS (ESI) m/z: 438.3 (M+H)+. 1H NMR (400 MHz, DMSO-$d_6$): δ 8.87 (d, J=2.0 Hz, 1H), 8.65 (dd, J=1.6, 5.2 Hz, 1H), 8.28 (t, J=5.6 Hz, 1H), 8.21 (d, J=8.0 Hz, 1H), 8.08 (d, J=6.0 Hz, 1H), 7.64 (dd, J=5.2, 8.0 Hz, 1H), 7.50 (d, J=16.0 Hz, 1H), 6.80 (d, J=16.0 Hz, 1H), 5.35-5.20 (m, 1H), 3.90 (dd, J=3.2, 11.6 Hz, 2H), 3.70 (s, 2H), 3.28 (q, J=6.4 Hz, 2H), 1.97-1.85 (m, 2H), 1.75-1.52 (m, 8H), 1.46 (q, J=6.8 Hz, 2H), 0.62 (td, J=3.6, 7.2 Hz, 1H).

Example 279: (1R,5S,6r)-tert-butyl 6-(2-((E)-3-(pyridin-3-yl)acrylamido)ethyl)-3-azabicyclo[3.1.0]hexane-3-carboxylate

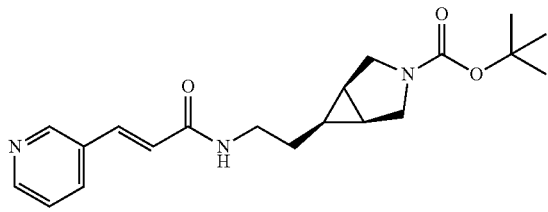 [SMILES: CC(C)(C)OC(=O)N1C[C@@H]2[C@H](CCNC(=O)/C=C/c3cccnc3)[C@@H]2C1]

To a 100 mL round-bottom flask equipped with a magnetic stir bar was added (1R,5S,6s)-tert-butyl 6-(hydroxymethyl)-3-azabicyclo[3.1.0]hexane-3-carboxylate (550 mg, 2.58 mmol) followed by the addition of dichloromethane (10 mL) and triethylamine (783 mg, 7.74 mmol, 1.08 mL). The solution was cooled to 0° C., and methanesulfonyl chloride (443 mg, 3.87 mmol) was added dropwise. The reaction mixture was allowed to warm to 20° C. and stir for 5 h. The mixture was diluted by slow addition of water (10 mL). The resulting mixture was transferred to a separatory funnel, and the aqueous layer mixture was extracted with dichloromethane (10 mL×3). The combined organic layers were washed with brine (10 mL), dried over anhydrous sodium sulfate, filtered, and concentrated under reduced pressure to afford a residue. The crude product was purified by silica gel column chromatography (petroleum ether/ethyl acetate, from 15/1 to 5/1) to give 410 mg (55%) of (1R,5S,6s)-tert-butyl 6-(((methylsulfonyl)oxy)methyl)-3-azabicyclo[3.1.0]hexane-3-carboxylate as yellow oil. 1H NMR (400 MHz, CDCl3): δ 4.28 (dd, J=2.2, 8.0 Hz, 2H), 3.57-3.49 (m, 4H), 3.01 (s, 3H), 1.83 (td, J=1.4, 8.0 Hz, 2H), 1.45 (s, 9H), 1.43-1.39 (m, 1H).

To a 100 mL round-bottom flask equipped with a magnetic stir bar was added (1R,5S,6s)-tert-butyl 6-(((methylsulfonyl)oxy)methyl)-3-azabicyclo[3.1.0]hexane-3-carboxylate (410 mg, 1.41 mmol) followed by the addition of acetonitrile (10 mL). Sodium cyanide (101 mg, 2.06 mmol) and sodium iodide (46 mg, 0.31 mmol) were added and the mixture was stirred at 20° C. for 12 h. The reaction mixture was filtered and the filtrate was concentrated to give a crude product. The crude residue was purified by silica gel column chromatography (petroleum ether/ethyl acetate, from 5/1 to 1/1) to give 200 mg (64%) of (1R,5S,6r)-tert-butyl 6-(cyanomethyl)-3-azabicyclo[3.1.0]hexane-3-carboxylate as a yellow oil. 1H NMR (400 MHz, CDCl3): δ 3.57 (dt, J=3.4, 11.4 Hz, 2H), 3.49-3.37 (m, 2H), 2.47-2.34 (m, 1H), 2.30-2.14 (m, 1H), 1.77 (dd, J=3.8, 8.0 Hz, 2H), 1.46 (s, 9H), 1.35-1.27 (m, 1H).

To a mixture of (1R,5S,6r)-tert-butyl 6-(cyanomethyl)-3-azabicyclo[3.1.0]hexane-3-carboxylate (150 mg, 0.675 mmol) in a solution of saturated ammonia in methanol (5 mL) was added Raney nickel (30 mg). The mixture was stirred at 25° C. under an atmosphere of hydrogen (15 psi) for 12 h. The suspension was filtered and the filter cake was washed with methanol (20 mL). The combined filtrates were concentrated under vacuum to give 150 mg of crude (1R, 5S,6r)-tert-butyl 6-(2-aminoethyl)-3-azabicyclo[3.1.0]hexane-3-carboxylate.

To a 40 mL vial equipped with a magnetic stir bar was added (E)-3-(pyridin-3-yl)acrylic acid (36 mg, 0.24 mmol) followed by the addition of dichloromethane (4 mL). 1-Ethyl-3-(3-dimethylaminopropyl)carbodiimide hydrochloride (51 mg, 0.27 mmol) and pyridine (70 mg, 0.88 mmol) were added into the mixture at 20° C., followed by the addition of (1R,5S,6r)-tert-butyl 6-(2-aminoethyl)-3-azabicyclo[3.1.0]hexane-3-carboxylate (50 mg, 0.22 mmol). The mixture was stirred at 20° C. for 2 h. The mixture was concentrated under reduced pressure to afford the crude product. The crude product was purified by preparative HPLC (Phenomenex Gemini C18 column (150×25 mm, 5 um); flow rate: 25 mL/min; gradient: 20%-50% B over 10 min; mobile phase A: 0.05% aqueous ammonia hydroxide, mobile phase B: acetonitrile) to give 21 mg (27%) of the title compound as a yellow gum. MS (ESI) m/z: 358.4 (M+H)+. 1H NMR (400 MHz, DMSO-$d_6$): δ 8.74 (s, 1H), 8.62-8.47 (m, 1H), 8.31-8.18 (m, 1H), 7.96 (br d, J=7.8 Hz, 1H), 7.50-7.38 (m, 2H), 6.72 (d, J=15.8 Hz, 1H), 3.44-3.38 (m, 2H), 3.27-3.21 (m, 4H), 1.66-1.54 (m, 2H), 1.36 (s, 9H), 1.33-1.22 (m, 2H), 0.88 (q, J=7.6 Hz, 1H).

Example 280: (E)-N-(2-((1R,5S,6r)-3-benzyl-3-azabicyclo[3.1.0]hexan-6-yl)ethyl)-3-(pyridin-3-yl)acrylamide

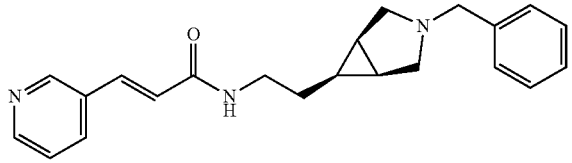 [SMILES: O=C(/C=C/c1cccnc1)NCC[C@H]1[C@H]2CN(Cc3ccccc3)C[C@@H]12]

To a 50 mL round-bottom flask equipped with a magnetic stir bar was added (1R,5S,6r)-tert-butyl 6-(2-((E)-3-(pyridin-3-yl)acrylamido)ethyl)-3-azabicyclo[3.1.0]hexane-3-carboxylate (120 mg, 0.311 mmol) followed by the addition of dichloromethane (5 mL). 2,2,2-Trifluoroacetic acid (3.08 g, 27.0 mmol, 2 mL) was added. The reaction mixture was stirred at 25° C. for 1 h. The mixture was concentrated under reduced pressure to afford 120 mg of crude (E)-N-(2-((1R,5S,6r)-3-azabicyclo[3.1.0]hexan-6-yl)ethyl)-3-(pyridin-3-yl)acrylamide as the TFA salt and as a yellow oil.

To a 40 mL vial equipped with a magnetic stir bar was added (E)-N-(2-((1R,5S,6r)-3-azabicyclo[3.1.0]hexan-6-yl)ethyl)-3-(pyridin-3-yl)acrylamide (60 mg, 0.16 mmol, TFA salt) followed by the addition of methanol (3 mL). Triethylamine (33 mg, 0.32 mmol) was added into the mixture followed by the addition of acetic acid (10 mg, 0.16 mmol). The pH of the mixture was about 5-6. Benzaldehyde (26 mg, 0.24 mmol) and sodium cyanoborohydride (15 mg, 0.24 mmol) were added. The mixture was stirred at 25° C. for 2 h. The mixture was quenched by slow addition of water (10 mL). The resulting mixture was transferred to a separatory funnel, and the aqueous layer mixture was extracted with ethyl acetate (20 mL×3). The combined organic layers were washed with brine (20 mL), dried over anhydrous sodium sulfate, filtered, and concentrated under reduced pressure to afford the crude product. The crude product was purified by preparative HPLC (Luna C18 column (150×25 mm, 5 um); flow rate: 25 mL/min; gradient: 1%-30% B over 9 min; mobile phase A: 0.075% aqueous trifluoroacetic acid, mobile phase B: acetonitrile) and the resulting impure product was further purified by preparative HPLC (Waters Xbridge C18 column (150×25 mm, 5 um); flow rate: 25 mL/min; gradient: 33%-60% B over 10 min; mobile phase A: 0.05% ammonia hydroxide, mobile phase B: acetonitrile) to give 8 mg (11%) of the title compound as a light yellow gum. MS (ESI) m/z: 348.4 (M+H)$^+$. $^1$H NMR (400 MHz, DMSO-$d_6$): δ 8.75 (d, J=2.0 Hz, 1H), 8.54 (dd, J=1.6, 4.8 Hz, 1H), 8.22 (br t, J=5.2 Hz, 1H), 7.97 (br d, J=7.8 Hz, 1H), 7.51-7.40 (m, 2H), 7.35-7.16 (m, 5H), 6.75 (d, J=16.0 Hz, 1H), 3.56 (s, 2H), 3.31-3.22 (m, 4H), 2.84 (d, J=9.2 Hz, 2H), 1.88 (q, J=7.2 Hz, 2H), 1.44 (br d, J=7.6 Hz, 2H), 0.80-0.72 (m, 1H).

Example 281: (E)-N-(2-((1R,5S,6r)-3-phenyl-3-azabicyclo[3.1.0]hexan-6-yl)ethyl)-3-(pyridin-3-yl)acrylamide

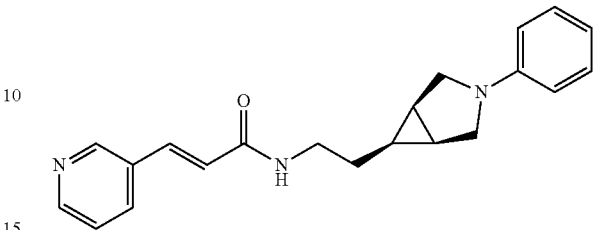

To a 10 mL vial equipped with a magnetic stir bar was added (1R,5S,6r)-tert-butyl 6-(cyanomethyl)-3-azabicyclo[3.1.0]hexane-3-carboxylate (60 mg, 270 umol) followed by the addition of dichloromethane (5 mL). 2,2,2-Trifluoroacetic acid (1.54 g, 13.5 mmol, 1 mL) was added. The mixture was stirred at 25° C. for 1 h. The mixture was concentrated under reduced pressure to afford 60 mg of crude 2-((1R,5S,6r)-3-azabicyclo[3.1.0]hexan-6-yl)acetonitrile as the TFA salt and as a yellow oil.

To a 50 mL three-neck round-bottom flask equipped with a magnetic stir bar and a reflux condenser was added 2-((1R,5S,6r)-3-azabicyclo[3.1.0]hexan-6-yl)acetonitrile (60 mg, 0.25 mmol, TFA salt) followed by the addition of 1,4-dioxane (10 mL). Cesium carbonate (248 mg, 0.762 mmol) was added. The mixture was stirred at 25° C. for 0.5 h. Bromobenzene (52 mg, 0.33 mmol), 2,2'-bis(diphenylphosphino)-1,1'-binaphthyl (16 mg, 0.025 mmol) and tris(dibenzylideneacetone)dipalladium(0) (12 mg, 0.013 mmol) were added into the mixture. The flask was evacuated and backfilled with nitrogen three times. The mixture was heated to 100° C. and stirred for 11.5 h. The reaction mixture was cooled to room temperature and quenched by slow addition of saturated aqueous ammonium chloride (1 mL). The suspension was filtered through a pad of Celite. The Celite pad was washed with ethyl acetate (15 mL) and water (15 mL). The aqueous phase was extracted with ethyl acetate (15 mL×3), and the combined organic phases were washed with brine (20 mL), dried over anhydrous sodium sulfate, filtered, and concentrated under reduced pressure to afford the crude product as a yellow oil. The crude product was purified by silica gel column chromatography (petroleum ether/ethyl acetate, from 20/1 to 5/1) to give 45 mg (70%) of 2-((1R,5S,6r)-3-phenyl-3-azabicyclo[3.1.0]hexan-6-yl)acetonitrile as a yellow oil.

To a 50 mL round-bottom flask equipped with a magnetic stir bar was added 2-((1R,5S,6r)-3-phenyl-3-azabicyclo[3.1.0]hexan-6-yl)acetonitrile (45 mg, 177 umol) followed by the addition of saturated ammonia in methanol (5 mL). Raney nickel (30 mg) was added into the mixture at 25° C. The flask was evacuated and backfilled with hydrogen three times. The mixture was stirred at 25° C. under an atmosphere of hydrogen (balloon) for 10 h. The suspension was filtered through a pad of Celite. The Celite pad was washed with methanol (20 mL). The filtrate was concentrated under reduced pressure to afford 35 mg of crude 2-((1R,5S,6r)-3-phenyl-3-azabicyclo[3.1.0]hexan-6-yl)ethanamine as a yellow oil.

To a 25 mL round-bottom flask equipped with a magnetic stir bar was added (E)-3-(pyridin-3-yl)acrylic acid (28 mg, 190 umol) followed by the addition of dichloromethane (4 mL). 1-Ethyl-3-(3-dimethylaminopropyl)carbodiimide hydrochloride (40 mg, 0.21 mmol) and pyridine (68 mg, 0.87 mmol) was added, followed by the addition of 2-((1R,5S,6r)-3-phenyl-3-azabicyclo[3.1.0]hexan-6-yl)ethanamine (35 mg, 0.17 mmol). The mixture was stirred at 25° C. for 2 h. The reaction mixture was quenched by slow addition of water (10 mL). The resulting mixture was transferred to a separatory funnel, and the aqueous layer was extracted with ethyl acetate (15 mL×3). The combined organic layers were washed with brine (15 mL), dried over anhydrous sodium sulfate, filtered, and concentrated under reduced pressure to afford the crude product. The crude product was purified by preparative HPLC (Phenomenex Luna C18 column (150×25 mm, 10 um); flow rate: 25 mL/min; gradient: 22%-52% B over 10 min; mobile phase A: 0.1% aqueous trifluoroacetic acid, mobile phase B: acetonitrile) to give 11.5 mg (14%) of the title compound as the TFA salt as a yellow solid. MS (ESI) m/z: 334.3 (M+H)$^+$. $^1$H NMR (400 MHz, DMSO-d$_6$): δ 8.77 (s, 1H), 8.57 (d, J=4.8 Hz, 1H), 8.28-8.15 (m, 1H), 8.04 (br d, J=8.4 Hz, 1H), 7.51 (dd, J=5.0, 8.0 Hz, 1H), 7.43 (d, J=16.0 Hz, 1H), 7.12 (t, J=8.0 Hz, 2H), 6.70 (d, J=16.0 Hz, 1H), 6.56 (t, J=7.4 Hz, 1H), 6.45 (d, J=7.8 Hz, 2H), 3.35 (br d, J=7.8 Hz, 2H), 3.29-3.21 (m, 4H), 1.78 (br d, J=8.2 Hz, 2H), 1.30 (q, J=7.2 Hz, 2H), 0.95 (q, J=7.6 Hz, 1H).

Example 282: 2-((5-fluoro-4-((1R,5S,6s)-6-(2-((E)-3-(pyridin-3-yl)acrylamido)ethyl)-3-azabicyclo[3.1.0]hexan-3-yl)pyrimidin-2-yl)oxy)acetic acid

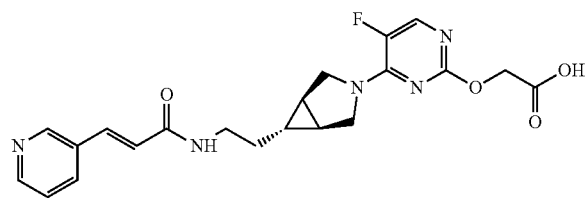 [SMILES: O=C(O)COc1ncc(F)c(N2C[C@@H]3[C@@H](CCNC(=O)/C=C/c4cccnc4)[C@@H]3C2)n1]

To a 50 mL round-bottom flask equipped with a magnetic stir bar was added sodium hydride (14 mg, 0.35 mmol, 60% dispersion in mineral oil) followed by the addition of tetrahydrofuran (4 mL). The solution was cooled to 0° C. tert-Butyl 2-hydroxyacetate (46 mg, 0.35 mmol, 0.02 mL) was added dropwise. The mixture was warmed to 25° C. and stirred for 0.5 h. The reaction mixture was re-cooled to 0° C., and a solution of the Compound 172 compound (70 mg, 0.17 mmol) in tetrahydrofuran (0.5 mL) was added dropwise. The mixture was stirred at 25° C. for 12 h under an atmosphere of nitrogen. The mixture was quenched with hydrogen chloride in 1,4-dioxane (4 M) to a pH of 6, diluted with methanol (10 mL), and filtered. The filtrate was concentrated under reduced pressure to afford a residue as a yellow oil. The residue was purified by preparative HPLC (Phenomenex Gemini C18 column (150×25 mm, 10 um); flow rate: 25 mL/min; gradient: 2%-27% B over 10 min; mobile phase A: 0.1% aqueous trifluoroacetic acid, mobile phase B: acetonitrile) to give an impure yellow gum which was further purified by preparative HPLC (Phenomenex Gemini C18 column (150×25 mm, 5 um); flow rate: 25 mL/min; gradient: 0%-30% B over 10 min; mobile phase A: 0.05% aqueous ammonia hydroxide, mobile phase B: acetonitrile) to give 4.6 mg (6%) of the title compound as a white solid. MS (ESI) m/z: 428.4 (M+H)$^+$. $^1$H NMR (400 MHz, DMSO-d$_6$): δ 8.74 (s, 1H), 8.53 (d, J=4.8 Hz, 1H), 8.30 (t, J=5.6 Hz, 1H), 7.97 (d, J=8.0 Hz, 1H), 7.89 (d, J=5.6 Hz, 1H), 7.50-7.38 (m, 2H), 6.77 (d, J=16.0 Hz, 1H), 4.43 (s, 2H), 3.84 (dd, J=3.2, 11.2 Hz, 2H), 3.56 (d, J=9.6 Hz, 2H), 3.26 (d, J=6.0 Hz, 2H), 1.49 (s, 2H), 1.43 (q, J=6.8 Hz, 2H), 0.64-0.55 (m, 1H).

Example 283: (E)-N-(2-((1R,5S,6s)-3-(2-amino-2-oxo-1-phenylethyl)-3-azabicyclo[3.1.0]hexan-6-yl)ethyl)-3-(pyridin-3-yl)acrylamide

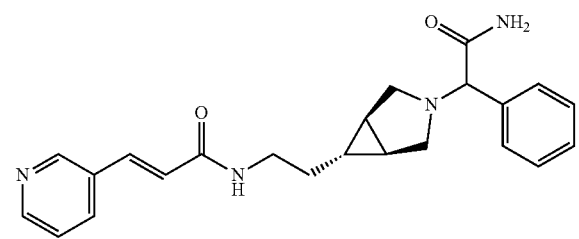 [SMILES: NC(=O)C(c1ccccc1)N1C[C@@H]2[C@@H](CCNC(=O)/C=C/c3cccnc3)[C@@H]2C1]

To a 50 mL round-bottom flask equipped with a magnetic stir bar was added (E)-N-(2-((1R,5S,6S)-3-azabicyclo[3.1.0]hexan-6-yl)ethyl)-3-(pyridin-3-yl)acrylamide (350 mg, 0.94 mmol, TFA salt) followed by the addition of dichloromethane (8 mL). N,N-diisopropylethylamine (364 mg, 2.83 mmol, 0.49 mL) was added. The mixture was stirred at 25° C. for 10 min, and a solution of methyl 2-bromo-2-phenylacetate (216 mg, 0.94 mmol, 0.15 mL) in dichloromethane (1 mL) was added dropwise and stirred for 1 h at 25° C. The resulting mixture was concentrated under reduced pressure to afford the crude product as a red oil. The resulting crude product was purified by silica gel column chromatography (petroleum ether/ethyl acetate, from 1/1 to 0/1, followed by ethyl acetate/methanol, 10/1) to give 290 mg (76%) of methyl 2-phenyl-2-((1R,5S,6s)-6-(2-((E)-3-(pyridin-3-yl)acrylamido)ethyl)-3-azabicyclo[3.1.0]hexan-3-yl)acetate as a yellow gum. MS (ESI) m/z: 406.2 (M+H)$^+$.

To a 50 mL round-bottom flask equipped with a magnetic stir bar was added methyl 2-phenyl-2-((1R,5S,6s)-6-(2-((E)-3-(pyridin-3-yl)acrylamido)ethyl)-3-azabicyclo[3.1.0]hexan-3-yl)acetate (290 mg, 0.72 mmol) followed by the addition of water (5 mL) and methanol (5 mL). Lithium hydroxide monohydrate (150 mg, 3.58 mmol) was then added. The mixture was stirred at 25° C. for 3 h. The reaction mixture was acidified with hydrogen chloride in methanol (4 M) to a pH of 5 and concentrated under high reduced pressure to give 270 mg of crude 2-phenyl-2-((1R,5S,6s)-6-(2-((E)-3-(pyridin-3-yl)acrylamido)ethyl)-3-azabicyclo[3.1.0]hexan-3-yl)acetic acid as a red solid. MS (ESI) m/z: 392.2 (M+H)$^+$.

To a 50 mL round-bottom flask equipped with a magnetic stir bar was added 2-phenyl-2-((1R,5S,6s)-6-(2-((E)-3-(pyridin-3-yl)acrylamido)ethyl)-3-azabicyclo[3.1.0]hexan-3-yl)acetic acid (70 mg, 0.18 mmol) and ammonium chloride (19 mg, 0.36 mmol) followed by the addition of N,N-dimethylacetamide (3 mL). N,N-Diisopropylethylamine (69 mg, 0.54 mmol, 0.09 mL) and 2-(3H-[1,2,3]triazolo[4,5-b]pyridin-3-yl)-1,1,3,3-tetramethylisouronium hexafluorophosphate(V) (136 mg, 0.36 mmol) were added. The mixture was stirred at 20° C. for 1 h. The reaction mixture was quenched by slow addition of water (15 mL). The resulting mixture was transferred to a separatory funnel, and the aqueous layer mixture was extracted with dichloromethane (20 mL×2). The combined organic layers were washed with brine (10 mL), dried over anhydrous sodium sulfate, filtered, and concentrated under reduced pressure to afford a residue as a yellow oil. The residue was purified by preparative HPLC (Phenomenex Gemini C18 column (150× 25 mm, 5 um); flow rate: 25 mL/min; gradient: 15%-45% B over 10 min; mobile phase A: 0.05% aqueous ammonia hydroxide, mobile phase B: acetonitrile) to give 35 mg (50%) of the title compound as a white solid. MS (ESI) m/z: 391.4 (M+H)+. 1H NMR (400 MHz, DMSO-d6): δ 8.74 (d, J=1.6 Hz, 1H), 8.54 (dd, J=1.6, 4.8 Hz, 1H), 8.15 (t, J=5.2 Hz, 1H), 7.97 (d, J=8.0 Hz, 1H), 7.48-7.40 (m, 2H), 7.40-7.32 (m, 3H), 7.32-7.21 (m, 3H), 7.00 (s, 1H), 6.72 (d, J=16.0 Hz, 1H), 3.66 (s, 1H), 3.22 (d, J=7.2 Hz, 2H), 3.09 (d, J=8.4 Hz, 1H), 2.58 (d, J=8.8 Hz, 1H), 2.34 (dd, J=3.6, 8.4 Hz, 1H), 2.07 (dd, J=3.6, 8.8 Hz, 1H), 1.34 (q, J=6.8 Hz, 2H), 1.28-1.16 (m, 2H), 1.11 (dd, J=3.2, 6.8 Hz, 1H).

Example 284: 3-((E)-3-((2-((1R,5S,6s)-3-(2-chloro-5-fluoropyrimidin-4-yl)-3-azabicyclo[3.1.0]hexan-6-yl)ethyl)amino)-3-oxoprop-1-en-1-yl)pyridine 1-oxide

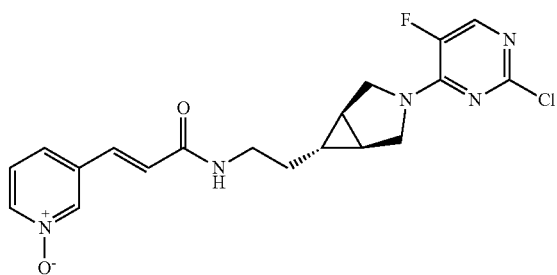

To a 100 mL round-bottom flask equipped with a magnetic stir bar was added the Example 172 compound (91 mg, 0.23 mmol, HCl salt) followed by the addition of chloroform (10 mL). The reaction mixture was cooled to 0° C. and m-chloroperoxybenzoic acid (40 mg, 0.23 mmol) was added in portions. The mixture was quenched by slow addition of aqueous sodium thiosulfate (0.3 mL) followed by the addition of water (5 mL). The resulting mixture was transferred to a separatory funnel, and the aqueous layer was extracted with dichloromethane (10×2). The organic layers were dried over anhydrous sodium sulfate, filtered, and concentrated under reduced pressure to afford a crude product. The crude product was purified by preparative HPLC (Phenomenex Gemini C18 column (150×25 mm, 5 um); flow rate: 25 mL/min; gradient: 10%-40% B over 10 min; mobile phase A: water (0.05% ammonia hydroxide), mobile phase B: acetonitrile) to give 38 mg (41%) of the title compound as a white solid. MS (ESI) m/z: 404.2 (M+H)+. 1H NMR (400 MHz, DMSO-d6): δ 8.46 (s, 1H), 8.22-8.17 (m, 1H), 8.10 (d, J=5.6 Hz, 1H), 7.52 (d, J=8.0 Hz, 1H), 7.43 (t, J=6.8 Hz, 1H), 7.34 (d, J=16.0 Hz, 1H), 6.74 (d, J=16.0 Hz, 1H), 3.84 (d, J=10.0 Hz, 2H), 3.65 (s, 2H), 3.25 (t, J=12.4 Hz, 2H), 1.53 (s, 2H), 1.46-1.41 (m, 2H), 0.63-0.60 (m, 1H).

Example 285: (E)-N-(2-((1R,5S,6s)-3-(2-(2-amino-2-oxoethoxy)-5-fluoropyrimidin-4-yl)-3-azabicyclo[3.1.0]hexan-6-yl)ethyl)-3-(pyridin-3-yl)acrylamide

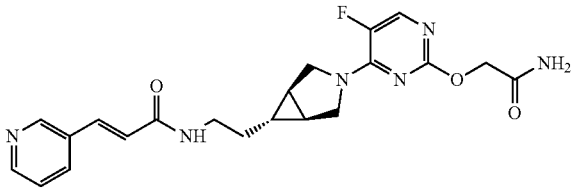 [SMILES: NC(=O)COc1ncc(F)c(N2C[C@@H]3[C@@H](CCNC(=O)/C=C/c4cccnc4)[C@@H]3C2)n1]

To a 50 mL round-bottom flask equipped with a magnetic stir bar was added the Example 282 compound (40 mg, 0.09 mmol) and ammonium chloride (10 mg, 0.19 mmol) followed by the addition of N,N-dimethylacetamide (1.5 mL). N,N-Diisopropylethylamine (36 mg, 0.28 mmol, 0.05 mL) and 2-(3H-[1,2,3]triazolo[4,5-b]pyridin-3-yl)-1,1,3,3-tetramethylisouronium hexafluorophosphate(V) (71 mg, 0.19 mmol) was added into the mixture at 20° C. The mixture was stirred at 20° C. for 1 h. The mixture was quenched by slow addition of water (0.5 mL). The resulting mixture was concentrated under high vacuum to give crude product as yellow oil. The residue was purified by preparative HPLC (Phenomenex Gemini C18 column (150×25 mm, 10 um); flow rate: 25 mL/min; gradient: 1%-25% B over 10 min; mobile phase A: 0.1% aqueous trifluoroacetic acid, mobile phase B: acetonitrile) to give 38.6 mg (47%) of the title compound as the TFA salt as a yellow gum. MS (ESI) m/z: 427.2 (M+H)+. 1H NMR (400 MHz, DMSO-d6): δ 8.91 (d, J=1.6 Hz, 1H), 8.68 (dd, J=1.2, 5.0 Hz, 1H), 8.28 (d, J=6.4 Hz, 2H), 8.03 (d, J=5.6 Hz, 1H), 7.70 (dd, J=5.2, 8.0 Hz, 1H), 7.51 (d, J=16.0 Hz, 1H), 7.40 (s, 1H), 7.15 (s, 1H), 6.81 (d, J=16.0 Hz, 1H), 4.58 (s, 2H), 3.87 (dd, J=2.8, 11.6 Hz, 2H), 3.64 (s, 2H), 3.27 (q, J=6.4 Hz, 2H), 1.54 (s, 2H), 1.45 (q, J=6.8 Hz, 2H), 0.61 (td, J=3.6, 6.8 Hz, 1H).

Example 286: (E)-N-(2-((1R,5S,6s)-3-(2-hydroxy-1-phenylethyl)-3-azabicyclo[3.1.0]hexan-6-yl)ethyl)-3-(pyridin-3-yl)acrylamide

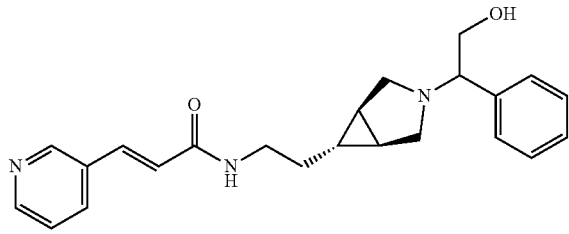 [SMILES: O=C(/C=C/c1cccnc1)NCC[C@@H]1[C@H]2CN(C(CO)c3ccccc3)C[C@@H]12]

To a 50 mL round-bottom flask equipped with a magnetic stir bar was added lithium aluminum hydride (11 mg, 0.30 mmol) followed by the addition of tetrahydrofuran (2 mL). A solution of methyl 2-phenyl-2-((1R,5S,6s)-6-(2-((E)-3-(pyridin-3-yl)acrylamido)ethyl)-3-azabicyclo[3.1.0]hexan-3-yl)acetate (60 mg, 0.15 mmol) in tetrahydrofuran (2 mL) was added dropwise at 0° C. The mixture was stirred at 0° C. for 0.5 h. The mixture was slowly poured into aqueous hydrogen chloride (1 mL, 1 M), then basified with saturated aqueous potassium carbonate to a pH of 6. The mixture was concentrated under high reduced pressure to give the crude product as a yellow solid. The residue was purified by preparative HPLC (Phenomenex Gemini C18 column (150× 25 mm, 10 um); flow rate: 25 mL/min; gradient: 5%-35% B over 10 min; mobile phase A: 0.1% aqueous trifluoroacetic acid, mobile phase B: acetonitrile) to give 28 mg (25%) of the title compound as the TFA salt as a white solid. MS (ESI) m/z: 378.3 (M+H)$^+$. $^1$H NMR (400 MHz, DMSO-d$_6$): δ 10.65 (s, 1H), 9.67 (s, 1H), 8.79 (d, J=1.6 Hz, 1H), 8.59 (dd, J=1.6, 4.8 Hz, 1H), 8.30-8.15 (m, 1H), 8.05 (d, J=8.0 Hz, 1H), 7.56-7.36 (m, 7H), 6.75 (d, J=16.0 Hz, 1H), 4.43-4.25 (m, 1H), 4.12 (d, J=5.6 Hz, 1H), 3.96-3.72 (m, 3H), 3.59-3.47 (m, 1H), 3.22 (d, J=8.8 Hz, 3H), 2.94 (d, J=7.6 Hz, 1H), 1.72-1.64 (m, 1H), 1.49 (td, J=4.0, 7.6 Hz, 1H), 1.44-1.30 (m, 2H), 1.21 (d, J=3.2 Hz, 1H).

Example 287: (E)-N-(2-((1R,5S,6s)-3-(5-fluoro-2-phenylpyrimidin-4-yl)-3-azabicyclo[3.1.0]hexan-6-yl)ethyl)-3-(pyridin-3-yl)acrylamide

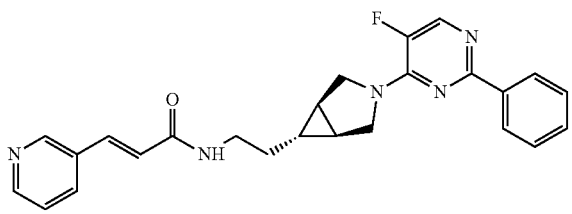 [SMILES: O=C(/C=C/c1cccnc1)NCC[C@@H]1[C@H]2CN(c3nc(-c4ccccc4)ncc3F)C[C@@H]12]

To a 50 mL round-bottom flask equipped with a magnetic stir bar was added the Example 172 compound (20 mg, 0.05 mmol, HCl salt) and phenylboronic acid (9 mg, 0.08 mmol) followed by the addition of 1,4-dioxane (5 mL) and water (1 mL). (1,1'-bis(diphenylphosphino)ferrocene)palladium(II) dichloride (2 mg, 0.003 mmol) and sodium bicarbonate (11 mg, 0.13 mmol) was added into the mixture at 20° C. The flask was then evacuated and backfilled with nitrogen three times. The mixture was stirred at 80° C. under an atmosphere of nitrogen for 12 h. The suspension was filtered and the filter cake was washed with tetrahydrofuran (10 mL) and the filtrate was diluted with water (15 mL). The resulting mixture was transferred to a separatory funnel and extracted with ethyl acetate (15 mL×2). The combined organic layers were washed with brine (10 mL), dried over anhydrous sodium sulfate, filtered, and concentrated under reduced pressure to afford a crude residue as a black oil. The residue was purified by preparative HPLC (Phenomenex Gemini C18 column (150×30 mm, 10 um); flow rate: 25 mL/min; gradient: 15%-35% B over 10 min; mobile phase A: 0.1% aqueous trifluoroacetic acid, mobile phase B: acetonitrile) to give 7 mg (7%) of the title compound as the TFA salt as a yellow gum. MS (ESI) m/z: 430.2 (M+H)$^+$. $^1$H NMR (400 MHz, DMSO-d$_6$): δ 8.83 (d, J=1.6 Hz, 1H), 8.62 (dd, J=1.2, 5.2 Hz, 1H), 8.33-8.20 (m, 4H), 8.13 (d, J=8.0 Hz, 1H), 7.57 (dd, J=5.2, 8.2 Hz, 1H), 7.52-7.43 (m, 4H), 6.78 (d, J=16.0 Hz, 1H), 4.03 (d, J=3.2 Hz, 2H), 4.01 (d, J=3.2 Hz, 2H), 3.30 (q, J=6.4 Hz, 2H), 1.58 (s, 2H), 1.48 (q, J=6.8 Hz, 2H), 0.68 (td, J=3.6, 6.8 Hz, 1H).

Example 288: (E)-N-(2-((1R,5S,6s)-3-(3-(dimethylphosphoryl)phenyl)-3-azabicyclo[3.1.0]hexan-6-yl)ethyl)-3-(pyridin-3-yl)acrylamide

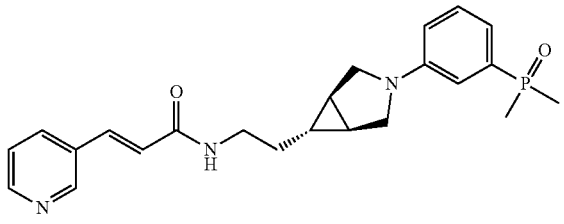 [SMILES: CP(C)(=O)c1cccc(N2C[C@@H]3[C@@H](CCNC(=O)/C=C/c4cccnc4)[C@@H]3C2)c1]

To a 100 mL round-bottom flask equipped with a magnetic stir bar was added 1-chloro-3-iodobenzene (400 mg, 1.68 mmol, 0.207 mL) and dimethyl phosphine oxide (144 mg, 1.85 mmol) in dimethylformide (5 mL) followed by the addition of potassium phosphate (374 mg, 1.76 mmol), (9,9-dimethyl-9H-xanthene-4,5-diyl)bis(diphenylphosphine) (49 mg, 0.084 mmol) and palladium diacetate (19 mg, 0.084 mmol). The reaction mixture was purged with nitrogen and stirred at 120° C. for 6 h. The suspension was filtered and the filter cake was washed with ethyl acetate (20 mL). The filtrate was concentrated under vacuum to give the crude product as a brown liquid. The crude product was diluted with water (5 mL) and extracted with ethyl acetate (10 mL×2) and the organic phase was concentrated under high vacuum to give 200 mg (63%) of (3-chlorophenyl) dimethylphosphine oxide as a brown oil. MS (ESI) m/z: 189.1 (M+H)$^+$. $^1$H NMR (400 MHz, CDCl$_3$): δ 7.72 (br d, J=12.0 Hz, 1H), 7.63 (br dd, J=7.6, 10.0 Hz, 1H), 7.54-7.50 (m, 1H), 7.48-7.42 (m, 1H), 2.98 (s, 1H), 2.89 (s, 1H), 1.81 (d, J=12.8 Hz, 6H).

To a 100 mL round-bottom flask equipped with a magnetic stir bar and a reflux condenser was added (E)-N-(2-((1R,5S,6s)-3-azabicyclo[3.1.0]hexan-6-yl)ethyl)-3-(pyridin-3-yl)acrylamide (70 mg, 0.19 mmol, TFA salt), cesium carbonate (307 mg, 0.943 mmol), dioxane (5 mL) and (3-chlorophenyl)dimethylphosphine oxide (80 mg, 0.42 mmol). 2,2'-bis(diphenylphosphino)-1,1'-binaphthyl (12 mg, 0.019 mmol) and tris(dibenzylideneacetone)dipalladium(0) (9 mg, 0.009 mmol) were added into the mixture at 25° C. The mixture was heated to 110° C. and stirred at that temperature for 48 h. The suspension was filtered and the filter cake was washed with methanol (10 mL). The filtrate was concentrated under vacuum to give the crude product. The crude product was purified by preparative HPLC (Phenomenex Gemini C18 column (150×25 mm, 10 um); flow rate: 25 mL/min; gradient: 15%-35% B over 10 min; mobile phase A: 0.1% aqueous trifluoroacetic acid, mobile phase B: acetonitrile) to give a product, but it was not pure, then it was purified by preparative HPLC (Phenomenex Gemini C18 column (150×25 mm, 10 um); flow rate: 25 mL/min; gradient: 15%-45% B over 10 min; mobile phase A: water (10 mM ammonium bicarbonate), mobile phase B: acetonitrile) to give 5 mg (6%) of the title compound as a white solid. MS (ESI) m/z: 410.4 (M+H)$^+$. $^1$H NMR (400 MHz, DMSO-d$_6$): δ 8.75 (d, J=2.1 Hz, 1H), 8.54 (dd, J=1.6, 4.8 Hz, 1H), 8.20 (br t, J=5.6 Hz, 1H), 7.97 (td, J=1.8, 7.9 Hz, 1H), 7.50-7.40 (m, 2H), 7.26 (dt, J=3.5, 7.8 Hz, 1H), 6.94 (dd, J=7.5, 11.2 Hz, 1H), 6.82 (br d, J=13.2 Hz, 1H), 6.74 (d, J=15.9 Hz, 1H), 6.66 (dd, J=1.7, 7.6 Hz, 1H), 3.53 (d, J=9.3 Hz, 2H), 3.28 (br s, 2H), 3.20 (br d, J=8.7 Hz, 2H), 1.59 (d, J=13.2 Hz, 6H), 1.55 (br s, 2H), 1.46 (q, J=6.8 Hz, 2H), 0.70 (tt, J=3.4, 6.9 Hz, 1H).

Example 289: (E)-N-(2-((1R,5S,6r)-3-benzyl-6-fluoro-3-azabicyclo[3.1.0]hexan-6-yl)ethyl)-3-(pyridin-3-yl)acrylamide

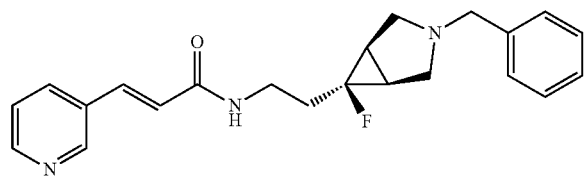 [SMILES: O=C(/C=C/c1cccnc1)NCC[C@@]1(F)[C@@H]2CN(Cc3ccccc3)C[C@@H]21]

A solution of ethyl 2-chloro-2-fluoroacetate (75 g, 534 mmol) in acetone (800 mL) was added dropwise into a stirred solution of sodium iodide (200 g, 1.33 mol). When the addition was completed, the reaction mixture was stirred at 55° C. for 5 h under an atmosphere of nitrogen. A second batch of 2-chloro-2-fluoroacetate (75 g, 534 mmol) was reacted under identical conditions. The two batches of crude reaction mixtures were combined and filtered, and the solid precipitate was washed with acetone (50 mL). The filtrate was concentrated under vacuum to remove most of the acetone. The residue was diluted with tert-butyl methyl ether (2000 mL), and washed with water (500 mL×2), a saturated solution of NaHSO₃ (500 mL), a saturated solution of Na₂S₂O₃ (500 mL), and brine (500 mL), then dried over anhydrous sodium sulfate, filtered, and concentrated under reduced pressure to afford 206 g ethyl 2-fluoro-2-iodoacetate as a yellow oil. $^1$H NMR (400 MHz, CDCl$_3$): δ 7.116 (d, J=51.2 Hz, 1H), 4.35 (q, J=7.2 Hz, 2H), 1.34 (t, J=7.2 Hz, 3H).

To a 1 L round bottom flask equipped with a magnetic stir bar was added tert-butyl 2,5-dihydro-1H-pyrrole-1-carboxylate (30 g, 178 mmol) and ethyl 2-fluoro-2-iodoacetate (103 g, 443 mmol) followed by the addition of acetonitrile (500 mL). Copper (16.9 g, 266 mmol) was added into the mixture at 25° C. The mixture was heated to 70° C. and stirred at that temperature for 6 h under an atmosphere of nitrogen. After cooling to room temperature, the resulting suspension was filtered, and the filter cake was washed with acetonitrile (30 mL). The filtrate was concentrated under reduced pressure to give the crude product as a brown oil. The crude product was purified by silica gel column chromatography (petroleum ether/ethyl acetate, from 30/1 to 5/1) to give 31 g (44%) of (3R,4R)-tert-butyl 3-(2-ethoxy-1-fluoro-2-oxoethyl)-4-iodopyrrolidine-1-carboxylate as a light yellow oil. MS (ESI) m/z: 346.0 (M-t-Bu+H)⁺.

To a 250 mL round-bottom flask equipped with a magnetic stir bar was added (3R,4R)-tert-butyl 3-(2-ethoxy-1-fluoro-2-oxoethyl)-4-iodopyrrolidine-1-carboxylate (5 g, 12.5 mmol) followed by the addition of tetrahydrofuran (60 mL). The solution was cooled to −78° C., and lithium bis(trimethylsilyl)amide (1 M, 27.2 mL) was added dropwise. The mixture was stirred at −78° C. for 2 h. The mixture was quenched by slow addition of saturated aqueous ammonium chloride (50 mL) at −78° C. and stirred for 10 min.

Five additional batches on the same scale were reacted under identical conditions. The six reaction mixtures were combined and transferred to a separatory funnel, and the aqueous layer was extracted with ethyl acetate (100 mL×2). The combined organic layers were washed with brine (50 mL), dried over anhydrous sodium sulfate, filtered, and concentrated under reduced pressure to afford the crude product as a yellow oil. The resulting crude product was purified by silica gel column chromatography (petroleum ether/ethyl acetate, from 20/1 to 5/1) to give 14 g (69%) of (1R,5S,6r)-3-tert-butyl 6-ethyl 6-fluoro-3-azabicyclo[3.1.0]hexane-3,6-dicarboxylate as a light yellow oil. $^1$H NMR (400 MHz, CDCl$_3$): δ 4.28 (q, J=7.2 Hz, 2H), 3.83-3.62 (m, 3H), 2.42-2.18 (m, 2H), 1.44 (s, 9H), 1.33 (t, J=7.2 Hz, 3H).

To a 100 mL round-bottom flask equipped with a magnetic stir bar was added (1R,5S,6r)-3-tert-butyl 6-ethyl 6-fluoro-3-azabicyclo[3.1.0]hexane-3,6-dicarboxylate (1.8 g, 6.6 mmol), followed by the addition of dichloromethane (15 mL). The solution was cooled to 0° C. 2,2,2-Trifluoroacetic acid (8.32 g, 72.9 mmol, 5.40 mL) was added in several portions. The mixture was warmed to 25° C. and stirred for 0.5 h. The reaction mixture was concentrated under reduced pressure to give 1.8 g (95%) of (1R,5S,6r)-ethyl 6-fluoro-3-azabicyclo[3.1.0]hexane-6-carboxylate as the TFA salt as a yellow oil.

To a 100 mL round-bottom flask equipped with a magnetic stir bar was added (1R,5S,6r)-ethyl 6-fluoro-3-azabicyclo[3.1.0]hexane-6-carboxylate (1.8 g, 6.3 mmol, TFA salt) followed by the addition of dichloromethane (10 mL) and triethylamine (1.90 g, 18.8 mmol, 2.62 mL). (Bromomethyl)benzene (1.18 g, 6.89 mmol, 0.82 mL) was added into the mixture at 0° C. The cooling bath was removed and the mixture was stirred at 25° C. for 0.5 h. The mixture was quenched by slow addition of water (10 mL). The resulting mixture was transferred to a separatory funnel, and the aqueous layer mixture was extracted with dichloromethane (30 mL×2). The combined organic layers were washed with brine (10 mL), dried over anhydrous sodium sulfate, filtered, and concentrated under reduced pressure to afford the crude product as a yellow oil. The resulting crude product was purified by silica gel column chromatography (petroleum ether/ethyl acetate, from 10/1 to 1/1) to give 0.85 g (47%) of (1R,5S,6r)-ethyl 3-benzyl-6-fluoro-3-azabicyclo[3.1.0] hexane-6-carboxylate as a yellow oil. MS (ESI) m/z: 264.2 (M+H)⁺.

To a 100 mL round-bottom flask equipped with a magnetic stir bar was added (1R,5S,6r)-ethyl 3-benzyl-6-fluoro-3-azabicyclo[3.1.0]hexane-6-carboxylate (0.85 g, 2.9 mmol), followed by the addition of tetrahydrofuran (10 mL). The solution was cooled to 0° C. and lithium aluminium hydride (167 mg, 4.41 mmol) was added in portions. The mixture was allowed to warm to 25° C. and stirred for 0.5 h. The mixture was quenched by slow addition of ethyl acetate (10 mL) and concentrated under reduced pressure affording the crude product as a white solid. The resulting crude product was purified by silica gel column chromatography (petroleum ether/ethyl acetate, from 5/1 to 0/1) to give 0.65 g (92%) of ((1R,5S,6r)-3-benzyl-6-fluoro-3-azabicyclo [3.1.0]hexan-6-yl)methanol as a colorless gum. MS (ESI) m/z: 222.1 (M+H)⁺.

To a 100 mL round-bottom flask equipped with a magnetic stir bar was added ((1R,5S,6r)-3-benzyl-6-fluoro-3-azabicyclo[3.1.0]hexan-6-yl)methanol (650 mg, 2.69 mmol) followed by the addition of tetrahydrofuran (10 mL) and triphenylphosphine (1.16 g, 4.42 mmol). The mixture was cooled to 0° C. and carbon tetrabromide (1.46 g, 4.40 mmol) was added. The mixture was allowed to warm to 25° C. and stirred for 0.5 h. The mixture was quenched by slow addition of water (1 mL) and concentrated under reduced pressure to afford the crude product as a white solid. The resulting crude product was purified by silica gel column chromatography (petroleum ether/ethyl acetate, from 5/1 to 1/1) to give 0.45 g (59%) of (1R,5S,6r)-3-benzyl-6-(bromomethyl)-6-fluoro-3-azabicyclo[3.1.0]hexane as a colorless oil. MS (ESI) m/z: 286.1 (M+H)$^+$.

To a 100 mL round-bottom flask equipped with a magnetic stir bar was added (1R,5S,6r)-3-benzyl-6-(bromomethyl)-6-fluoro-3-azabicyclo[3.1.0]hexane (0.45 g, 1.58 mmol) followed by the addition of acetonitrile (10 mL) and sodium cyanide (78 mg, 1.58 mmol). The mixture was stirred at 25° C. for 1 h. The mixture was diluted by the slow addition of water (50 mL). The resulting mixture was transferred to a separatory funnel, and the aqueous layer was extracted with ethyl acetate (30 mL×2). The combined organic layers were washed with brine (10 mL), dried over anhydrous sodium sulfate, filtered, and concentrated under reduced pressure to afford the crude product as a yellow oil. The resulting crude product was purified by silica gel column chromatography (petroleum ether/ethyl acetate, from 5/1 to 1/1) to give 0.15 g (40%) of 2-((1R,5S,6r)-3-benzyl-6-fluoro-3-azabicyclo[3.1.0]hexan-6-yl)acetonitrile as a colorless oil. MS (ESI) m/z: 231.3 (M+H)$^+$.

To a 100 mL round-bottom flask equipped with a magnetic stir bar was added 2-((1R,5S,6r)-3-benzyl-6-fluoro-3-azabicyclo[3.1.0]hexan-6-yl)acetonitrile (50 mg, 0.21 mmol, three batches) followed by the addition of methanol (6 mL) and Raney nickel (5 mg). The reaction mixture was stirred under a hydrogen balloon at 25° C. for 2 h. Two additional batches on the same scale were reacted under identical conditions. The three reaction mixtures were combined and filtered, and the filter cake was washed with methanol (5 mL). The filtrate was concentrated under reduced pressure to give 0.15 g (98%) of 2-((1R,5S,6r)-3-benzyl-6-fluoro-3-azabicyclo[3.1.0]hexan-6-yl)ethanamine as a colorless oil.

To a solution of (E)-3-(pyridin-3-yl)acrylic acid (80 mg, 0.54 mmol) and 2-((1R,5S,6r)-3-benzyl-6-fluoro-3-azabicyclo[3.1.0]hexan-6-yl)ethanamine (126 mg, 0.54 mmol) in pyridine (3 mL) was added 1-ethyl-3-(3-dimethylaminopropyl)carbodiimide hydrochloride (134 mg, 0.70 mmol) in one portion. The mixture was stirred at 25° C. for 1 h. The mixture was concentrated under reduced pressure to afford the crude product as a yellow oil. The resulting residue was purified by preparative HPLC (Phenomenex Gemini C18 column (150×50 mm, 10 um); flow rate: 25 mL/min; gradient: 23%-53% B over 10 min; mobile phase A: 0.1% aqueous ammonium bicarbonate, mobile phase B: acetonitrile) to give 35 mg (18%) of the title compound as a white solid. MS (ESI) m/z: 366.4 (M+H)$^+$. $^1$H NMR (400 MHz, DMSO-d$_6$): δ 8.74 (d, J=2.0 Hz, 1H), 8.54 (dd, J=1.6, 4.8 Hz, 1H), 8.23 (t, J=5.6 Hz, 1H), 7.97 (td, J=1.8, 8.0 Hz, 1H), 7.49-7.39 (m, 2H), 7.33-7.25 (m, 4H), 7.24-7.17 (m, 1H), 6.71 (d, J=16.0 Hz, 1H), 3.55 (s, 2H), 3.37 (d, J=6.8 Hz, 2H), 3.00-2.88 (m, 2H), 2.63 (d, J=9.6 Hz, 2H), 1.95-1.81 (m, 2H), 1.68 (s, 2H).

Example 290: (E)-3-(6-aminopyridin-3-yl)-N-(2-((1R,5S,6r)-6-fluoro-3-(pyrimidin-2-yl)-3-azabicyclo[3.1.0]hexan-6-yl)ethyl)acrylamide

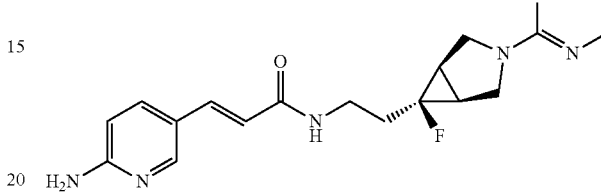

To a 100 mL round-bottom flask equipped with a magnetic stir bar was added (1R,5S,6r)-ethyl 6-fluoro-3-azabicyclo[3.1.0]hexane-6-carboxylate (1.7 g, 5.92 mmol, TFA salt) followed by the addition of N,N-dimethylformamide (15 mL). Cesium carbonate (5.79 g, 17.8 mmol) was added into the mixture at 25° C. and stirred for 0.5 h, then 2-chloropyrimidine (814 mg, 7.10 mmol) was added. The mixture was heated to 60° C. and stirred at that temperature for 12 h. The suspension was filtered and the filter cake was washed with ethyl acetate (5 mL). The filtrate was concentrated under reduced pressure to give the crude product as a brown oil. The crude product was purified by silica gel column chromatography (petroleum ether/ethyl acetate, from 20/1 to 3/1) to give 520 mg (35%) of (1R,5S,6r)-ethyl 6-fluoro-3-(pyrimidin-2-yl)-3-azabicyclo[3.1.0]hexane-6-carboxylate as a white solid. MS (ESI) m/z: 252.1 (M+H)$^+$.

To a 100 mL round-bottom flask equipped with a magnetic stir bar was added (1R,5S,6r)-ethyl 6-fluoro-3-(pyrimidin-2-yl)-3-azabicyclo[3.1.0]hexane-6-carboxylate (520 mg, 2.07 mmol) followed by the addition of tetrahydrofuran (10 mL). The solution was cooled to 0° C. Lithium aluminum hydride (94 mg, 2.48 mmol) was added into the mixture and stirred at 0° C. for 0.5 h. The mixture was quenched by slow addition of water (10 mL). The resulting mixture was transferred to a separatory funnel, and the aqueous layer mixture was extracted with ethyl acetate (20 mL×3). The combined organic layers were washed with brine (10 mL), dried over anhydrous sodium sulfate, filtered, and concentrated under reduced pressure to afford the crude product as a white solid. The crude product was purified by silica gel column chromatography (petroleum ether/ethyl acetate, from 1/1 to 0/1) to give 400 mg (92%) of ((1R,5S,6r)-6-fluoro-3-(pyrimidin-2-yl)-3-azabicyclo[3.1.0]hexan-6-yl)methanol as a white solid. $^1$H NMR (400 MHz, CDCl$_3$): δ 8.31 (d, J=4.8 Hz, 2H), 6.50 (t, J=4.8 Hz, 1H), 3.96-3.81 (m, 6H), 2.28-2.17 (m, 1H), 1.98 (br s, 2H).

To a 100 mL round-bottom flask equipped with a magnetic stir bar was added ((1R,5S,6r)-6-fluoro-3-(pyrimidin-2-yl)-3-azabicyclo[3.1.0]hexan-6-yl)methanol (400 mg, 1.91 mmol) and triphenylphosphine (903 mg, 3.44 mmol) followed by the addition of tetrahydrofuran (6 mL). The mixture was cooled to 0° C. A solution of carbon tetrabromide (1.14 g, 3.44 mmol) in dichloromethane (6 mL) was added. The reaction mixture was warmed to 25° C. and stirred at that temperature for 12 h. The mixture was quenched by slow addition of water (20 mL). The resulting mixture was transferred to a separatory funnel, and the aqueous layer mixture was extracted with ethyl acetate (30 mL×3). The combined organic layers were washed with brine (20 mL), dried over anhydrous sodium sulfate, filtered, and concentrated under reduced pressure to afford the crude product as a white solid. The crude product was purified by silica gel column chromatography (petroleum ether/ethyl acetate, from 5/1 to 1/1) to give 455 mg (88%) of (1R,5S, 6r)-6-(bromomethyl)-6-fluoro-3-(pyrimidin-2-yl)-3-azabicyclo[3.1.0]hexane as a white solid. MS (ESI) m/z: 274.1 (M+H)+. 1H NMR (400 MHz, CDCl3): δ 8.31 (d, J=4.8 Hz, 2H), 6.50 (t, J=4.8 Hz, 1H), 3.98-3.84 (m, 4H), 3.74-3.63 (m, 2H), 2.09-2.02 (m, 2H).

To a 100 mL round-bottom flask equipped with a magnetic stir bar was added (1R,5S,6r)-6-(bromomethyl)-6-fluoro-3-(pyrimidin-2-yl)-3-azabicyclo[3.1.0]hexane (250 mg, 0.919 mmol) followed by the addition of N,N-dimethylformamide (5 mL). The solution was cooled to 0° C. Sodium cyanide (45 mg, 0.92 mmol) was added, and the mixture was warmed to 25° C. and stirred at that temperature for 12 h. The reaction mixture was diluted with ethyl acetate (20 mL) and washed with brine (10 mL×3). The organic layer was concentrated under reduced pressure to give the crude product. The crude product was purified by preparative HPLC (Phenomenex Gemini C18 column (150×40 mm, 15 um); flow rate: 25 mL/min; gradient: 1%-25% B over 10 min; mobile phase A: 0.1% aqueous trifluoroacetic acid, mobile phase B: acetonitrile) to give 55 mg (18%) of 2-((1R,5S,6r)-6-fluoro-3-(pyrimidin-2-yl)-3-azabicyclo [3.1.0]hexan-6-yl)acetonitrile as the TFA salt as a white solid. MS (ESI) m/z: 219.1 (M+H)+.

To a solution of 2-((1R,5S,6r)-6-fluoro-3-(pyrimidin-2-yl)-3-azabicyclo[3.1.0]hexan-6-yl)acetonitrile (45 mg, 0.21 mmol) in methanol (5 mL) was added Raney nickel (18 mg, 0.21 mmol). The suspension was degassed under reduced pressure and purged with hydrogen three times. The mixture was stirred under a balloon of hydrogen at 25° C. for 6 h. The suspension was filtered and the filter cake was washed with methanol (5 mL). The filtrate was concentrated under reduced pressure to give 48 mg of crude 2-((1R,5S,6r)-6-fluoro-3-(pyrimidin-2-yl)-3-azabicyclo[3.1.0]hexan-6-yl) ethanamine as a yellow gum. MS (ESI) m/z: 223.1 (M+H)+.

To a solution of (E)-3-(6-aminopyridin-3-yl)acrylic acid (35 mg, 0.21 mmol) and 2-((1R,5S,6r)-6-fluoro-3-(pyrimidin-2-yl)-3-azabicyclo[3.1.0]hexan-6-yl)ethanamine (47 mg, 0.21 mmol) in pyridine (3 mL) was added 1-ethyl-3-(3-dimethylaminopropyl)carbodiimide hydrochloride (53 mg, 0.28 mmol) in one portion. The mixture was stirred at 25° C. for 1 h. The mixture was concentrated under reduced pressure to afford the crude product as a colorless oil. The crude product was purified by preparative HPLC (Phenomenex Gemini C18 column (150×25 mm, 5 um); flow rate: 25 mL/min; gradient: 14%-41% B over 10 min; mobile phase A: 0.05% ammonia hydroxide, mobile phase B: acetonitrile) to give 17 mg (21%) of (E)-3-(6-aminopyridin-3-yl)-N-(2-((1R,5S,6r)-6-fluoro-3-(pyrimidin-2-yl)-3-azabicyclo[3.1.0] hexan-6-yl)ethyl)acrylamide as a yellow solid. MS (ESI) m/z: 469.4 (M+H)+. 1H NMR (400 MHz, DMSO-d6): δ 8.31 (d, J=4.8 Hz, 2H), 8.06 (d, J=2.4 Hz, 1H), 8.00 (t, J=5.6 Hz, 1H), 7.59 (dd, J=2.4, 8.8 Hz, 1H), 7.27 (d, J=15.6 Hz, 1H), 6.59 (t, J=4.8 Hz, 1H), 6.46 (d, J=8.8 Hz, 1H), 6.42-6.26 (m, 3H), 3.78-3.67 (m, 4H), 3.42-3.35 (m, 2H), 1.98 (br t, J=7.2 Hz, 1H), 1.94-1.85 (m, 3H).

Example 291: (1R,5S,6r)-tert-butyl 6-fluoro-6-(2-((E)-3-(pyridin-3-yl)acrylamido)ethyl)-3-azabicyclo [3.1.0]hexane-3-carboxylate

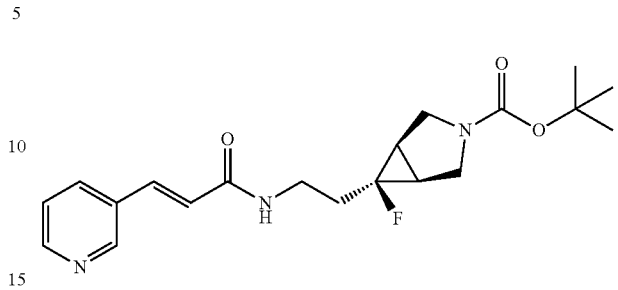

To a 100 mL round-bottom flask equipped with a magnetic stir bar was added (1R,5S,6r)-3-tert-butyl 6-ethyl 6-fluoro-3-azabicyclo[3.1.0]hexane-3,6-dicarboxylate (2 g, 7.32 mmol) followed by the addition of tetrahydrofuran (30 mL). The solution was cooled to 0° C. Lithium aluminum hydride (392 mg, 10.3 mmol) was added in several portions at 0° C. and the mixture was allowed to warm to 25° C. and stir for 3 h. The reaction mixture was cooled to 0° C. and quenched with water (0.4 mL), followed by the addition of aqueous 15% sodium hydroxide (0.4 mL) and then water (1.2 mL). The suspension was filtered and the filtrate was concentrated to give a crude product. The crude product was purified by silica gel column chromatography (petroleum ether/ethyl acetate, from 5/1 to 1/1) to give 1.2 g (71%) of (1R,5S,6r)-tert-butyl 6-fluoro-6-(hydroxymethyl)-3-azabicyclo[3.1.0]hexane-3-carboxylate as a white solid.

To a 100 mL round-bottom flask equipped with a magnetic stir bar was added (1R,5S,6r)-tert-butyl 6-fluoro-6-(hydroxymethyl)-3-azabicyclo[3.1.0]hexane-3-carboxylate (1 g, 4.32 mmol) followed by the addition of dichloromethane (20 mL) and triphenylphosphine (2.27 g, 8.65 mmol). The mixture was cooled to at 0° C. and carbon tetrabromide (2.87 g, 8.65 mmol) was added in portions. The mixture was warmed to and stirred at 25° C. for 2 h. The mixture was concentrated under reduced pressure to afford the crude product as a yellow oil. The crude product was purified by silica gel column chromatography (petroleum ether/ethyl acetate, from 10/1 to 5/1) to give 1.1 g (84%) of (1R,5S, 6r)-tert-butyl 6-(bromomethyl)-6-fluoro-3-azabicyclo [3.1.0]hexane-3-carboxylate as a colorless oil. MS (ESI) m/z: 238.1 (M-t-Bu+H)+.

To a 25 mL round-bottom flask equipped with a magnetic stir bar was added (1R,5S,6r)-tert-butyl 6-(bromomethyl)-6-fluoro-3-azabicyclo[3.1.0]hexane-3-carboxylate (100 mg, 0.33 mmol) followed by the addition of N,N-dimethylformamide (1 mL) and potassium cyanide (22 mg, 0.33 mmol). The mixture was stirred at 25° C. for 2 h. The reaction mixture was diluted with ethyl acetate (5 mL) and washed with brine (5 mL×3). The organic layer was concentrated to give a crude product. The crude product was purified by silica gel column chromatography (petroleum ether/ethyl acetate, from 10/1 to 5/1) to give 55 mg (69%) of (1R,5S, 6r)-tert-butyl 6-(cyanomethyl)-6-fluoro-3-azabicyclo[3.1.0] hexane-3-carboxylate as a white solid. 1H NMR (400 MHz, CDCl3): δ 3.79-3.65 (m, 4H), 3.08-2.99 (m, 1H), 2.90-2.80 (m, 1H), 1.92-1.86 (m, 2H), 1.46 (s, 9H).

To a solution of (1R,5S,6r)-tert-butyl 6-(cyanomethyl)-6-fluoro-3-azabicyclo[3.1.0]hexane-3-carboxylate (40 mg, 0.17 mmol) in saturated ammonia in methanol (5 mL) was added Raney nickel (5 mg, 0.058 mmol) under an atmosphere of nitrogen. The suspension was degassed under vacuum and purged with hydrogen several times. The mixture was stirred under a balloon of hydrogen at 25° C. for 2 h. The suspension was filtered and the filtrate was concentrated to give 35 mg (86%) of (1R,5S,6r)-tert-butyl 6-(2-aminoethyl)-6-fluoro-3-azabicyclo[3.1.0]hexane-3-carboxylate as a yellow oil.

To a 25 round-bottom flask equipped with a magnetic stir bar was added (E)-3-(pyridin-3-yl)acrylic acid (20 mg, 0.13 mmol), pyridine (1 mL), and 1-ethyl-3-(3-dimethylaminopropyl)carbodiimide hydrochloride (31 mg, 0.16 mmol), followed by (1R,5S,6r)-tert-butyl 6-(2-aminoethyl)-6-fluoro-3-azabicyclo[3.1.0]hexane-3-carboxylate (35 mg, 0.14 mmol). The reaction mixture was stirred at 25° C. for 2 h. The mixture was concentrated under reduced pressure to afford the crude product as a yellow oil. The crude product was purified by preparative HPLC (Waters Xbridge C18 (150×25 mm, 5 um); flow rate: 25 mL/min; gradient: 23%-53% B over 10 min; mobile phase A: 10 mM ammonium bicarbonate, mobile phase B: acetonitrile) to give 25 mg (48%) of (1R,5S,6r)-tert-butyl 6-fluoro-6-(2-((E)-3-(pyridin-3-yl)acrylamido)ethyl)-3-azabicyclo[3.1.0]hexane-3-carboxylate as a white solid. MS (ESI) m/z: 438.3 (M+H)$^+$. $^1$H NMR (400 MHz, DMSO-d$_6$): δ 8.75 (d, J=2.0 Hz, 1H), 8.55 (dd, J=1.6, 4.8 Hz, 1H), 8.26 (t, J=5.6 Hz, 1H), 7.98 (td, J=2.0, 8.0 Hz, 1H), 7.49-7.43 (m, 2H), 6.73 (d, J=16.0 Hz, 1H), 3.55-3.37 (m, 6H), 1.99-1.84 (m, 2H), 1.76 (br s, 2H), 1.37 (s, 9H).

Example 292: (E)-N-(2-((1R,5S,6r)-3-(2-chloro-5-fluoropyrimidin-4-yl)-6-fluoro-3-azabicyclo[3.1.0]hexan-6-yl)ethyl)-3-(pyridin-3-yl)acrylamide

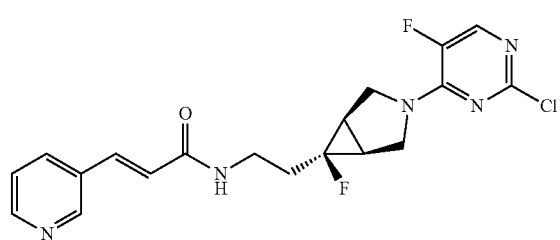 [SMILES: O=C(/C=C/c1cccnc1)NCC[C@@]1(F)[C@@H]2CN(c3nc(Cl)ncc3F)C[C@@H]21]

To a 50 mL round-bottom flask equipped with a magnetic stir bar was added the Example 291 compound (220 mg, 0.586 mmol) followed by the addition of dichloromethane (5 mL). Trifluoroacetic acid (1.54 g, 13.5 mmol, 1 mL) was added into the mixture at 25° C. The mixture was stirred at 25° C. for 10 min. The mixture was concentrated under reduced pressure to afford 240 mg of crude (E)-N-(2-((1R,5S,6r)-6-fluoro-3-azabicyclo[3.1.0]hexan-6-yl)ethyl)-3-(pyridin-3-yl)acrylamide as a TFA salt as a yellow oil. MS (ESI) m/z: 276.2 (M+H)$^+$.

To a 50 mL round-bottom flask equipped with a magnetic stir bar was added (E)-N-(2-((1R,5S,6r)-6-fluoro-3-azabicyclo[3.1.0]hexan-6-yl)ethyl)-3-(pyridin-3-yl)acrylamide (120 mg, 0.31 mmol, TFA salt) followed by the addition of dioxane (5 mL) and N,N-diisopropylethylamine (159 mg, 1.23 mmol, 0.215 mL). 2,4-Dichloro-5-fluoropyrimidine (51 mg, 0.31 mmol) was added and the mixture was heated at 60° C. for 1 h. The mixture was concentrated under reduced pressure to afford the crude product as a black oil. The crude product was purified by preparative HPLC (Phenomenex Gemini C18 column (150×25 mm, 10 um); flow rate: 25 mL/min; gradient: 10%-40% B over 10 min; mobile phase A: 0.1% aqueous trifluoroacetic acid, mobile phase B: acetonitrile) to give 26 mg (16%) of (E)-N-(2-((1R,5S,6r)-3-(2-chloro-5-fluoropyrimidin-4-yl)-6-fluoro-3-azabicyclo[3.1.0]hexan-6-yl)ethyl)-3-(pyridin-3-yl)acrylamide was obtained as the TFA salt as a yellow solid. MS (ESI) m/z: 406.0 (M+H)$^+$. $^1$H NM R (400 MHz, DMSO-d$_6$+D$_2$O): δ 8.88 (d, J=1.6 Hz, 1H), 8.65 (dd, J=1.2, 5.2 Hz, 1H), 8.28 (br d, J=8.0 Hz, 1H), 8.09 (d, J=5.6 Hz, 1H), 7.68 (dd, J=5.2, 8.0 Hz, 1H), 7.50 (d, J=16 Hz, 1H), 6.80 (d, J=16 Hz, 1H), 4.16-4.00 (m, 1H), 3.91-3.73 (m, 3H), 3.44-3.40 (m, 2H), 2.05-1.88 (i, 4H).

Examples 293-342

The following compounds were prepared substantially according to the procedures described in the referenced examples:

| Ex. No. | Chemical structure | Chemical name | MS (ESI) m/z (M + H)$^+$ | Prep. as in Ex. No. |
|---|---|---|---|---|
| 293 | 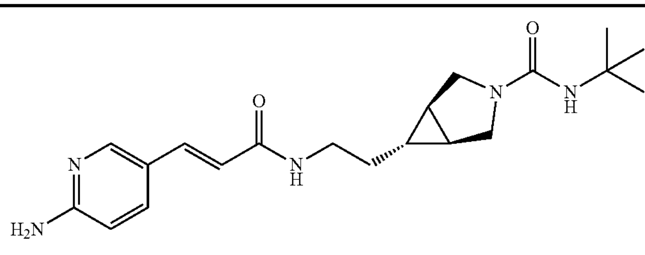 | (1R,5S,6s)-6-(2-((E)-3-(6-aminopyridin-3-yl)acrylamido)ethyl)-N-(tert-butyl)-3-azabicyclo[3.1.0]hexane-3-carboxamide | 372.4 | 21 |
| 294 | 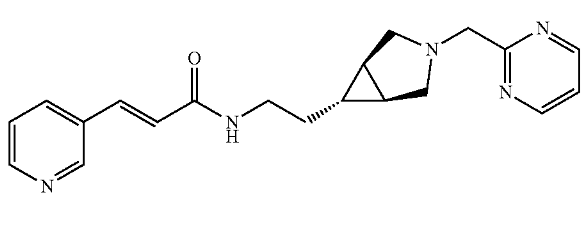 [SMILES: O=C(/C=C/c1cccnc1)NCC[C@@H]1[C@H]2CN(Cc3ncccn3)C[C@@H]12] | (E)-3-(Pyridin-3-yl)-N-(2-((1R,5S,6s)-3-(pyrimidin-2-ylmethyl)-3-azabicyclo[3.1.0]hexan-6-yl)ethyl)acrylamide | 350.1 | 243 |

-continued

| Ex. No. | Chemical name | MS (ESI) m/z (M + H)+ | Prep. as in Ex. No. |
|---|---|---|---|
| 295 | (E)-N-(2-((1R,5S,6s)-3-phenethyl-3-azabicyclo[3.1.0]hexan-6-yl)ethyl)-3-(pyridin-3-yl)acrylamide | 362.3 | 243 |
| 296 | (E)-3-(pyridin-3-yl)-N-(2-((1R,5S,6s)-3-(2,2,2-trifluoro-1-phenylethyl)-3-azabicyclo[3.1.0]hexan-6-yl)ethyl)acrylamide | 416.3 | 276 |
| 297 | (E)-N-(2-((1R,5S,6s)-3-(5-fluoro-2-methoxypyrimidin-4-yl)-3-azabicyclo[3.1.0]hexan-6-yl)ethyl)-3-(pyridin-3-yl)acrylamide | 384.3 | 278 |
| 298 | (E)-3-(pyridin-3-yl)-N-(2-((1R,5S,6s)-3-(pyrimidin-5-ylmethyl)-3-azabicyclo[3.1.0]hexan-6-yl)ethyl)acrylamide | 350.2 | 243 |
| 299 | (E)-N-(2-((1R,5S,6s)-3-(2-(difluoromethoxy)pyridin-4-yl)-3-azabicyclo[3.1.0]hexan-6-yl)ethyl)-3-(pyridin-3-yl)acrylamide | 401.3 | 117 |
| 300 | (E)-N-(2-((1R,5S,6s)-3-(2-chlorobenzyl)-3-azabicyclo[3.1.0]hexan-6-yl)ethyl)-3-(pyridin-3-yl)acrylamide | 382.2 | 243 |

-continued

| Ex. No. | Chemical structure | Chemical name | MS (ESI) m/z (M + H)+ | Prep. as in Ex. No. |
|---|---|---|---|---|
| 301 | 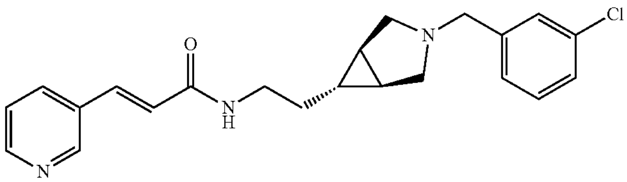 [SMILES: O=C(/C=C/c1cccnc1)NCC[C@@H]1[C@H]2CN(Cc3cccc(Cl)c3)C[C@@H]12] | (E)-N-(2-((1R,5S,6s)-3-(3-chlorobenzyl)-3-azabicyclo[3.1.0]hexan-6-yl)ethyl)-3-(pyridin-3-yl)acrylamide | 382.2 | 243 |
| 302 | 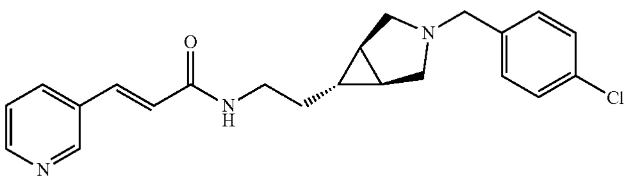 | (E)-N-(2-((1R,5S,6s)-3-(4-chlorobenzyl)-3-azabicyclo[3.1.0]hexan-6-yl)ethyl)-3-(pyridin-3-yl)acrylamide | 382.1 | 243 |
| 303 | 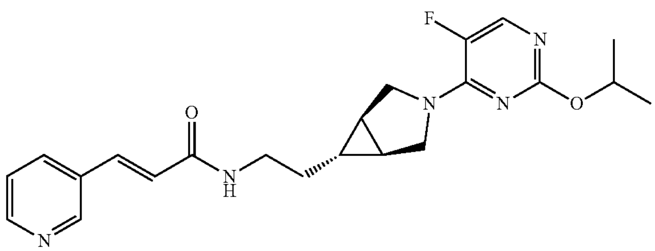 [SMILES: CC(C)Oc1ncc(F)c(N2C[C@@H]3[C@@H](CCNC(=O)/C=C/c4cccnc4)[C@@H]3C2)n1] | (E)-N-(2-((1R,5S,6s)-3-(5-fluoro-2-isopropoxypyrimidin-4-yl)-3-azabicyclo[3.1.0]hexan-6-yl)ethyl)-3-(pyridin-3-yl)acrylamide | 412.3 | 278 |
| 304 | 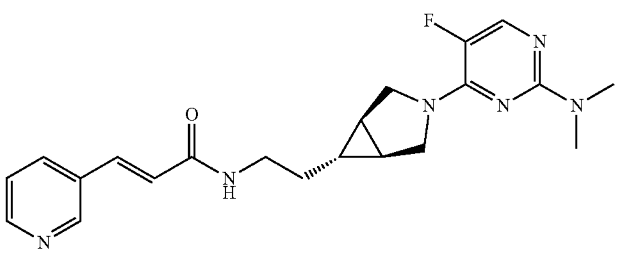 [SMILES: CN(C)c1ncc(F)c(N2C[C@@H]3[C@@H](CCNC(=O)/C=C/c4cccnc4)[C@@H]3C2)n1] | (E)-N-(2-((1R,5S,6s)-3-(2-(dimethylamino)-5-fluoropyrimidin-4-yl)-3-azabicyclo[3.1.0]hexan-6-yl)ethyl)-3-(pyridin-3-yl)acrylamide | 397.3 | 277 |
| 305 | 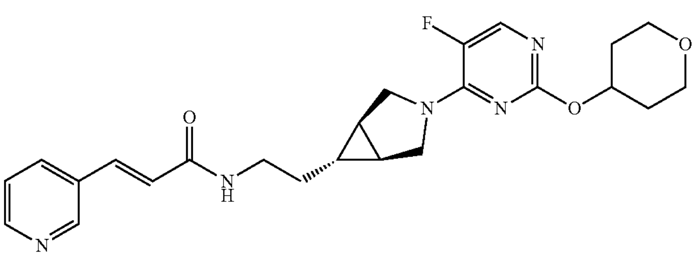 [SMILES: O=C(/C=C/c1cccnc1)NCC[C@@H]1[C@H]2CN(c3nc(OC4CCOCC4)ncc3F)C[C@@H]12] | (E)-N-(2-((1R,5S,6s)-3-(5-fluoro-2-((tetrahydro-2H-pyran-4-yl)oxy)pyrimidin-4-yl)-3-azabicyclo[3.1.0]hexan-6-yl)ethyl)-3-(pyridin-3-yl)acrylamide | 454.4 | 278 |
| 306 | 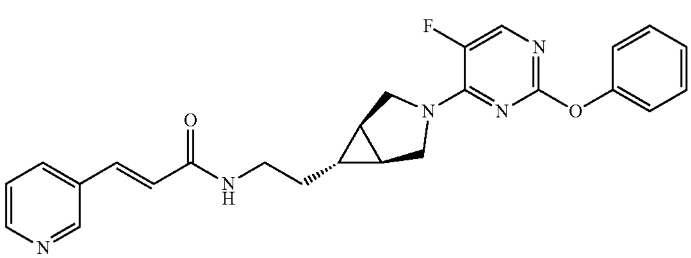 [SMILES: O=C(/C=C/c1cccnc1)NCC[C@@H]1[C@H]2CN(c3nc(Oc4ccccc4)ncc3F)C[C@@H]12] | (E)-N-(2-((1R,5S,6s)-3-(5-fluoro-2-phenoxypyrimidin-4-yl)-3-azabicyclo[3.1.0]hexan-6-yl)ethyl)-3-(pyridin-3-yl)acrylamide | 446.3 | 278 |

-continued

| Ex. No. | Chemical structure | Chemical name | MS (ESI) m/z (M + H)+ | Prep. as in Ex. No. |
|---|---|---|---|---|
| 307 | 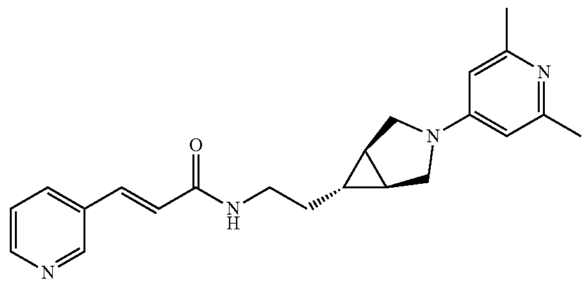 [SMILES: Cc1cc(N2C[C@@H]3[C@@H](CCNC(=O)/C=C/c4cccnc4)[C@@H]3C2)cc(C)n1] | (E)-N-(2-((1R,5S,6s)-3-(2,6-dimethylpyridin-4-yl)-3-azabicyclo[3.1.0]hexan-6-yl)ethyl)-3-(pyridin-3-yl)acrylamide | 363.3 | 117 |
| 308 | 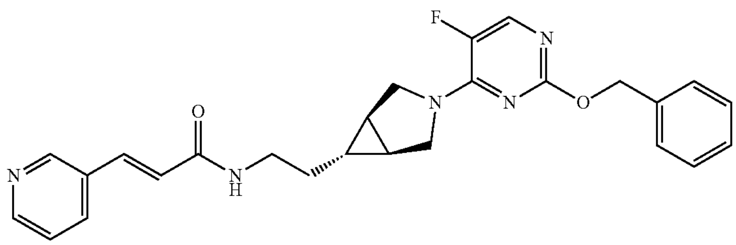 [SMILES: O=C(/C=C/c1cccnc1)NCC[C@@H]1[C@H]2CN(c3nc(OCc4ccccc4)ncc3F)C[C@@H]12] | (E)-N-(2-((1R,5S,6s)-3-(2-(benzyloxy)-5-fluoropyrimidin-4-yl)-3-azabicyclo[3.1.0]hexan-6-yl)ethyl)-3-(pyridin-3-yl)acrylamide | 460.1 | 278 |
| 309 | 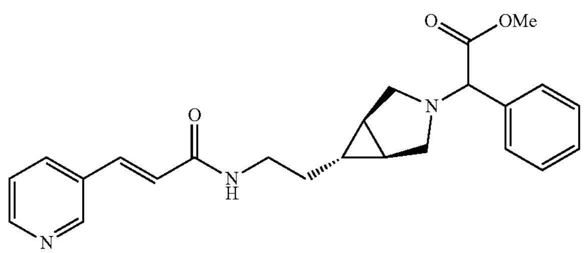 [SMILES: COC(=O)C(c1ccccc1)N1C[C@@H]2[C@@H](CCNC(=O)/C=C/c3cccnc3)[C@@H]2C1] | methyl 2-phenyl-2-((1R,5S,6s)-6-(2-((E)-3-(pyridin-3-yl)acrylamido)ethyl)-3-azabicyclo[3.1.0]hexan-3-yl)acetate | 406.3 | 276 |
| 310 | 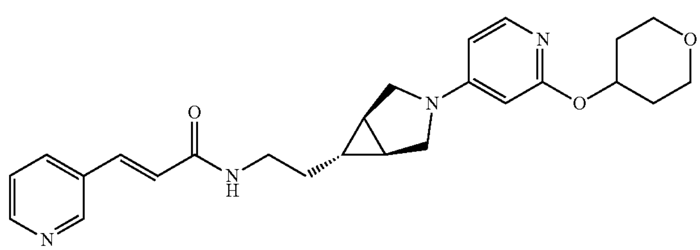 [SMILES: O=C(/C=C/c1cccnc1)NCC[C@@H]1[C@H]2CN(c3ccnc(OC4CCOCC4)c3)C[C@@H]12] | (E)-3-(Pyridin-3-yl)-N-(2-((1R,5S,6s)-3-(2-((tetrahydro-2H-pyran-4-yl)oxy)pyridin-4-yl)-3-azabicyclo[3.1.0]hexan-6-yl)ethyl)acrylamide | 435.3 | 117 |
| 311 | 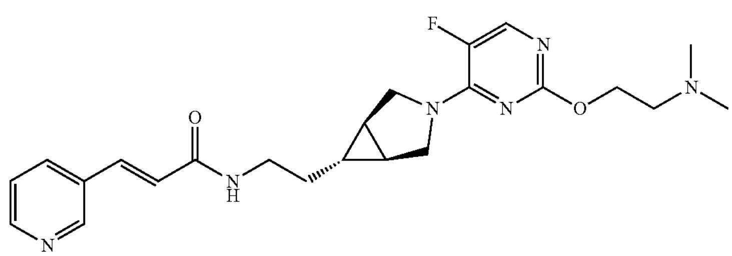 [SMILES: CN(C)CCOc1ncc(F)c(N2C[C@@H]3[C@@H](CCNC(=O)/C=C/c4cccnc4)[C@@H]3C2)n1] | (E)-N-(2-((1R,5S,6s)-3-(2-(2-(dimethylamino)ethoxy)-5-fluoropyrimidin-4-yl)-3-azabicyclo[3.1.0]hexan-6-yl)ethyl)-3-(pyridin-3-yl)acrylamide | 441.4 | 278 |
| 312 | 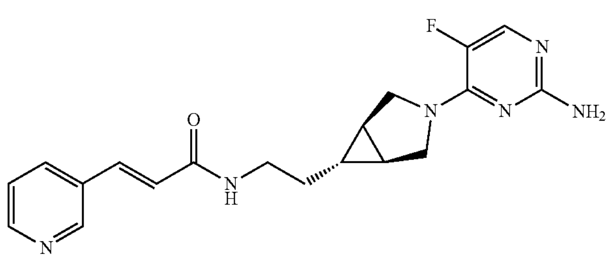 [SMILES: Nc1ncc(F)c(N2C[C@@H]3[C@@H](CCNC(=O)/C=C/c4cccnc4)[C@@H]3C2)n1] | (E)-N-(2-((1R,5S,6s)-3-(2-amino-5-fluoropyrimidin-4-yl)-3-azabicyclo[3.1.0]hexan-6-yl)ethyl)-3-(pyridin-3-yl)acrylamide | 369.1 | 277 |

-continued

| Ex. No. | Chemical structure | Chemical name | MS (ESI) m/z (M + H)+ | Prep. as in Ex. No. |
|---|---|---|---|---|
| 313 | 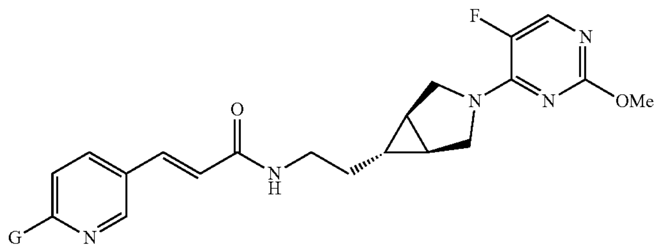 | (E)-N-(2-((1R,5S,6s)-3-(5-fluoro-2-methoxypyrimidin-4-yl)-3-azabicyclo[3.1.0]hexan-6-yl)ethyl)-3-(6-fluoropyridin-3-yl)acrylamide | 402.4 | 189 |
| 314 | 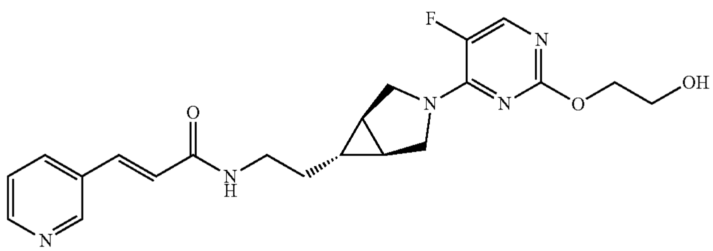 [SMILES: O=C(/C=C/c1cccnc1)NCC[C@@H]1[C@H]2CN(c3nc(OCCO)ncc3F)C[C@@H]12] | (E)-N-(2-((1R,5S,6s)-3-(5-fluoro-2-(2-hydroxyethoxy)pyrimidin-4-yl)-3-azabicyclo[3.1.0]hexan-6-yl)ethyl)-3-(pyridin-3-yl)acrylamide | 414.3 | 278 |
| 315 | 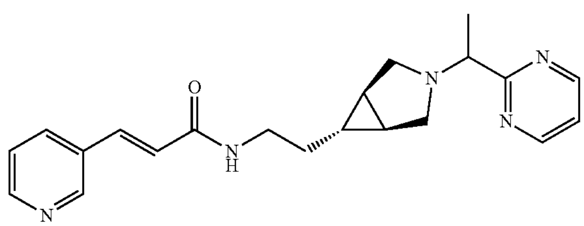 [SMILES: CC(c1ncccn1)N1C[C@@H]2[C@@H](CCNC(=O)/C=C/c3cccnc3)[C@@H]2C1] | (E)-3-(pyridin-3-yl)-N-(2-((1R,5S,6s)-3-(1-(pyrimidin-2-yl)ethyl)-3-azabicyclo[3.1.0]hexan-6-yl)ethyl)acrylamide | 364.2 | 243 |
| 316 | 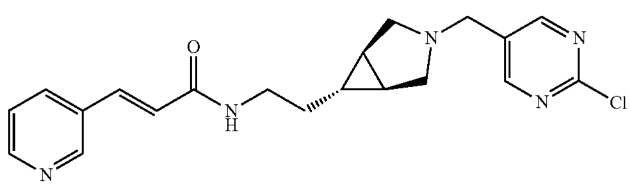 | (E)-N-(2-((1R,5S,6s)-3-((2-chloropyrimidin-5-yl)methyl)-3-azabicyclo[3.1.0]hexan-6-yl)ethyl)-3-(pyridin-3-yl)acrylamide | 384.1 | 276 |
| 317 | 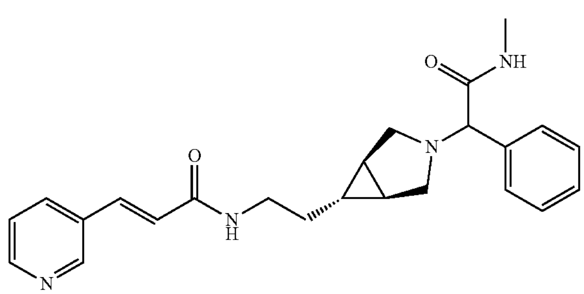 [SMILES: CNC(=O)C(c1ccccc1)N1C[C@@H]2[C@@H](CCNC(=O)/C=C/c3cccnc3)[C@@H]2C1] | (E)-N-(2-((1R,5S,6s)-3-(2-(methylamino)-2-oxo-1-phenylethyl)-3-azabicyclo[3.1.0]hexan-6-yl)ethyl)-3-(pyridin-3-yl)acrylamide | 405.4 | 283 |
| 318 | 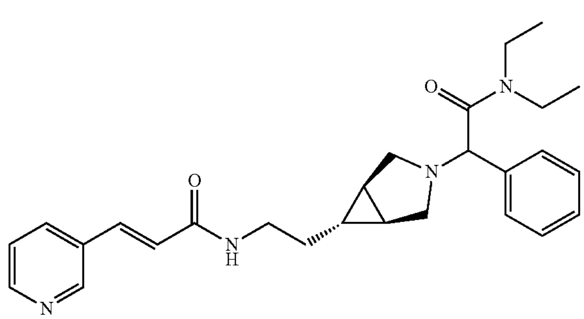 [SMILES: CCN(CC)C(=O)C(c1ccccc1)N1C[C@@H]2[C@@H](CCNC(=O)/C=C/c3cccnc3)[C@@H]2C1] | (E)-N-(2-((1R,5S,6s)-3-(2-(diethylamino)-2-oxo-1-phenylethyl)-3-azabicyclo[3.1.0]hexan-6-yl)ethyl)-3-(pyridin-3-yl)acrylamide | 447.5 | 283 |

-continued

| Ex. No. | Chemical structure | Chemical name | MS (ESI) m/z (M + H)+ | Prep. as in Ex. No. |
|---|---|---|---|---|
| 319 | 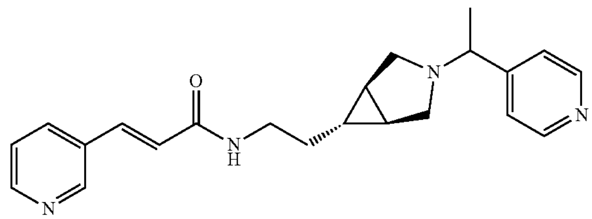 [SMILES: CC(c1ccncc1)N1C[C@@H]2[C@@H](CCNC(=O)/C=C/c3cccnc3)[C@@H]2C1] | (E)-3-(pyridin-3-yl)-N-(2-((1R,5S,6s)-3-(1-(pyridin-4-yl)ethyl)-3-azabicyclo[3.1.0]hexan-6-yl)ethyl)acrylamide | 363.3 | 243 |
| 320 | 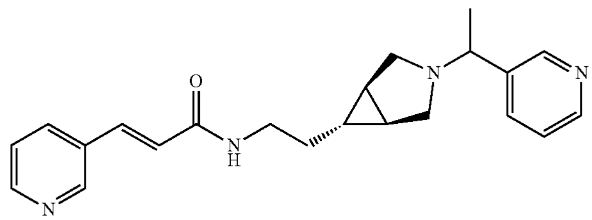 [SMILES: CC(c1cccnc1)N1C[C@@H]2[C@@H](CCNC(=O)/C=C/c3cccnc3)[C@@H]2C1] | (E)-3-(pyridin-3-yl)-N-(2-((1R,5S,6s)-3-(1-(pyridin-3-yl)ethyl)-3-azabicyclo[3.1.0]hexan-6-yl)ethyl)acrylamide | 363.3 | 243 |
| 321 | 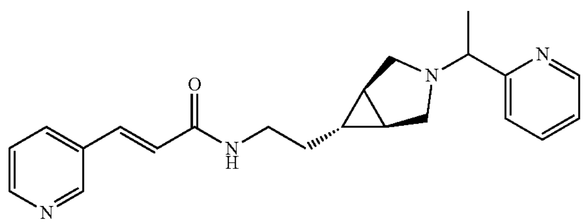 [SMILES: CC(c1ccccn1)N1C[C@@H]2[C@@H](CCNC(=O)/C=C/c3cccnc3)[C@@H]2C1] | (E)-N-(2-((1R,5S,6s)-3-(1-(pyridin-2-yl)ethyl)-3-azabicyclo[3.1.0]hexan-6-yl)ethyl)-3-(pyridin-3-yl)acrylamide | 363.2 | 243 |
| 322 | 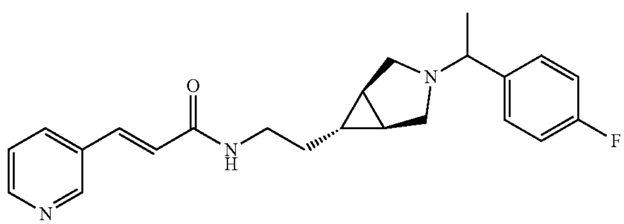 [SMILES: CC(c1ccc(F)cc1)N1C[C@@H]2[C@@H](CCNC(=O)/C=C/c3cccnc3)[C@@H]2C1] | (E)-N-(2-((1R,5S,6s)-3-(1-(4-fluorophenyl)ethyl)-3-azabicyclo[3.1.0]hexan-6-yl)ethyl)-3-(pyridin-3-yl)acrylamide | 380.4 | 243 |
| 323 | 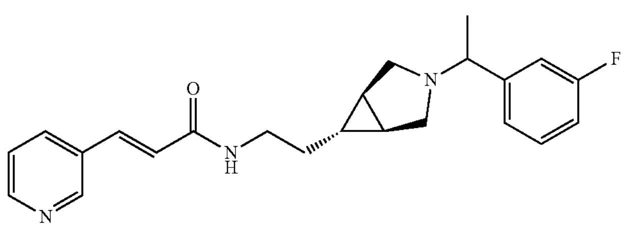 [SMILES: CC(c1cccc(F)c1)N1C[C@@H]2[C@@H](CCNC(=O)/C=C/c3cccnc3)[C@@H]2C1] | (E)-N-(2-((1R,5S,6s)-3-(1-(3-fluorophenyl)ethyl)-3-azabicyclo[3.1.0]hexan-6-yl)ethyl)-3-(pyridin-3-yl)acrylamide | 380.4 | 243 |
| 324 | 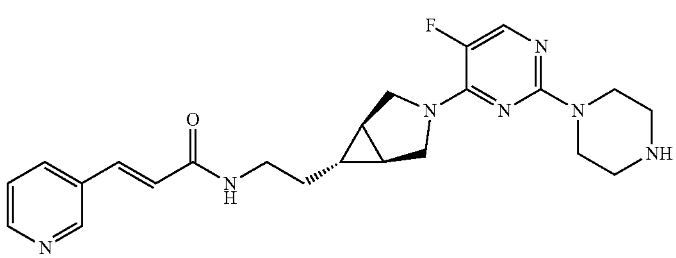 [SMILES: O=C(/C=C/c1cccnc1)NCC[C@@H]1[C@H]2CN(c3nc(N4CCNCC4)ncc3F)C[C@@H]12] | (E)-N-(2-((1R,5S,6s)-3-(5-fluoro-2-(piperazin-1-yl)pyrimidin-4-yl)-3-azabicyclo[3.1.0]hexan-6-yl)ethyl)-3-(pyridin-3-yl)acrylamide | 438.3 | 277 |

| Ex. No. | Chemical structure | Chemical name | MS (ESI) m/z (M + H)+ | Prep. as in Ex. No. |
|---|---|---|---|---|
| 325 | 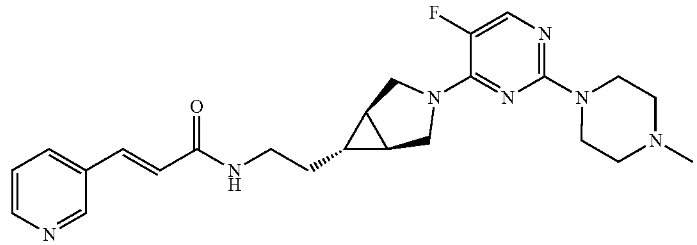 [SMILES: CN1CCN(c2ncc(F)c(N3C[C@@H]4[C@@H](CCNC(=O)/C=C/c5cccnc5)[C@@H]4C3)n2)CC1] | (E)-N-(2-((1R,5S,6s)-3-(5-fluoro-2-(4-methylpiperazin-1-yl)pyrimidin-4-yl)-3-azabicyclo[3.1.0]hexan-6-yl)ethyl)-3-(pyridin-3-yl)acrylamide | 452.3 | 277 |
| 326 | 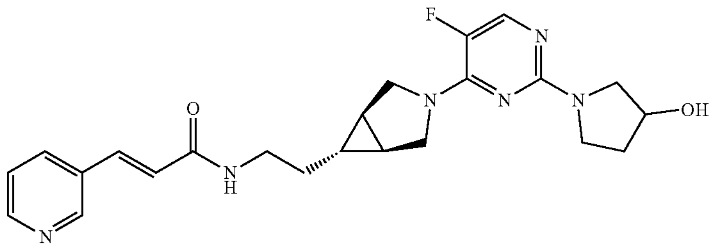 [SMILES: O=C(/C=C/c1cccnc1)NCC[C@@H]1[C@H]2CN(c3nc(N4CCC(O)C4)ncc3F)C[C@@H]12] | (E)-N-(2-((1R,5S,6s)-3-(5-fluoro-2-(3-hydroxypyrrolidin-1-yl)pyrimidin-4-yl)-3-azabicyclo[3.1.0]hexan-6-yl)ethyl)-3-(pyridin-3-yl)acrylamide | 439.3 | 277 |
| 327 | 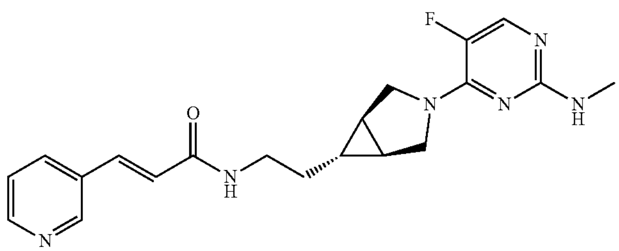 [SMILES: CNc1ncc(F)c(N2C[C@@H]3[C@@H](CCNC(=O)/C=C/c4cccnc4)[C@@H]3C2)n1] | (E)-N-(2-((1R,5S,6s)-3-(5-fluoro-2-(methylamino)pyrimidin-4-yl)-3-azabicyclo[3.1.0]hexan-6-yl)ethyl)-3-(pyridin-3-yl)acrylamide | 383.2 | 277 |
| 328 | 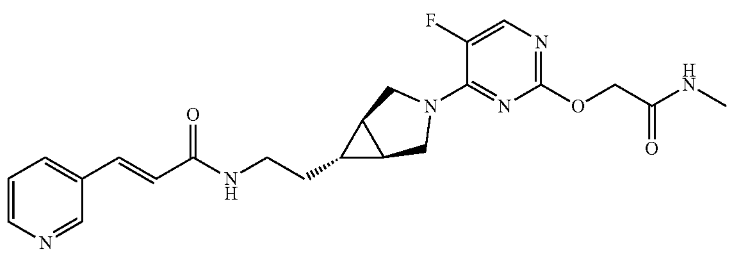 [SMILES: CNC(=O)COc1ncc(F)c(N2C[C@@H]3[C@@H](CCNC(=O)/C=C/c4cccnc4)[C@@H]3C2)n1] | (E)-N-(2-((1R,5S,6s)-3-(5-fluoro-2-(2-(methylamino)-2-oxoethoxy)pyrimidin-4-yl)-3-azabicyclo[3.1.0]hexan-6-yl)ethyl)-3-(pyridin-3-yl)acrylamide | 441.2 | 285 |
| 329 | 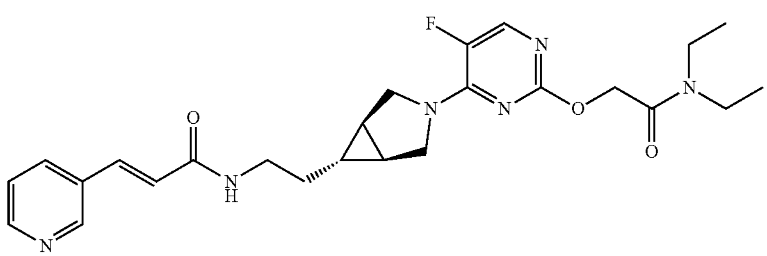 [SMILES: CCN(CC)C(=O)COc1ncc(F)c(N2C[C@@H]3[C@@H](CCNC(=O)/C=C/c4cccnc4)[C@@H]3C2)n1] | (E)-N-(2-((1R,5S,6s)-3-(2-(2-(diethylamino)-2-oxoethoxy)-5-fluoropyrimidin-4-yl)-3-azabicyclo[3.1.0]hexan-6-yl)ethyl)-3-(pyridin-3-yl)acrylamide | 483.3 | 285 |
| 330 | 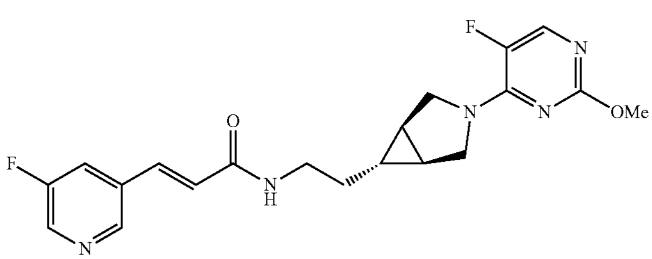 [SMILES: COc1ncc(F)c(N2C[C@@H]3[C@@H](CCNC(=O)/C=C/c4cncc(F)c4)[C@@H]3C2)n1] | (E)-N-(2-((1R,5S,6s)-3-(5-fluoro-2-methoxypyrimidin-4-yl)-3-azabicyclo[3.1.0]hexan-6-yl)ethyl)-3-(5-fluoropyridin-3-yl)acrylamide | 402.3 | 189 |

-continued

| Ex. No. | Chemical structure | Chemical name | MS (ESI) m/z (M + H)+ | Prep. as in Ex. No. |
|---|---|---|---|---|
| 331 | 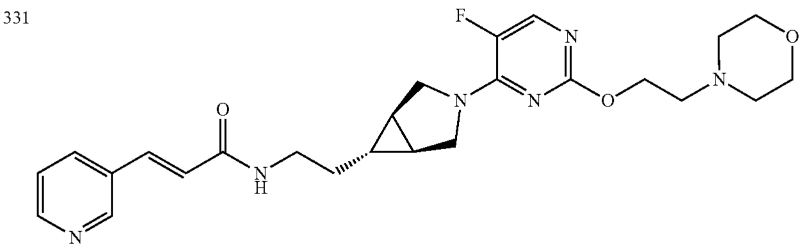 | (E)-N-(2-((1R,5S,6s)-3-(5-fluoro-2-(2-morpholinoethoxy)pyrimidin-4-yl)-3-azabicyclo[3.1.0]hexan-6-yl)ethyl)-3-(pyridin-3-yl)acrylamide | 483.4 | 278 |
| 332 | 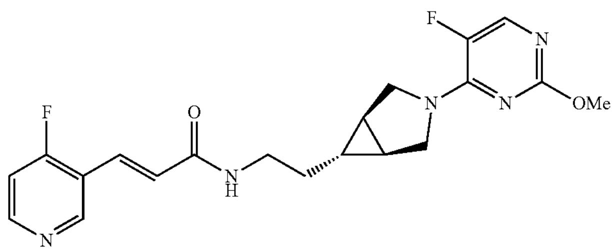 [SMILES: COc1ncc(F)c(N2C[C@@H]3[C@@H](CCNC(=O)/C=C/c4cnccc4F)[C@@H]3C2)n1] | (E)-N-(2-((1R,5S,6s)-3-(5-fluoro-2-methoxypyrimidin-4-yl)-3-azabicyclo[3.1.0]hexan-6-yl)ethyl)-3-(4-fluoropyridin-3-yl)acrylamide | 402.2 | 189 |
| 333 | 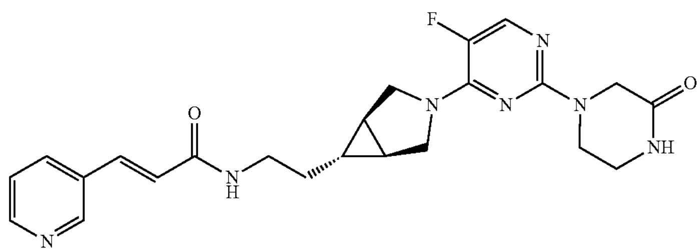 [SMILES: O=C(/C=C/c1cccnc1)NCC[C@@H]1[C@H]2CN(c3nc(N4CCNC(=O)C4)ncc3F)C[C@@H]12] | (E)-N-(2-((1R,5S,6s)-3-(5-fluoro-2-(3-oxopiperazin-1-yl)pyrimidin-4-yl)-3-azabicyclo[3.1.0]hexan-6-yl)ethyl)-3-(pyridin-3-yl)acrylamide | 452.2 | 277 |
| 334 | 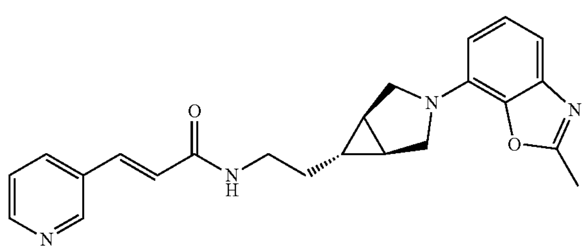 [SMILES: Cc1nc2cccc(N3C[C@@H]4[C@@H](CCNC(=O)/C=C/c5cccnc5)[C@@H]4C3)c2o1] | (E)-N-(2-((1R,5S,6s)-3-(2-methylbenzo[d]oxazol-7-yl)-3-azabicyclo[3.1.0]hexan-6-yl)ethyl)-3-(pyridin-3-yl)acrylamide | 389.3 | 189 |
| 335 | 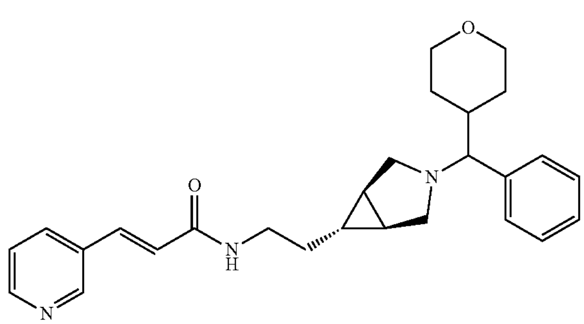 [SMILES: O=C(/C=C/c1cccnc1)NCC[C@@H]1[C@H]2CN(C(c3ccccc3)C3CCOCC3)C[C@@H]12] | (E)-N-(2-((1R,5S,6s)-3-(phenyl(tetrahydro-2H-pyran-4-yl)methyl)-3-azabicyclo[3.1.0]hexan-6-yl)ethyl)-3-(pyridin-3-yl)acrylamide | 432.3 | 243 |

-continued

| Ex. No. | Chemical structure | Chemical name | MS (ESI) m/z (M + H)+ | Prep. as in Ex. No. |
|---|---|---|---|---|
| 336 | 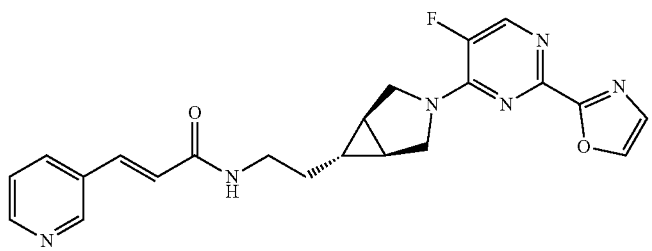 [SMILES: O=C(/C=C/c1cccnc1)NCC[C@@H]1[C@H]2CN(c3nc(-c4ncco4)ncc3F)C[C@@H]12] | (E)-N-(2-((1R,5S,6s)-3-(5-fluoro-2-(oxazol-2-yl)pyrimidin-4-yl)-3-azabicyclo[3.1.0]hexan-6-yl)ethyl)-3-(pyridin-3-yl)acrylamide | 421.4 | 287 |
| 337 | 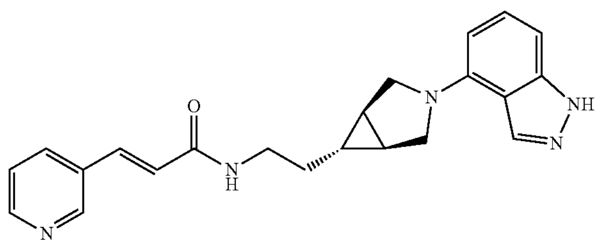 [SMILES: O=C(/C=C/c1cccnc1)NCC[C@@H]1[C@H]2CN(c3cccc4[nH]ncc34)C[C@@H]12] | (E)-N-(2-((1R,5S,6s)-3-(1H-indazol-4-yl)-3-azabicyclo[3.1.0]hexan-6-yl)ethyl)-3-(pyridin-3-yl)acrylamide | 374.3 | 117 |
| 338 | 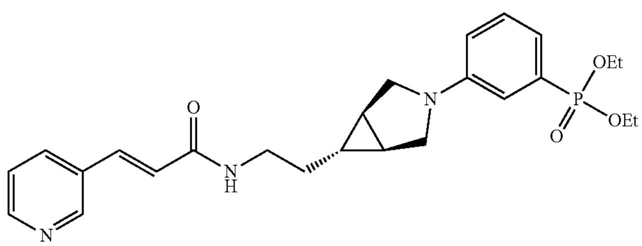 [SMILES: CCOP(=O)(OCC)c1cccc(N2C[C@@H]3[C@@H](CCNC(=O)/C=C/c4cccnc4)[C@@H]3C2)c1] | diethyl (3-((1R,5S,6s)-6-(2-((E)-3-(pyridin-3-yl)acrylamido)ethyl)-3-azabicyclo[3.1.0]hexan-3-yl)phenyl)phosphonate | 470.2 | 288 |
| 339 | 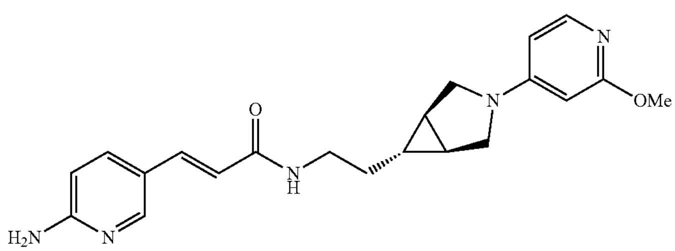 [SMILES: COc1cc(N2C[C@@H]3[C@@H](CCNC(=O)/C=C/c4ccc(N)nc4)[C@@H]3C2)ccn1] | (E)-3-(6-aminopyridin-3-yl)-N-(2-((1R,5S,6s)-3-(2-methoxypyridin-4-yl)-3-azabicyclo[3.1.0]hexan-6-yl)ethyl)acrylamide | 380.3 | 189 |
| 340 | 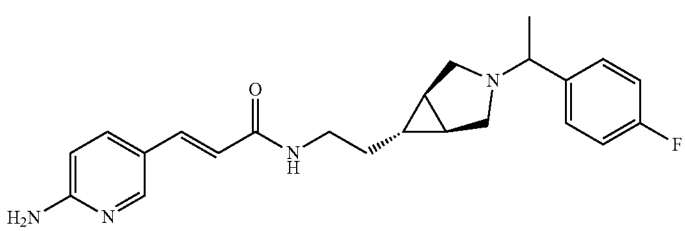 [SMILES: CC(c1ccc(F)cc1)N1C[C@@H]2[C@@H](CCNC(=O)/C=C/c3ccc(N)nc3)[C@@H]2C1] | (E)-3-(6-aminopyridin-3-yl)-N-(2-((1R,5S,6s)-3-(1-(4-fluorophenyl)ethyl)-3-azabicyclo[3.1.0]hexan-6-yl)ethyl)acrylamide | 395.1 | 243 |
| 341 | 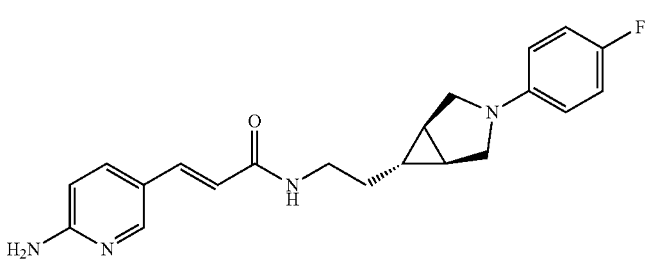 [SMILES: Nc1ccc(/C=C/C(=O)NCC[C@@H]2[C@H]3CN(c4ccc(F)cc4)C[C@@H]23)cn1] | (E)-3-(6-aminopyridin-3-yl)-N-(2-((1R,5S,6s)-3-(4-fluorophenyl)-3-azabicyclo[3.1.0]hexan-6-yl)ethyl)acrylamide | 367.2 | 189 |

| Ex. No. | Chemical structure | Chemical name | MS (ESI) m/z (M + H)+ | Prep. as in Ex. No. |
|---|---|---|---|---|
| 342 | 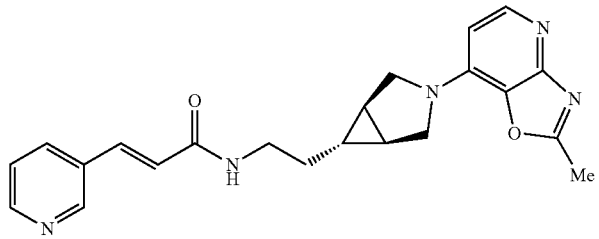 [SMILES: Cc1nc2nccc(N3C[C@@H]4[C@@H](CCNC(=O)/C=C/c5cccnc5)[C@@H]4C3)c2o1] | (E)-N-(2-((1R,5S,6s)-3-(2-methyloxazolo[4,5-b]pyridin-7-yl)-3-azabicyclo[3.1.0]hexan-6-yl)ethyl)-3-(pyridin-3-yl)acrylamide | 390.1 | 117 |

Biological Example 1: NAMPT Assay

To test the inhibition activity ($IC_{50}$) of the compounds of the disclosure against the enzymatic activity of NAMPT, the compounds were dissolved in 100% DMSO to a final concentration of 3 mM. The compounds were then diluted 20 fold in an intermediate dilution to 5% DMSO and water. Finally 10 μL of each compound was added to the assay plate, in duplicate, with highest concentration at 30 μM and the lowest at 0.001 μM in a final volume of 50 μL and 1% DMSO concentration. Each assay also tested, in parallel, two reference compounds, FK866 and GMX1778, with highest concentration at 10 μM and lowest at 0.0003 μM. 200 ng of human NAMPT enzyme (His-hNAMPT obtained from *E. coli* expression system) diluted in TEST (tris-buffered saline-Polysorbate 20) 1× was added to each well in a volume of 10 μL and the compounds were incubated with the enzyme at room temperature for 20 minutes. After the incubation, 30 μL of master mixture were added to each well. The master mixture contained: 50 mM Tris-HCl, pH 8.0, 12.5 mM $MgCl_2$, 20 μM nicotinamide, 40 μM phosphoribosyl pyrophosphate (PRPP), 20 μM adenosine triphosphate (ATP), 30 μg/mL of alcohol dehydrogenase, 10 μg/mL of NMNAT, 1.5% alcohol, 1 mM dithiothreitol (DTT), 0.02% bovine serum albumin (BSA), 0.01% Tween 20. The reaction was performed at 30° C. for 60 minutes. Fluorescence intensity was measured at an excitation of 340 nm and an emission of 460 nm using a Tecan Infinite M1000 microplate reader. The fluorescence values indicated increase of NADH product.

Enzyme activity assay was performed in duplicate at each concentration. The fluorescence data was analyzed and compared. In the absence of the compound, the intensity (Ce) in each data set was defined as 100% activity. In the absence of enzyme, the intensity ($C_0$) in each data set was defined as 0% activity. The percent activity in the presence of each compound was calculated according to the following equation: % activity=$(C-C_0)/(Ce-C_0)$, where C is the fluorescence in the presence of the compound.

The % activity vs. compound concentrations were then plotted using non-linear regression analysis of Sigmoidal dose-response curve generated with the equation $Y=B+(T-B)/1+10^{(Log\ EC50-X)\times Hill\ Slope}$, where Y is percent activity, B is minimum percent activity, T is maximum percent activity, X is logarithm of compound and Hill Slope=slope factor or Hill coefficient.

The results of NAMPT inhibition assay of the compounds of the disclosure are provided in Table 1. $IC_{50}$ activity of 1-29 μM is labeled "+", $IC_{50}$ activity of 0.5-0.99 μM is labeled "++", $IC_{50}$ activity of 0.01-0.49 μM is labeled "+++", $IC_{50}$ activity of <0.01 μM is labeled "++++", and $IC_{50}$ activity of <50% inhibition at 30 μM is labeled "±"

TABLE 1

| Ex. No. | NAMPT $IC_{50}$ (μM) [BPS] | NAMPT $IC_{50}$ (μM) [HDB] |
|---|---|---|
| 1 | ++++ | |
| 2 | +++ | |
| 3 | +++ | |
| 4 | +++ | |
| 5 | +++ | |
| 6 | +++ | |
| 7 | +++ | |
| 8 | ± | |
| 9 | | +++ |
| 10 | +++ | |
| 11 | ++ | |
| 12 | ++++ | |
| 13 | | +++ |
| 14 | ± | |
| 15 | +++ | |
| 16 | +++ | |
| 17 | +++ | ++++ |
| 18 | +++ | |
| 19 | +++ | |
| 20 | +++ | |
| 21 | +++ | |
| 22 | +++ | |
| 23 | +++ | +++ |
| 24 | +++ | |
| 25 | +++ | +++ |
| 26 | +++ | |
| 27 | +++ | |
| 28 | +++ | |
| 29 | +++ | |
| 30 | +++ | +++ |
| 31 | +++ | |
| 32 | +++ | |
| 33 | +++ | |
| 34 | +++ | |
| 35 | + | |
| 36 | +++ | |
| 37 | +++ | |
| 38 | +++ | |
| 39 | +++ | |
| 40 | +++ | |
| 41 | +++ | |
| 42 | +++ | |
| 43 | +++ | |
| 44 | +++ | |
| 45 | +++ | |
| 46 | +++ | |
| 47 | +++ | |
| 48 | +++ | |
| 49 | + | |
| 50 | +++ | |

TABLE 1-continued

| Ex. No. | NAMPT IC$_{50}$ (μM) [BPS] | NAMPT IC$_{50}$ (μM) [HDB] |
| --- | --- | --- |
| 51 | +++ | |
| 52 | +++ | |
| 53 | +++ | |
| 54 | + | |
| 55 | ± | |
| 56 | +++ | |
| 57 | +++ | |
| 58 | +++ | |
| 59 | ++ | |
| 60 | +++ | |
| 61 | +++ | |
| 62 | + | |
| 63 | +++ | |
| 64 | +++ | |
| 65 | + | |
| 66 | + | |
| 67 | +++ | |
| 68 | + | |
| 69 | ++ | |
| 70 | +++ | |
| 71 | +++ | |
| 72 | +++ | |
| 73 | + | |
| 74 | +++ | |
| 75 | +++ | |
| 76 | +++ | |
| 77 | +++ | |
| 78 | ++ | |
| 79 | +++ | |
| 80 | + | |
| 81 | ++++ | |
| 82 | +++ | |
| 83 | +++ | |
| 84 | ++ | |
| 85 | | +++ |
| 86 | +++ | |
| 87 | +++ | |
| 88 | +++ | |
| 89 | +++ | |
| 90 | +++ | |
| 91 | +++ | |
| 92 | +++ | |
| 93 | +++ | |
| 94 | +++ | |
| 95 | +++ | |
| 96 | +++ | |
| 97 | +++ | |
| 98 | +++ | |
| 99 | +++ | |
| 100 | ++ | |
| 101 | +++ | |
| 102 | +++ | |
| 103 | +++ | |
| 104 | +++ | |
| 105 | +++ | |
| 106 | +++ | |
| 107 | +++ | |
| 108 | +++ | |
| 109 | +++ | |
| 110 | +++ | |
| 111 | +++ | |
| 112 | +++ | |
| 113 | +++ | |
| 114 | | +++ |
| 115 | | ++++ |
| 116 | | +++ |
| 117 | +++ | |
| 118 | +++ | |
| 119 | +++ | |
| 120 | +++ | |
| 121 | +++ | |
| 122 | +++ | |
| 123 | +++ | |
| 124 | +++ | |
| 125 | +++ | |
| 126 | +++ | |
| 127 | +++ | |
| 128 | +++ | |
| 129 | +++ | |
| 130 | +++ | |
| 131 | +++ | |
| 132 | +++ | |
| 133 | +++ | |
| 134 | | ++++ |
| 135 | | +++ |
| 136 | | ++++ |
| 137 | | +++ |
| 138 | | +++ |
| 139 | | +++ |
| 140 | | +++ |
| 141 | | ++++ |
| 142 | | ++++ |
| 143 | | +++ |
| 144 | | +++ |
| 145 | | +++ |
| 146 | | +++ |
| 147 | | ++++ |
| 148 | | ++++ |
| 149 | | +++ |
| 150 | | +++ |
| 151 | | ++++ |
| 152 | | +++ |
| 153 | | +++ |
| 154 | | +++ |
| 155 | | +++ |
| 156 | | +++ |
| 157 | | ++++ |
| 158 | | ++++ |
| 159 | | ++++ |
| 160 | | ++++ |
| 161 | | +++ |
| 162 | | +++ |
| 163 | | +++ |
| 164 | | +++ |
| 165 | | +++ |
| 166 | | +++ |
| 167 | | +++ |
| 168 | | +++ |
| 169 | | ++++ |
| 170 | | +++ |
| 171 | | ++++ |
| 172 | | ++++ |
| 173 | | +++ |
| 174 | | ++++ |
| 175 | | +++ |
| 176 | | +++ |
| 177 | | +++ |
| 178 | +++ | |
| 179 | + | ++ |
| 180 | ++ | |
| 181 | + | |
| 182 | | +++ |
| 183 | | +++ |
| 184 | | +++ |
| 185 | | +++ |
| 186 | | +++ |
| 187 | | +++ |
| 188 | | ++++ |
| 189 | +++ | |
| 190 | +++ | |
| 191 | +++ | |
| 192 | +++ | |
| 193 | | ++++ |
| 194 | | +++ |
| 195 | | +++ |
| 196 | | +++ |
| 197 | | +++ |
| 198 | | +++ |
| 199 | | +++ |
| 200 | | +++ |
| 201 | | ++++ |
| 202 | | +++ |
| 203 | | +++ |
| 204 | | +++ |

TABLE 1-continued

| Ex. No. | NAMPT IC$_{50}$ (μM) [BPS] | NAMPT IC$_{50}$ (μM) [HDB] |
|---|---|---|
| 205 | | ++++ |
| 206 | | +++ |
| 207 | | ++++ |
| 208 | | ++++ |
| 209 | | +++ |
| 210 | | +++ |
| 211 | | +++ |
| 212 | | +++ |
| 213 | | +++ |
| 214 | | +++ |
| 215 | | + |
| 216 | | + |
| 217 | | +++ |
| 218 | | +++ |
| 219 | | +++ |
| 220 | | +++ |
| 221 | | +++ |
| 222 | | ++++ |
| 223 | | +++ |
| 224 | | +++ |
| 225 | | ++++ |
| 226 | | +++ |
| 227 | | +++ |
| 228 | +++ | |
| 229 | +++ | |
| 230 | +++ | |
| 231 | + | |
| 232 | +++ | |
| 233 | ± | + |
| 234 | + | |
| 235 | + | |
| 236 | ± | |
| 237 | ++ | |
| 238 | + | |
| 239 | + | |
| 240 | + | |
| 241 | + | |
| 242 | ± | |
| 243 | | +++ |
| 244 | | +++ |
| 245 | | + |
| 246 | | ++ |
| 247 | | +++ |
| 248 | | +++ |
| 249 | | +++ |
| 250 | | +++ |
| 251 | | +++ |
| 252 | + | |
| 253 | +++ | |
| 254 | +++ | |
| 255 | +++ | |
| 256 racemic | +++ | +++ |
| 256 isomer A | | +++ |
| 256 isomer B | | +++ |
| 257 | +++ | |
| 258 | +++ | |
| 259 | +++ | |
| 260 | ++ | |
| 261 | | +++ |
| 262 | | +++ |
| 263 | | +++ |
| 264 | | +++ |
| 265 | | +++ |
| 266 | | +++ |
| 267 | +++ | |
| 268 | ++ | |
| 269 | + | |
| 270 | +++ | |
| 271 | + | |
| 272 | +++ | |
| 273 | + | |
| 274 | +++ | |
| 275 | ++ | |
| 276 | | ++++ |
| 277 | | ++++ |
| 278 | | ++++ |
| 279 | | +++ |
| 280 | | +++ |
| 281 | | +++ |
| 282 | | +++ |
| 283 | | ++++ |
| 284 | | ++++ |
| 285 | | ++++ |
| 286 | | +++ |
| 287 | | ++++ |
| 288 | | +++ |
| 289 | | +++ |
| 290 | | +++ |
| 291 | | +++ |
| 292 | | +++ |
| 293 | +++ | |
| 294 | | +++ |
| 295 | | +++ |
| 296 | | ++++ |
| 297 | | ++++ |
| 298 | | ++++ |
| 299 | | ++++ |
| 300 | | +++ |
| 301 | | ++++ |
| 302 | | +++ |
| 303 | | +++ |
| 304 | | ++++ |
| 305 | | ++++ |
| 306 | | +++ |
| 307 | | +++ |
| 308 | | ++++ |
| 309 | | ++++ |
| 310 | | +++ |
| 311 | | ++++ |
| 312 | | ++++ |
| 313 | | ++++ |
| 314 | | +++ |
| 315 | | +++ |
| 316 | | +++ |
| 317 | | ++++ |
| 318 | | ++++ |
| 319 | | ++++ |
| 320 | | ++++ |
| 321 | | +++ |
| 322 | | +++ |
| 323 | | ++++ |
| 324 | | +++ |
| 325 | | ++++ |
| 326 | | ++++ |
| 327 | | ++++ |
| 328 | | +++ |
| 329 | | +++ |
| 330 | | +++ |
| 331 | | ++++ |
| 332 | | ++++ |
| 333 | | ++++ |
| 334 | | ++++ |
| 335 | | +++ |
| 336 | | ++++ |
| 337 | | +++ |
| 338 | | +++ |
| 339 | | +++ |
| 340 | | +++ |
| 341 | | +++ |
| 342 | | +++ |

Biological Example 2: Cell Viability Assay

To assess cell viability, H1975 (MYC amplified lung), HT1080 (IDH1$^{R132C}$ mutant fibrosarcoma), and UACC257 (melanoma, wildtype at the MYC and IDH1/2 genes) cells were seeded into 96-well plates at 7,000-8,000 cells/well. After 12-24 hours, the compounds of the disclosure, and/or nicotinamide mononucleotide (NMN), nicotinic acid (NA), nicotinamide adenine dinucleotide (NAD+), FK866, and GMX1778 were serially diluted and added to wells. Cell viability was measured by CellTiter-Glo® (Promega) cell viability assay and the $IC_{50}$ values (compound concentrations causing 50% viability of cells) were determined.

To determine cytotoxicity, 7,000-8,000 cells were treated with DMSO, the compounds of the disclosure, FK866, or GMX1778, and the number of viable cells that excluded trypan blue was counted using TE2000-U inverted microscope (Nikon) at 48, 72, and 96 hrs after treatment.

As noted above, H1975 is MYC amplified, HT1080 is IDH1 mutant, and UACC257 has neither MYC or IDH mutation. The results of the cell viability assay show that the compounds of the disclosure generally have potent activity in H1975 and HT1080 cells (e.g., low nanomolar, or even picomolar, $IC_{50}$ values), and low activity in UACC257 (e.g., more than 10 μM). That is, the compounds of the disclosure have selectivity for MYC and IDH1/2 mutant cancers and are less active against cancers that don't have these mutations.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Various exemplary embodiments of the disclosure include, but are not limited to the enumerated embodiments listed below, which can be combined in any number and in any combination that is not technically or logically inconsistent.

Embodiment 1 provides a compound of the formula (I) as described above, provided that the compound of formula (I) is not
ethyl 5-((((2-(2-(5-bromopyridin-2-yl)octahydrocyclopenta[c]pyrrol-5-yl)ethyl)carbamoyl)oxy)methyl)isoxazole-3-carboxylate;
ethyl 5-((((2-(2-(tert-butoxycarbonyl)octahydrocyclopenta[c]pyrrol-5-yl)ethyl)carbamoyl)oxy)methyl)isoxazole-3-carboxylate;
(3-carbamoylisoxazol-5-yl)methyl (2-(2-(5-bromopyridin-2-yl)octahydrocyclopenta[c]pyrrol-5-yl)ethyl)carbamate;
(3-(methylcarbamoyl)isoxazol-5-yl)methyl (2-(2-(5-bromopyridin-2-yl)octahydrocyclopenta[c]pyrrol-5-yl)ethyl)carbamate; or
ethyl 7-(6-(2-((tert-butoxycarbonyl)amino)ethyl)-3-azabicyclo[3.1.0]hexan-3-yl)-1-(2,4-difluorophenyl)-6-fluoro-4-oxo-1,4-dihydro-1,8-naphthyridine-3-carboxylate.

Embodiment 2 provides the compound of embodiment 1, wherein m is 1, and both n and p are 0.

Embodiment 3 provides the compound of embodiment 1, wherein m is 1, and both n and p are 1; or m is 2, and both n and p are 1.

Embodiment 4 provides the compound of embodiment 1, wherein m is 1, n is 2, and p is 1.

Embodiment 5 provides the compound of any of embodiments 1-4, wherein R is hydrogen.

Embodiment 6 provides the compound of any of embodiments 1-5, wherein L is ethylene optionally substituted with one or more $R_{15}$.

Embodiment 7 provides the compound of embodiment 6, wherein each $R_{15}$ is independently halogen, $C_1$-$C_3$ alkyl, —OH, $C_1$-$C_3$ alkoxy, or $C_1$-$C_3$ haloalkoxy, or two $R_{15}$ groups form a $C_3$-$C_4$ cyclyl.

Embodiment 8 provides the compound of embodiment 6, wherein each $R_{15}$ is independently halogen, $C_1$-$C_3$ alkyl, or —OH, or two $R_{15}$ groups form a $C_3$-$C_4$ cyclyl.

Embodiment 9 provides the compound of any of embodiments 1-5, wherein L is ethylene optionally substituted with one $R_{15}$, and wherein $R_{15}$ is independently halogen or —OH.

Embodiment 10 provides the compound of any of embodiments 1-5, wherein L is ethylene optionally substituted with two $R_{15}$ groups that form a $C_3$-$C_4$ cyclyl (e.g., cyclopropyl).

Embodiment 11 provides the compound of any of embodiments 1-5, wherein L is unsubstituted ethylene.

Embodiment 12 provides the compound of any of embodiments 1-5, wherein L is ethylene, —$CH_2$—CHF—, —$CH_2$—CHOH—, or —C(cyclopropyl)-$CH_2$—.

Embodiment 13 provides the compound of any of embodiments 1-5, wherein L is $C_3$-$C_4$ alkylene linker optionally substituted with one or more $R_{15}$, wherein each $R_{15}$ is independently halogen, $C_1$-$C_3$ alkyl, —OH, $C_1$-$C_3$ alkoxy, or $C_1$-$C_3$ haloalkoxy, or two $R_{15}$ groups form a $C_3$-$C_4$ cyclyl.

Embodiment 14 provides the compound of any of embodiments 1-13, wherein X represents O.

Embodiment 15 provides the compound of any of embodiments 1-13, wherein X represents N—CN.

Embodiment 16 provides the compound of any of embodiments 1-15, wherein $R_1$ is —$R_7$, —$NHR_7$, or —$CH_2$—$OR_7$.

Embodiment 17 provides the compound of any of embodiments 1-15, wherein $R_1$ is —$R_7$, —$NHR_7$, or —$OR_7$.

Embodiment 18 provides the compound of any of embodiments 1-15, wherein $R_1$ is —$R_7$ or —$NHR_7$.

Embodiment 19 provides the compound of any of embodiments 1-15, wherein $R_1$ is —$R_7$.

Embodiment 20 provides the compound of any of embodiments 1-15, wherein $R_1$ is —$R_7$, which is $C_1$-$C_6$ alkyl optionally substituted with one or more $R_{10}$, aryl($C_0$-$C_2$ alkyl) optionally substituted with one or more $R_{11}$, aryl($C_2$-$C_3$ alkenyl) optionally substituted with one or more $R_{11}$, heteroaryl($C_0$-$C_2$ alkyl) optionally substituted with one or more $R_{11}$, heteroaryl($C_2$-$C_3$ alkenyl) optionally substituted with one or more $R_{11}$, heterocyclyl($C_0$-$C_2$ alkyl) optionally substituted with one or more $R_{11}$, or cyclyl($C_0$-$C_2$ alkyl) optionally substituted with one or more $R_{11}$.

Embodiment 21 provides the compound of embodiment 20, wherein $R_1$ is $C_1$-$C_6$ alkyl optionally substituted with one or more $R_{10}$, aryl optionally substituted with one or more $R_{11}$, aryl(ethenyl) optionally substituted with one or more $R_{11}$, heteroaryl optionally substituted with one or more $R_{11}$, heteroaryl(ethenyl) optionally substituted with one or more $R_{11}$, heterocyclyl optionally substituted with one or more $R_{11}$, or cyclyl optionally substituted with one or more $R_{11}$.

Embodiment 22 provides the compound of embodiment 20, wherein $R_1$ is $C_1$-$C_6$ alkyl, aryl optionally substituted with one or more $R_{11}$, aryl(ethenyl) optionally substituted with one or more $R_{11}$, heteroaryl optionally substituted with one or more $R_{11}$, heteroaryl(ethenyl) optionally substituted with one or more $R_{11}$, heterocyclyl optionally substituted with one or more $R_{11}$, or cyclyl optionally substituted with one or more $R_{11}$.

Embodiment 23 provides the compound of embodiment 20, wherein $R_1$ is $C_1$-$C_6$ alkyl, aryl optionally substituted with one or more $R_{11}$, heteroaryl optionally substituted with one or more $R_{11}$, heteroaryl(ethenyl) optionally substituted with one or more $R_{11}$, heterocyclyl optionally substituted with one or more $R_{11}$, or cyclyl optionally substituted with one or more $R_{11}$.

Embodiment 24 provides the compound of embodiment 20, wherein $R_1$ is aryl optionally substituted with one or more $R_{11}$, heteroaryl optionally substituted with one or more $R_{11}$, heteroaryl(ethenyl) optionally substituted with one or more $R_{11}$, heterocyclyl optionally substituted with one or more $R_{11}$, or cyclyl optionally substituted with one or more $R_{11}$.

Embodiment 25 provides the compound of embodiment 20, wherein $R_1$ is heteroaryl optionally substituted with one or more $R_{11}$, heteroaryl(ethenyl) optionally substituted with one or more $R_{11}$, or heterocyclyl optionally substituted with one or more $R_{11}$; or wherein $R_1$ is heteroaryl optionally substituted with one or more $R_{11}$ or heteroaryl(ethenyl) optionally substituted with one or more $R_{11}$.

Embodiment 26 provides the compound of embodiment 20, wherein $R_1$ is heteroaryl(ethenyl) optionally substituted with one or more $R_{11}$; or $R_1$ is 4-pyridinyl(ethenyl), 3-pyridinyl(ethenyl), or 2-pyridinyl(ethenyl), each optionally substituted with one or more $R_{11}$.

Embodiment 27 provides the compound of any of embodiments 1-15, wherein $R_1$ is —$NHR_7$, wherein $R_7$ is $C_1$-$C_6$ alkyl optionally substituted with one or more $R_{10}$, aryl($C_0$-$C_2$ alkyl) optionally substituted with one or more $R_{11}$, aryl($C_2$-$C_3$ alkenyl) optionally substituted with one or more $R_{11}$, heteroaryl($C_0$-$C_2$ alkyl) optionally substituted with one or more $R_{11}$, heteroaryl($C_2$-$C_3$ alkenyl) optionally substituted with one or more $R_{11}$, heterocyclyl($C_0$-$C_2$ alkyl) optionally substituted with one or more $R_{11}$, or cyclyl($C_0$-$C_2$ alkyl) optionally substituted with one or more $R_{11}$.

Embodiment 28 provides the compound of embodiment 27, wherein $R_7$ is $C_1$-$C_6$ alkyl optionally substituted with one or more $R_{10}$, aryl optionally substituted with one or more $R_{11}$, aryl(methyl) optionally substituted with one or more $R_{11}$, heteroaryl optionally substituted with one or more $R_{11}$, heteroaryl(methyl) optionally substituted with one or more $R_{11}$, heterocyclyl optionally substituted with one or more $R_{11}$, or cyclyl optionally substituted with one or more $R_{11}$.

Embodiment 29 provides the compound of embodiment 27, wherein $R_7$ is $C_1$-$C_6$ alkyl, aryl optionally substituted with one or more $R_{11}$, aryl(methyl) optionally substituted with one or more $R_{11}$, heteroaryl optionally substituted with one or more $R_{11}$, heteroaryl(methyl) optionally substituted with one or more $R_{11}$, heterocyclyl optionally substituted with one or more $R_{11}$, or cyclyl optionally substituted with one or more $R_{11}$.

Embodiment 30 provides the compound of embodiment 27, wherein $R_7$ is heteroaryl optionally substituted with one or more $R_{11}$, heteroaryl(methyl) optionally substituted with one or more $R_{11}$, or heterocyclyl optionally substituted with one or more $R_{11}$.

Embodiment 31 provides the compound of embodiment 27, wherein $R_7$ is pyridinyl, 4-pyridinyl(methyl), 3-pyridinyl(methyl), or 2-pyridinyl(methyl), each optionally substituted with one or more $R_{11}$.

Embodiment 32 provides the compound of any one of embodiments 1-31, wherein each $R_{11}$ is independently selected from the group consisting of halogen, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, aryl optionally substituted with one or more $R_{12}$, heteroaryl optionally substituted with one or more $R_{12}$, and heterocyclyl optionally substituted with one or more $R_{12}$.

Embodiment 33 provides the compound of any one of embodiments 1-31, wherein each $R_{11}$ is independently selected from the group consisting of halogen, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, and heteroaryl optionally substituted with one or more $R_{12}$.

Embodiment 34 provides the compound of any one of embodiments 1-31, wherein each $R_{11}$ is independently selected from the group consisting of halogen, —$NH_2$, —$NH(C_1$-$C_6$ alkyl), —$N(C_1$-$C_6$ alkyl)$_2$, —OH, $C_1$-$C_6$ alkoxy, and $C_1$-$C_6$ haloalkoxy.

Embodiment 35 provides the compound of any one of embodiments 1-31, wherein each $R_{11}$ is independently selected from the group consisting of halogen, —$NH_2$, —$NH(C_1$-$C_6$ alkyl), —$N(C_1$-$C_6$ alkyl)$_2$, —OH, and $C_1$-$C_6$ alkoxy; or wherein each $R_{11}$ is independently selected from the group consisting of halogen, —$NH_2$, —$NH(C_1$-$C_6$ alkyl), and —$N(C_1$-$C_6$ alkyl)$_2$; or wherein each $R_{11}$ is independently selected from the group consisting of halogen, —$NH_2$, and —OH; or wherein each $R_{11}$ is independently selected from the group consisting of halogen, and —$NH_2$.

Embodiment 36 provides the compound of any one of embodiments 1-31, wherein $R_7$ is unsubstituted or substituted with one $R_{11}$ selected from halogen and —$NH_2$.

Embodiment 37 provides the compound of any one of embodiments 1-31, wherein $R_7$ is unsubstituted or substituted with one $R_{11}$, which is —$NH_2$.

Embodiment 38 provides the compound of any of embodiments 1-37, wherein $R_2$ is hydrogen or methyl.

Embodiment 39 provides the compound of any of embodiments 1-37, wherein $R_2$ is hydrogen.

Embodiment 40 provides the compound of any of embodiments 1-39, wherein $R_3$ is selected from the group consisting of —$R_8$, —C(O)$R_8$, —C(O)O$R_8$, —C(O)$NH_2$, —C(O)$NHR_8$, and —S(O)$_2R_8$.

Embodiment 41 provides the compound of any of embodiments 1-39, wherein $R_3$ is selected from the group consisting of aryl($C_0$-$C_4$ alkyl) optionally substituted with one or more $R_{13}$, heteroaryl($C_0$-$C_4$ alkyl) optionally substituted with one or more $R_{13}$, heterocyclyl($C_0$-$C_4$ alkyl) optionally substituted with one or more $R_{13}$, cyclyl($C_0$-$C_4$ alkyl) optionally substituted with one or more $R_{13}$, —C(O)$R_8$, —C(O)O$R_8$, —C(O)$NH_2$, —C(O)$NHR_8$, and —S(O)$_2R_8$.

Embodiment 42 provides the compound of any of embodiments 1-39, wherein $R_3$ is selected from the group consisting of aryl($C_0$-$C_4$ alkyl) optionally substituted with one or more $R_{13}$, heteroaryl($C_0$-$C_4$ alkyl) optionally substituted with one or more $R_{13}$, —C(O)$R_8$, —C(O)O$R_8$, —C(O)$NH_2$, —C(O)$NHR_8$, and —S(O)$_2R_8$.

Embodiment 43 provides the compound of any of embodiments 1-39, wherein $R_3$ is selected from the group consisting of aryl optionally substituted with one or more $R_{13}$, aryl(methyl) optionally substituted with one or more $R_{13}$, heteroaryl optionally substituted with one or more $R_{13}$, heteroaryl(methyl) optionally substituted with one or more $R_{13}$, —C(O)$R_8$, —C(O)O$R_8$, —C(O)$NH_2$, —C(O)$NR_8R_9$, and —S(O)$_2$—$R_8$; or wherein $R_3$ is selected from the group consisting of aryl optionally substituted with one or more $R_{13}$, aryl(methyl) optionally substituted with one or more $R_{13}$, heteroaryl optionally substituted with one or more $R_{13}$, —C(O)$R_8$, —C(O)O$R_8$, —C(O)NH$_2$, —C(O)NH$R_8$, and —S(O)$_2R_8$.

Embodiment 44 provides the compound of any of embodiments 1-39, wherein $R_3$ is selected from the group consisting of —C(O)$R_8$, —C(O)O$R_8$, —C(O)NH$_2$, —C(O)N$R_8R_9$, and —S(O)$_2$—$R_8$; or wherein $R_3$ is selected from the group consisting of —C(O)$R_8$, —C(O)O$R_8$, —C(O)NH$R_8$, and —S(O)$_2R_8$; or wherein $R_3$ is selected from the group consisting of —C(O)$R_8$, —C(O)O$R_8$, and —C(O)NH$R_8$; or wherein $R_3$ is selected from the group consisting of —C(O)$R_8$, —C(O)O$R_8$, and —S(O)$_2R_8$; or wherein $R_3$ is —C(O)$R_8$ or —C(O)O$R_8$.

Embodiment 45 provides the compound of any of embodiments 40-44, wherein each $R_8$ is independently selected from the group consisting of $C_1$-$C_8$ alkyl optionally substituted with one or more $R_{13}$, aryl($C_0$-$C_1$ alkyl) optionally substituted with one or more $R_{13}$, heteroaryl($C_0$-$C_1$ alkyl) optionally substituted with one or more $R_{13}$, heterocyclyl($C_0$-$C_1$ alkyl) optionally substituted with one or more $R_{13}$, and cyclyl($C_0$-$C_1$ alkyl) optionally substituted with one or more $R_{13}$.

Embodiment 46 provides the compound of any of embodiments 40-44, wherein each $R_8$ is independently selected from the group consisting of $C_1$-$C_6$ alkyl, aryl($C_0$-$C_1$ alkyl) optionally substituted with one or more $R_{13}$, heteroaryl($C_0$-$C_1$ alkyl) optionally substituted with one or more $R_{13}$, and heterocyclyl($C_0$-$C_1$ alkyl) optionally substituted with one or more $R_{13}$.

Embodiment 47 provides the compound of any of embodiments 40-44, wherein each $R_8$ is independently selected from the group consisting of $C_1$-$C_6$ alkyl, aryl optionally substituted with one or more $R_{13}$, heteroaryl optionally substituted with one or more $R_{13}$, heteroaryl(methyl) optionally substituted with one or more $R_{13}$, heterocyclyl optionally substituted with one or more $R_{13}$, and heterocyclyl(methyl) optionally substituted with one or more $R_{13}$.

Embodiment 48 provides the compound of any of embodiments 40-44, wherein each $R_8$ is independently selected from the group consisting of $C_1$-$C_6$ alkyl, aryl optionally substituted with one or more $R_{13}$, heteroaryl optionally substituted with one or more $R_{13}$, heterocyclyl optionally substituted with one or more $R_{13}$, and heterocyclyl(methyl) optionally substituted with one or more $R_{13}$.

Embodiment 49 provides the compound of any of embodiments 40-44, wherein each $R_8$ is independently selected from the group consisting of $C_1$-$C_4$ alkyl, aryl optionally substituted with one or more $R_{13}$, heteroaryl optionally substituted with one or more $R_{13}$, heterocyclyl optionally substituted with one or more $R_{13}$, and heterocyclyl(methyl) optionally substituted with one or more $R_{13}$.

Embodiment 50 provides the compound of any of embodiments 40-44, wherein each $R_3$ is independently selected from the group consisting of aryl optionally substituted with one or more $R_{13}$, heteroaryl optionally substituted with one or more $R_{13}$, heterocyclyl optionally substituted with one or more $R_{13}$; and heterocyclyl(methyl) optionally substituted with one or more $R_{13}$; or wherein each $R_3$ is independently selected from the group consisting of aryl optionally substituted with one or more $R_{13}$, heteroaryl optionally substituted with one or more $R_{13}$, and heterocyclyl optionally substituted with one or more $R_{13}$.

Embodiment 51 provides the compound of any of embodiments 1-50, wherein $R_{13}$ is independently selected from the group consisting of halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy optionally substituted with one or more $R_{16}$, $C_1$-$C_6$ haloalkoxy, —CONH$_2$, —CONH($C_1$-$C_6$ alkyl), —CON($C_1$-$C_6$ alkyl)$_2$, —CONH—OH, —CO$_2$H, —CO$_2$($C_1$-$C_6$ alkyl), aryl optionally substituted with one or more $R_{14}$, heteroaryl optionally substituted with one or more $R_{14}$, and heterocyclyl optionally substituted with one or more $R_{14}$; or two $R_{13}$ groups when attached to the same carbon atom form =O.

Embodiment 52 provides the compound of any of embodiments 1-50, wherein $R_{13}$ is independently selected from the group consisting of halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy optionally substituted with one or more $R_{16}$, $C_1$-$C_6$ haloalkoxy, —CONH$_2$, —CONH($C_1$-$C_6$ alkyl), —CON($C_1$-$C_6$ alkyl)$_2$, —CONH—OH, —CO$_2$H, and —CO$_2$($C_1$-$C_6$ alkyl).

Embodiment 53 provides the compound of any of embodiments 1-50, wherein $R_{13}$ is independently selected from the group consisting of halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CONH$_2$, —CONH($C_1$-$C_6$ alkyl), —CON($C_1$-$C_6$ alkyl)$_2$, —CO$_2$H, and —CO$_2$($C_1$-$C_6$ alkyl).

Embodiment 54 provides the compound of any of embodiments 1-50, wherein $R_{13}$ is independently selected from the group consisting of halogen, —CN, —CH$_3$, halomethyl, —NH$_2$, —NH(CH$_3$), —N(CH$_3$)$_2$, —OH, methoxy, halomethoxy, —CONH$_2$, —CONH(CH$_3$), —CON(CH$_3$)$_2$, —CO$_2$H, and —CO$_2$(CH$_3$).

Embodiment 55 provides the compound of any of embodiments 1-50, wherein $R_{13}$ is independently selected from the group consisting of halogen, —CN, —CH$_3$, halomethyl, —NH$_2$, —NH(CH$_3$), —N(CH$_3$)$_2$, —OH, methoxy, halomethoxy, —CONH$_2$, and —CO$_2$H.

Embodiment 56 provides the compound of any one of embodiments 1-50, wherein Ra is unsubstituted, or substituted with one or more $R_{11}$ selected from halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CONH$_2$, —CONH($C_1$-$C_6$ alkyl), —CON($C_1$-$C_6$ alkyl)$_2$, —CO$_2$H, and —CO$_2$($C_1$-$C_6$ alkyl).

Embodiment 57 provides the compound of any one of embodiments 1-50, wherein Ra is unsubstituted, or substituted with one $R_{11}$ selected from halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CONH$_2$, —CONH($C_1$-$C_6$ alkyl), —CON($C_1$-$C_6$ alkyl)$_2$, —CO$_2$H, and —CO$_2$($C_1$-$C_6$ alkyl).

Embodiment 58 provides the compound of any one of embodiments 1-50, wherein Ra is unsubstituted, or substituted with one or more $R_{11}$ selected from halogen, —CN, —CH$_3$, halomethyl, —NH$_2$, —NH(CH$_3$), —N(CH$_3$)$_2$, —OH, methoxy, halomethoxy, —CONH$_2$, and —CO$_2$H.

Embodiment 59 provides the compound of any one of embodiments 1-50, wherein Ra is unsubstituted, or substituted with one $R_{11}$ selected from halogen, —CN, —CH$_3$, halomethyl, —NH$_2$, —NH(CH$_3$), —N(CH$_3$)$_2$, —OH, methoxy, halomethoxy, —CONH$_2$, and —CO$_2$H.

Embodiment 60 provides the compound of any of embodiments 1-59, wherein each $R_4$ is independently selected from hydrogen and $C_1$-$C_6$ alkyl; or wherein each $R_4$ is independently selected from hydrogen and methyl.

Embodiment 61 provides the compound of any of embodiments 1-59, wherein each $R_4$ is independently hydrogen.

Embodiment 62 provides the compound of any of embodiments 1-61, wherein each $R_5$ is independently selected from hydrogen and $C_1$-$C_6$ alkyl; or wherein each $R_5$ is independently selected from hydrogen and methyl.

Embodiment 63 provides the compound of any of embodiments 1-61, wherein each $R_5$ is independently hydrogen.

Embodiment 64 provides the compound of any of embodiments 1-63, wherein each $R_6$ is independently selected from hydrogen and $C_1$-$C_6$ alkyl, or two $R_6$ groups form an oxo group Embodiment 65 provides the compound of any of embodiments 1-63, wherein each $R_6$ is independently selected from hydrogen and methyl, or two $R_6$ groups form an oxo group.

Embodiment 66 provides the compound of any of embodiments 1-63, wherein each $R_6$ is hydrogen, or two $R_6$ groups form an oxo group.

Embodiment 67 provides the compound of any of embodiments 1-66, wherein each $R_6$ is hydrogen.

Embodiment 68 provides the compound of any of embodiments 1-66, wherein two $R_6$ groups form an oxo group.

Embodiment 69 provides the compound of embodiment 1 according to any of examples disclosed herein (such as, e.g., examples 1-230 and 241-342) or a pharmaceutically acceptable salt thereof.

Embodiment 70 provides a compound of the formula (II) as described above.

Embodiment 71 provides the compound of embodiment 70, wherein q is 1, and both w and z are 0.

Embodiment 72 provides the compound of embodiment 70, wherein q is 1, and both w and z are 1.

Embodiment 73 provides the compound of embodiment 70, wherein q is 2, and both w and z are 1.

Embodiment 74 provides the compound of embodiment 70, wherein q is 1, w is 2, and z is 1.

Embodiment 75 provides the compound of any of embodiments 70-74, wherein Y represents O.

Embodiment 76 provides the compound of any of embodiments 70-74, wherein Y represents N—CN.

Embodiment 77 provides the compound of any of embodiments 70-76, wherein $R_{21}$ is —$R_{25}$ or —$NHR_{27}$.

Embodiment 78 provides the compound of any of embodiments 70-76, wherein $R_{21}$ is —$R_{25}$.

Embodiment 79 provides the compound of any of embodiments 70-76, wherein $R_{21}$ is —$NHR_{27}$, wherein $R_{27}$ is $C_1$-$C_6$ alkyl optionally substituted with one or more $R_{30}$, aryl($C_0$-$C_2$ alkyl) optionally substituted with one or more $R_{31}$, aryl($C_2$-$C_3$ alkenyl) optionally substituted with one or more $R_{31}$, heteroaryl($C_0$-$C_2$ alkyl) optionally substituted with one or more $R_{31}$, heteroaryl($C_2$-$C_3$ alkenyl) optionally substituted with one or more $R_{31}$, heterocyclyl($C_0$-$C_2$ alkyl) optionally substituted with one or more $R_{31}$, or cyclyl($C_0$-$C_2$ alkyl) optionally substituted with one or more $R_{31}$.

Embodiment 80 provides the compound of embodiment 79, wherein $R_{27}$ is $C_1$-$C_6$ alkyl optionally substituted with one or more $R_{30}$, aryl optionally substituted with one or more $R_{31}$, aryl(methyl) optionally substituted with one or more $R_{31}$, heteroaryl optionally substituted with one or more $R_{31}$, heteroaryl(methyl) optionally substituted with one or more $R_{31}$, heterocyclyl optionally substituted with one or more $R_{31}$, or cyclyl optionally substituted with one or more $R_{31}$.

Embodiment 81 provides the compound of embodiment 79, wherein $R_{27}$ is $C_1$-$C_6$ alkyl, aryl optionally substituted with one or more $R_{31}$, aryl(methyl) optionally substituted with one or more $R_{31}$, heteroaryl optionally substituted with one or more $R_{31}$, heteroaryl(methyl) optionally substituted with one or more $R_{31}$, heterocyclyl optionally substituted with one or more $R_{31}$, or cyclyl optionally substituted with one or more $R_{31}$.

Embodiment 82 provides the compound of embodiment 79, wherein $R_{27}$ is heteroaryl optionally substituted with one or more $R_{31}$, heteroaryl(methyl) optionally substituted with one or more $R_{31}$, or heterocyclyl optionally substituted with one or more $R_{31}$.

Embodiment 83 provides the compound of embodiment 79, wherein $R_{27}$ is pyridinyl, 4-pyridinyl(methyl), 3-pyridinyl(methyl), or 2-pyridinyl(methyl), each optionally substituted with one or more $R_{31}$.

Embodiment 84 provides the compound of any one of embodiments 70-83, wherein each $R_{31}$ is independently selected from the group consisting of halogen, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, aryl optionally substituted with one or more $R_{32}$, heteroaryl optionally substituted with one or more $R_{32}$, and heterocyclyl optionally substituted with one or more $R_{32}$.

Embodiment 85 provides the compound of any one of embodiments 70-83, wherein each $R_{31}$ is independently selected from the group consisting of halogen, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, and heteroaryl optionally substituted with one or more $R_{32}$.

Embodiment 86 provides the compound of any one of embodiments 70-83, wherein each $R_{31}$ is independently selected from the group consisting of halogen, —$NH_2$, —$NH(C_1$-$C_6$ alkyl), —$N(C_1$-$C_6$ alkyl)$_2$, —OH, $C_1$-$C_6$ alkoxy, and $C_1$-$C_6$ haloalkoxy.

Embodiment 87 provides the compound of any one of embodiments 70-83, wherein each $R_{31}$ is independently selected from the group consisting of halogen, —$NH_2$, —$NH(C_1$-$C_6$ alkyl), —$N(C_1$-$C_6$ alkyl)$_2$, —OH, and $C_1$-$C_6$ alkoxy; or wherein each $R_{31}$ is independently selected from the group consisting of halogen, —$NH_2$, —$NH(C_1$-$C_6$ alkyl), and —$N(C_1$-$C_6$ alkyl)$_2$; or wherein each $R_{31}$ is independently selected from the group consisting of halogen, —$NH_2$, and —OH; or wherein each $R_{31}$ is independently selected from the group consisting of halogen, and —$NH_2$.

Embodiment 88 provides the compound of any one of embodiments 70-87, wherein $R_{27}$ is unsubstituted or substituted with one $R_{31}$ selected from halogen and —$NH_2$.

Embodiment 89 provides the compound of any one of embodiments 70-87, wherein $R_{27}$ is unsubstituted or substituted with one $R_{31}$, which is —$NH_2$.

Embodiment 90 provides the compound of any of embodiments 70-89, wherein $R_{22}$ is hydrogen or methyl.

Embodiment 91 provides the compound of any of embodiments 70-89, wherein $R_{22}$ is hydrogen.

Embodiment 92 provides the compound of any of embodiments 70-91, wherein $R_{23}$ is selected from the group consisting of —$R_{28}$, —C(O)$R_{28}$, —C(O)O$R_{28}$, —C(O)$NH_2$, —C(O)$NHR_{28}$, and —S(O)$_2R_{28}$.

Embodiment 93 provides the compound of any of embodiments 70-91, wherein $R_{23}$ is selected from the group consisting of aryl($C_0$-$C_4$ alkyl) optionally substituted with one or more $R_{33}$, heteroaryl($C_0$-$C_4$ alkyl) optionally substituted with one or more $R_{33}$, heterocyclyl($C_0$-$C_4$ alkyl) optionally substituted with one or more $R_{33}$, cyclyl($C_0$-$C_4$ alkyl) optionally substituted with one or more $R_{33}$, —C(O)$R_{28}$, —C(O)O$R_{28}$, —C(O)$NH_2$, —C(O)$NHR_{28}$, and —S(O)$_2R_{28}$.

Embodiment 94 provides the compound of any of embodiments 70-91, wherein $R_{23}$ is selected from the group consisting of aryl($C_0$-$C_4$ alkyl) optionally substituted with one or more $R_{33}$, heteroaryl($C_0$-$C_4$ alkyl) optionally substituted with one or more $R_{33}$, —C(O)$R_{28}$, —C(O)O$R_{28}$, —C(O)NH$_2$, —C(O)NH$R_{28}$, and —S(O)$_2R_{28}$.

Embodiment 95 provides the compound of any of embodiments 70-91, wherein $R_{23}$ is selected from the group consisting of aryl optionally substituted with one or more $R_{33}$, aryl(methyl) optionally substituted with one or more $R_{33}$, heteroaryl optionally substituted with one or more $R_{33}$, heteroaryl(methyl) optionally substituted with one or more $R_{33}$, —C(O)$R_{28}$, —C(O)O$R_{28}$, —C(O)NH$_2$, —C(O)N$R_{28}R_9$, and —S(O)$_2$—$R_{28}$; or wherein $R_{23}$ is selected from the group consisting of aryl optionally substituted with one or more $R_{33}$, aryl(methyl) optionally substituted with one or more $R_{33}$, heteroaryl optionally substituted with one or more $R_{33}$, —C(O)$R_{28}$, —C(O)O$R_{28}$, —C(O)NH$_2$, —C(O)NH$R_{28}$, and —S(O)$_2R_{28}$.

Embodiment 96 provides the compound of any of embodiments 70-91, wherein $R_{23}$ is selected from the group consisting of —C(O)$R_{28}$, —C(O)O$R_{28}$, —C(O)NH$_2$, —C(O)N$R_{28}R_9$, and —S(O)$_2$—$R_{28}$; or wherein $R_{23}$ is selected from the group consisting of —C(O)$R_{28}$, —C(O)O$R_{28}$, —C(O)NH$R_{28}$, and —S(O)$_2R_{28}$; or wherein $R_{23}$ is selected from the group consisting of —C(O)$R_{28}$, —C(O)O$R_{28}$, and —C(O)NH$R_{28}$; or wherein $R_{23}$ is selected from the group consisting of —C(O)$R_{28}$, —C(O)O$R_{28}$, and —S(O)$_2R_{28}$; or wherein $R_{23}$ is —C(O)$R_{28}$ or —C(O)O$R_{28}$.

Embodiment 97 provides the compound of any of embodiments 92-96, wherein each $R_{28}$ is independently selected from the group consisting of $C_1$-$C_6$ alkyl optionally substituted with one or more $R_{33}$, aryl($C_0$-$C_1$ alkyl) optionally substituted with one or more $R_{33}$, heteroaryl($C_0$-$C_1$ alkyl) optionally substituted with one or more $R_{33}$, heterocyclyl($C_0$-$C_1$ alkyl) optionally substituted with one or more $R_{33}$, and cyclyl($C_0$-$C_1$ alkyl) optionally substituted with one or more $R_{33}$.

Embodiment 98 provides the compound of any of embodiments 92-96, wherein each $R_{28}$ is independently selected from the group consisting of $C_1$-$C_6$ alkyl, aryl($C_0$-$C_1$ alkyl) optionally substituted with one or more $R_{33}$, heteroaryl($C_0$-$C_1$ alkyl) optionally substituted with one or more $R_{33}$, and heterocyclyl($C_0$-$C_1$ alkyl) optionally substituted with one or more $R_{33}$.

Embodiment 99 provides the compound of any of embodiments 92-96, wherein each $R_{28}$ is independently selected from the group consisting of $C_1$-$C_6$ alkyl, aryl optionally substituted with one or more $R_{33}$, heteroaryl optionally substituted with one or more $R_{33}$, heteroaryl(methyl) optionally substituted with one or more $R_{33}$, heterocyclyl optionally substituted with one or more $R_{33}$, and heterocyclyl(methyl) optionally substituted with one or more $R_{33}$.

Embodiment 100 provides the compound of any of embodiments 92-96, wherein each $R_{28}$ is independently selected from the group consisting of $C_1$-$C_6$ alkyl, aryl optionally substituted with one or more $R_{33}$, heteroaryl optionally substituted with one or more $R_{33}$, heterocyclyl optionally substituted with one or more $R_{33}$, and heterocyclyl(methyl) optionally substituted with one or more $R_{33}$.

Embodiment 101 provides the compound of any of embodiments 92-96, wherein each $R_{28}$ is independently selected from the group consisting of $C_1$-$C_4$ alkyl, aryl optionally substituted with one or more $R_{33}$, heteroaryl optionally substituted with one or more $R_{33}$, heterocyclyl optionally substituted with one or more $R_{33}$, and heterocyclyl(methyl) optionally substituted with one or more $R_{33}$.

Embodiment 102 provides the compound of any of embodiments 92-96, wherein each $R_{28}$ is independently selected from the group consisting of aryl optionally substituted with one or more $R_{33}$, heteroaryl optionally substituted with one or more $R_{33}$, heterocyclyl optionally substituted with one or more $R_{33}$; and heterocyclyl(methyl) optionally substituted with one or more $R_{33}$; or wherein each $R_{28}$ is independently selected from the group consisting of aryl optionally substituted with one or more $R_{33}$, heteroaryl optionally substituted with one or more $R_{33}$, and heterocyclyl optionally substituted with one or more $R_{33}$.

Embodiment 103 provides the compound of any of embodiments 70-102, wherein $R_{33}$ is independently selected from the group consisting of halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CONH$_2$, —CONH($C_1$-$C_6$ alkyl), —CON($C_1$-$C_6$ alkyl)$_2$, —CONH—OH, —CO$_2$H, —CO$_2$($C_1$-$C_6$ alkyl), aryl optionally substituted with one or more $R_{34}$, heteroaryl optionally substituted with one or more $R_{34}$, and heterocyclyl optionally substituted with one or more $R_{34}$; or two $R_{33}$ groups when attached to the same carbon atom form =O.

Embodiment 104 provides the compound of any of embodiments 70-102, wherein $R_{33}$ is independently selected from the group consisting of halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CONH$_2$, —CONH($C_1$-$C_6$ alkyl), —CON($C_1$-$C_6$ alkyl)$_2$, —CONH—OH, —CO$_2$H, and —CO$_2$($C_1$-$C_6$ alkyl).

Embodiment 105 provides the compound of any of embodiments 70-102, wherein $R_{33}$ is independently selected from the group consisting of halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CONH$_2$, —CONH($C_1$-$C_6$ alkyl), —CON($C_1$-$C_6$ alkyl)$_2$, —CO$_2$H, and —CO$_2$($C_1$-$C_6$ alkyl).

Embodiment 106 provides the compound of any of embodiments 70-102, wherein $R_{33}$ is independently selected from the group consisting of halogen, —CN, —CH$_3$, halomethyl, —NH$_2$, —NH(CH$_3$), —N(CH$_3$)$_2$, —OH, methoxy, halomethoxy, —CONH$_2$, —CONH(CH$_3$), —CON(CH$_3$)$_2$, —CO$_2$H, and —CO$_2$(CH$_3$).

Embodiment 107 provides the compound of any of embodiments 70-102, wherein $R_{33}$ is independently selected from the group consisting of halogen, —CN, —CH$_3$, halomethyl, —NH$_2$, —NH(CH$_3$), —N(CH$_3$)$_2$, —OH, methoxy, halomethoxy, —CONH$_2$, and —CO$_2$H.

Embodiment 108 provides the compound of any one of embodiments 70-102, wherein $R_{28}$ is unsubstituted, or substituted with one or more $R_{31}$ selected from halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CONH$_2$, —CONH($C_1$-$C_6$ alkyl), —CON($C_1$-$C_6$ alkyl)$_2$, —CO$_2$H, and —CO$_2$($C_1$-$C_6$ alkyl).

Embodiment 109 provides the compound of any one of embodiments 70-102, wherein $R_{28}$ is unsubstituted, or substituted with one $R_{31}$ selected from halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CONH$_2$, —CONH($C_1$-$C_6$ alkyl), —CON($C_1$-$C_6$ alkyl)$_2$, —CO$_2$H, and —CO$_2$($C_1$-$C_6$ alkyl).

Embodiment 110 provides the compound of any one of embodiments 70-102, wherein $R_{28}$ is unsubstituted, or substituted with one or more $R_{31}$ selected from halogen, —CN, —CH$_3$, halomethyl, —NH$_2$, —NH(CH$_3$), —N(CH$_3$)$_2$, —OH, methoxy, halomethoxy, —CONH$_2$, and —CO$_2$H.

Embodiment 111 provides the compound of any one of embodiments 70-102, wherein $R_{28}$ is unsubstituted, or substituted with one $R_{31}$ selected from halogen, —CN, —CH$_3$, halomethyl, —NH$_2$, —NH(CH$_3$), —N(CH$_3$)$_2$, —OH, methoxy, halomethoxy, —CONH$_2$, and —CO$_2$H.

Embodiment 112 provides the compound of any of embodiments 70-111, wherein each $R_{24}$ is independently selected from hydrogen and $C_1$-$C_6$ alkyl; or wherein each $R_{24}$ is independently selected from hydrogen and methyl.

Embodiment 113 provides the compound of any of embodiments 70-111, wherein each $R_{24}$ is independently hydrogen.

Embodiment 114 provides the compound of any of embodiments 70-111, wherein each $R_{25}$ is independently selected from hydrogen and $C_1$-$C_6$ alkyl; or wherein each $R_{25}$ is independently selected from hydrogen and methyl.

Embodiment 115 provides the compound of any of embodiments 70-114, wherein each $R_{25}$ is independently hydrogen.

Embodiment 116 provides the compound of any of embodiments 70-115, wherein each $R_{26}$ is independently selected from hydrogen and $C_1$-$C_6$ alkyl, or two $R_{26}$ groups form an oxo group; or wherein each $R_{26}$ is independently selected from hydrogen and methyl, or two $R_{26}$ groups form an oxo group.

Embodiment 117 provides the compound of any of embodiments 70-115, wherein each $R_{26}$ is hydrogen, or two $R_{26}$ groups form an oxo group.

Embodiment 118 provides the compound of any of embodiments 70-115, wherein each $R_{26}$ is hydrogen.

Embodiment 119 provides the compound of any of embodiments 70-115, wherein two $R_{21}$ groups form an oxo group.

Embodiment 120 provides the compound of embodiment 70 according to any of examples disclosed herein (such as, e.g., examples 231-240) or a pharmaceutically acceptable salt thereof.

Embodiment 121 provides a pharmaceutical composition comprising a compound according to any one of embodiments 1-120 and a pharmaceutically acceptable carrier, solvent, adjuvant or diluent.

Embodiment 122 provides a method of treating cancer, the method comprising administering to a subject in need of such treatment one or more compounds according to any one of embodiments 1-120 or a pharmaceutical composition according to embodiment 121.

Embodiment 123 provides the method of embodiment 122, wherein the cancer is a solid tumor (e.g., carcinomas, sarcomas, and astrocytomas).

Embodiment 124 provides the method of embodiment 122, wherein the cancer is a hematological malignancy (e.g., leukemia or lymphoma).

Embodiment 125 provides the method of embodiment 122, wherein the cancer is an IDH1 mutant cancer; or an IDH2 mutant cancer; or the cancer includes mutation or gene amplification of the MYC, MYCN, and/or MYCL genes; or the cancer includes reduced expression of NAPRT1 or DNA methylation of the NAPRT1 promoter.

Embodiment 126 provides a method of inhibiting nicotinamide phosphoribosyltransferase (NAMPT), the method comprising administering one or more compounds according to any one of embodiments 1-120 or a pharmaceutical composition according to embodiment 121.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A compound which is:
tert-butyl 6-(2-((E)-3-(pyridin-3-yl)acrylamido)ethyl)-3-azabicyclo[3.1.0]hexane-3-carboxylate;
tert-butyl 6-(2-(2-(pyridin-3-yloxy) acetamido)ethyl)-3-azabicyclo[3.1.0]hexane-3-carboxylate;
tert-butyl 6-(2-(thieno [2,3-b]pyridine-2-carboxamido) ethyl)-3-azabicyclo[3.1.0]hexane-3-carboxylate;
tert-butyl 6-(2-((E)-3-(6-aminopyridin-3-yl)acrylamido) ethyl)-3-azabicyclo[3.1.0]hexane-3-carboxylate;
tert-butyl 6-(2-(furo [2,3-b]pyridine-2-carboxamido) ethyl)-3-azabicyclo[3.1.0]hexane-3-carboxylate;
tert-butyl 6-(2-(benzo [b]thiophene-5-carboxamido) ethyl)-3-azabicyclo[3.1.0]hexane-3-carboxylate;
tert-butyl 6-(2-(imidazo [1,2-a]pyridine-6-carboxamido) ethyl)-3-azabicyclo[3.1.0]hexane-3-carboxylate;
tert-butyl 6-(2-pivalamidoethyl)-3-azabicyclo[3.1.0] hexane-3-carboxylate;
tert-butyl 6-(2-((E)-3-(3-methylisoxazolo [5,4-b]pyridin-5-yl)acrylamido)ethyl)-3-azabicyclo[3.1.0]hexane-3-carboxylate;
tert-butyl 6-(2-(2-(pyridin-3-yl)cyclopropanecarboxamido)ethyl)-3-azabicyclo[3.1.0]hexane-3-carboxylate;
tert-butyl 6-(2-(thiazolo [5,4-c]pyridine-2-carboxamido) ethyl)-3-azabicyclo[3.1.0]hexane-3-carboxylate;
tert-butyl 6-(2-(5-(pyridin-3-yl) isoxazole-3-carboxamido)ethyl)-3-azabicyclo[3.1.0]hexane-3-carboxylate;
ter-butyl 6-(2-(5-aminothieno [2,3-c]pyridine-2-carboxamido)ethyl)-3-azabicyclo[3.1.0]hexane-3-carboxylate;
tert-butyl 6-(2-acetamidoethyl)-3-azabicyclo[3.1.0] hexane-3-carboxylate;
tert-butyl 6-(2-(isoindoline-2-carboxamido)ethyl)-3-azabicyclo[3.1.0]hexane-3-carboxylate;
tert-butyl 6-(2-(4,5,6,7-tetrahydrothieno [3,2-c]pyridine-5-carboxamido)ethyl)-3-azabicyclo[3.1.0]hexane-3-carboxylate;
tert-butyl 6-(2-(3-(pyridin-3-yl)azetidine-1-carboxamido) ethyl)-3-azabicyclo[3.1.0]hexane-3-carboxylate;
tert-butyl 6-(2-((E)-2-cyano-3-(pyridin-4-yl)guanidino) ethyl)-3-azabicyclo[3.1.0]hexane-3-carboxylate;
tert-butyl 6-(2-(3-((pyridin-3-yl)methyl) ureido)ethyl)-3-azabicyclo[3.1.0]hexane-3-carboxylate;
tert-butyl 6-(2-(2,3-dihydro-1H-pyrrolo [3,4-c]pyridine-2-carboxamido)ethyl)-3-azabicyclo[3.1.0]hexane-3-carboxylate;
3-methyloxetan-3-yl 6-(2-((E)-3-(pyridin-3-yl)acrylamido)ethyl)-3-azabicyclo[3.1.0]hexane-3-carboxylate;
(E)-N-(2-(3-benzoyl-3-azabicyclo[3.1.0]hexan-6-yl) ethyl)-3-(pyridin-3-yl)acrylamide;
(E)-N-(2-(3-(phenylsulfonyl)-3-azabicyclo[3.1.0]hexan-6-yl)ethyl)-3-(pyridin-3-yl)acrylamide;
3-methyloxetan-3-yl 6-(2-((E)-3-(6-aminopyridin-3-yl) acrylamido)ethyl)-3-azabicyclo[3.1.0]hexane-3-carboxylate;
(E)-3-(6-aminopyridin-3-yl)-N-(2-(3-benzoyl-3-azabicyclo[3.1.0]hexan-6-yl)ethyl)acrylamide;
3-methyloxetan-3-yl 6-(2-(thieno [2,3-c]pyridine-2-carboxamido)ethyl)-3-azabicyclo[3.1.0]hexane-3-carboxylate;

3-methyloxetan-3-yl 6-(2-(furo [2,3-c]pyridine-2-carboxamido)ethyl)-3-azabicyclo[3.1.0]hexane-3-carboxylate;
6-(2-((E)-3-(6-aminopyridin-3-yl)acrylamido)ethyl)-N-benzyl-3-azabicyclo[3.1.0]hexane-3-carboxamide;
(E)-3-(6-aminopyridin-3-yl)-N-(2-(3-(morpholine-4-carbonyl)-3-azabicyclo[3.1.0]hexan-6-yl)ethyl)acrylamide;
N-(2-(3-benzoyl-3-azabicyclo[3.1.0]hexan-6-yl)ethyl) furo [2,3-c]pyridine-2-carboxamide;
6-(2-((E)-3-(6-aminopyridin-3-yl)acrylamido)ethyl)-N-phenyl-3-azabicyclo[3.1.0]hexane-3-carboxamide;
6-(2-((E)-3-(6-aminopyridin-3-yl)acrylamido)ethyl)-N-(tetrahydro-2H-pyran-4-yl)-3-azabicyclo[3.1.0]hexane-3-carboxamide;
6-(2-((E)-3-(6-aminopyridin-3-yl)acrylamido)ethyl)-N,N-diethyl-3-azabicyclo[3.1.0]hexane-3-carboxamide;
cyclopentyl 6-(2-((E)-3-(6-aminopyridin-3-yl)acrylamido)ethyl)-3-azabicyclo[3.1.0]hexane-3-carboxylate;
3-methyloxetan-3-yl 6-(2-((E)-3-(pyridin-4-yl)acrylamido)ethyl)-3-azabicyclo[3.1.0]hexane-3-carboxylate;
3-methyloxetan-3-yl 6-(2-(1H-pyrrolo [3,2-c]pyridine-2-carboxamido)ethyl)-3-azabicyclo[3.1.0]hexane-3-carboxylate;
3-methyloxetan-3-yl 6-(2-(thieno [3,2-c]pyridine-2-carboxamido)ethyl)-3-azabicyclo[3.1.0]hexane-3-carboxylate;
3-methyloxetan-3-yl 6-(2-(imidazo [1,2-a]pyridine-6-carboxamido)ethyl)-3-azabicyclo[3.1.0]hexane-3-carboxylate;
(E)-3-(6-aminopyridin-3-yl)-N-(2-(3-(pyrrolidine-1-carbonyl)-3-azabicyclo[3.1.0]hexan-6-yl)ethyl)acrylamide;
phenyl 6-(2-((E)-3-(6-aminopyridin-3-yl)acrylamido)ethyl)-3-azabicyclo[3.1.0]hexane-3-carboxylate;
tetrahydro-2H-pyran-4-yl 6-(2-((E)-3-(6-aminopyridin-3-yl)acrylamido)ethyl)-3-azabicyclo[3.1.0]hexane-3-carboxylate;
3-methyloxetan-3-yl 6-(2-(5-fluoroisoindoline-2-carboxamido)ethyl)-3-azabicyclo[3.1.0]hexane-3-carboxylate;
3-methyloxetan-3-yl 6-(2-(imidazo [1,2-a]pyrimidine-6-carboxamido)ethyl)-3-azabicyclo[3.1.0]hexane-3-carboxylate;
3-methyloxetan-3-yl 6-(2-(benzo [d]thiazole-6-carboxamido)ethyl)-3-azabicyclo[3.1.0]hexane-3-carboxylate;
(E)-3-(6-aminopyridin-3-yl)-N-(2-(3-(phenylsulfonyl)-3-azabicyclo[3.1.0]hexan-6-yl)ethyl)acrylamide;
(E)-3-(6-aminopyridin-3-yl)-N-(2-(3-((4-fluorophenyl) sulfonyl)-3-azabicyclo[3.1.0]hexan-6-yl)ethyl)acrylamide;
(E)-3-(6-aminopyridin-3-yl)-N-(2-(3-((tetrahydro-2H-pyran-4-yl) sulfonyl)-3-azabicyclo[3.1.0]hexan-6-yl)ethyl)acrylamide;
(E)-3-(6-aminopyridin-3-yl)-N-(2-(3-(cyclopentylsulfonyl)-3-azabicyclo[3.1.0]hexan-6-yl)ethyl)acrylamide;
3-methyloxetan-3-yl 6-(2-(2-aminobenzo [d]thiazole-6-carboxamido)ethyl)-3-azabicyclo[3.1.0]hexane-3-carboxylate;
3-methyloxetan-3-yl 6-(2-(5-(pyridin-3-yl) isoxazole-3-carboxamido)ethyl)-3-azabicyclo[3.1.0]hexane-3-carboxylate;
2,3-dihydro-1H-inden-2-yl 6-(2-((E)-3-(6-aminopyridin-3-yl)acrylamido)ethyl)-3-azabicyclo[3.1.0]hexane-3-carboxylate;
(1-methylpiperidin)-4-yl 6-(2-((E)-3-(6-aminopyridin-3-yl)acrylamido)ethyl)-3-azabicyclo[3.1.0]hexane-3-carboxylate;
3-methyloxetan-3-yl 6-(2-(2-(pyridin-3-yl)cyclopropanecarboxamido)ethyl)-3-azabicyclo[3.1.0]hexane-3-carboxylate;
3-methyloxetan-3-yl 6-(2-((E)-3-(2-aminopyrimidin-5-yl)acrylamido)ethyl)-3-azabicyclo[3.1.0]hexane-3-carboxylate;
3-methyloxetan-3-yl 6-(2-(1/-pyrazolo [3,4-b]pyridine-5-carboxamido)ethyl)-3-azabicyclo[3.1.0]hexane-3-carboxylate;
N-(2-(3-(tert-butylcarbamoyl)-3-azabicyclo[3.1.0]hexan-6-yl)ethyl) furo [2,3-c]pyridine-2-carboxamide;
N-(2-(3-(phenylcarbamoyl)-3-azabicyclo[3.1.0]hexan-6-yl)ethyl) furo [2,3-c]pyridine-2-carboxamide;
N-(2-(3-(morpholine-4-carbonyl)-3-azabicyclo[3.1.0]hexan-6-yl)ethyl) furo [2,3-c]pyridine-2-carboxamide;
N-(2-(3-((tetrahydro-2H-pyran-4-yl) carbamoyl)-3-azabicyclo[3.1.0]hexan-6-yl)ethyl) furo [2,3-c] pyridine-2-carboxamide;
N-(2-(3-(diethylcarbamoyl)-3-azabicyclo[3.1.0]hexan-6-yl)ethyl) furo [2,3-c]pyridine-2-carboxamide;
tetrahydro-2H-pyran-4-yl 6-(2-(furo [2,3-c]pyridine-2-carboxamido)ethyl)-3-azabicyclo[3.1.0]hexane-3-carboxylate;
3-methyloxetan-3-yl 6-(2-(thiazolo [5,4-c]pyridine-2-carboxamido)ethyl)-3-azabicyclo[3.1.0]hexane-3-carboxylate;
N-(2-(3-benzoyl-3-azabicyclo[3.1.0]hexan-6-yl)ethyl) imidazo [1,2-a]pyridine-6-carboxamide;
N-(2-(3-(tert-butylcarbamoyl)-3-azabicyclo[3.1.0]hexan-6-yl)ethyl) imidazo [1,2-a]pyridine-6-carboxamide;
N-(2-(3-(phenylcarbamoyl)-3-azabicyclo[3.1.0]hexan-6-yl)ethyl) imidazo [1,2-a]pyridine-6-carboxamide;
N-(2-(3-(pyrrolidine-1-carbonyl)-3-azabicyclo[3.1.0]hexan-6-yl)ethyl) imidazo [1,2-a]pyridine-6-carboxamide;
tetrahydro-2H-pyran-4-yl 6-(2-(imidazo [1,2-a]pyridine-6-carboxamido)ethyl)-3-azabicyclo[3.1.0]hexane-3-carboxylate;
N-(2-(3-((tetrahydro-2H-pyran-4-yl) sulfonyl)-3-azabicyclo[3.1.0]hexan-6-yl)ethyl) imidazo [1,2-a]pyridine-6-carboxamide;
N-(2-(3-(neopentylcarbamoyl)-3-azabicyclo[3.1.0] hexan-6-yl)ethyl) furo [2,3-c]pyridine-2-carboxamide;
N-(2-(3-(pyrrolidine-1-carbonyl)-3-azabicyclo[3.1.0] hexan-6-yl)ethyl) furo [2,3-c]pyridine-2-carboxamide;
(cyclopentyl) 6-(2-(furo [2,3-c]pyridine-2-carboxamido) ethyl)-3-azabicyclo[3.1.0]hexane-3-carboxylate;
N-(2-(3-((4-fluorophenyl) sulfonyl)-3-azabicyclo[3.1.0] hexan-6-yl)ethyl) furo [2,3-c]pyridine-2-carboxamide;
N-(2-(3-((tetrahydro-2H-pyran-4-yl) sulfonyl)-3-azabicyclo[3.1.0]hexan-6-yl)ethyl) furo [2,3-c] pyridine-2-carboxamide;
3-methyloxetan-3-yl 6-(2-(5-aminothieno [2,3-c]pyridine-2-carboxamido)ethyl)-3-azabicyclo[3.1.0] hexane-3-carboxylate;
N-(tert-butyl)-6-(2-((E)-3-(pyridin-3-yl)acrylamido) ethyl)-3-azabicyclo[3.1.0]hexane-3-carboxamide;
N-(2-(3-benzoyl-3-azabicyclo[3.1.0]hexan-6-yl)ethyl) imidazo [1,2-a]pyrimidine-6-carboxamide;
N-(2-(3-(tert-butylcarbamoyl)-3-azabicyclo[3.1.0]hexan-6-yl)ethyl) imidazo [1,2-a]pyrimidine-6-carboxamide;

N-(2-(3-(phenylcarbamoyl)-3-azabicyclo[3.1.0]hexan-6-yl)ethyl) imidazo [1,2-a]pyrimidine-6-carboxamide;

tetrahydro-2H-pyran-4-yl 6-(2-(imidazo [1,2-a]pyrimidine-6-carboxamido)ethyl)-3-azabicyclo[3.1.0]hexane-3-carboxylate;

N-(2-(3-((tetrahydro-2H-pyran-4-yl) sulfonyl)-3-azabicyclo[3.1.0]hexan-6-yl)ethyl) imidazo [1,2-a]pyrimidine-6-carboxamide;

N-(2-(3-(tert-butylcarbamoyl)-3-azabicyclo[3.1.0]hexan-6-yl)ethyl)-5-(pyridin-3-yl) isoxazole-3-carboxamide;

N-(2-(3-(tert-butylcarbamoyl)-3-azabicyclo[3.1.0]hexan-6-yl)ethyl)-1H-pyrrolo [3,2-c]pyridine-2-carboxamide;

tetrahydro-2H-pyran-4-yl 6-(2-(1H-pyrrolo [3,2-c]pyridine-2-carboxamido)ethyl)-3-azabicyclo[3.1.0]hexane-3-carboxylate;

N-(2-(3-((tetrahydro-2H-pyran-4-yl) sulfonyl)-3-azabicyclo[3.1.0]hexan-6-yl)ethyl)-1H-pyrrolo [3,2-c]pyridine-2-carboxamide;

tetrahydro-2H-pyran-4-yl 6-(2-(thieno [2,3-c]pyridine-2-carboxamido)ethyl)-3-azabicyclo[3.1.0]hexane-3-carboxylate;

(E)-3-(6-aminopyridin-3-yl)-N-(2-(3-(4-fluorobenzoyl)-3-azabicyclo[3.1.0]hexan-6-yl)ethyl)acrylamide;

(E)-3-(6-aminopyridin-3-yl)-N-(2-(3-(2,4-dimethyloxazole-5-carbonyl)-3-azabicyclo[3.1.0]hexan-6-yl)ethyl) acrylamide;

(E)-3-(6-aminopyridin-3-yl)-N-(2-(3-(1,3,5-trimethyl-1H-pyrazole-4-carbonyl)-3-azabicyclo[3.1.0]hexan-6-yl)ethyl)acrylamide;

(E)-3-(6-aminopyridin-3-yl)-N-(2-(3-(3-fluorobenzoyl)-3-azabicyclo[3.1.0]hexan-6-yl)ethyl)acrylamide;

(E)-3-(6-aminopyridin-3-yl)-N-(2-(3-(4-(difluoromethoxy)benzoyl)-3-azabicyclo[3.1.0]hexan-6-yl)ethyl)acrylamide;

(E)-3-(6-aminopyridin-3-yl)-N-(2-(3-(3-(difluoromethoxy)benzoyl)-3-azabicyclo[3.1.0]hexan-6-yl)ethyl)acrylamide;

(E)-3-(6-aminopyridin-3-yl)-N-(2-(3-(4-methylnicotinoyl)-3-azabicyclo[3.1.0]hexan-6-yl)ethyl)acrylamide;

(E)-3-(6-aminopyridin-3-yl)-N-(2-(3-(4-(1-methylpiperidin-4-yl)benzoyl)-3-azabicyclo[3.1.0]hexan-6-yl)ethyl)acrylamide;

(E)-3-(6-aminopyridin-3-yl)-N-(2-(3-(2-(tetrahydro-2H-pyran-4-yl) acetyl)-3-azabicyclo[3.1.0]hexan-6-yl)ethyl)acrylamide;

(E)-3-(6-aminopyridin-3-yl)-N-(2-(3-(tetrahydro-2H-pyran-4-carbonyl)-3-azabicyclo[3.1.0]hexan-6-yl)ethyl)acrylamide;

6-(2-((E)-3-(6-aminopyridin-3-yl)acrylamido)ethyl)-N-neopentyl-3-azabicyclo[3.1.0]hexane-3-carboxamide;

N-(2-(3-(4-fluorobenzoyl)-3-azabicyclo[3.1.0]hexan-6-yl)ethyl) furo [2,3-c]pyridine-2-carboxamide;

N-(2-(3-(2,4-dimethyloxazole-5-carbonyl)-3-azabicyclo[3.1.0]hexan-6-yl)ethyl) furo [2,3-c]pyridine-2-carboxamide;

N-(2-(3-(2-(tetrahydro-2H-pyran-4-yl) acetyl)-3-azabicyclo[3.1.0]hexan-6-yl)ethyl) furo [2,3-c] pyridine-2-carboxamide;

N-(2-(3-(tetrahydro-2H-pyran-4-carbonyl)-3-azabicyclo[3.1.0]hexan-6-yl)ethyl) furo [2,3-c] pyridine-2-carboxamide;

N-(2-(3-(2-(tetrahydro-2H-pyran-4-yl) acetyl)-3-azabicyclo[3.1.0]hexan-6-yl)ethyl) imidazo [1,2-a] pyridine-6-carboxamide;

N-(2-(3-(4-fluorobenzoyl)-3-azabicyclo[3.1.0]hexan-6-yl)ethyl) imidazo [1,2-a]pyridine-6-carboxamide;

N-(2-(3-(2,4-dimethyloxazole-5-carbonyl)-3-azabicyclo[3.1.0]hexan-6-yl)ethyl) imidazo [1,2-a]pyridine-6-carboxamide;

(E)-3-(pyridin-3-yl)-N-((3-(2-(tetrahydro-2H-pyran-4-yl) acetyl)-3-azabicyclo[3.1.0]hexan-6-yl)methyl)acrylamide;

(E)-N-(2-(3-(2,4-dimethyloxazole-5-carbonyl)-3-azabicyclo[3.1.0]hexan-6-yl)ethyl)-3-(pyridin-3-yl)acrylamide;

N-(2-(3-(2-(tetrahydro-2H-pyran-4-yl) acetyl)-3-azabicyclo[3.1.0]hexan-6-yl)ethyl) imidazo [1,2-a]pyrimidine-6-carboxamide;

N-(2-(3-(4-fluorobenzoyl)-3-azabicyclo[3.1.0]hexan-6-yl)ethyl) imidazo [1,2-a]pyrimidine-6-carboxamide;

N-(2-(3-(2,4-dimethyloxazole-5-carbonyl)-3-azabicyclo[3.1.0]hexan-6-yl)ethyl) imidazo [1,2-a]pyrimidine-6-carboxamide;

5-(pyridin-3-yl)-N-(2-(3-(2-(tetrahydro-2H-pyran-4-yl) acetyl)-3-azabicyclo[3.1.0]hexan-6-yl)ethyl) isoxazole-3-carboxamide;

N-(2-(3-(4-fluorobenzoyl)-3-azabicyclo[3.1.0]hexan-6-yl)ethyl)-5-(pyridin-3-yl) isoxazole-3-carboxamide;

N-(2-(3-(2,4-dimethyloxazole-5-carbonyl)-3-azabicyclo[3.1.0]hexan-6-yl)ethyl)-5-(pyridin-3-yl) isoxazole-3-carboxamide;

N-(2-(3-(2-(tetrahydro-2H-pyran-4-yl) acetyl)-3-azabicyclo[3.1.0]hexan-6-yl)ethyl)-1H-pyrrolo [3,2-c] pyridine-2-carboxamide;

N-(2-(3-(2,4-dimethyloxazole-5-carbonyl)-3-azabicyclo[3.1.0]hexan-6-yl)ethyl)-1H-pyrrolo [3,2-c] pyridine-2-carboxamide;

N-(2-(3-(2,4-dimethyloxazole-5-carbonyl)-3-azabicyclo[3.1.0]hexan-6-yl)ethyl) thieno [2,3-c]pyridine-2-carboxamide;

3-(6-(2-((E)-3-(pyridin-3-yl)acrylamido)ethyl)-3-azabicyclo[3.1.0]hexane-3-carbonyl)benzamide;

N-(2-(3-(3-carbamoylbenzoyl)-3-azabicyclo[3.1.0]hexan-6-yl)ethyl)-1H-pyrrolo [3,2-c]pyridine-2-carboxamide;

(E)-N-(2-(3-phenyl-3-azabicyclo[3.1.0]hexan-6-yl)ethyl)-3-(pyridin-3-yl)acrylamide;

N-(2-(3-(pyrimidin-2-yl)-3-azabicyclo[3.1.0]hexan-6-yl)ethyl) imidazo [1,2-a]pyridine-6-carboxamide;

N-(2-(3-(pyrimidin-2-yl)-3-azabicyclo[3.1.0]hexan-6-yl)ethyl) furo [2,3-c]pyridine-2-carboxamide;

N-(2-(3-(benzo [d]thiazol-2-yl)-3-azabicyclo[3.1.0]hexan-6-yl)ethyl) furo [2,3-c]pyridine-2-carboxamide;

N-(2-(3-(naphthalen-1-yl)-3-azabicyclo[3.1.0]hexan-6-yl)ethyl) furo [2,3-c]pyridine-2-carboxamide;

N-(2-(3-(quinazolin-2-yl)-3-azabicyclo[3.1.0]hexan-6-yl)ethyl) furo [2,3-c]pyridine-2-carboxamide;

(E)-3-(pyridin-3-yl)-N-(2-(3-(pyrimidin-2-yl)-3-azabicyclo[3.1.0]hexan-6-yl)ethyl)acrylamide;

(E)-N-(2-(3-(benzo [d]thiazol-2-yl)-3-azabicyclo[3.1.0]hexan-6-yl)ethyl)-3-(pyridin-3-yl)acrylamide;

(E)-3-(pyridin-3-yl)-N-(2-(3-(quinazolin-2-yl)-3-azabicyclo[3.1.0]hexan-6-yl)ethyl)acrylamide;

(E)-N-(2-(3-(naphthalen-1-yl)-3-azabicyclo[3.1.0]hexan-6-yl)ethyl)-3-(pyridin-3-yl)acrylamide;

(E)-N-(2-(3-(naphthalen-2-yl)-3-azabicyclo[3.1.0]hexan-6-yl)ethyl)-3-(pyridin-3-yl)acrylamide;

(E)-N-(2-(3-(3-fluorophenyl)-3-azabicyclo[3.1.0]hexan-6-yl)ethyl)-3-(pyridin-3-yl)acrylamide;

(E)-N-(2-(3-(3-methoxyphenyl)-3-azabicyclo[3.1.0]hexan-6-yl)ethyl)-3-(pyridin-3-yl)acrylamide;

N-(2-(3-(3-methoxyphenyl)-3-azabicyclo[3.1.0]hexan-6-yl)ethyl) furo [2,3-c]pyridine-2-carboxamide;

5-(pyridin-3-yl)-N-(2-(3-(pyrimidin-2-yl)-3-azabicyclo[3.1.0]hexan-6-yl)ethyl) isoxazole-3-carboxamide;
(E)-3-(pyridin-3-yl)-N-(2-(3-(o-tolyl)-3-azabicyclo[3.1.0]hexan-6-yl)ethyl)acrylamide;
(E)-N-(2-(3-(2,6-dimethylphenyl)-3-azabicyclo[3.1.0]hexan-6-yl)ethyl)-3-(pyridin-3-yl)acrylamide;
N-(2-(3-phenyl-3-azabicyclo[3.1.0]hexan-6-yl)ethyl)-5-(pyridin-3-yl) isoxazole-3-carboxamide;
(E)-N-(2-(3-(2-cyanophenyl)-3-azabicyclo[3.1.0]hexan-6-yl)ethyl)-3-(pyridin-3-yl)acrylamide;
(E)-N-(2-(3-(3-cyanophenyl)-3-azabicyclo[3.1.0]hexan-6-yl)ethyl)-3-(pyridin-3-yl)acrylamide;
(E)-N-(2-(3-(4-cyanophenyl)-3-azabicyclo[3.1.0]hexan-6-yl)ethyl)-3-(pyridin-3-yl)acrylamide;
(E)-3-(pyridin-3-yl)-N-(2-(3-(3-(trifluoromethyl)phenyl)-3-azabicyclo[3.1.0]hexan-6-yl)ethyl)acrylamide;
(E)-3-(pyridin-3-yl)-N-(2-(3-(4-(trifluoromethyl)phenyl)-3-azabicyclo[3.1.0]hexan-6-yl)ethyl)acrylamide;
(E)-3-(pyridin-3-yl)-N-(2-(3-(2-(trifluoromethyl)phenyl)-3-azabicyclo[3.1.0]hexan-6-yl)ethyl)acrylamide;
(E)-N-(2-(3-(isoquinolin-7-yl)-3-azabicyclo[3.1.0]hexan-6-yl)ethyl)-3-(pyridin-3-yl)acrylamide;
(E)-N-(2-(3-(isoquinolin-6-yl)-3-azabicyclo[3.1.0]hexan-6-yl)ethyl)-3-(pyridin-3-yl)acrylamide;
(E)-3-(pyridin-3-yl)-N-(2-(3-(quinolin-4-yl)-3-azabicyclo[3.1.0]hexan-6-yl)ethyl)acrylamide;
(E)-N-(2-(3-(2-chlorophenyl)-3-azabicyclo[3.1.0]hexan-6-yl)ethyl)-3-(pyridin-3-yl)acrylamide;
(E)-N-(2-(3-(3-chlorophenyl)-3-azabicyclo[3.1.0]hexan-6-yl)ethyl)-3-(pyridin-3-yl)acrylamide;
(E)-N-(2-(3-(4-chlorophenyl)-3-azabicyclo[3.1.0]hexan-6-yl)ethyl)-3-(pyridin-3-yl)acrylamide;
(E)-N-(2-(3~ (3,4-dichlorophenyl)-3-azabicyclo[3.1.0]hexan-6-yl)ethyl)-3-(pyridin-3-yl)acrylamide;
(E)-N-(2-(3-(3,5-dichlorophenyl)-3-azabicyclo[3.1.0]hexan-6-yl)ethyl)-3-(pyridin-3-yl)acrylamide;
(E)-3-(pyridin-3-yl)-N-(2-(3-(pyridin-3-yl)-3-azabicyclo[3.1.0]hexan-6-yl)ethyl)acrylamide;
(E)-N-(2-(3-(5-chloro-2-fluorophenyl)-3-azabicyclo[3.1.0]hexan-6-yl)ethyl)-3-(pyridin-3-yl)acrylamide;
(E)-N-(2-(3-(3-(methylthio)phenyl)-3-azabicyclo[3.1.0]hexan-6-yl)ethyl)-3-(pyridin-3-yl)acrylamide;
(E)-N-(2-(3-(3-(methylsulfonyl)phenyl)-3-azabicyclo[3.1.0]hexan-6-yl)ethyl)-3-(pyridin-3-yl)acrylamide;
(E)-N-(2-(3-(3-chloro-4-fluorophenyl)-3-azabicyclo[3.1.0]hexan-6-yl)ethyl)-3-(pyridin-3-yl)acrylamide;
(E)-3-(pyridin-3-yl)-N-(2-(3-(pyridin-4-yl)-3-azabicyclo[3.1.0]hexan-6-yl)ethyl)acrylamide;
(E)-N-(2-(3-(3-(tert-butyl)phenyl)-3-azabicyclo[3.1.0]hexan-6-yl)ethyl)-3-(pyridin-3-yl)acrylamide;
(E)-N-(2-(3-(3-(tert-butoxy)phenyl)-3-azabicyclo[3.1.0]hexan-6-yl)ethyl)-3-(pyridin-3-yl)acrylamide;
(E)-3-(pyridin-3-yl)-N-(2-(3-(2-(trifluoromethyl) pyridin-4-yl)-3-azabicyclo[3.1.0]hexan-6-yl)ethyl)acrylamide;
(E)-N-(2-(3-(2-chloropyridin-4-yl)-3-azabicyclo[3.1.0]hexan-6-yl)ethyl)-3-(pyridin-3-yl)acrylamide;
(E)-N-(2-(3-(2-methoxypyridin-4-yl)-3-azabicyclo[3.1.0]hexan-6-yl)ethyl)-3-(pyridin-3-yl)acrylamide;
(E)-3-(pyridin-3-yl)-N-(2-(3-(5-(trifluoromethyl)pyrimidin-2-yl)-3-azabicyclo[3.1.0]hexan-6-yl)ethyl)acrylamide;
(E)-N-(2-(3-(5-fluoropyrimidin-2-yl)-3-azabicyclo[3.1.0]hexan-6-yl)ethyl)-3-(pyridin-3-yl)acrylamide;
(E)-N-(2-(3-(5-chloropyrimidin-2-yl)-3-azabicyclo[3.1.0]hexan-6-yl)ethyl)-3-(pyridin-3-yl)acrylamide;
(E)-3-(6-aminopyridin-3-yl)-N-(2-(3-(quinazolin-2-yl)-3-azabicyclo[3.1.0]hexan-6-yl)ethyl)acrylamide;
(E)-N-(2-(3-(7,8-dihydro-5H-pyrano[4,3-d]pyrimidin-2-yl)-3-azabicyclo[3.1.0]hexan-6-yl)ethyl)-3-(pyridin-3-yl)acrylamide;
(E)-N-(2-(3-(6-fluoroquinazolin-2-yl)-3-azabicyclo[3.1.0]hexan-6-yl)ethyl)-3-(pyridin-3-yl)acrylamide;
(E)-3-(pyridin-3-yl)-N-(2-(3-(pyrimidin-4-yl)-3-azabicyclo[3.1.0]hexan-6-yl)ethyl)acrylamide;
(E)-3-(pyridin-3-yl)-N-(2-(3-(4-(trifluoromethyl)pyrimidin-2-yl)-3-azabicyclo[3.1.0]hexan-6-yl)ethyl)acrylamide;
(E)-N-(2-(3-(1,3,5-triazin-2-yl)-3-azabicyclo[3.1.0]hexan-6-yl)ethyl)-3-(pyridin-3-yl)acrylamide;
2-(6-(2-((E)-3-(pyridin-3-yl)acrylamido)ethyl)-3-azabicyclo[3.1.0]hexan-3-yl)pyrimidine-4-carboxamide;
(E)-N-(2-(3-(2-chloro-5-fluoropyrimidin-4-yl)-3-azabicyclo[3.1.0]hexan-6-yl)ethyl)-3-(pyridin-3-yl)acrylamide;
(E)-N-(2-(3-(5-fluoro-4-methoxypyrimidin-2-yl)-3-azabicyclo[3.1.0]hexan-6-yl)ethyl)-3-(pyridin-3-yl)acrylamide;
2-(6-(2-((E)-3-(pyridin-3-yl)acrylamido)ethyl)-3-azabicyclo[3.1.0]hexan-3-yl)pyrimidine-5-carboxamide;
(E)-3-(pyridin-3-yl)-N-(2-(3-(4-(trifluoromethyl) thiazol-2-yl)-3-azabicyclo[3.1.0]hexan-6-yl)ethyl)acrylamide;
(E)-N-(2-(3-(pyridin-2-yl)-3-azabicyclo[3.1.0]hexan-6-yl)ethyl)-3-(pyridin-3-yl)acrylamide;
(E)-N-(2-(3-(pyrazin-2-yl)-3-azabicyclo[3.1.0]hexan-6-yl)ethyl)-3-(pyridin-3-yl)acrylamide;
3-(6-(2-((E)-3-(6-aminopyridin-3-yl)acrylamido)ethyl)-3-azabicyclo[3.1.0]hexane-3-carbonyl)benzoic acid;
4-(6-(2-((E)-3-(6-aminopyridin-3-yl)acrylamido)ethyl)-3-azabicyclo[3.1.0]hexane-3-carbonyl)benzoic acid;
3-(6-(2-(furo [2,3-c]pyridine-2-carboxamido)ethyl)-3-azabicyclo[3.1.0]hexane-3-carbonyl)benzoic acid;
3-(6-(2-(imidazo [1,2-a]pyridine-6-carboxamido)ethyl)-3-azabicyclo[3.1.0]hexane-3-carbonyl)benzoic acid;
3-(6-(2-(imidazo [1,2-a]pyrimidine-6-carboxamido)ethyl)-3-azabicyclo[3.1.0]hexane-3-carbonyl)benzoic acid;
3-(6-(2-((E)-3-(pyridin-3-yl)acrylamido)ethyl)-3-azabicyclo[3.1.0]hexan-3-yl)benzamide;
(E)-N-(2-(3-(3-acetamidophenyl)-3-azabicyclo[3.1.0]hexan-6-yl)ethyl)-3-(pyridin-3-yl)acrylamide;
(E)-N-(2-(3-(3-(methylsulfonamido)phenyl)-3-azabicyclo[3.1.0]hexan-6-yl)ethyl)-3-(pyridin-3-yl)acrylamide;
4-(6-(2-((E)-3-(pyridin-3-yl)acrylamido)ethyl)-3-azabicyclo[3.1.0]hexan-3-yl)benzamide;
(E)-N-(2-(3-(5-fluoro-4-hydroxypyrimidin-2-yl)-3-azabicyclo[3.1.0]hexan-6-yl)ethyl)-3-(pyridin-3-yl)acrylamide;
(E)-N-(2-(3-(4-chloro-5-fluoropyrimidin-2-yl)-3-azabicyclo[3.1.0]hexan-6-yl)ethyl)-3-(pyridin-3-yl)acrylamide;
(E)-3-(6-aminopyridin-3-yl)-N-(2-(3-(pyrimidin-2-yl)-3-azabicyclo[3.1.0]hexan-6-yl)ethyl)acrylamide;
(E)-3-(6-aminopyridin-3-yl)-N-(2-(3-(benzo[d]thiazol-2-yl)-3-azabicyclo[3.1.0]hexan-6-yl)ethyl)acrylamide;
(E)-3-(6-aminopyridin-3-yl)-N-(2-(3-(naphthalen-1-yl)-3-azabicyclo[3.1.0]hexan-6-yl)ethyl)acrylamide;
(E)-3-(6-aminopyridin-3-yl)-N-(2-(3-phenyl-3-azabicyclo[3.1.0]hexan-6-yl)ethyl)acrylamide;
N-(2-(3-phenyl-3-azabicyclo[3.1.0]hexan-6-yl)ethyl) furo [2,3-c]pyridine-2-carboxamide;
N-(2-(3-(pyrimidin-2-yl)-3-azabicyclo[3.1.0]hexan-6-yl)ethyl)-1H-pyrrolo [3,2-c]pyridine-2-carboxamide;

(E)-N-(2-(3-(4-fluorophenyl)-3-azabicyclo[3.1.0]hexan-6-yl)ethyl)-3-(pyridin-3-yl)acrylamide;

N-(2-(3-(4-fluorophenyl)-3-azabicyclo[3.1.0]hexan-6-yl)ethyl) furo [2,3-c]pyridine-2-carboxamide;

N-(2-(3-(3-fluorophenyl)-3-azabicyclo[3.1.0]hexan-6-yl)ethyl) furo [2,3-c]pyridine-2-carboxamide;

N-(2-(3-phenyl-3-azabicyclo[3.1.0]hexan-6-yl)ethyl)-1H-pyrrolo [3,2-c]pyridine-2-carboxamide;

N-(2-(3-(pyrimidin-2-yl)-3-azabicyclo[3.1.0]hexan-6-yl)ethyl) imidazo [1,2-a]pyrimidine-6-carboxamide;

N-(2-(3-(pyrimidin-2-yl)-3-azabicyclo[3.1.0]hexan-6-yl)ethyl) thieno [2,3-c]pyridine-2-carboxamide;

(E)-3-(6-aminopyridin-3-yl)-N-(2-(3-(3-fluorophenyl)-3-azabicyclo[3.1.0]hexan-6-yl)ethyl)acrylamide;

(E)-3-(6-aminopyridin-3-yl)-N-(2-(3-(3-(trifluoromethyl)phenyl)-3-azabicyclo[3.1.0]hexan-6-yl)ethyl)acrylamide;

N-(2-(3-(2-chloro-5-fluoropyrimidin-4-yl)-3-azabicyclo[3.1.0]hexan-6-yl)ethyl) imidazo [1,2-a]pyridine-6-carboxamide;

N-(2-(3-(2-chloro-5-fluoropyrimidin-4-yl)-3-azabicyclo[3.1.0]hexan-6-yl)ethyl)-1H-pyrrolo [3,2-c] pyridine-2-carboxamide;

(E)-N-(2-(3-(2-chloro-5-fluoropyrimidin-4-yl)-3-azabicyclo[3.1.0]hexan-6-yl)ethyl)-3-(6-chloropyridin-3-yl)acrylamide;

(E)-3-(6-aminopyridin-3-yl)-N-(2-(3-(2-chloro-5-fluoropyrimidin-4-yl)-3-azabicyclo[3.1.0]hexan-6-yl)ethyl)acrylamide;

N-(2-(3-(2-chloro-5-fluoropyrimidin-4-yl)-3-azabicyclo[3.1.0]hexan-6-yl)ethyl)-3-(pyridin-3-yl) propanamide;

N-(2-(3-(2-chloro-5-fluoropyrimidin-4-yl)-3-azabicyclo[3.1.0]hexan-6-yl)ethyl)-5-(pyridin-3-yl) isoxazole-3-carboxamide;

(E)-N-(2-(3-(2-chloro-5-fluoropyrimidin-4-yl)-3-azabicyclo[3.1.0]hexan-6-yl)ethyl)-3-(pyridin-2-yl)acrylamide;

N-(2-(3-(2-chloro-5-fluoropyrimidin-4-yl)-3-azabicyclo[3.1.0]hexan-6-yl)ethyl) cinnamamide;

(E)-N-(2-(3-(2-chloro-5-fluoropyrimidin-4-yl)-3-azabicyclo[3.1.0]hexan-6-yl)ethyl)-3-(6-hydroxypyridin-3-yl)acrylamide;

(E)-N-(2-(3-(2-chloro-5-fluoropyrimidin-4-yl)-3-azabicyclo[3.1.0]hexan-6-yl)ethyl)-3-(6-methoxypyridin-3-yl)acrylamide;

N-(2-(3-(2-chloro-5-fluoropyrimidin-4-yl)-3-azabicyclo[3.1.0]hexan-6-yl)ethyl) imidazo [1,2-a]pyrimidine-6-carboxamide;

(E)-N-(2-(3-(2-chloro-5-fluoropyrimidin-4-yl)-3-azabicyclo[3.1.0]hexan-6-yl)ethyl)-3-(pyridin-4-yl)acrylamide;

N-(2-(3-(2-chloro-5-fluoropyrimidin-4-yl)-3-azabicyclo[3.1.0]hexan-6-yl)ethyl)-3-(pyridin-4-yl) propanamide;

N-(2-(3-(2-chloro-5-fluoropyrimidin-4-yl)-3-azabicyclo[3.1.0]hexan-6-yl)ethyl)-[1,2,4]triazolo [4,3-a]pyridine-6-carboxamide;

N-(2-(3-(2-chloro-5-fluoropyrimidin-4-yl)-3-azabicyclo[3.1.0]hexan-6-yl)ethyl)-[1,2,4]triazolo [1,5-a]pyridine-6-carboxamide;

N-(2-(3-(2-chloro-5-fluoropyrimidin-4-yl)-3-azabicyclo[3.1.0]hexan-6-yl)ethyl)-3-(pyridin-2-yl) propanamide;

N-(2-(3-(2-chloro-5-fluoropyrimidin-4-yl)-3-azabicyclo[3.1.0]hexan-6-yl)ethyl)-2-(pyridin-3-yloxy) acetamide;

N-(2-(3-(2-chloro-5-fluoropyrimidin-4-yl)-3-azabicyclo[3.1.0]hexan-6-yl)ethyl) thieno [2',3': 4,5] imidazo [2,1-b]thiazole-2-carboxamide;

N-(2-(3-(2-chloro-5-fluoropyrimidin-4-yl)-3-azabicyclo[3.1.0]hexan-6-yl)ethyl) furo [2,3-c]pyridine-2-carboxamide;

(E)-N-(2-(3-(2-chloro-5-fluoropyrimidin-4-yl)-3-azabicyclo[3.1.0]hexan-6-yl)ethyl)-3-(6-fluoropyridin-3-yl)acrylamide;

N-(2-(3-(2-chloro-5-fluoropyrimidin-4-yl)-3-azabicyclo[3.1.0]hexan-6-yl)ethyl) thieno [2,3-c] pyridine-2-carboxamide;

N-(2-(3-(2-chloro-5-fluoropyrimidin-4-yl)-3-azabicyclo[3.1.0]hexan-6-yl)ethyl)-1H-pyrazolo [3,4-b] pyridine-5-carboxamide;

N-(2-(3-(2-chloro-5-fluoropyrimidin-4-yl)-3-azabicyclo[3.1.0]hexan-6-yl)ethyl) isoindoline-2-carboxamide;

N-(2-(3-(2-chloro-5-fluoropyrimidin-4-yl)-3-azabicyclo[3.1.0]hexan-6-yl)ethyl)-1H-pyrrolo [3,4-c] pyridine-2(3H)-carboxamide;

N-(2-(3-(2-chloro-5-fluoropyrimidin-4-yl)-3-azabicyclo[3.1.0]hexan-6-yl)ethyl)-5H-pyrrolo [3,4-b] pyridine-6(7H)-carboxamide;

(E)-1-(2-(3-benzoyl-3-azabicyclo[3.1.0]hexan-6-yl)ethyl)-2-cyano-3-(pyridin-4-yl)guanidine;

3-methyloxetan-3-yl 6-(2-((E)-2-cyano-3-(pyridin-4-yl)guanidino)ethyl)-3-azabicyclo[3.1.0]hexane-3-carboxylate;

3-methyloxetan-3-yl 6-(2-(isoindoline-2-carboxamido)ethyl)-3-azabicyclo[3.1.0]hexane-3-carboxylate;

(E)-N-((3-benzoyl-3-azabicyclo[3.1.0]hexan-6-yl)methyl)-3-(pyridin-3-yl)acrylamide;

tert-butyl 6-((1-((E)-3-(6-aminopyridin-3-yl)acrylamido)cyclopropyl)methyl)-3-azabicyclo[3.1.0]hexane-3-carboxylate;

tert-butyl 6-((1-((E)-3-(pyridin-3-yl)acrylamido)cyclopropyl)methyl)-3-azabicyclo[3.1.0]hexane-3-carboxylate;

(E)-N-(2-(3-benzyl-3-azabicyclo[3.1.0]hexan-6-yl)ethyl)-3-(pyridin-3-yl)acrylamide;

(E)-3-(pyridin-3-yl)-N-(2-(3-(4-(trifluoromethyl)benzyl)-3-azabicyclo[3.1.0]hexan-6-yl)ethyl)acrylamide;

(E)-N-(2-(3-isopropyl-3-azabicyclo[3.1.0]hexan-6-yl)ethyl)-3-(pyridin-3-yl)acrylamide;

(E)-3-(pyridin-3-yl)-N-(2-(3-((tetrahydro-2H-pyran-4-yl)methyl)-3-azabicyclo[3.1.0]hexan-6-yl)ethyl)acrylamide;

(E)-N-(2-(3-(4-fluorobenzyl)-3-azabicyclo[3.1.0]hexan-6-yl)ethyl)-3-(pyridin-3-yl)acrylamide;

(E)-N-(2-(3-(2,4-difluorobenzyl)-3-azabicyclo[3.1.0]hexan-6-yl)ethyl)-3-(pyridin-3-yl)acrylamide;

(E)-N-(2-(3-(1-phenylethyl)-3-azabicyclo[3.1.0]hexan-6-yl)ethyl)-3-(pyridin-3-yl)acrylamide;

(E)-N-(2-(3-(4-fluorophenethyl)-3-azabicyclo[3.1.0]hexan-6-yl)ethyl)-3-(pyridin-3-yl)acrylamide;

(E)-N-(2~ (3-(3,5-dichlorobenzyl)-3-azabicyclo[3.1.0]hexan-6-yl)ethyl)-3-(pyridin-3-yl)acrylamide;

tert-butyl 6-(2-((E)-3-(6-aminopyridin-3-yl)acrylamido)-1-hydroxyethyl)-3-azabicyclo[3.1.0]hexane-3-carboxylate;

tert-butyl 6-(1-hydroxy-2-((E)-3-(pyridin-3-yl)acrylamido)ethyl)-3-azabicyclo[3.1.0]hexane-3-carboxylate;

tert-butyl 6-(2-((E)-3-(6-aminopyridin-3-yl)acrylamido)-1-fluoroethyl)-3-azabicyclo[3.1.0]hexane-3-carboxylate;

tert-butyl 6-(1-fluoro-2-((E)-3-(pyridin-3-yl)acrylamido)ethyl)-3-azabicyclo[3.1.0]hexane-3-carboxylate;
(E)-N-(2-(2-oxo-3-phenyl-3-azabicyclo[3.1.0]hexan-6-yl)ethyl)-3-(pyridin-3-yl)acrylamide;
(E)-N-(2-(3-benzyl-2-oxo-3-azabicyclo[3.1.0]hexan-6-yl)ethyl)-3-(pyridin-3-yl)acrylamide;
(E)-3-(6-aminopyridin-3-yl)-N-(2-(3-benzyl-2-oxo-3-azabicyclo[3.1.0]hexan-6-yl)ethyl)acrylamide;
(E)-3-(6-aminopyridin-3-yl)-N-(2-(2-oxo-3-phenyl-3-azabicyclo[3.1.0]hexan-6-yl)ethyl)acrylamide;
N-(2-(2-oxo-3-phenyl-3-azabicyclo[3.1.0]hexan-6-yl)ethyl) furo [2,3-c]pyridine-2-carboxamide;
N-(2-(2-oxo-3-phenyl-3-azabicyclo[3.1.0]hexan-6-yl)ethyl)-5-(pyridin-3-yl) isoxazole-3-carboxamide;
(E)-N-(2-(2-oxo-3-(3-(trifluoromethyl)phenyl)-3-azabicyclo[3.1.0]hexan-6-yl)ethyl)-3-(pyridin-3-yl)acrylamide;
(E)-3-(6-aminopyridin-3-yl)-N-(2-(2-oxo-3-(3-(trifluoromethyl)phenyl)-3-azabicyclo[3.1.0]hexan-6-yl)ethyl)acrylamide;
(E)-N-(2-(3-(4-fluorophenyl)-2-oxo-3-azabicyclo[3.1.0]hexan-6-yl)ethyl)-3-(pyridin-3-yl)acrylamide;
N-(2-(3-(4-fluorophenyl)-2-oxo-3-azabicyclo[3.1.0]hexan-6-yl)ethyl)-5-(pyridin-3-yl) isoxazole-3-carboxamide;
N-(2-(3-(4-fluorophenyl)-2-oxo-3-azabicyclo[3.1.0]hexan-6-yl)ethyl) isoindoline-2-carboxamide;
(E)-N-(2-(3-benzhydryl-3-azabicyclo[3.1.0]hexan-6-yl)ethyl)-3-(pyridin-3-yl)acrylamide;
(E)-N-(2-(3-(5-fluoro-2-morpholinopyrimidin-4-yl)-3-azabicyclo[3.1.0]hexan-6-yl)ethyl)-3-(pyridin-3-yl)acrylamide;
(E)-N-(2-(3-(2-(cyclopentyloxy)-5-fluoropyrimidin-4-yl)-3-azabicyclo[3.1.0]hexan-6-yl)ethyl)-3-(pyridin-3-yl)acrylamide;
tert-butyl 6-(2-((E)-3-(pyridin-3-yl)acrylamido)ethyl)-3-azabicyclo[3.1.0]hexane-3-carboxylate;
(E)-N-(2-(3-benzyl-3-azabicyclo[3.1.0]hexan-6-yl)ethyl)-3-(pyridin-3-yl)acrylamide;
(E)-N-(2-(3-phenyl-3-azabicyclo[3.1.0]hexan-6-yl)ethyl)-3-(pyridin-3-yl)acrylamide;
2-((5-fluoro-4-(6-(2-((E)-3-(pyridin-3-yl)acrylamido)ethyl)-3-azabicyclo[3.1.0]hexan-3-yl)pyrimidin-2-yl)oxy) acetic acid;
(E)-N-(2-(3-(2-amino-2-oxo-1-phenylethyl)-3-azabicyclo[3.1.0]hexan-6-yl)ethyl)-3-(pyridin-3-yl)acrylamide;
3-((E)-3-((2-(3-(2-chloro-5-fluoropyrimidin-4-yl)-3-azabicyclo[3.1.0]hexan-6-yl)ethyl)amino)-3-oxoprop-1-en-1-yl)pyridine 1-oxide;
(E)-N-(2-(3-(2-(2-amino-2-oxoethoxy)-5-fluoropyrimidin-4-yl)-3-azabicyclo[3.1.0]hexan-6-yl)ethyl)-3-(pyridin-3-yl)acrylamide;
(E)-N-(2-(3-(2-hydroxy-1-phenylethyl)-3-azabicyclo[3.1.0]hexan-6-yl)ethyl)-3-(pyridin-3-yl)acrylamide;
(E)-N-(2-(3-(5-fluoro-2-phenylpyrimidin-4-yl)-3-azabicyclo[3.1.0]hexan-6-yl)ethyl)-3-(pyridin-3-yl)acrylamide;
(E)-N-(2-(3-(3-(dimethylphosphoryl)phenyl)-3-azabicyclo[3.1.0]hexan-6-yl)ethyl)-3-(pyridin-3-yl)acrylamide;
(E)-N-(2-(3-benzyl-6-fluoro-3-azabicyclo[3.1.0]hexan-6-yl)ethyl)-3-(pyridin-3-yl)acrylamide;
(E)-3-(6-aminopyridin-3-yl)-N-(2-(6-fluoro-3-(pyrimidin-2-yl)-3-azabicyclo[3.1.0]hexan-6-yl)ethyl)acrylamide;
tert-butyl 6-fluoro-6-(2-((E)-3-(pyridin-3-yl)acrylamido)ethyl)-3-azabicyclo[3.1.0]hexane-3-carboxylate;
(E)-N-(2-(3-(2-chloro-5-fluoropyrimidin-4-yl)-6-fluoro-3-azabicyclo[3.1.0]hexan-6-yl)ethyl)-3-(pyridin-3-yl)acrylamide;
6-(2-((E)-3-(6-aminopyridin-3-yl)acrylamido)ethyl)-N-(tert-butyl)-3-azabicyclo[3.1.0]hexane-3-carboxamide;
6-(2-((E)-3-(6-aminopyridin-3-yl)acrylamido)ethyl)-N-(tert-butyl)-3-azabicyclo[3.1.0]hexane-3-carboxamide;
(E)-3-(pyridin-3-yl)-N-(2-(3-(pyrimidin-2-ylmethyl)-3-azabicyclo[3.1.0]hexan-6-yl)ethyl)acrylamide;
(E)-N-(2-(3-phenethyl-3-azabicyclo[3.1.0]hexan-6-yl)ethyl)-3-(pyridin-3-yl)acrylamide;
(E)-3-(pyridin-3-yl)-N-(2-(3-(2,2,2-trifluoro-1-phenylethyl)-3-azabicyclo[3.1.0]hexan-6-yl)ethyl)acrylamide;
(E)-N-(2-(3-(5-fluoro-2-methoxypyrimidin-4-yl)-3-azabicyclo[3.1.0]hexan-6-yl)ethyl)-3-(pyridin-3-yl)acrylamide;
(E)-3-(pyridin-3-yl)-N-(2-(3-(pyrimidin-5-ylmethyl)-3-azabicyclo[3.1.0]hexan-6-yl)ethyl)acrylamide;
(E)-N-(2-(3-(2-(difluoromethoxy)pyridin-4-yl)-3-azabicyclo[3.1.0]hexan-6-yl)ethyl)-3-(pyridin-3-yl)acrylamide;
(E)-N-(2-(3-(2-chlorobenzyl)-3-azabicyclo[3.1.0]hexan-6-yl)ethyl)-3-(pyridin-3-yl)acrylamide;
(E)-N-(2-(3-(3-chlorobenzyl)-3-azabicyclo[3.1.0]hexan-6-yl)ethyl)-3-(pyridin-3-yl)acrylamide;
(E)-N-(2-(3-(4-chlorobenzyl)-3-azabicyclo[3.1.0]hexan-6-yl)ethyl)-3-(pyridin-3-yl)acrylamide;
(E)-N-(2-(3-(5-fluoro-2-isopropoxypyrimidin-4-yl)-3-azabicyclo[3.1.0]hexan-6-yl)ethyl)-3-(pyridin-3-yl)acrylamide;
(E)-N-(2-(3-(2-(dimethylamino)-5-fluoropyrimidin-4-yl)-3-azabicyclo[3.1.0]hexan-6-yl)ethyl)-3-(pyridin-3-yl)acrylamide;
(E)-N-(2-(3-(5-fluoro-2-((tetrahydro-2H-pyran-4-yl)oxy)pyrimidin-4-yl)-3-azabicyclo[3.1.0]hexan-6-yl)ethyl)-3-(pyridin-3-yl)acrylamide;
(E)-N-(2-(3-(5-fluoro-2-phenoxypyrimidin-4-yl)-3-azabicyclo[3.1.0]hexan-6-yl)ethyl)-3-(pyridin-3-yl)acrylamide;
(E)-N-(2-(3-(2,6-dimethylpyridin-4-yl)-3-azabicyclo[3.1.0]hexan-6-yl)ethyl)-3-(pyridin-3-yl)acrylamide;
(E)-N-(2-(3-(2-(benzyloxy)-5-fluoropyrimidin-4-yl)-3-azabicyclo[3.1.0]hexan-6-yl)ethyl)-3-(pyridin-3-yl)acrylamide;
methyl 2-phenyl-2-(6-(2-((E)-3-(pyridin-3-yl)acrylamido)ethyl)-3-azabicyclo[3.1.0]hexan-3-yl)acetate;
(E)-3-(pyridin-3-yl)-N-(2-(3-(2-((tetrahydro-2H-pyran-4-yl)oxy)pyridin-4-yl)-3-azabicyclo[3.1.0]hexan-6-yl)ethyl)acrylamide;
(E)-N-(2-(3-(2-(2-(dimethylamino)ethoxy)-5-fluoropyrimidin-4-yl)-3-azabicyclo[3.1.0]hexan-6-yl)ethyl)-3-(pyridin-3-yl)acrylamide;
(E)-N-(2-(3-(2-amino-5-fluoropyrimidin-4-yl)-3-azabicyclo[3.1.0]hexan-6-yl)ethyl)-3-(pyridin-3-yl)acrylamide;
(E)-N-(2-(3-(5-fluoro-2-methoxypyrimidin-4-yl)-3-azabicyclo[3.1.0]hexan-6-yl)ethyl)-3-(6-fluoropyridin-3-yl)acrylamide;
(E)-N-(2-(3-(5-fluoro-2-(2-hydroxyethoxy)pyrimidin-4-yl)-3-azabicyclo[3.1.0]hexan-6-yl)ethyl)-3-(pyridin-3-yl)acrylamide;
(E)-3-(pyridin-3-yl)-N-(2-(3-(1-(pyrimidin-2-yl)ethyl)-3-azabicyclo[3.1.0]hexan-6-yl)ethyl)acrylamide;
(E)-N-(2-(3-((2-chloropyrimidin-5-yl)methyl)-3-azabicyclo[3.1.0]hexan-6-yl)ethyl)-3-(pyridin-3-yl)acrylamide;

(E)-N-(2-(3-(2-(methylamino)-2-oxo-1-phenylethyl)-3-azabicyclo[3.1.0]hexan-6-yl)ethyl)-3-(pyridin-3-yl)acrylamide;
(E)-N-(2-(3-(2-(diethylamino)-2-oxo-1-phenylethyl)-3-azabicyclo[3.1.0]hexan-6-yl)ethyl)-3-(pyridin-3-yl)acrylamide;
(E)-3-(pyridin-3-yl)-N-(2-(3-(1-(pyridin-4-yl)ethyl)-3-azabicyclo[3.1.0]hexan-6-yl)ethyl)acrylamide;
(E)-3-(pyridin-3-yl)-N-(2-(3-(1-(pyridin-3-yl)ethyl)-3-azabicyclo[3.1.0]hexan-6-yl)ethyl)acrylamide;
(E)-N-(2-(3-(1-(pyridin-2-yl)ethyl)-3-azabicyclo[3.1.0]hexan-6-yl)ethyl)-3-(pyridin-3-yl)acrylamide;
(E)-N-(2-(3-(1-(4-fluorophenyl)ethyl)-3-azabicyclo[3.1.0]hexan-6-yl)ethyl)-3-(pyridin-3-yl)acrylamide;
(E)-N-(2-(3-(1-(3-fluorophenyl)ethyl)-3-azabicyclo[3.1.0]hexan-6-yl)ethyl)-3-(pyridin-3-yl)acrylamide;
(E)-N-(2-(3-(5-fluoro-2-(piperazin-1-yl)pyrimidin-4-yl)-3-azabicyclo[3.1.0]hexan-6-yl)ethyl)-3-(pyridin-3-yl)acrylamide;
(E)-N-(2-(3-(5-fluoro-2-(4-methylpiperazin-1-yl)pyrimidin-4-yl)-3-azabicyclo[3.1.0]hexan-6-yl)ethyl)-3-(pyridin-3-yl)acrylamide;
(E)-N-(2-(3-(5-fluoro-2-(3-hydroxypyrrolidin-1-yl)pyrimidin-4-yl)-3-azabicyclo[3.1.0]hexan-6-yl)ethyl)-3-(pyridin-3-yl)acrylamide;
(E)-N-(2-(3-(5-fluoro-2-(methylamino)pyrimidin-4-yl)-3-azabicyclo[3.1.0]hexan-6-yl)ethyl)-3-(pyridin-3-yl)acrylamide;
(E)-N-(2-(3-(5-fluoro-2-(2-(methylamino)-2-oxoethoxy)pyrimidin-4-yl)-3-azabicyclo[3.1.0]hexan-6-yl)ethyl)-3-(pyridin-3-yl)acrylamide;
(E)-N-(2-(3-(2-(2-(diethylamino)-2-oxoethoxy)-5-fluoropyrimidin-4-yl)-3-azabicyclo[3.1.0]hexan-6-yl)ethyl)-3-(pyridin-3-yl)acrylamide;
(E)-N-(2-(3-(5-fluoro-2-methoxypyrimidin-4-yl)-3-azabicyclo[3.1.0]hexan-6-yl)ethyl)-3-(5-fluoropyridin-3-yl)acrylamide;
(E)-N-(2-(3-(5-fluoro-2-(2-morpholinoethoxy)pyrimidin-4-yl)-3-azabicyclo[3.1.0]hexan-6-yl)ethyl)-3-(pyridin-3-yl)acrylamide;
(E)-N-(2-(3-(5-fluoro-2-methoxypyrimidin-4-yl)-3-azabicyclo[3.1.0]hexan-6-yl)ethyl)-3-(4-fluoropyridin-3-yl)acrylamide;
(E)-N-(2-(3-(5-fluoro-2-(3-oxopiperazin-1-yl)pyrimidin-4-yl)-3-azabicyclo[3.1.0]hexan-6-yl)ethyl)-3-(pyridin-3-yl)acrylamide;
(E)-N-(2-(3-(2-methylbenzo[d]oxazol-7-yl)-3-azabicyclo[3.1.0]hexan-6-yl)ethyl)-3-(pyridin-3-yl)acrylamide;
(E)-N-(2-(3-(phenyl(tetrahydro-2H-pyran-4-yl)methyl)-3-azabicyclo[3.1.0]hexan-6-yl)ethyl)-3-(pyridin-3-yl)acrylamide;
(E)-N-(2-(3-(5-fluoro-2-(oxazol-2-yl)pyrimidin-4-yl)-3-azabicyclo[3.1.0]hexan-6-yl)ethyl)-3-(pyridin-3-yl)acrylamide;
(E)-N-(2-(3-(1H-indazol-4-yl)-3-azabicyclo[3.1.0]hexan-6-yl)ethyl)-3-(pyridin-3-yl)acrylamide;
diethyl(3-(6-(2-(E)-3-(pyridin-3-yl)acrylamido)ethyl)-3-azabicyclo[3.1.0]hexan-3-yl)phenyl)phosphonate;
(E)-3-(6-aminopyridin-3-yl)-N-(2-(3-(2-methoxypyridin-4-yl)-3-azabicyclo[3.1.0]hexan-6-yl)ethyl)acrylamide;
(E)-3-(6-aminopyridin-3-yl)-N-(2-(3-(1~ (4-fluorophenyl)ethyl)-3-azabicyclo[3.1.0]hexan-6-yl)ethyl)acrylamide;
(E)-3-(6-aminopyridin-3-yl)-N-(2-(3-(4-fluorophenyl)-3-azabicyclo[3.1.0]hexan-6-yl)ethyl)acrylamide;
(E)-N-(2-(3-(2-methyloxazolo[4,5-b]pyridin-7-yl)-3-azabicyclo[3.1.0]hexan-6-yl)ethyl)-3-(pyridin-3-yl)acrylamide; or
a pharmaceutically acceptable salt thereof.

2. A pharmaceutical composition comprising a compound according to claim 1 and a pharmaceutically acceptable carrier, solvent, adjuvant or diluent.

3. A method of treating lung cancer, fibrosarcoma or melanoma, the method comprising administering to a subject in need of such treatment one or more compounds according to claim 1.

4. A method of treating a cancer selected from lung cancer fibrosarcoma and melanoma, the method comprising administering to a subject in need of such treatment one or more compounds according to claim 1, and wherein the cancer is an IDH1 mutant cancer, an IDH2 mutant cancer, a cancer which includes mutation or gene amplification of at least one of the MYC, MYCN, and MYCL genes, or a cancer which includes reduced expression of NAPRT1 or DNA methylation of the NAPRT1 promoter.

5. A method of treating lung cancer, fibrosarcoma or melanoma by inhibiting nicotinamide phosphoribosyltransferase (NAMPT), the method comprising administering one or more compounds according to claim 1 to a subject in need of such treatment.

6. A compound which is:
tert-butyl 6-((5-(pyridin-3-yl) isoxazole-3-carboxamido)methyl)-3-azabicyclo[3.1.0]hexane-3-carboxylate;
tert-butyl 6-(((E)-3-(pyridin-3-yl)acrylamido)methyl)-3-azabicyclo[3.1.0]hexane-3-carboxylate;
tert-butyl 6-((2-(pyridin-3-yloxy) acetamido)methyl)-3-azabicyclo[3.1.0]hexane-3-carboxylate;
tert-butyl 6-(((E)-3-(6-aminopyridin-3-yl)acrylamido)methyl)-3-azabicyclo[3.1.0]hexane-3-carboxylate;
tert-butyl 6-((furo[2,3-c]pyridine-2-carboxamido)methyl)-3-azabicyclo[3.1.0]hexane-3-carboxylate;
tert-butyl 6-((thieno[2,3-c]pyridine-2-carboxamido)methyl)-3-azabicyclo[3.1.0]hexane-3-carboxylate;
3-methyloxetan-3-yl 6-(((E)-3-(pyridin-3-yl)acrylamido)methyl)-3-azabicyclo[3.1.0]hexane-3-carboxylate;
3-methyloxetan-3-yl 6-(((E)-3-(6-aminopyridin-3-yl)acrylamido)methyl)-3-azabicyclo[3.1.0]hexane-3-carboxylate;
(E)-3-(6-aminopyridin-3-yl)-N-((3-benzoyl-3-azabicyclo[3.1.0]hexan-6-yl)methyl)acrylamide;
tert-butyl 5-((3-(pyridin-3-ylmethyl) ureido)methyl) hexahydro-1H-isoindole-2 (3H)-carboxylate;
tert-butyl 5-((2,3-dihydro-1H-pyrrolo[3,4-c]pyridine-2-carboxamido)methyl) hexahydro-1H-isoindole-2 (3H)-carboxylate; or
a pharmaceutically acceptable salt thereof.

7. A pharmaceutical composition comprising a compound according to claim 6 and a pharmaceutically acceptable carrier, solvent, adjuvant or diluent.

8. A method of treating lung cancer, fibrosarcoma or melanoma, the method comprising administering to a subject in need of such treatment one or more compounds according to claim 6.

9. A method of treating lung cancer, fibrosarcoma or melanoma by inhibiting nicotinamide phosphoribosyltransferase (NAMPT), the method comprising administering one or more compounds according to claim 6 to a subject in need of such treatment.

10. A method of treating cancer selected from lung cancer, fibrosarcoma and melanoma, the method comprising administering to a subject in need of such treatment one or more compounds according to claim 6, and wherein the cancer is an IDH1 mutant cancer, an IDH2 mutant cancer, a cancer which includes mutation or gene amplification of at least one of the MYC, MYCN, and MYCL genes, or a cancer which includes reduced expression of NAPRT1 or DNA methylation of the NAPRT1 promoter.

* * * * *